US010058599B2

(12) United States Patent
Singh et al.

(10) Patent No.: US 10,058,599 B2
(45) Date of Patent: Aug. 28, 2018

(54) SUPPRESSOR CELL FUNCTION INHIBITION FOLLOWING *LISTERIA* VACCINE TREATMENT

(71) Applicant: Advaxis, Inc., Princeton, NJ (US)

(72) Inventors: Reshma Singh, Princeton, NJ (US); Anu Wallecha, Yardley, PA (US)

(73) Assignee: ADVAXIS, INC., Princeton, NJ (US)

( * ) Notice: Subject to any disclaimer, the term of this patent is extended or adjusted under 35 U.S.C. 154(b) by 0 days.

(21) Appl. No.: 14/383,970

(22) PCT Filed: Mar. 12, 2013

(86) PCT No.: PCT/US2013/030521
§ 371 (c)(1),
(2) Date: Sep. 9, 2014

(87) PCT Pub. No.: WO2013/138337
PCT Pub. Date: Sep. 19, 2013

(65) Prior Publication Data
US 2015/0098964 A1    Apr. 9, 2015

Related U.S. Application Data

(60) Provisional application No. 61/609,627, filed on Mar. 12, 2012.

(51) Int. Cl.
*A61K 39/02* (2006.01)
*A61K 39/00* (2006.01)
*A61K 39/12* (2006.01)
*A61K 35/74* (2015.01)
*A61K 48/00* (2006.01)
*A61K 35/00* (2006.01)

(52) U.S. Cl.
CPC .......... *A61K 39/0208* (2013.01); *A61K 35/74* (2013.01); *A61K 39/0011* (2013.01); *A61K 39/12* (2013.01); *A61K 48/00* (2013.01); *A61K 2035/11* (2013.01); *A61K 2039/522* (2013.01); *A61K 2039/523* (2013.01); *A61K 2039/55594* (2013.01); *A61K 2039/585* (2013.01); *A61K 2039/6068* (2013.01); *C12N 2710/20034* (2013.01)

(58) Field of Classification Search
None
See application file for complete search history.

(56) References Cited

U.S. PATENT DOCUMENTS

| 4,458,066 | A | 7/1984 | Caruthers et al. |
|---|---|---|---|
| 4,521,382 | A | 6/1985 | Kessick |
| 4,816,567 | A | 3/1989 | Cabilly et al. |
| 5,204,253 | A | 4/1993 | Sanford et al. |
| 5,262,177 | A | 11/1993 | Brown et al. |
| 5,580,859 | A | 12/1996 | Felgner et al. |
| 5,589,466 | A | 12/1996 | Felgner et al. |
| 5,643,599 | A | 7/1997 | Lee et al. |
| 5,679,647 | A | 10/1997 | Carson et al. |
| 5,681,570 | A | 10/1997 | Yang |
| 5,736,524 | A | 4/1998 | Content et al. |
| 5,739,118 | A | 4/1998 | Carrano et al. |
| 5,804,566 | A | 9/1998 | Carson et al. |
| 5,824,538 | A | 10/1998 | Branstorm et al. |
| 5,830,702 | A | 11/1998 | Portnoy et al. |
| 5,858,682 | A | 1/1999 | Gruenwald et al. |
| 5,877,159 | A | 3/1999 | Powell et al. |
| 5,922,583 | A | 7/1999 | Morsey et al. |
| 5,922,687 | A | 7/1999 | Mann et al. |
| 6,004,815 | A | 12/1999 | Portnoy et al. |
| 6,015,567 | A | 1/2000 | Hudziak et al. |
| 6,017,705 | A | 1/2000 | Lurquin et al. |
| 6,051,237 | A | 4/2000 | Paterson et al. |
| 6,099,848 | A | 8/2000 | Frankel et al. |
| 6,287,556 | B1 | 9/2001 | Portnoy et al. |
| 6,306,404 | B1 | 10/2001 | LaPosta et al. |
| 6,329,511 | B1 | 12/2001 | Vasquez et al. |
| 6,479,258 | B1 | 11/2002 | Short |
| 6,500,432 | B1 | 12/2002 | Dalemans et al. |
| 6,504,020 | B1 | 1/2003 | Frankel et al. |
| 6,521,449 | B1 | 2/2003 | Polack et al. |
| 6,565,852 | B1 | 5/2003 | Paterson |
| 6,599,502 | B2 | 7/2003 | Portnoy et al. |
| 6,635,749 | B2 | 10/2003 | Frankel et al. |
| 6,641,814 | B1 | 11/2003 | Andersen |
| 6,740,516 | B2 | 5/2004 | Savitzky et al. |
| 6,767,542 | B2 | 7/2004 | Paterson et al. |
| 6,773,900 | B2 | 8/2004 | Short et al. |
| 6,855,320 | B2 | 2/2005 | Paterson et al. |
| 6,991,785 | B2 | 1/2006 | Frey, II |
| 7,135,188 | B2 | 11/2006 | Paterson et al. |

(Continued)

FOREIGN PATENT DOCUMENTS

| CN | 1763093 A | 4/2006 |
|---|---|---|
| CN | 103687611 A | 3/2014 |

(Continued)

OTHER PUBLICATIONS

Singh et al. (Human Vaccines, 7:497-505, 2011).*
Yamamoto et al. (Clin Experiment. Immunol., 144:475-484, 2006).*
U.S. Appl. No. 60/490,089, filed Jul. 24, 2003, Thomas W. Dubensky.
Abachin et al., Formation of D-alanyl-lipoteichoic acid is required for adhesion and virulence of Listeria monocytogenes 2002, Mol Microbiol 43:1-14.
Adams et al., 1992, "Cre-lox recombination in *Escherichia coli* cells Mechanistic differences from the in vitro reaction", J. Mol. Biol. 226:661-673.

(Continued)

*Primary Examiner* — Brian Gangle
(74) *Attorney, Agent, or Firm* — Alston & Bird LLP

(57) ABSTRACT

This invention provides methods and compositions for using a live attenuated *Listeria* for inhibiting cell-mediated suppression of anti-disease infiltrating T lymphocytes in a subject having the disease.

14 Claims, 42 Drawing Sheets
Specification includes a Sequence Listing.

(56) References Cited

U.S. PATENT DOCUMENTS

| | | |
|---|---|---|
| 7,375,091 B2 | 5/2008 | Cheever et al. |
| 7,425,449 B2 | 9/2008 | Portnoy et al. |
| 7,488,487 B2 | 2/2009 | Frankel et al. |
| 7,488,802 B2 | 2/2009 | Collins et al. |
| 7,521,051 B2 | 4/2009 | Collins et al. |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,662,396 B2 | 2/2010 | Paterson et al. |
| 7,691,393 B2 | 4/2010 | Dubensky et al. |
| 7,700,344 B2 | 4/2010 | Paterson et al. |
| 7,786,288 B2 | 8/2010 | Karp |
| 7,790,177 B2 | 9/2010 | Karp |
| 7,794,728 B2 | 9/2010 | Portnoy et al. |
| 7,794,729 B2 | 9/2010 | Paterson et al. |
| 7,820,180 B2 | 10/2010 | Paterson et al. |
| 7,842,289 B2 | 11/2010 | Dubensky et al. |
| 7,855,064 B2 | 12/2010 | Paterson et al. |
| 7,858,097 B2 | 12/2010 | Paterson et al. |
| 7,871,604 B1 | 1/2011 | Curtiss, III et al. |
| 7,887,822 B2 | 2/2011 | Ferrone et al. |
| 7,935,804 B2 | 5/2011 | Dubensky et al. |
| 8,008,449 B2 | 8/2011 | Korman et al. |
| 8,114,414 B2 | 2/2012 | Paterson |
| 8,168,757 B2 | 5/2012 | Finnefrock et al. |
| 8,241,636 B2 | 8/2012 | Paterson et al. |
| 8,268,326 B2 | 9/2012 | Paterson et al. |
| 8,287,883 B2 | 10/2012 | Dubensky et al. |
| 8,337,861 B2 | 12/2012 | Paterson et al. |
| 8,354,509 B2 | 1/2013 | Carven et al. |
| 8,383,796 B2 | 2/2013 | Korman et al. |
| 8,771,702 B2 | 7/2014 | Paterson et al. |
| 8,778,329 B2 | 7/2014 | Sewell |
| 8,791,237 B2 | 7/2014 | Paterson et al. |
| 8,906,664 B2 | 12/2014 | Paterson et al. |
| 8,956,621 B2 | 2/2015 | Paterson et al. |
| 9,012,141 B2 | 4/2015 | Paterson et al. |
| 9,017,660 B2 | 4/2015 | Shahabi et al. |
| 9,084,747 B2 | 7/2015 | Shahabi et al. |
| 9,226,958 B2 | 1/2016 | Harn et al. |
| 9,408,898 B2 | 8/2016 | Seavey et al. |
| 9,463,227 B2 * | 10/2016 | Rothman ............... A61K 35/74 |
| 9,492,527 B2 | 11/2016 | Paterson et al. |
| 9,499,602 B2 | 11/2016 | Paterson et al. |
| 9,549,973 B2 | 1/2017 | Paterson et al. |
| 9,644,212 B2 | 5/2017 | Maciag et al. |
| 9,650,639 B2 | 5/2017 | Maciag et al. |
| 9,700,608 B2 | 7/2017 | Paterson et al. |
| 2002/0025323 A1 | 2/2002 | Paterson et al. |
| 2002/0028206 A1 | 3/2002 | Paterson |
| 2002/0136737 A1 | 9/2002 | Frankel et al. |
| 2002/0165172 A1 | 11/2002 | Sallberg et al. |
| 2003/0202985 A1 | 10/2003 | Paterson |
| 2003/0219802 A1 | 11/2003 | Dhaini et al. |
| 2003/0220239 A1 | 11/2003 | Simard et al. |
| 2004/0013685 A1 | 1/2004 | Andersen et al. |
| 2004/0013690 A1 | 1/2004 | Portnoy et al. |
| 2004/0031690 A1 | 1/2004 | Portnoy et al. |
| 2004/0058342 A1 | 3/2004 | Yousef |
| 2004/0228877 A1 | 11/2004 | Dubensky et al. |
| 2005/0048081 A1 | 3/2005 | Frankel |
| 2005/0118184 A1 | 6/2005 | Paterson et al. |
| 2005/0129715 A1 | 6/2005 | Paterson et al. |
| 2005/0281783 A1 | 12/2005 | Kinch et al. |
| 2006/0051380 A1 | 3/2006 | Schulick et al. |
| 2006/0073170 A1 | 4/2006 | Papierok |
| 2006/0093582 A1 | 5/2006 | Paterson et al. |
| 2006/0104991 A1 | 5/2006 | Paterson et al. |
| 2006/0121053 A1 | 6/2006 | Sweeney et al. |
| 2006/0204516 A1 | 9/2006 | Paterson et al. |
| 2006/0205067 A1 | 9/2006 | Paterson et al. |
| 2006/0210540 A1 | 9/2006 | Paterson et al. |
| 2006/0233835 A1 | 10/2006 | Paterson et al. |
| 2006/0269561 A1 | 11/2006 | Paterson et al. |
| 2007/0003567 A1 | 1/2007 | Paterson et al. |
| 2007/0154953 A1 | 7/2007 | Brunner et al. |
| 2007/0207170 A1 | 9/2007 | Dubensky et al. |
| 2007/0207171 A1 | 9/2007 | Dubensky et al. |
| 2007/0253976 A1 | 11/2007 | Paterson et al. |
| 2007/0264279 A1 | 11/2007 | Paterson et al. |
| 2008/0124354 A1 | 5/2008 | Paterson et al. |
| 2008/0131456 A1 | 6/2008 | Paterson et al. |
| 2008/0213295 A1 | 9/2008 | Cheever et al. |
| 2008/0241069 A1 | 10/2008 | Paterson |
| 2009/0081248 A1 | 3/2009 | Paterson et al. |
| 2009/0081250 A1 | 3/2009 | Paterson et al. |
| 2009/0186051 A1 | 7/2009 | Paterson et al. |
| 2009/0202587 A1 | 8/2009 | Paterson et al. |
| 2009/0143085 A1 | 11/2009 | Lauer et al. |
| 2010/0069344 A1 | 3/2010 | Wang et al. |
| 2010/0189739 A1 | 7/2010 | Frankel et al. |
| 2010/0233212 A1 | 9/2010 | Dubensky |
| 2010/0291140 A1 | 11/2010 | Paterson et al. |
| 2011/0129499 A1 | 6/2011 | Maciag et al. |
| 2011/0142791 A1 | 6/2011 | Shahabi et al. |
| 2011/0223107 A1 | 9/2011 | Tremblay et al. |
| 2011/0223187 A1 | 9/2011 | Shahabi et al. |
| 2011/0271358 A1 | 11/2011 | Freeman et al. |
| 2011/0305724 A1 | 12/2011 | Paterson et al. |
| 2012/0014984 A1 | 1/2012 | Shahabi |
| 2012/0114685 A1 | 5/2012 | Sewell |
| 2012/0135033 A1 | 5/2012 | Wallecha |
| 2012/0177678 A1 | 7/2012 | Paterson et al. |
| 2013/0259891 A1 | 10/2013 | Harn et al. |
| 2014/0186387 A1 | 7/2014 | Lauer et al. |
| 2014/0199258 A1 | 7/2014 | Rothman |
| 2014/0234370 A1 | 8/2014 | Shahabi |
| 2014/0248304 A1 | 9/2014 | Paterson et al. |
| 2014/0314708 A1 | 10/2014 | Maciag et al. |
| 2014/0335120 A1 | 11/2014 | Maciag et al. |
| 2015/0079034 A1 | 3/2015 | Seavey et al. |
| 2015/0125480 A1 | 5/2015 | Paterson et al. |
| 2015/0196628 A1 | 7/2015 | Mason et al. |
| 2015/0238584 A1 | 8/2015 | Shahabi et al. |
| 2015/0297702 A1 | 10/2015 | Shahabi |
| 2015/0335721 A1 | 11/2015 | Paterson et al. |
| 2015/0343047 A1 | 12/2015 | Paterson et al. |
| 2015/0366955 A9 | 12/2015 | Shahabi et al. |
| 2016/0022814 A1 | 1/2016 | Petit et al. |
| 2016/0024173 A1 | 1/2016 | Paterson et al. |
| 2016/0158331 A1 | 6/2016 | Paterson et al. |
| 2016/0206716 A1 | 7/2016 | Seavey et al. |
| 2016/0220652 A1 | 8/2016 | Petit et al. |
| 2016/0228530 A1 | 8/2016 | Paterson |
| 2016/0256538 A1 | 9/2016 | Harn et al. |
| 2016/0324903 A1 | 11/2016 | Rothman et al. |
| 2016/0361401 A1 | 12/2016 | Shahabi et al. |
| 2016/0367650 A1 | 12/2016 | Paterson |
| 2017/0028045 A1 | 2/2017 | Paterson et al. |
| 2017/0042996 A1 | 2/2017 | Wallecha et al. |
| 2017/0049867 A1 | 2/2017 | Seavey et al. |
| 2017/0080064 A1 | 3/2017 | Petit et al. |
| 2017/0100469 A1 | 4/2017 | Paterson et al. |
| 2017/0106072 A1 | 4/2017 | Petit |
| 2017/0204361 A1 | 7/2017 | Eapen et al. |
| 2017/0246273 A1 | 8/2017 | Wallecha et al. |
| 2017/0281691 A1 | 10/2017 | Paterson et al. |

FOREIGN PATENT DOCUMENTS

| | | |
|---|---|---|
| EP | 0902086 | 3/1999 |
| EP | 1408048 | 4/2004 |
| JP | 2007-161700 A | 6/2007 |
| JP | 2008-509677 T | 4/2008 |
| JP | 2013-526837 | 6/2013 |
| RU | 2009122560 A | 12/2010 |
| WO | WO 1990/012594 | 11/1990 |
| WO | WO 1992/020356 | 11/1992 |
| WO | WO 1993/015212 | 8/1993 |
| WO | WO 1994/017192 | 8/1994 |
| WO | WO 1996/014087 A1 | 5/1996 |
| WO | WO 1996/034631 | 11/1996 |
| WO | WO 1996/039154 | 12/1996 |
| WO | WO 1997/003211 | 1/1997 |

(56) References Cited

FOREIGN PATENT DOCUMENTS

| WO | WO 1998/004720 | 2/1998 |
|---|---|---|
| WO | WO 1998/048026 | 10/1998 |
| WO | WO 1999/007861 | 2/1999 |
| WO | WO 1999/025376 | 5/1999 |
| WO | WO 2001/072329 | 10/2001 |
| WO | WO 2001/079274 | 10/2001 |
| WO | WO 2001/079274 | 7/2002 |
| WO | WO 2003/045318 A2 | 6/2003 |
| WO | WO 2003/092600 | 11/2003 |
| WO | WO 2003/102168 | 12/2003 |
| WO | WO 2004/004771 | 1/2004 |
| WO | WO 2004/006837 | 1/2004 |
| WO | WO 2004/056875 | 7/2004 |
| WO | WO 2004/062597 A2 | 7/2004 |
| WO | WO 2004/072286 | 8/2004 |
| WO | WO 2004/084936 | 10/2004 |
| WO | WO 2004/110481 | 12/2004 |
| WO | WO 2005/009463 | 2/2005 |
| WO | WO 2005/037233 | 4/2005 |
| WO | WO 2005/061534 | 7/2005 |
| WO | WO 2005/071088 | 8/2005 |
| WO | WO 2006/017856 | 2/2006 |
| WO | WO 2006/036550 | 4/2006 |
| WO | WO 2007/061848 | 5/2007 |
| WO | WO 2007/103225 | 9/2007 |
| WO | WO 2007/106476 A2 | 9/2007 |
| WO | WO 2007/130455 A2 | 11/2007 |
| WO | WO 2007/137258 A2 | 11/2007 |
| WO | WO 2008/045148 A2 | 4/2008 |
| WO | WO 2008/079172 A2 | 7/2008 |
| WO | WO 2008/109155 | 9/2008 |
| WO | WO 2008/130551 | 10/2008 |
| WO | WO 2008/140812 A2 | 11/2008 |
| WO | WO 2009/110950 | 9/2009 |
| WO | WO2009/143085 | 11/2009 |
| WO | WO 2009/143167 | 11/2009 |
| WO | WO 2010/008782 A1 | 1/2010 |
| WO | WO 2010/011870 | 1/2010 |
| WO | WO 2010/027827 | 3/2010 |
| WO | WO 2010/040135 A1 | 4/2010 |
| WO | WO 2010/077634 | 7/2010 |
| WO | WO 2010/102140 A1 | 9/2010 |
| WO | WO 2011/060260 A2 | 5/2011 |
| WO | WO 2011/066342 | 6/2011 |
| WO | WO 2011/100754 A1 | 8/2011 |
| WO | WO 2012/12551 | 9/2012 |
| WO | WO 2012/138377 A2 | 10/2012 |
| WO | WO 2013/019906 A1 | 2/2013 |
| WO | WO 2013/025925 A1 | 2/2013 |
| WO | WO 2013/138337 A1 | 9/2013 |
| WO | WO 2014/100079 | 6/2014 |
| WO | WO 2015/126921 A1 | 8/2015 |
| WO | WO 2015/130810 A2 | 9/2015 |
| WO | WO 2015/134722 A2 | 9/2015 |
| WO | WO 2015/164121 A1 | 10/2015 |
| WO | WO 2015/167748 A1 | 11/2015 |
| WO | WO 2016/011320 | 1/2016 |
| WO | WO 2016/011353 A1 | 1/2016 |
| WO | WO 2016/011357 A1 | 1/2016 |
| WO | WO 2016/011362 A1 | 1/2016 |
| WO | WO 2016/061182 A1 | 4/2016 |
| WO | WO 2016/061277 A1 | 4/2016 |
| WO | WO 2016/100924 A1 | 6/2016 |
| WO | WO 2016/100929 A1 | 6/2016 |
| WO | WO 2016/126876 | 8/2016 |
| WO | WO 2016/126878 A2 | 8/2016 |
| WO | WO 2016/141121 A1 | 9/2016 |
| WO | WO 2016/154412 A2 | 9/2016 |
| WO | WO 2016/183361 A1 | 11/2016 |
| WO | WO 2016/191545 A1 | 12/2016 |
| WO | WO 2016/207859 A1 | 12/2016 |
| WO | WO 2017/048714 A1 | 3/2017 |
| WO | WO 2017/048850 A1 | 3/2017 |
| WO | WO 2017/049218 A2 | 3/2017 |
| WO | WO 2017/066706 A1 | 4/2017 |
| WO | WO 2017/085691 A1 | 5/2017 |
| WO | WO 2017/106754 A2 | 6/2017 |
| WO | WO 2017/132547 A1 | 8/2017 |

OTHER PUBLICATIONS

Ahmadzadeh et al. Tumor antigen-specific CD8 T cells infiltrating the tumor express high levels of PD-1 and are functionally impaired. Blood (2009) 114: 1537-1544.

Alexander et al, Characterization of an Aromatic Amino Acid-Dependent Listeria Monocytogenes Mutant: Attenuation, Persistence, and Ability to Induce Protective Immunity in Mice 1993, Infection and Immunity 10 61 :2245-2248.

Al-Lazikani et al. JMB Standard Conformations for the Canonical Structures of Immunoglobulins., J. Mol. Biol. 273:927-948 (1997).

Allision et al., 1997, "Cloning and characterization of a Prevotella melaninogenica hemolysin", Infect. Immun. 65(7):2765-71.

Altschul et al. Basic Local Alignment Search Tool Basic Local Alignment Search Tool; J. Mol. Biol. 215:403-410 (1990).

Altschul "Amino Acid Substitution Matrices from an Information Theoretic Perspective", J. Mol. Biol. 219:555-565 (1991).

Altschul et al. A Protein Alignment Scoring System Sensitive at all Evolutionary Distances; J. Mol. Evol. 36:290-300 (1993).

Altschul et al., "Gapped BLAST and PSI-BLAST: a new generation of protein database search programs" (1997) Nucleic Acids Res. 25:3389-3402.

Amersham. Introduction to Glutathione S-transferase (GST) Gene Fusion System , Pharmacia Biotech; BioDirectory, Piscataway, N.J., ( pp. 384-391) (2001).

An et al., 1996, "A recombinant minigene vaccine containing a nonameric cytotoxic-T-Lymphocyte epitope confers limited protection against Listeria monocytogenes infection", Infect. Immun., vol. 64, No. 5, p. 1685-1693.

Anderson, 1998, "Human gene therapy ", Nature, Apr. 30; 392 (6679 Suppl):25-30.

Angelakopoulos et al., "Safety and shedding of an attenuated strain of listeria Monocytogenes with a delection of actA/plcB in adult volunteers: a dose escalation study of oral innoculation", Infection and Immunity 2002, 70(7): 3592-3601.

Anthony "Precursor Lesions for Liver Cancer in Humans" Cancer Res. (1976) 36:2579-2583.

Attwood et al., "The Babel of Bioinformatics", Science, vol. 290, No. 5491: 471-473, 2000.

Auchtung et al "Regulation of a Bacillus subtilis mobile genetic element by intercellular signaling and the global DNA damage response". Proc Natl Acad Sci USA. Aug. 30, 2005;102 (35):12554-9.

Auerbuch, et al. "Development of a Competitive Index Assay to Evaluate the Virulence of Listeria monocytogenes actA Mutants during Primary and Secondary Infection of Mice " (2001) Infect. Immunity 69:5953-5957.

Awwad, 1989, "Cyclophosphamide-induced immunologically mediated regression of a cyclophosphamide-resistant murine tumor: a consequence of eliminating precursor L3T4+ suppresor T-cells", Cancer Res., 49(7):1649-1654.

Baca et al. "Protein Chemistry and Structure: Antibody Humanization Using Monovalent Phage Display", (1997) J. Biol. Chem. 272:10678-10684.

Baert et al. "Influence of Immunogenicity on the Long-Term Efficacy of Infliximab in Crohn's Disease " (2003) New Engl. J. Med. 348:601-608.

Baloglu et al. "Immune Responses of Mice to Vaccinia Virus Recombinants Expressing Either Listeria Monocytogenes Partial Listeriolysin or *Brucella abortus* Ribosomal L7/L12 Protein" Vet Microbiol.; 109(1-2) M, Aug. 10, 2005.

Bargmann et al. "The neu oncogene encodes an epidermal growth factor receptor-related protein" Nature 319, 226-230, Jan. 16, 1986.

Bear, 1986, "Tumor-specific suppressor T-cells which inhibit the in vitro generation of cytolytic T-cells from immune and early tumor-bearing host spleens", Cancer Res., Apr.; 46(4 Pt 1):1805-12.

Beattie et al. "Cloning and charcterization of T-cell-reactive protein antigens from Listeria monocytogenes", infect. Immune. Sep. 1990, 58(9):2792-803.

(56) References Cited

OTHER PUBLICATIONS

Beatty et al., IFN-gamma-dependent inhibition of tumor angiogenesis by tumor-infiltrating CD4+ T cells requires tumor responsiveness to IFN-gamma.J Immunol. Feb. 15, 2001;166(4):2276-82.
Beaucage et al. "Deoxynucleoside Phosphoramidites—A New Class of Key Intermediates for Deoxypolynucleotide Synthesis" Tetra. Lett. 22:1859-1862, (1981).
Becker at al., The changes in the T helper 1 (Th1) and T helper 2 (Th2) cytokine balance 3,4during HIV-1 infection are indicative of an allergic response to viral proteins that may bereversed by Th2 cytokine inhibitors and immune response modifiers—a review and hypothesis; Viruses Genes 28:5-18 (2004).
Belt et al (1991) Efficient cDNA cloning by direct phenotypic correction of a mutant human cell line (HPRT2) using an Epstein-Barr virus-derived cDNA expression vector. Nucleic Acids Res. 19, 4861-4866.
Beniaminovitz et al. "Prevention of Rejection in Cardiac Transplantation by Blockade of the Interleukin-2 Receptor With a Monoclonal Antibody" (2000) New Engl. J. Med. 342:613-619.
Benvegnu, et al. Space Occupying lesions of the liver detected by ultrasonography and their relation to hypatocellular Carcinoma in Cirrhosis; Liver 12:80-83 (1992).
Bernhard et al., 2002, "Vaccination against the HER-2/neu oncogenic protein", Endocrine-Related Cancer, 9:33-44.
Bielecki et al. "Bacillus subtilis expressing a haemolysin gene from Lesteria monocytogenes can grow in mammalian cells", Nature 1990, 354:175-176.
Billaut-Mulot et al. Interleukin-18 modulates immune responses induced by HIV-1 Nef DNA prime/protein boost vaccine; Vaccine 19:95-102 (2000).
Billington et al., 1997, "The Arcanobacterium (Actinomyces) pyogenes hemolysin, pyolysin, is a novel member of the thiol-activated cytolysin family", J. Bacteriol. Oct; 179(19):6100-6.
Bird et al. "An autologous dendritic cell canine mammary tumor hybrid-cell fusion vaccine", Cancer Immunol Immunother. Jan. 2011;60(1):87-97.
Bishop et al. "Adoptive Transfer of Immunity to Listeria Monocytogenes the Influence of In Vitro Stimulationon Lymphocyte Subset Requirements", J. Immunol. 139: 2005-2009 (1987).
Bodmer et al., 1988, "Enhanced recognition of a modified peptide antigen by cytotoxic T cells specific for influenza nucleoprotein", Cell 52:253-258.
Boon et al., 2006, "Human T-cell responses against melanoma" Annu. Rev. Immunol. 24:175-208.
Bourquin et al., 2000, "Myelin oligodendrocyte glycoprotein-DNA vaccination induces antibody-mediated autoaggression in experimental autoimmune encephalomyelitis" Eur. J. Immunol. 30:3663-3671.
Bouwer et al. Acquired immunity to an intracellular pathogen: immunologic recognition of L. monocytogenes-infected cells, Immunol. Rev. Aug. 1997; 158:137-46.
Bouwer et al. Cytotoxic-T-lymphocyte responses to epitopes of listeriolysin O and p60 following infection with Listeria monocytogenes, Infect. Immune. Jul. 1996; 64(7):2515-22.
Boyer et al., "DNA prime Listeria boost induces a cellular immune response to SIV antigens in the Rhesus Macaque model that is capable of limited suppression of SIV239 viral replication", Virology. 333: 88-101, 2005.
Brantl et al, "Molecular analysis of the replication region of the conjugative Streptococcus agalactiae plasmid pIP501 in Bacillus subtilis. Comparison with plasmids pAM31 and pSM1 9035" Nucleic Acid Res 18: 4783-4790, 1990.
Brett et al. "Comparison of antigen presentation of influenza A nucleoprotein expressed in attenuated AroA-*Salmonella typhimurium* with that of live virus", J Immunol. Apr. 1, 1993;150(7):2869-84.
Brockstedt et al, "Listeria-based cancer vaccines that segregate immunogenicity from toxicity" 2004, PNAS, 101:13832-13837.

Bron et al, "Use of the air Gene as a Food-Grade Selection Marker in Lactic Acid Bacteria" 2002, Appl Environ Microbiol, 68: 5663-70.
Bron et al., 2004, "Identification of Lactobacillus plantarum genes that are induced in the gastrointestinal tract of mice", J. Bacteriol. Sep.; 186(17):5721-9.
Brown et al., 1988, "Site-specific integration in Saccharopolyspora erthraea and multisite integration in Streptomyces lividans of actinomycete plasmid pSE101", J. Bacteriology 170: 2287-2295.
Brown et al. "Chemical synthesis and cloning of a tyrosine tRNA gene" 1979, Meth. Enzymol. 68:109-151.
Bruder et al. "Efficient induction of cytotoxic CD8+ T cells against exogenous proteins: establishment and characterization of a T cell line specific for the membrane protein ActA of Listeria monocytogenes", Eur. J. Immunol. Sep. 1998; 28(9):2630-9.
Bruhn et al., 2005, "Characterization of anti-self CD8 T-cell responses stimulated by recombinant Listeria monocytogenes expressing the melanoma antigen TRP-2", Vaccine, Jul. 21; 23(33):4263-72.
Brundage et al, 1993. Expression and phosphorylation of the Listeria monocytogenes ActA protein in mammalian cells, Proc. Natl. Acad. Sci., USA, 90:11890-11894.
Bubert et al., 1997, "The Listeria monocytogenes iap gene as an indicator gene for the study of PrfA-dependent regulation", Mol. Gen. Genet. Sep.; 256(1):54-62.
Calendar et al., Poster presented at the ISOPOL Meeting 2001, http://64.233.169.104/search?q=cache:mA_uJpQsCrcJ:www.ma.uni-heidelberg.de/inst/imh/download/isopol.doc+Portnoy+Isopol+2001&hl=en&ct=clnk&cd=3&gl=us.
Camilli et al., 1993, "Daul roles of plcA in Listeria monocytogenes pathogenesis", Mol. Microbiol. 8:143-157.
Camilli et al. "Insertional mutagenesis of Listeria monocytogenes with a novel Tn917 derivative that allows direct cloning of DNA flanking transposon insertions", J Bacteriol, Jul. 1990;172(7):3738-44.
Camilli et al, 1991, Listeria monocytogenes mutants lacking phosphatidylinositol-specific phospholipase C area virulent, J. Exp. Med., 173:751-754.
Carbone, 1989, "Induction of ovalbumin-specific cytotoxic T cells by in vivo peptide immunization" J. Exp. Med. 169:603-612.
Carbone, 1990, "Class I-restricted processing and presentation of exogenous cell-associated antigen in vivo", J. Exp. Med. 171:377-387.
Carpenter et al. Non-Fc Receptor-Binding Humanized Anti-CD3 Antibodies Induce Apoptosis of Activated Human T Cells; J. Immunol. 165:6205-6213 (2000).
Catic et al. "Introduction of protein or DNA delivered via recombinant *Salmonella typhimurium* into the major histocompatibility complex class I presentation pathway of macrophages", Microbes Infect., Feb. 1999, 1(2):113-21.
Cenatiempo, "Prokaryotic gene expression in vitro: transcription-translation coupled systems." 1986, Biochimie 68:505-516.
Chen et al. "Episomal Expression of Truncated Listeriolysin O in LmddA-LLO-E7 Vaccine Enhances Antitumor Efficacy by Preferentially Inducing Expansions of CD4FoxP3_ andCD8 T Cells", Cancer Immunol Res; 2(9) Sep. 2014, pp. 911-922.
Chen, B.J. et al., "PD-L1 Expression Is Characteristic of a Subset of Aggressive B-cell Lymphomas and Virus-Associated Malignancies" Clin Cancer Res 19: 3462-3473 (2013).
Chothia et al. Canonical Structures for the Hypervariable Regions of Immunoglobulins; J Mol. Biol. 196:901-917 (1987).
Chothia et al. Confirmations of immunoglobulin hypervariable Regions; Nature 342:878-883 (1989).
Ciesielski et al. "Therapeutic Effect of a T Helper Cell Supported CTL Response Induced by a Survivin Peptide Vaccine against Murine Cerebral Glioma"; Cancer Immunol Immunother; 57(12): 1827-1835 (2008).
Clackson et al. Making Antibody Fragments Using Phage Display Libraries; Nature 352: 624-628 (1991).
Clark et al., "Clinical use of streptolysin-O to facilitate antisense oligodeoxyribonucleotide delivery for purging autografts in chronic myeloid leukaemia", Bone Marrow Transplantation, vol. 23, No. 12, 1999, pp. 1303/1308.

(56) References Cited

OTHER PUBLICATIONS

Clifton et al., "Overcoming cancer immune tolerance and escape", Clinical Cancer Research : An Official Journal of the American Association for Cancer Research 2009, vol. 15, No. 3, pp. 749-751.
Collins et al. "Directional cloning of DNA fragments at a large distance from an initial probe: a circularization method", Proc Natl Acad Sci U S A. Nov. 1984;81(21):6812-6.
Courvalin et al., 1995, "Gene transfer from bacteria to mammalian cells", C R Acad Sci III, Dec; 318(12):1207-12.
Coynault et al. "Virulence and vaccine potential of *Salmonella typhimurium* mutants deficient in the expression of the RpoS (sigma S) regulon", Mol Microbiol. Oct. 1996;22(1):149-60.
Cunto-Amesty et al., 2003, "Strategies in cancer vaccines development", Int. J. Parasitol. 33(5-6):597-613.
Da'Dara et al. Elimination of helminth infection restores HIV-1C vaccine-specific T cellresponses independent of helminth-induced IL-10; Vaccine; 3;28(5):1310-7 (2010).
Dakappagari et al., 2000, "Prevention of mammary tumors with a chimeric HER-2 B-cell epitope peptide vaccine", Cancer Res. Jul. 15; 60(14):3782-9.
Darji et al. The role of the bacterial membrane protein ActA in immunity and protection against Listeria monocytogenes, J. Immunol. Sep. 1, 1998, 161(5):2414-20.
Darji et al. "Antigen-specific T cell receptor antagonism by antigen-presenting cells treated with the hemolysin of Listeria monocytogenes: a noval type of immune escape", Eur. J. Immunol. Jul. 1997; 27(7):1696-703.
Darji et al. T-cell energy induced by antigen presenting cells treated with the hemolysin of Listeria monocytogenes, Immunol. Lett. Jun. 1, 1997, 57(1-3):33-7.
Darji et al., 1995, "Hyperexpression of listeriolysin in the nonpathogenic species *Listeria innocua* and high yield purification", J. Biotechnol. Dec. 15; 43(3):205-12.
Darji et al., 1995, "Listeriolysin generates a route for the presentation of exogenous antigens by major histocompatibility complex class I", Eur. J. Immunol. Oct.; 25(10):2967-71.
Darji et al., 1997, "Oral somatic transgene vaccination using attenuated S. typhimurium" Cell 91:765-775.
Darji et al., 1997, "TAP-dependent major histocompatibility complex class I presentation of soluble proteins using listeriolysin", Eur. J. Immunol. Jun; 27(6):1353-9.
Darji et al., 2003, "Induction of immune responses by attenuated isogenic mutant strains of Listeria monocytoge" Vaccine 1; 21 Suppl. 2:S102-9.
De Boer et al, "A division inhibitor and a topological specificity factor coded for by the minicell locus determine proper placement of the division septum in *E. coli*" 1989, Cell 56:641-649.
De Bruin et al. Selection of high-affinity phage antibodies from phage display libraries; Nature Biotechnol. 17:397-399 (1999).
Decatur et al., "A PEST-Like Sequence in Listeriolysin O Essential for Listeria monocytogenes Pathogenicity", Science 2000, 290:992-995.
Dell'Erba et al., "Immunohistochemical reactivity of anti-melanoma monoclonal antibody 225.28S in Human Breast Cancer Biopsies", Anticancer Res. 2001, vol. 21, No. 2A, pp. 925-930.
Dembo et al. Limit Distribution of Maximal Non-Aligned Two-Sequence Segmental Score Ann. Prob. 22:2022-2039; (1994).
Dermime et al., 2004, "Vaccine and antibody-directed T cell tumour immunotherapy" Biochim Biophys Acta. 1704(1):11-35.
Deshpande et al., 1997, "Isolation of a contact-dependent haemolysin from *Mycobacterium tuberculosis*", J. Med. Microbiol. Mar.; 46(3):233-8.
Dietrich et al., 2001, "From evil to good: a cytolysin in vaccine development", Trends Microbiol. Jan.; 9(1):23-8.
Disis, "Generation of immunity to the HER-2/neu oncogenic protein in patients with breast and ovarian cancer using a peptide-based vaccine" Clin Cancer Res. 5(6):1289-97, Jun. 1999.
Doling et al. Cytotoxic T-lymphocyte epitopes fused to anthrax toxin induce protective antiviral immunity, Infect. Immun. Jul. 1999; 67(7):3290-6.

Dominiecki et al. Tumor sensitivity to IFN-γ is required for successful antigen-specific immunotherapy of a transplantable mouse tumor model for HPV-transformed tumors; Cancer Immunol Immunother ;54(5):477-88 (2005).
Dons et al. "Cloning and characterization of a gene encoding flagellin of Listeria monocytogenes", Mol Microbiol. Oct. 1992;6(20):2919-29.
Dramsi et al., 1995, "Entry of Listeria monocytogenes into hepatocytes requires expression of inIB, a surface protein of the internalin multigene family", Mol. Microbiol. 16(2):251-61.
Dunn et al., 1991, "Selective radiation resistance of immunologically induced T cells as the basis for irradiation-induced T-cell-mediated regression of immunogenic tumor", J. Leukoc Biol. 49(4):388-396.
Dustoor, "Antitumor activity of listeria monocytogenes on a guinea pig fibrosarcoma", Infection and Immunity, 1979, vol. 23, No. 1, pp. 54-60.
Dzojic et al "Adenovirus-mediated CD40 ligand therapy induces tumor cell apoptosis and systemic immunity in the TRAMP-C2 mouse prostate cancer model" The Prostate 66: 831-838 (2006).
Ebert et al., 1990, "Selective immunosuppressive action of a factor produced by colon cancer cells", Cancer Res. 50(19):6158-6161.
Edman et al. A Protein Sequenator; Eur. J. Biochem . 80: 116-132, (1967).
Eisenhauer et al. New response evaluation criteria in solid tumours: Revised Recist guideline (version 1.1), Eur. J Cancer 45:228-247 (2009).
Emond et al. "A ribosomal DNA fragment of Listeria monocytogenes and its use as a genus-specific probe in an aqueous-phase hybridization assay", Appl Environ Microbiol. Aug. 1993;59(8):2690-7.
Ercolini et al., "Identification and characterization of the immunodominant rat HER-2/neu MHC class I epitope presented by spontaneous mammary tumors from Her-2/neu transgenic mice", Journal of Immunology, 2003, vol. 170, No. 8, pp. 4273-4280.
Everts et al. Selective Intracellular Delivery of Dexamethasone into Activated Endothelial Cells Using an E-Selectin-Directed Immunoconjugate; J. Immunol. 168:883-889 (2002).
Ezzel, 1995, "Cancer Vaccines: An Idea Whose Time Has Come?" J. NIH Res., 7:46-49.
Falk et al., 1991, "Identification of naturally processed viral nonapeptides allows their quantification in infected cells and suggests an allele-specific T cell epitope forecast" J. Exp. Med. 174(2):425-434.
Ferrari et al. "Isolation of an Alanine Racemase Gene from Bacillus subtilis and its Use for Plasmid Maintenance in B. subtilis", Nature Biotechnology 3, 1003-1007 (1985).
Flint et al., "Overexpression of the erbB-2 proto-oncogene in canine osteosarcoma cell lines and tumors", Vet. Pathol. 41: 291-296, 2004.
Foote et al. "Antibody Framework Residues Affecting the Conformation of the Hypervariable Loops", J. Mol. Biol. 224:487-499 (1992).
Fouts et al. "Construction and immunogenicity of *Salmonella typhimurium* vaccine vectors that express HIV-1 gp120", Vaccine. Dec. 1995;13(17):1697-705.
Frankel et al. "Induction of cell-mediated immune responses to human immunodeficiency virus type 1 Gag protein by using Listeria monocytogenes as a live vaccine vector", J Immunol. Nov. 15, 1995;155(10):4775-82.
Frey, 1993, "Rat adenocarcinoma 13762 expresses tumor rejection antigens but tumor-bearing animals exhibit tumor-specific immunosuppression", Clin. Immunol. Immunopathol. 69(2):223-233.
Friedman et al., 2000, "Induction of human immunodeficiency virus (HIV)-specific CD8 T-cell responses by Listeria monocytogenes and a hyperattenuated Listeria strain engineered to express HIV antigens" J. Virology 74 9987-9993.
Fu et al., 1990, "Expansion of Immunoregulatory macrophages by granulocyte-macrophage colony-stimulating factor derived from a murine mammary tumor", Cancer Res. 50(2):227-234.
Fuji, 1987, "Significance of suppressor macrophages for immunosurveillance of tumor bearing mice" J. Natl. Cancer Inst. 78(3):509-517.

(56) References Cited

OTHER PUBLICATIONS

Furukawa, 1993, "Nude mouse metastatic models of human stomach cancer constructed using orthotopic implantation of histologically intact tissue" Cancer Res. 53(5):1204-1208.
Gadiot et al., "Overall survival and PD-L1 expression in metastasized malignant melanoma" Cancer 117:2192-2201 (2011).
Galakatos et al. "Biosynthetic alr alanine racemase from *Salmonella typhimurium:* DNA and protein sequence determination", Biochemistry. Jun. 3, 1986;25(11):3255-60.
Galen et al., 2001, "Can a 'flawless' live vector vaccine strain be engineered?", Trends Microbiol. 9(8):372-6.
Gao et al. Overexpression of PD-L1 significantly associates with tumor aggressiveness and postoperative recurrence in human hepatocellular carcinoma. Clinical Cancer Research (2009) 15: 971-979.
Garay-Malpartida et al. Bioinformatics. Jun. 2005;21 Suppl 1 :i169-76.
Gentschev et al. "*Salmonella* Strain Secreting Active Listeriolysin Changes Its Intracellular Localization", Infect. Immun., 1995, 63:4202-4205.
Gentschev et al. 1996, "Development of antigen-delivery systems, based on the *Escherichia coli* hemolysin secreatiohn pathway" Gene 179:133-140.
Ghebeh et al. The B7-H1 (PD-L1) T lymphocyte-inhibitory molecule is expressed in breast cancer patients with infiltrating ductal carcinoma: correlation with important high-risk propgnostic factors. Neoplasia (2006) 8: 190-198.
Ghebeh Foxp3+ tregs and B7-H1+/PD-1+ T lymphocytes co-infiltrate the tumor tissues of high-risk breast cancer patients: implication for immunotherapy. BMC Cancer. Feb. 23, 2008;8:57.
Ghosh et al. "Natalizumab for Active Crohn's Disease" (2003) New Engl. J. Med. 348:24-32.
Giannini et al. Morphological Precursors of Hepatocellular Carcinoma: A Morphometrical Analysis; Hepatogastroenterol. 34:95-97 (1987).
Gibellini et al. Extracellular HIV-1 Tat Protein Induces the Rapid Ser 133 Phosphorylation and Activation of CREB Transcription Factor in Both Jurkat Lymphoblastoid T Cells and Primary Peripheral Blood Mononuclear Cells; J. Immunol. 160:3891-3898 (1998).
Gilbert et al. Enhanced CD8 T cell immunogenicity and protective efficacyin a mouse malaria model using a recombinant adenoviral vaccine in heterologous prime-boost immunization regimes; Vaccine 20:1039-45 (2002).
Gilman et al. "Isolation of sigma-28-specific promoters from Bacillus subtilis DNA" 1984, Gene 32:11-20.
Gilmore et al., 1989, "A Bacillus cereus cytolytic determinant, cereolysin AB, which comprises the phospholipase C and sphingomyelinase genes: nucleotide sequenc and genetic linkage", J. Bacteriol. Feb.; 171(2):744-53.
Gish et al. Identification of protein coding regions by database similarity search; Nature Genet. 3:266-272 (1993).
Glick (1987). Factors affecting the expression of foreign proteins in *Escherichia coli,* J. Ind. Microbiol. 1:277-282.
Glomski et al., 2002, "The Listeria monocytogenes hemolysin has an acidic pH optimum to compartmentalize activity and pevent damage to infected host cells" J. Cell Biol. Mar. 18; 156(6):1029-38.
Goebel et al., 1993, "Listeria monocytogenes—a model system for studying the pathomechanisms of an intracellular microorganism", Zbl. Bakt. 278:334-347.
Gold et al., "Translational initiation in prokaryotes." 1981, Ann. Rev. Microbiol. 35:365-404.
Gonzalo et al. A heterologous prime-boost regime using DNA and recombinant vaccinia virus expressing the Leishmania infantum P36/LACK antigen protects BALB/c mice from cutaneous leishmaniasis; Vaccine 20:1226-31 (2002).
Goossens et al., 1992, "Induction of protective CD8+ T lymphocytes by an attenuated Listeria monocytogenes actA mutant" Int. Immunol. Dec.; 4(12):1413-8.

Goossens et al., 1995, "Attenuated Listeria monocytogenes as a live vector for induction of CD8+ T cells in vivo: a study with the nucleoprotein of the lymphocytic choriomeningitis virus", Int. Immunol. May; 7(5):797-805.
Gottesman, (1984). Bacterial regulation: global regulatory networks Annu Rev Genet, Ann. Rev. Genet. 18:415-442.
Graham et al. "Candidate AIDS vaccines", N Engl J Med. Nov. 16, 1995;333(20):1331-9.
Gregory et al., 1997, "Internalin B promotes the replication of Listeria monocytogenes in mouse hepatocytes" Infect. Immun. 65(12):5137-41.
Gunn et al., 2002, "Recombinant Intra-cellular Bacteria as Carriers for Tumor Antigens", In Vaccine Delivery Strategies, Chapter 14, Eds. Guido Dietrich and Werner Goebel, Horizon Scientific Press, UK.
Gunn et al., "Two Listeria monocytogenes vaccine vectors that express different molecular forms of human papilloma virus-16 E7 induce qualitatively different T cell immunity that correlated with their avility to induce regression of established tumors immortalized by HPV-16", Journal of Immunology, vol. 167, No. 11, 2001, pp. 6471-6479.
Guzman et al. "Attenuated Listeria monocytogenes carrier strains can deliver an HIV-1 gp120 T helper epitope to MHC class II-restricted human CD4+ T cells", European Journal of Immunology, vol. 28, No. 6, Jun. 1998, pp. 1807-1814.
Hamanishi et al. Programmed cell death 1 ligand 1 and tumor-infiltrating CD8+ T lymphocytes are prognostic factors of human ovarian cancer. Proceeding of the National Academy of Sciences (2007): 104: 3360-3365.
Hancock et al. SIMPLE34: An Improved and Enhanced Implementation for VAX and Sun computers of the Simple algorithm for analysis of clustered repetitive motifs in nucleotide sequences; Comput. Appl. Biosci. 10:67-70 (1994).
Harty et al. "CD8 T lymphocytes specific for the secreted p60 antigen protect against Listeria monocytogenes infection", J. Immunol. May 1, 1995; 154(9):4642-50.
Harty et al. "CD8+ T cells specific for a single nonamer epitope of Listeria monocytogenes are protective in vivo", J Exp Med. Jun. 1, 1992;175(6):1531-8.
Hassan et al., 2004, "Mesothelin: a new target for immunotherapy" Clin. Cancer Res. 10(12 Pt 1):3937-42.
Hauf et al., 1997, "Listeria monocytogenes infection of P388D1 macrophages results in a biphasic NF-kappaB (RelA/p50) activation induced by lipoteichoic acid and Bacterial phospholipases and mediated by IkappaBalpha and IkappaBbeta degradation", Proc. Natl. Acad. Sci. U.S.A. Aug. 19; 94(17):9394-9.
Haynes et al. "Update on the issues of HIV vaccine development", Ann Med. Feb. 1996;28(1):39-41.
Haynes et al. "Scientific and social issues of human immunodeficiency virus vaccine development", Science. May 28, 1993;260(5112):1279-86.
He et al. Humanization and Pharmacokinetics of a Monoclonal Antibody with Specificity for Both E- and P-Selectin; J. Immunol. 160:1029 (1998).
Heinrich et al (Vaccination against prostate cancer using a live tissue factor deficient cell line in Lobund-Wistar rats. Cancer Immunol Immunother 2007;56(5):725-30).
Henikoff et al., "Amino acid substitution matrices from protein blocks" (1992) Proc. Natl. Acad. Sci. USA 89:10915-10919.
Herold et al. "Anti-Cd3 Monoclonal Antibody in New-Onset Type 1 Diabetes Mellitus" (2002) New Engl. J. Med. 346:1692-1698.
Hess et al., 1995, "Listeria monocytogenes p60 supports host cell invasion by and in vivo survival of attenuated *Salmonella typhimurium*" Infect. Immun. May; 63(5):2047-53.
Hess et al., 1996, "*Salmonella typhimurium* aroA-infection in gene-targeted immunodeficient mice: major role of CD4+ TCR-alpha beta cells and IFN-gamma in bacterial clearance independent of intracellular location" J. Immunol. May 1; 156(9):3321-6.
Hess et al., 1996, "Superior efficacy of secreted over somatic antigen display in recombinant *Salmonella* vaccine induced protection against listeriosis" Proc. Nat. Acad. Sci. 93:1458-1463.
Hess et al., 1997, "Protection against murine listeriosis by an attenuated recombinant *Salmonella typhimurium* vaccine strain that

(56) References Cited

OTHER PUBLICATIONS secretes the naturally somatic antigen superoxide dismutase", Infect. Immun. Apr.; 65(4):1286-92.
Hess et al, "*Mycobacterium bovis* Bacille Calmette-Guerin strains secreting listeriolysin of Listeria monocytogenes", Proc. Natl. Acad. Sci. U.S.A. Apr. 28, 1998; 95(9):5299-304.
Hess et al. Abstract, "Live antigen carriers as tools for improved anti-tuberculosis vaccines", FEMS Immunol. Med. Microbiol. Feb. 1999; 23(2):165-73.
Higgins et al., Abstract, "Delivery of protein to the cytosol of macrophages using *Escherichia coli* K-12", Mol. Microbiol. Mar. 31, 1999(6):1631-41.
Higgins et al., 1998, "Bacterial delivery of DNA evolves" Nat. Biotechnol. Feb.; 16(2):138-9.
Hiltbold et al. "The presentation of class I and class II epitopes of listeriolysin O is regulated by intracellular localization and by intracelluar spread of Listeria monocytogenes", J. Immunol. Aug. 1, 1996; 157(3):1163-75.
Hiltbold et al. "Mechanisms of processing and presentation of the antigens of Listeria monocytogenes", Infect. Agents Dis. Oct. 1993; 2(5):314-23.
Hino et al. Tumor cell expression of programmed cell death-1 is a prognostic factor for malignant melanoma. Cancer (2010 116(7):1757-66.
Hjortland et al., "Immunotoxin treatment targeted to the higher-molecular weight melanoma-associated antigen prolonging the survival of immunodeficient rats with invasive intracranial human glioblastoma multiforme", J. Neurosurg. 2004, vol. 100, No. 2, pp. 320-327.
Hodgson, 2000, "Generalized transduction of serotype 1/2 and serotype 4b strains of Listeria monocytogenes", Mol. Microbiol. 35(2):312-23.
Hoogenboom et al. "Natural and designer binding sites made by phage display technology", Immunol. Today 21:371-377 (2000).
Hsing et al. "Requirement for Nuclear Factor-kB Activation by a Distinct Subset of CD40-Mediated Effector Functions in B Lymphocytes", J. Immunol. 162:2804-2811 (1999).
Huang et al., 1994, "Role of bone marrow-derived cells in presenting MHC class I-restricted tumor antigens" Science 264:961-965.
Hussain et al., "What is needed for effective antitumor immunotherapy? Lessons learned using Listeria Monocytogenes as a live vector for HPV-associated tumors", Cancer Immunology, Immunotherapy, vol. 54, No. 6, 2005, pp. 577-586.
Hussain et al., "CD4+CD25+ Regulatory T Cells That Secrete TGF and IL-10 Are Preferentially Induced by a Vaccine Vector", 2004, J Immunother 27( 5):339-346.
Ikonomidis et al., 1994, Abstract E-90, Abstracts, 94th General Meeting of the American society for Microbiology, May 23-27.
Ikonomidis et al., "Influenze-specific immunity induced by recombinant Listeria monoctogenese vaccines", Vaccine, vol. 15, No. 4, 1997, pp. 433-440.
Ikonomidis et al. "Delivery of a viral antigen to the class I processing and presentation pathway by Listeria monocytogenes", J Exp Med. Dec. 1, 1994;180(6):2209-18.
Inman et al. PD-L1 (B7-H1) expression by urothelial carcinoma of the bladder and BCG-induced granulomata: associations with localized stage progression. Cancer (2007): 109: 1499-1505.
International Search for PCT Application No. PCT/US13/030521 dated May 14, 2013.
Jensen et al., 1997, "Recombinant Listeria monocytogenes as a live vaccine vehicle and a probe for studying-cell-mediated immunity" Immunological Review 158:147-157.
Jensen, 1997, "Recombinant Listeria monocytogenes vaccination eliminates papillomavirus-induced tumors and prevents papilloma formation from viral DNA", J. Virol. 71(11):8467-8474.
Jiang et al. "Characterization of a mutant Listeria monocytogenes strain expressing green fluorescent protein" Acta. Biochim. Biophys Sin (Shanghai), 37(1): 19-24, (2005).

Johnson et al., "Kabat database and its applications: 30 years after the first variability plot", Nucleic Acids Research, 2000, vol. 28, No. 1, pp. 214-218.
Jones et al. "Characterization of Listeria monocytogenes pathogenesis in a strain expressing perfringolysin O in place of listeriolysin O." (1994) Infect. Immunity 65: 5608-5613.
Kabat et al., "Unusual distributions of amino acids in complementarity-determining (hypervariable) segments of heavy and light chains of immunoglobulins and their possible roles in specificity of antibody-combining sites" (1977) J. Biol. Chem. 252:6609-6616.
Kabat "The Structural Basis of Antibody Complementarity", Adv. Prot. Chem. 32:1-75 (1978).
Kaithamana et al. Induction of Experimental Autoimmune Graves' Disease in BALB/c Mice; J. Immunol. 163:5157-5164 (1999).
Karlin et al., "Methods for assessing the statistical significance of molecular sequence features by using general scoring schemes" (1990) Proc. Natl. Acad. Sci. USA 87:2264-2268.
Karlin et al., "Applications and statistics for multiple high-scoring segments in molecular sequences" (1993) Proc. Natl. Acad. Sci. USA 90:5873-5877.
Kaufman et al., "Impact of intracellular location of and antigen display by intracellular bacteria:implications for vaccine development", J. Immunol. Lett. 1999, 65(1-2):81-84.
Kaufmann "Immunity to intracellular bacteria", Annu Rev Immunol. 1993;11:129-63.
Kim et al., "Coexpression of BiP increased antithrombotic hirudin production in recombinant *Saccharomyces cerevisiae*", Journal of Biotechnology, vol. 101, No. 1, pp. 81-87, 2003.
King et. al., "Amplification of a novel v-erbB-related gene in a human mammory carcinoma" (1985). Science 229:974-976.
Knutson et al., "Immunization with a HER-2/neu helper peptide vaccine generates HER-2/neu CD8 T-cell immunity in cancer patients." The Journal of Clinical Investigation, 107:477-484, 2001.
Kocks et al., 1992, "L monocytogenes-induced act in assembly requires the actA gene product", Cell, vol. 68, No. 3, p. 521-531.
Kohler et al, "Expression of the iap gene coding for protein p60 of Listeria monocytogenes is controlled on the posttranscriptional level" J Bacteriol 173: 4668-74, 1991.
Kohler et al. Continuous Cultures of Fused Cells Secreting Antibody of Predefined Specificity; Nature 256: 495 (1975).
Kovacsovics-Bankowski et al., 1993, "Efficient major histocompatibility complex class I peresentation of exogenous antigen upon phagocytosis by macrophages", Proc. Natl. Acad. Sci. USA 90:4942-4946.
Kucera et al., "Prostate Specific Antigen (PSA) in Breat and Ovarian Cancer", Anticancer Res 1997, vol. 17, No. 60, pp. 4735-4737.
Kyte et al., "A simple method for displaying the hydropathic character of a protein", J. Mol. Biol. 157, 105 (1982).
Lampson et al., 1993, "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ", Cancer Research 53:176-182.
Landy, Mechanistic and structural complexity in the site-specific recombination pathways of Int and FLP Current Opinion in Genetics & Development 3:699-707; (1993).
Lasa et al., 1997, "Identification of two regions in the N-terminal domain of ActA involved in the actin comet tail formation by Listeria monocytogenes" EMBO 16(7):1531-40.
Lauer et al., "Characterization of the Attachment Site of Bacteriophage U153 within the Listeria monocytogenes comK Gene" ASM Meeting, Abstract 1999.
Lauer et al., "Systematic mutational analysis of the amino-terminal domain of the Listeria monocytogenes ActA protein reveals novel functions in actin-based motility" Molecular Microbiology 42(5):1163-1177, 2001.
Lauer et al., "Construction, characterization, and use of two LM site-specific phageintegration vectors", 2002 J Bacteliol, 184:4177-4186.
Le Doussal et al. Enhanced In Vivo Targeting of an Asymmetric Bivalent Hapten Antibody Conjugate CocktailsTo Double-Antigen-Positive Mouse B Cells With Monoclonal ; J. Immunol. 146:169-175 (1991).

(56) References Cited

OTHER PUBLICATIONS

Leao et al., 1995, "A species-specific nucleotide sequence of *Mycobacterium tuberculosis* encodes a protein that exhibts hemolytic activity when expressed in *Escherichia coli*" Infect. Immun. Nov.; 63(11):4301-6.

Lebrun et al., Aug. 1996, "Internallan must be on the Bacterial Surface to mediate Entry of Listeria monocytogenes into Epilhalial Cells", Molecullar Microbiolgy 21:579-592.

Lee et al., 1991, "Construction of single-copy integration vectors for *Staphylococcus aureus*", Gene 103:101-5.

Lee et al. Delivery of macromolecules into cytosol using liposomes containig hemolysin from Listeria monocytogenes, J. Biol. Chem., Mar. 29, 1996, 271(13):7249-52.

Lehner et al., 1996, "Processing and delivery of peptides presented by MHC class I molecules", Curr. Opin. Immunol. 8(1):59-67.

Lejeune, 1994, "Nitric oxide involvement in tumor-induced immunosuppression" J. Immunol. 152(10):5077-5083.

Lenz, "Stable integration vector for nutrient broth-based selection of attenuated Listeria monocytogenes strains with recombinant antigen expression" Clin Vaccine Immunol. 15(9):1414-1419. Sep. 2008.

Li et al., "Conditional lethality yields a new vaccine strain of listeria monocytogenes for the induction of cell-mediated immunity", Infection and Immunity, 2005, 73(8): 5065-5073.

Liau et al., 2002, "Tumor immunity within the central nervous system stimulated by recombinant Listeria monocytogenes vaccination", Cancer Res., 62(8):2287-93.

Lieberman et al. "Engineered Listeria monocytogenes as an AIDS vaccine", Vaccine. May 6, 2002;20(15):2007-10.

Lin et al., "Treatment of Established Tumors with a Novel Vaccine that Enhances Major Histocompatibility Class II Presentation of Tumor Antigen", Cancer Res. 1996, 56:21-26.

Lin et al., 2002, "Oral vaccination with recombinant Listeria monocytogenes expressing human papillomavirus type 16 E7 can cause tumor growth in mice to regress" Int. J. Cancer, Dec. 20; 102(6):629-37.

Lingnau et al., 1995, "Expression of the Listeria monocytogenes Egd inlA and inlB genes, whose products mediate bacterial entry into tissue culture cell lines, by PrfA-dependent and independent mechanisms" Infect. Immun. Oct.; 63(10):3896-903.

Lipford et al. "Vaccination with immunodominant peptides encapsulated in Quil A-containing liposomes induces peptide-specific primary CD8+ cytotoxic T cells", Vaccine Jan. 1994; 12(1):73-80.

Lipsky et al. "Infliximab and Methotrexate in the Treatment of Rheumatoid Arthritis" (2000) New Engl. J. Med. 343:1594-1602.

Liu et al. "Randomised, double blind, placebo controlled study of interferon beta-1a in relapsing-remitting multiple sclerosis analysed by area under disability/time curves" (1999) J. Neurol. Neurosurg. Psych. 67:451-456.

Lobocka et al. "Organization and expression of the *Escherichia coli* K-12 dad operon encoding the smaller subunit of D-amino acid dehydrogenase and the catabolic alanine racemase", J Bacteriol. Mar. 1994;176(5):1500-10.

Loeffler et al., 2006, "Comparison of different live vaccine strategies in vivo for delivery of protein antigen or antigen-encoding DNA and mRNA by virulence-attenuated Listeria monocytogenes" Infect. Immun. Jul; 74(7):3946-57.

Loessner et al., 1995, "Heterogeneous endolysins in Listeria monocytogenes bacteriophages: a new class of enzymes and evidence for conserved holin genes within the siphoviral lysis cassettes", Mol. Microbiol. Jun.; 16(6):1231-41.

Loessner et al., 2000, "Complete nucleotide sequence, molecular analysis and genome structure of bacteriophage A118 of Listeria monocytogenes: implications for phage evolution", Molecular Microbiology 35(2):324-40.

Loessner et al. 1994. Structural proteins and DNA characteristics of 14 Listeria typing bacteriophages. J. Gen. Virol. 75:701-710.

Maciag et al. "The first clinical use of a live-attenuated Listeria monocytogenes vaccine: a Phase I safety study of Lm-LLO-E7 in patients with advanced carcinoma of the cervix", Vaccine. Jun. 19, 2009;27(30):3975-83.

Madden et al. Applications of Network BLAST Server; Meth. Enzymol. 266:131-141 (1996).

Makela et al., Hand book of Experimental Immunology vol. 1, Chapter 3—"Haptens and carriers", pp. 3.1-3.13; 1987.

Manjili et al., 2003, "HSP110-HER2/neu chaperone complex vaccine induces protective immunity against spontaneous mammary tumors in HER-2/neu trangenic mice" J. Immunol. Oct. 15; 171(8):4054-61.

Marks et al. By-passing Immunization Human Antibodies from V-gene Libraries Displayed on Phage; J. Mol. Biol. 222: 581-597 (1991).

Marquis et al., 1997, "Proteolytic pathways of activation and degradation of a bacterial phospholipase C during intracellular infection by Listeria monocytogenes" J. Cell Biol. 137:1381-1392.

Marquis et al. "Intracytoplasmic growth and virulence of Listeria monocytogenes auxotrophic mutants", Infect Immun. Sep. 1993;61(9):3756-60.

Martin et al., 1986, "Nucleotide sequence of the tetM tetracycline resistance determinant of the streptococcal conjugative shuttle transposon Tn1545", Nucleic Acid Res. 14:7047-7058.

Marx et al., 2002, "Broad-host-range cre-lox system for antibiotic marker recycling in gramnegativ bacteria" Biotechniques, Nov.; 33(5):1062-7.

Mata et al. "Evaluation of a recombinant Listeria monocytogenes expressing an HIV protein that protects mice against viral challenge", Vaccine 19:1435-45, 2001.

Mata et al. Th1 T.cell responses to HIV•1 Gag protein delivered by Listeria monocytogenes vaccine are similar to those induced by endogenous listerial antigen's; J. Immunol 163:1449-1456. (1999).

Mata (1997). A hexameric phosphorothioate oligonucleotide telomerase inhibitor arrests growth of Burkitt's lymphoma cells in vitro and in vivo. Toxicol. Appi. Pharmacol. 144:189-197.

Mazda et al. (1997) Extremely efficient gene transfection into lympho-hematopoietic cell lines by Epstein-Barr virus-based vectors. J. Immunol. Methods 204, 143-151.

Mazzaccaro et al. "Major histocompatibility class I presentation of soluble antigen facilitated by Mycobacterium tuberculosis infection", Proc. Natl. Acad. Sci. U.S.A. Oct. 15, 1996; 93(21):11786-91.

McLaughlan et al., 1998, "Molecular characterization of an autolytic amidase of Listeria monocytogenes EGD", Microbiology, May; 144(Pt 5):1359-67.

Mendez et al. Functional Transplant of Megabase Humanimmunoglobulin Loci Recapitulates Human Antibody Response in Mice; Nature Genetics 15:146-156 (1997).

Mengaud et al., 1988, "Expression in *Escherichia coli* and sequence analysis of the listeriolysin O determinant of listeria monocytogenes", Infect. Immun., vol. 56, No. 4, 766-772.

Mengaud et al., "Transcriptional mapping and nucleotide sequence of the Listeria monocytogenes hlyA region reveal structural features that may be involved in regulation" Infect. Immun. 1989 57, 3695-3701.

Menne, et al. "A comparison of signal sequence predition methods using a test set of signal peptides" (2000) Bioinformatics 16: 741-742.

Merrifield et al., "Solid phase peptide synthesis. 1. The synthesis of a tetrapeptide" J. Am. Chem. Soc., 85:2149-2156 (1963).

Meyaard et al. "LAIR-1, a Novel Inhibitory Receptor Expressed on Human Mononuclear Leukocytes" (1997) Immunity 7:283-290.

Mikayama et al. "Molecular cloning and functional expression of a cDNA encoding gycosylation-inhibiting factor", Nov. 1993, Pro Natl. Acad. Sci., USA, vol. 90:10056-10060.

Milgrom et al. "Treatment of Allergic Asthma With Monoclonal Anti-Ige Antibody" (1999) New Engl. J. Med. 341:1966-1973.

Miller et al, "Targeted vectors for gene therapy" 1995, FASEB J., 9:190-199.

Milligan (1993) "Current concepts in antisense drug design", J. Med. Chem. 36:1923-1937; Antisense Research and Applications (1993, CRC Press).

(56) References Cited

OTHER PUBLICATIONS

Mkrtichyan et al. "Anti-PD-1 antibody significantly increases therapeutic efficacy of Listeria monocytogenes (Lm)-LLO immunotherapy", Journal for ImmunoTherapy of Cancer 2013, 1:15.

Mlynarova et al., 2002, "The promiscuity of heterospecific lox sites increases dramatically in the presence of palindromic DNA", Gene, Aug. 21; 296(1-2):129-37.

Mollet et al., 1993, "Directed genomic integratoin, gene replacement, and integrative gene expression in *Streptococcus thermophilus*" J. Bacteriology 175:4315-4324.

Moriishi et al., 1998, "Sequence analysis of the actA gene of Listeria monocytogenes isolated from human", Microbiol. Immunol., vol. 42, No. 2, p. 129-132.

Nagai et al, 1991 Isolation and partial characterization of major protein antigens in the culture fluid of *Mycobacterium tuberculosis*. Infect Immun. Jan. 1991;59(1):372-82.

Nakanuma, et al. Anatomic and molecular pathology of intrahepatic cholangiocarcinoma, J. Hepatobiliary Pancreat. Surg. 10:265-281 (2003).

Narang et al. (1979). Improved Phosphotriester Method for the Synthesis of Gene Fragments, Meth. Enzymol. 68: 90-99.

Naruishi et al (Adenoviral vector-mediated RTVP-1 gene-modified tumor cell-based vaccine suppresses the development of experimental prostate cancer. Cancer Gene Ther. Jul. 2006;13(7):658-63).

Naz et al "Novel human prostate-specific cDNA: molecular cloning, expression, and immunobiology of the recombinant protein" Biochem Biophys Res Commun. 297:1075-84, 2002.

Ngo et al., 1994, "The Protein Folding Problem and Tertiary Structure Prediction", pp. 492-495.

Nielsen, (1999). Peptide nucleic acids as therapeutic agents Current Opin Struct Biol 9:353-57.

Nikodinovic et al., A second generation snp-derived *Escherichia coli*-Streptomyces shuttle expression vector that is generally transferable by conjugation. Plasmid. Nov. 2006;56(3):223-7.

Nitcheu-Tefit et al. "Listeriolysin O Expressed in a Bacterial Vaccine Suppresses CD4 CD25high Regulatory T Cell Function In Vivo", J Immunol. Aug. 1, 2007;179(3):1532-41.

Nomi et al. Clinical significance and therapeutic potential of the programmed death-1 ligand/programmed death-1 pathway in human pancreatic cancer. Clinical Cancer Research (2007);13:2151-2157.

Noriega et al. "Engineered deltaguaB-A deltavirG Shigella flexneri 2a strain CVD 1205: construction, safety, immunogenicity, and potential efficacy as a mucosal vaccine", Infect Immun. Aug. 1996;64(8):3055-61.

Ochsenbein et al., 1999, "A comparison of T cell memory against the same antigen induced by virus versus intracellular bacteria" Proc. Natl. Acad Sci U.S.A. Aug. 3; 96(16):9293-8.

Offit et al. "Addressing Parents' Concerns: Do Multiple Vaccines Overwhelm or Weaken the Infant's Immune System?", Pediatrics vol. 109 No. 1 Jan. 2002.

Ogasawara et al A strategy for making synthetic peptide vaccines Proc. Nati. Acad. Sci. USA vol. 89, pp. 8995-8999, Oct. 1992.

Ohigashi et al. Clinical significance of programmed death-1 ligand-1 and programmed death-1 ligand 2 expression in human esophageal cancer. Clin. Cancer Research (2005): 11: 2947-2953.

O'Riordan et al. Listeria Intracellular Growth and Virulence Require Host-Derived Lipoic Acid, Science 302: 462-464(2003).

Oscarsson et al., 1996, "Induction of haemolytic activity in *Escherichia coli* by the slyA gene product" Mol. Microbiol. Apr.; 20(1):191-9.

Ostrand-Rosenberg "Myeloid-derived suppressor cells: linking inflammation and cancer", J Immunol. Apr. 15, 2009;182(8):4499-506.

Paglia et al., 1997, "The defined attenuated Listeria monocytogenes delta mp12 mutant is an effective oral vaccine carrier to trigger a long-lasting immune response against a mouse fibrosarcoma" Eur. J. Immunol. 27:1570-1575.

Palmeros et al., 2000, "A family of removable cassettes designed to obtain antibiotic-resistance-free genomic modifications of *Escherichia coli* and other bacteria" Gene, Apr. 18; 247(1-2):255-64.

Pamer et al. "Precise prediction of a dominant class I MHC-restricted epitope of Listeria monocytogenes", Nature. Oct. 31, 1991;353(6347):852-5.

Pan et al., "Regression of Established Tumors in Mice Mediated by the Oral Administration of a Recombinant Listeria monocytogenes Vaccine", Cancer Res., 1995, 55:4776-4779.

Pan et al., 1995, "A recombinant Listeria monocytogenes vaccine expressing a model tumour antigen protects mice against lethal tumour cell challenge and causes regression of established tumours" Nature Med. 1:471-477.

Parsa et al., "Engineering bacterial vectors for delivery of genes and proteins to antigen-presenting cells", Molecular Pharmaceutics, vol. 4, No. 1, 2007, pp. 4-17.

Passos et al. Recombinant Leishmania Antigens for Serodiagnosis of Visceral Leishmaniasis Clinical and Diagnostic Laboratory Immunology, Oct. 2005, p. 1164-1167, vol. 12, No. 10.

Paterson et al., "Listeria-based vaccines for cancer treatment", Current Opinion in Molecular Therapeutics, vol. 7, No. 5, 2005, pp. 454-460.

Paterson, "Rational approaches to immune regulation", Immunologic Research, 2003; 27/2-3:451-462.

Paterson et al. "Recombinant Listeria monocytogenes cancer vaccines", Curr Opin Immunol. Oct. 1996;8(5):664-9.

Paul et al. Frequent associations between CTl and T-Helper epitopes in HIV-1 genomes and 12, 13 implications for multi-epitope vaccine designs. BMC Microbiology 10:1-16 (2010).

Pawelek et al. "Tumor-targeted *Salmonella* as a novel anticancer vector", Cancer Res. Oct. 15, 1997;57(20):4537-44.

Peng et al. "Adjuvant properties of listeriolysin O in a DNA vaccine strategy", Cancer Immunol Immunother, Jun. 2007;56(6):797-806.

Penichet et al., 2001, "Antibody-cytokine fusion proteins for the therapy of cancer" J. Immunological Methods 248:91-101.

Peters et al. "Tailoring host immune responses to Listeria by manipulation of virulence genes—the interface between innate and acquired immunity", FEMS Immunol Med Microbiol. Apr. 1, 2003;35(3):243-53.

Peters et al. The Induction of HIV Gag-Specific CD8+ T Cells in the Spleen and Gut-Associated Lymphoid Tissue by Parenteral or Mucosal monocytogenes HIV Gag Immunization with Recombinant Listeria; J Immunol; 170:5176-5187 ( 2003).

Peters et al. "Enhancing the immunogenicity of bioengineered Listeria monocytogenes by passaging through live animal hosts", Vaccine. 21.:1187-94. (2003).

Pfeifer et al., 1993, "Phagocytic processing of bacterial antigens for class I MHC presentation to T cells" Nature, Jan. 28; 361(6410):359-62.

Portielji et al. IL-12: a promising adjuvant for cancer vaccination, Cancer Immunol. Immunother. 52:133-144 (2003).

Portnoy et al. "Molecular determinants of Listeria monocytogenes pathogenesis", Infect Immun. Apr. 1992;60(4):1263-7.

Presta "Selection, design, and engineering of therapeutic antibodies" (2005) J. Allergy Clin. Immunol. 116:731.

Pucci et al, "*Staphylococcus haemolyticus* Contains Two D-Glutamic Acid Biosynthetic Activities, a Glutamate Racemase and a D-Amino Acid Transaminase" 1995, J Bacteriol. 177: 336-342.

Pupa et al., 2001, "Prevention of spontaneous neu-expressing mammary tumor development in mice transgenic for rat proto-neu by DNA vaccination" Gene Ther. Jan.; 8(1):75-9.

Purchio et al. "Methods in Enzymology: Methods for molecular cloning in eukaryotic cells", (2003).

Quenee et al., 2005, "Combined sacB-based negative selection and cre-lox antibiotic marker recycling for efficient gene deletion in pseudomonas aeruginosa", Biotechniques, Jan.; 38(1):63-7.

Raveneau et al., 1992, "Reduced virulence of a Listeria monocytogenes phospholipase-deficient mutant obtained by transposon insertion into the zinc metalloproteas gene" Infect. Immune., 60:916-921.

(56) References Cited

OTHER PUBLICATIONS

Realini et al., "Proposed roles in protein-protein association and presentation of peptides by MHC Class I receptors", FEBS Lett., 1994, 348:109-113.
Rechsteiner et al (PEST sequences and regulation by proteolysis. Trends Biochem Sci 1996; 21(7) :267-71.
Reiter et al., 1989, "Transfer RNA genes frequently serve as integration sites for porkaryotic genetic elements", Nucleic Acids Research 17(5):1907-14.
Renard et al., "HER-2 DNA and protein vaccines containing potent Th cell epitopes induce distinct protective and therapeutic antitumor responses in HER-2 transgenic mice", The Journal of Immunology, 171(3):1588-1595, 2003.
Repique, 1992, "Immunosuppression derived from human B-lymphoblastoid and melanoma cell lines" Cancer Invest. 10(3):201-208.
Riegler. Preneoplastic Conditions of the Liver; Seminars in Gastrointestinal Disease vol. 7, No. 2:pp. 74-87 (1996).
Riera et al. Evaluation of a latex agglutination test (KAtex) for detection of Leishmania antigen in urine of patients with HIV-Leishmania coinfection: value in diagnosis and post-treatment follow-up. Eur J Clin Microbiol Infect Dis. Dec;23 (12):899-904 (2004).
Robinson et al. "New Hope for an Aids Vaccine", Nat. Rev. Immunol. 2:239-50 (2002).
Rocken et al. "Pathology and Pathogenesis of Hepatocellular", Digestive Diseases 19:269-278 (2001).
Roden et al., 2004, "Vaccination to prevent and treat cervical cancer", Hum. Pathol. 35(8):971-82.
Rogers et al. "Amino acid sequences common to rapidly degraded proteins: the PEST hypothesis", Science 1986; 234(4774):364-8.
Rothman et. al. "The use of living listeria monocytogenes as an active immunotherapy for the treatment of cancer", Emerging Cancer Therapy: Microbial Approaches and Biotechnological Tools, Edited by Arsénio M. Fialho and Ananda M. Chakrabarty Copyright © 2010 John Wiley & Sons, Inc.
Rubin et al. "Cloning, sequence determination, and regulation of the ribonucleotide reductase subunits from Plasmodium falciparum: a target for antimalarial therapy", Proc Natl Acad Sci U S A. Oct. 15, 1993;90(20):9280-4.
Russmann et al., 1998, "Delivery of epitopes by the *Salmonella* type III secretion system for vaccine system for vaccine development", Science, Jul. 24; 281(5376):565-8.
Safley et al., "Role of listeriolysin-O (LLO) in the T lymphocyte response to infection with Listeria monocytogenes. Identification of T cell epitopes of LLO" J. Immunology 146(10):3604-3616; May 1991.
Samstag (1996). Synthesis and properties of new antisense oligodeoxynucleotides containing benzylphosphonate linkages. Antisense Nucleic Acid Drug Dev. 6:153-156.
Schafer et al. "Induction of a cellular immune response to a foreign antigen by a recombinant Listeria monocytogenes vaccine", J Immunol. Jul. 1, 1992;149(1):53-9.
Scheirlinck et al., 1989, "Integration and expression of alpha-amylase and endoglucanase genes in the Lactobacillus plantarum chromosome", Appl. Environ Microbiol. 55(9):2130-7.
Scher et al., (2008) "Design and End Points of Clinical Trials for Patients With Progressive Prostate Cancer and Castrate Levels of Testosterone: Recommendations of the Prostate Cancer Clinical Trials Working Group" J. Clin. Oncol. 26(7):1148-159.
Schmidt et al., 1995, "Molecular Analysis of the Plasmid-Encoded Hemolysin of *Escherichia coli* O157:H7 Strain EDL 933", Infection and Immunity, 63(3):1055-1061.
Schneider et al. Induction of CD8+ T cells using heterologous prime-boost immunisation strategies, Immunol.Rev. 170:29-38 (1999).
Schnupf et al., "Phosphorylation, ubiquitination and degradation of listeriolysic O in mammalian cells: role of the PEST-like sequence" Cellular microbiology 8(2):353-364, 2006.
Schnupf et al. "ListeriolysinO: a phagosome-specific lysine", Microbes & Infect. 2007, 9:1176-1187.
Scortti et al., 2007, "The PrfA virulence regulon", Microbes Infect. Aug.; 9(10):1196-207.
Seavey "A novel human Her-2/neu chimeric molecule expressed by Listeria monocytogenes can elicit potent HLA-A2 restricted CD8-positive T cell responses and impact the growth and spread of Her-2/neu-positive breast tumors" Clin Cancer Res. 15(3):924-32, Feb. 1, 2009.
Sehgal I et al "Prostate cancer cells show elevated urokinase receptor in a mouse model of metastasis " Cancer Cell Int. Aug. 23, 2006;6:21.
Sewell et al., "Recombinant Listeria Vaccines Containing PEST Sequences are potent immune adjuvants for the tumor-associates antigen human pappilomavirus-16 E7", Cancer Research, American Association for Cancer Research, vol. 64, No. 24, 2004, pp. 8821-8825.
Sewell et al. Regression of HPV-Positive Tumors Treated with a New Listeria monocytogenes Vaccine Arch Otolaryngol., Head Neck Surg., Jan. 2004, vol. 130, pp. 92-97.
Shahabi et al. "A live, attenuated Listeria-based immunotherapeutic for the treatment of breast cancer", 2009 ASCO Breast cancer Symposium, Oct. 8, 2009, abstract.
Shahabi et al. "Development of a live and highly attenuated Listeria monocytogenes-based vaccine for the treatment of Her2/neu-overexpressing cancers in human", Cancer Gene Therapy, vol. 18, No. 1, Jan. 1, 2011, pp. 53-62.
Shahabi et al., "Development of a Listeria monocytogenes based vaccine against prostate cancer" Cancer Immunol Immunother (2008) 57:1301-1313.
Shahabi et al., "Live, attenuated strains of Listeria and *Salmonella* as vaccine vectors in cancer treatment", Bioeng. Bugs, 2010, vol. 1, No. 4, pp. 235-243.
Sharpe et al. "The function of programmed cell death 1 and its ligands in regulating autoimmunity and infection", Nature Immunology ; 8:239-245 (2007).
Shaw et al. "Complete nucleotide sequence of macrolide-lincosamide-streptogramin B-resistance transposon Tn917 in *Streptococcus faecalis*", J Bacteriol. Nov. 1985; 164(2):782-96.
Shen et al., 1995, "Recombinant Listeria monocytogenes as a live vaccine vehicle for the induction of protective anti-viral cell-mediated immunity" Proc. Nat'l Acad Sci U.S.A., 92(9):3987-91.
Shen et al., 1998, "Compartmentalization of bacterial antigens: diffrential effects on priming of CD8 T cells and protective immunity" Cell., Feb. 20; 92(4):535-45.
Shetron-Rama et al., 2002, "Intracellular induction of Listeria monocytogenes actA expression" Infect. Immun. 70:1087-1096.
Shimauchi et al. Augmented expression of programmed death-1 in both neoplasmatic and nonneoplastic CD4+ T-cells in adult T-cell Leukemia/ Lymphoma. Int. J. Cancer (2007): 121:2585-2590.
Shimizu et al., 1994, "Effects of CD4+ and CD8+ T cells in tumor-bearing mice on antibody production" Cancer Immunol. Immunother 38(4):272-276.
Shiver et al., Replication-incompetent adenoviral vaccine vector elicits effective antiimmunode® ciency-virus immunity, Nature 415: 331-5 (2002).
Sin et al. DNA Priming-Protein Boosting Enhances Both Antigen-Specific Antibody and Th1-Type Cellular Immune Responses in a Murine Herpes Simplex Virus-2 gD Vaccine Model, DNA Cell Biol. 18:771-9 (1999).
Singh et al. "Immunoediting sculpts tumor epitopes during immunotherapy", Cancer Res.67(5):1887-92. Mar. 1, 2007.
Singh et al., "Fusion to Listeriolysin O and Delivery by Listeria monocytogenes Enhances the Immunogenicity of HER-2/neu and Reveals Subdominant Epitopes in the FVB/N Mouse", The Journal of Immunology 2005, vol. 175, No. 6, pp. 3663-3673.
Sirard et al., 1997, "Intrtracytoplasmic delivery of Lidteriolysin O by vaccinal strain of Bacillus anthracis induces CD8-mediated protection against listeria monocytogenes", J. Immunology, vol. 159, p. 4435-4443.
Sizemore et al. "Attenuated Shigella as a DNA delivery vehicle for DNA-mediated immunization", Science. Oct. 13, 1995;270(5234):299-302.

(56) References Cited

OTHER PUBLICATIONS

Skoble, et al. "Three Regions within ActA Promote Arp2/3 Complex-mediated Actin Nucleation and Listeria monocytogenes Motility" 2000, J. Cell Biol. 150: 527-538.
Skolnick et al. "Form genes to protein structure and function: novel applications of computational approaches in the genomic era", Jan. 2000, Trends in Biotech., 18(1):34-39.
Slamon et al. "Use of Chemotherapy Plus a Monoclonal Antibody Against Her2 for Metastatic Breast Cancer That Overexpresses Her2" 2001, New Engl. J. Med. 344:783-792.
Slifka et al., 1996, "Antiviral cytotoxic T-cell memory by vaccination with recombinant Listeria monocytogenes" J. Virol. 70(5):2902-10.
Smith et al., 1995, "The two distinct phospholipases C of Listeria monocytogenes have overlapping roles in escape from a vacuole and cell-to-cell spread", Infect. Immun. 63:4231-4237.
Smith et al., Sep. 1995, "Asymmetric Distribution of the Listeria monocytogenes ActA Protein is Required and Sufficient to Direct Actin-Based Motility", Molecular Microbiology 17:945-951.
Smith et al., Biochimie. 1992. Use of a new integrational vector to investigate comparement-specific expression of the Bacillus subtilis spoIIM gene; 74 (7-8) p. 705-711.
Souders et al., 2006, "In vivo bactofection: listeriacan function as a DNA-cancer vaccine" DNA Cell Biol. Mar.; 25(3):142-51.
Soussi et al., "Effect of intragastric and intraperitoneal immunization with attenuated and wild-type LACK-expressing Listeria monocytogenes on control murine Leishmania major infection", Vaccine, vol. 20, No. 21-22, 2002, pp. 2702-2712.
Soussi et al., "Listeria monocytogenes as a short lived delivery system for the induction of type 1 cell-mediated immunity againdt the p36/LACK antigen of Leishmania major", Infection and Immunity, vol. 68, No. 3, 2000, pp. 1498-1506.
Strauss-Soukup, "Effects of Neutralization Pattern and Stereochemistry on DNA Bending by Methylphosphonate Substitutions", 1997, Biochemistry 36:8692-8698.
Strych et al, "Mutant Analysis Shows that Alanine Racemases from *Pseudomonas aeruginosa* and *Escherichia coli* Are Dimeric" 2002, J. Bacteriol. 184:4321-4325.
Stahl et al., 1984, "Replacement of the Bacillus subtilisin structural gene with an in vitro-derived deletion mutation", J. Bacteriol. 158:411-418.
States et al. Improved Sensitivity of Nucleic Acid Database Searches Using Application-Specific Scoring Matrices, Methods 3:66-70 (1991).
Stitz et al., 1990, "Characterization and immunological properties of influenza a virus nucleoprotein (NP): cell-associated NP isolated from infected cells or viral NP expressed by vaccinia recombinant virus do not confer protection" J. Gen. Virol., 71(Pt 5):1169-1179.
Strungnell et al., 1990, "Stable expression of forgein antigens from the chromosome of *Salmonella typhimurium* vaccine strains", Gene 88:57-63.
Stryer et al., "Levels of structure in protein architecture", Biochemistry, Third Edition, W H Freeman Company, New York, pp. 31-33, 1998.
Su et al., "Relevance of Hepatic Preneoplasia for Human Hepatocarcinogenesis" (2003) Toxicol. Pathol. 31:126-133.
Sun et al. "Isolation of Listeria monocytogenes small-plaque mutants defective for intracellular growth and cell-to-cell spread", Infect Immun. Nov. 1990;58(11):3770-8.
Supplementary European Search Report for European Application No. 13761946.6 dated Sep. 8, 2015.
Szalay et al. "Presentation of Listeria monocytogenes antigenes by major histocompatibility complex class I molecules to CD8 cytotoxic T lymphocytes independent of listeriolysin secretion and virulence", Eur. J. Immunol. Jul. 1994; 24(7):1471-7.
Tanabe et al., "Induction of Protective T Cells against Listeria monocytogenes in Mice by Immunization with a Listeriolysin O-Negative Avirulent Strain of Bacteria and Liposome-Encapsulated Listeriolysin O", Infect. Immun., 1999, 67(2):568-575.

Tang et al., "Protein Chemistry and Structure: Use of a Peptide Mimotope to Guide the Humanization of MRK-16, an Anti-P-glycoprotein Monoclonal Antibody", 1999 J. Biol. Chem. 274:27371-27378.
Tanghe "Improved Immunogenicity and Protective Efficacy of a Tuberculosis DNA Vaccine Encoding Ag85 by Protein Boosting" Infect. Immun. 69:3041-7 (2001).
Tanizawa et al. "The primary structure of thermostable D-amino acid aminotransferase from a thermophilic *Bacillus* species and its correlation with L-amino acid aminotransferases", J Biol Chem. Feb. 15, 1989;264(5):2450-4.
Tanizawa et al. "Thermostable alanine racemase from Bacillus stearothermophilus: DNA and protein sequence determination and secondary structure prediction", Biochemistry. Feb. 23, 1988;27(4):1311-6.
Tauch et al, "The alanine racemase gene alr is an alternative to antibiotic resistance genes in cloning systems for industrial Corynebacterium glutamicum strains" 2002, J. Biotechnol 99:79-91.
Teitelbaum et al. "Mycobacterial infection of macrophages results in membrane-permeable phagosomes", Proc. Natl. Acad. Sci. U.S. A, Dec. 21, 1999, 96(26):15190-5.
Terracciano et al. "Cytogenetic alterations in liver cell tumors as detected by Comparitive Genomic Hybridization", Pathologica 95:71-82 (2003).
Thomas-Kaskel et al (Vaccination of advanced prostate cancer patients with PSCA and PSA peptide-loaded dendritic cells induces DTH responses that correlate with superior overall survival. Int J Cancer. Nov. 15, 2006;119(10):2428-34).
Thompson et al. "Pathogenicity and immunogenicity of a Listeria monocytogenes strain that requires D-alanine for growth", Infect Immun. Aug. 1998;66(8):3552-61.
Thompson et al., "Costimulatory B7-H1 in renal cell carcinoma patients: Indicator of tumor aggressiveness and potential therapeutic target" PNAS 101 (49); 17174-17179 (2004).
Thompson et al. "PD-1 is expressed by tumor infiltrating cells and is associated with poor outcome for patients with renal carcinoma" Clinical Cancer Research (2007) 15: 1757-1761.
Tilney et al., 1989, "Actin filaments and the growth, movement, and spread of the intracellular bacterial parasite, Listeria monocytogenes" J. Cell Biol., Oct.; 109(4 Pt 1):1597-608.
Toplian et al., "Safety, Activity, and Immune Correlates of Anti-PD-1 Antibody in Cancer" New Eng. J Med. 366 (26): 2443-2454 (2012).
Triglia et al. "A procedure for in vitro amplification of DNA segments that lie outside the boundaries of known sequences", Nucleic Acids Res. Aug. 25, 1988;16(16):8186.
Uenaka et al (T cell immunomonitoring and tumor responses in patients immunized with a complex of cholesterol-bearing hydrophobized pullulan (CHP) and NY-ESO-1 protein. Cancer Immun. Apr. 19, 2007;7:9).
Ulmanen et al, "Transcription and Translation of Foreign Genes in Bacillus subtilis by the Aid of a Secretion Vector" 1985. J. Bacteriol. 162:176-182.
Vasil et al., 1982, "Cloning of a phosphate-regulated hemolysin gene (phospholipase C) from Pseudomonas aeruginosa" J. Bacteriol. Oct.; 152(1):431-40.
Vaughan et al. Human Antibodies with Sub-nanomolar Affinities Isolated from a Large Non-immunized Phage Display Library, Nature Biotechnol. 14:309-314 (1996).
Vazquez et al. Differential regulation of Ia expression and antigen presentation by listeriolysin-producing versus non-producing strains of Listeria monocytogenes, J. Leukoc Biol. May 1996; 59(5):683-90.
Vazquez-Boland et al., 1992, "Nucleotide sequence of the lecithinase operon of Listeria monocytogenes and possible role of lecithinase in cell-to-cell spread" Infect. Immun. 60:219-230.
Verch et al., Listeria monocytogenes-Based Antibiotic Resistance Gene-Free Antigen Delivery System Applicable to Other Bacterial Vectors and DNA Vaccines. Infect Immun, 2004. 72(11):6418-25.
Verma et al., 1995, "Delivery of class I and class II MHC-restricted T-cell epitopes of listeriolysin of listeria monocytogenes by attenuated salmonella", Vaccine, vol. 13, No. 2, p. 142-150.

(56) References Cited

OTHER PUBLICATIONS

Villanueva et al. "Listeriolysin is processed efficiently into an MHC class I-associated epitope in Listeria monocytogenes-infected cells", J. Immunol. Dec. 1, 1995; 155(11):5227-33.

Vines et al. "Identfication and characterization of nucleotide sequence difference in three virulence-associate genes of listeria monocytogenes strains representing clinically important serotypes", Current Microbiology, May 1998, vol. 36, No. 5, pp. 309-318.

Von Heijne. Patterns of Amino Acids near Signal-Sequence Cleavage Sites Eur. J. Biochem. 133:17-21 (1983).

Von Heijne, "A new method for predicting signal sequence cleavage sites" (1986) Nucleic Acids Res. 14:4683-4690.

Walker et al., 1994, "Tumor growth Alters T cell and macrophage production of and responsiveness to granulocyte-macrophage colony-stimulating factor: partial dysregulation through interleukin-10" Cell Immunol. 154(1):342-357.

Wallecha et al. "Construction and characterization of an attenuated Listeria monocytogenes strain for clinical use in cancer immunotherapy" Clin Vaccine Immunol. 16(1):96-103, Jan. 2009.

Wallecha et al., "Multiple effector mechanisms induced by recombinant listeria monocytogenes anticancer immunotherapeutics", Advances in Applied Microbiology, vol. 66, 2009, pp. 1-27.

Ward et al, 1986. Construction and characterisation of a series of multi-copy promoter-probe plasmid vectors for Streptomyces using the aminoglycoside phosphotransferase gene from Tn5 as indicator, Mol. Gen. Genet. 203:468-478.

Wasserman et al. "Catabolic alanine racemase from Salmonella typhimurium: DNA sequence, enzyme purification, and characterization", Biochemistry. Oct. 23, 1984;23(22):5182-7.

Watson et al., 1991, "Splenic macrophages from tumor-bearing mice co-expressing MAC-1 and MAC-2 antigen exert immunoregulatory functions via two distinct mechanisms" J. Leukoc Biol. 49(2):126-138.

Weber, "Assessing Tumor Response to Therapy" Nucl. Med. 50:1S-10S (2009).

Wei et al., 2005, "Listeria monocytogenes phosphatidylinositol-specific phospholipase C has evolved for virulence by greatly reduced activity on GPI anchors" Proc. Natl. Acad. Sci. U.S.A. 102:12927-12931.

Weidt et al., 1994, "CD8+ T lymphocyte-mediated antiviral immunity in mice as a result of injection of recombinant viral proteins", J. Immunol. Sep. 15; 153(6):2554-61.

Weiskirch "Listeria monocytogenes: a potent vaccine vector for neoplastic and infectious disease" Immunol. Rev., vol. 158, Aug. 1997, p. 159-169.

Welch et al., Jul. 3, 1998, "Interaction of Human Arp2/3 Complex and the Listeria monocytogenes ActA Protein in Actin Filament Nucleation" Science 281:105-108; pa-998020.

Wilson et al. "Transient expression of bacterial gene fragments in eukaryotic cells: implications for CD8(+) T cell epitope analaysis", J. Immunol. Methods, Feb. 3, 2000; 234 (1-2):137-47.

Wipke et al. "Variable binding affinities of listeriolysin O peptides for the H-2Kd class I molecule", Eur J Immunol. Aug. 1993;23(8):2005-10.

Wirth et al, "Highly efficient protoplast transformation system for *Streptococcus faecalis* and a new *Escherichia coli-S. faecalis* shuttle vector", J Bacteriol, 165: 831, 1986.

Wolff et. al. "Direct Gene Transfer into Mouse Muscle in Vivo", Science 247:1465(1990).

Wood et al. "Cancer immunotherapy using Listeria monocytogenes and listerial virulence factors" Immunol Res. ; 42(1-3):233-45. (2008).

Wootton et al. Statistics of Local Complexity in Amino Acid Sequences and Sequence Databases, Comput. Chem. 17:149-163 (1993).

Wright et al. "Lymphoid/Neuronal Cell Surface OX2 Glycoprotein Recognizes a Novel Receptor on Macrophages Implicated in the Control of Their Function ", (2000) Immunity 13:233-242.

Wu et al., "Engineering an itracellular pathway for major histrocompatibility complex class II presentation of antigens", Proc. Natl. Acad. Sci. USA, 1995, 92:11671-5.

Yang et al. "A Randomized Trial of Bevacizumab, an Anti—Vascular Endothelial Growth Factor Antibody, for Metastatic Renal Cancer" (2003) New Engl. J. Med. 349:427-434.

Young et al., 1992, "Tumor-derived cytokines induce bone marrow suppressor cells that mediate immunosuppression through transforming growth factor beta", Cancer Immunol. Immunother. 35(1)14-18.

Young et al., 1995, "Holins: form and function in bacteriophage lysis" FEMS Microbiol Rev., Aug., 17 (1-2):191-205.

Zhang et al., 1993, "Functional replacement of the hemolysin A transport signal by a different primary sequence", Proc. Natl. Acad. Sci. U.S.A May 1; 90(9):4211-5.

Zhang et al., "PowerBLAST: A New Network BLAST Application for Interactive or Automated Sequence Analysis and Annotation" (1997) Genome Res. 7:649-656.

Zhao et al. "Pathogenicity and immunogenicity of a vaccine strain of Listeria monocytogenes that relies on a suicide plasmid to supply an essential gene product", Infect Immun. Sep. 2005;73(9):5789-98.

Ahmed et al., "Immunotherapy of Osteosarcoma: Genetic Modification of T cells Overcomes Low Levels of Tumor Antigen Expression," Molecular Therapy, 17(10):1779-1787, (2009).

Alpdogan et al., "Interleukin-15 enhances immune reconstitution after allogeneic bone marrow transplantation," Blood, 105(2):865-873, (2005).

Baumhoer et al., "Aberrant expression of the human epidermal growth factor receptor 2 oncogene is not a common feature in osteosarcoma," Human Pathology, 42(6):859-866, (2011).

Braun et al., "InlB: an invasion protein of Listeria monocytogenes with a novel type of surface association," Mol Microbiol. Jul. 1997; 25(2):285-294.

Broad, "The case of the unmentioned malignancy," Science, 210(4475):1229-1230, (1980).

Bruhn et al., "Listeria as a Vaccine Vector," Microbes and Infection, 9(10):1226-1235, (2007).

Caudy et al., "Fragile X-related protein and VIG associate with the RNA interference machinery" Genes and Development 16: 2491-2496, (2002).

Da'Dara et al., "Helminth infection suppresses T-cell immune response to HIV-DNA-based vaccine in mice," Vaccine 24(24): 5211-5219, (2006).

De Las Mulas et al., "Oncogene HER-2 in canine mammary gland carcinomas," Breast cancer research and treatment, 80(3):363-367, (2003).

De Maria et al., "Spontaneous Feline Mammary Carcinoma Is a Model of HER2 Overexpressing Poor Prognosis Human Breast Cancer," Cancer Research, 65(3):907-912, (2005).

Dietrich et al., 1998, "Delivery of antigen-encoding plasmid DNA into the cytosol of macrophages by attenuated suicide Listeria monocytogenes," Nature Biotechnology 15:181-185.

Ebbeson et al., "Rhabdomyolysis, acute renal failure, and compartment syndrome in a child with parainfluenza type 1 infection," The Pediatric Infectious Disease Journal vol. 28, No. 9, pp. 850-852, Sep. 2009.

Finn et al., 2003, "Cancer vaccines: between the idea and the reality," Nature Reviews Immunology 3:630-641.

Glaser et al., "Comparative genomics of *Listeria* species," Science. Oct. 26, 2001;294(5543):849-852.

GenBank: "Listeria monocytogenes EGD-e chromosome, complete genome," Dec. 2014. [Retrieved from the Internet Jul. 21, 2015: <URL:http://www.ncbi.nlm.nih.gov/nuccore/NC_003210. 1?report=genbank&log$=seqview>].

GenBank: "Listeria monocytogenes actin nucleator protein ActA (actA) gene, complete cds," Nov. 1999. [Retrieved from the Internet Jun. 17, 2015: <URL:http://www.ncbi.nlm.nih.gov/nuccore/AF103807>].

GenBank: "Listeria monocytogenes strain HCC23 listeriolysin positive regulatory protein (prfA), phosphatidylinositol-specific phospholipase C (plcA) and listeriolysin O precursor (hly) genes, complete cds," Feb. 2005. [Retrieved from the Internet Jun. 17, 2015: <URL:http://www.ncbi.nlm.nih.gov/nuccore/AY878649>].

(56) References Cited

OTHER PUBLICATIONS

GenBank: "Listeria monocytogenes isolate H4 Hly (hly) gene, complete cds," Aug. 2006. [Retrieved from the Internet Jun. 17, 2015: <URL: http://www.ncbi.nlm.nih.gov/nuccore/DQ054588>].
GenBank: "Listeria monocytogenes strain 10403S Hly (hly) gene, complete cds," Aug. 2006. [Retrieved from the Internet Jun. 17, 2015: <URL: http://www.ncbi.nlm.nih.gov/nuccore/DQ054589>].
GenBank: "Listeria monocytogenes F6789 listeriolysin O (hly) gene, complete cds," Jul. 2001, [Retrieved from the Internet Jun. 17, 2015: <URL: http://www.ncbi.nlm.nih.gov/nuccore/U25452>].
Gouin et al., "The Listeria monocytogenes InlC protein interferes with innate immune responses by targeting the IκB kinase subunit IKKα," Proceedings of the National Academy of Sciences, 107(40):17333-17338, (2010).
Kawashima, et al., "Identification of HLA-A3-restricted Cytotoxic T Lymphocyte Epitopes from Carcinoembryonic Antigen and HER-2/neu by Primary in Vitro Immunization with Peptide-pulsed Dendritic Cells," Cancer Research, 59:431-435, (1999).
Keegan, et al., "An IL-4 receptor region containing an insulin receptor motif is important for IL-4-mediated IRS-1 phosphorylation and cell growth," Cell, 76(5):811-820, (1994).
Kim et al., "High efficacy of a Listeria-based vaccine against metastatic breast cancer reveals a dual mode of action," Cancer Res. 69(14):5860-5866, (2009).
Kumar, et al., "Prognostic and predictive value of c-erbB2 overexpression in osteogenic sarcoma," Journal of Cancer Research and Therapeutics, 2(1):20, (2006).
Kyte et al., "A simple method for displaying the hydropathic character of a protein," J. Mol. Biol., 157(1):105-132, (1982).
Li et al., "A meta-analysis on the association of HER-2 oveoreoxpression with prognosis in human osteosarcoma," European Journal of Cancer Care, 19(3):313-316, (2010).
Lucey et al., "Henrietta Lacks, HeLa cells, and cell culture contamination," Archives of Pathology & Laboratory Medicine, 133(9):1463-1467, (2009).
Ma et al., "Expression of HER 2 in Human Osteosarcoma," Science Technology and Engineering, 11(13):3045-3048, (2011).
Mitchell et al., "Avoidace f Autophagy Mediated by PlcA or ActA Is Required for Listeria monocytogenes Growth in Macrophages," Infect Immun. May 2015;83(5):2175-2184.
Mustafa, et al., "Listeria Monocytogenes Delivery of HPV-16 Major Capsid Protein L1 Induces Systemic and Mucosal Cell-Mediated CD4+ and CD8+ T-Cell Responses After Oral Immunization," Viral Immunology, 22(3):195-204, (2009).
Ogasawara Database EMBL, Oct. 13, 1997, "Bacillus subtilis Genome Sequence."
Parida et al., 1998, "Internalin B is essential for adhesion and mediates the invasion of Listeria monocytogenes into human endothelial cells" Mol. Microbiol. Apr.; 28(1):81-93.
Roback, "Vaccine-enhanced donor lymphocyte infusion (veDLI)," ASH Education Program Book, 2006(1):486-491, (2006).
Rongcun et al., "Identification of New HER/2neu-Derived Peptide Epitopes That Can Elicit Specific CTL Against Autologous and Allogeneic Carcinomas and Melanomas," The Journal of Immunology, 163(2):1037-1044, (1999).
Seggewiss et al., "Immune reconstitution after allogeneic transplantation and expanding options for immunomodulation: an update," Blood, 115(19):3861-3868, (2010).
Shahabi et al., "Development of a live and highly attenuated Listeria monocytogenes-based vaccine for the treatment of Her2/neu-overexpressing cancers in human," Cancer Gene Therapy, vol. 18, No. 1, Jan. 1, 2011, pp. 53-62.
Starks et al., "Listeria monocytogenes as a Vaccine Vector: Virulence Attenuation or Existing Antivector Immunity Does Not Diminish Therapeutic Efficacy," The Journal of Immunology, 173(1):420-427, (2004).
Strych et al., "Characterization of the alanine racemases from two Mycobacteria," FEMS Microbiol Lett. Mar. 15, 2001;196(2):93-98.

Taube, J. M. et al., "Colocalization of Inflammatory Response with B7-H1 Expression in Human Melanocytic Lesions Supports an Adaptive Resistance Mechanism of Immune Escape," Sci Transl Med 4(127):127ra37 (2012).
Thompson, et al., "Tumor B7-H1 is associated with poor prognosis in renal cell carcinoma patients with long-term follow-up," Cancer Research, 66(7):3381-3385, (2006). [Retrieved from Internet Nov. 28, 2017: <http://cancerres.aacrjournals.org/content/canres/66/7/3381.full.pdf>].
Yalçin et al., "C-erbB-2 expression and prognostic significance in osteosarcoma," Pediatric Blood & Cancer, 51(2):222-227, (2008).
Yeung et al., "Heat-killed Listeria monocytogenes as an Adjuvant Converts Established Murine Th2-Dominated Immune Response into Th1-Dominated Responses," The Journal of Immunology, 161(8):4146-4152, (1998).
Zakrzewski et al., "Adoptive transfer of T-cell precursors enhances T-cell reconstitution after allogeneic hematopoietic stem cell transplantation," Nature Medicine,12(9):1039-1047, (2006).
Zwickey et al., "Antigen Secreted from Noncytosolic Listeria monocytogenes Is Processed by the Classical MHC Class I Processing Pathway," J. Immunol. Jun. 1, 1999; 162(11):6341-6350.
Zwickey et al., "Peptide Epitopes from Noncytosolic Listeria monocytogenes Can Be Presented by Major Histocompatibility Complex Class I Molecules," Infect. Immun. May 1996; 64(5):1870-1872.
EP Supplementary European Search Report for application 15758226.3 dated Aug. 7, 2014.
EP Supplementary European Search Report for application EP15755609.3 dated Aug. 1, 2017.
European Search Report Application No. 09751395.6 dated Jul. 11, 2012.
European Search Report Application No. 10830785.1 dated Dec. 10, 2013
European Search Report Application No. 14190388.0 dated Mar. 2, 2015.
International Search report Application No. PCT/US 10/56534 dated Jun. 27, 2011.
International Search report Application No. PCT/US2012/051187 dated Jan. 23, 2013.
International Search Report for PCT Application No. PCT/US15/040911 dated Nov. 2, 2015.
International Search Report for PCT Application No. PCT/US15/40855 dated Dec. 18, 2015.
PCT International Preliminary Report on Patentability for application PCT/US2009/044538 dated Nov. 23, 2010.
PCT International Preliminary Report on Patentability for application PCT/US2010/056534 dated May 15, 2012.
PCT International Preliminary Report on Patentability for application PCT/US2012/028757 dated Sep. 17, 2013.
PCT International Preliminary Report on Patentability for application PCT/US2013/030521 dated Sep. 16, 2014.
PCT International Preliminary Report on Patentability for application PCT/US2015/017559 dated Aug. 30, 2016.
PCT International Preliminary Report on Patentability for application PCT/US2015/040911 dated Jan. 24, 2017.
PCT International Preliminary Report on Patentability for application PCT/US2016/016452 dated Aug. 8, 2017.
PCT International Preliminary Report on Patentability for application PCT/US2012/051187 dated Feb. 18, 2014.
PCT International Preliminary Report on Patentability for application PCT/US2015/018915 dated Sep. 6, 2016.
PCT International Preliminary Report on Patentability for application PCT/US2015/040855 dated Jan. 24, 2017.
PCT International Search Report and Written Opinion of the International Searching Authority for application PCT/US2015/040855 dated Dec. 18, 2015.
PCT International Search Report and Written Opinion of the International Searching Authority for application PCT/US2016/016452 dated Aug. 24, 2016.
PCT International Search Report for application PCT/US2015/018915 dated Jun. 19, 2015.
PCT Written Opinion of the International Searching Authority for application PCT/US2012/051187 dated Jan. 23, 2013.

(56) References Cited

OTHER PUBLICATIONS

PCT Written Opinion of the International Searching Authority for application PCT/US2009/044538 dated Aug. 14, 2009.
PCT Written Opinion of the International Searching Authority for application PCT/US2010/056534 dated Jun. 27, 2011.
PCT Written Opinion of the International Searching Authority for application PCT/US2012/028757 dated Aug. 27, 2012.
PCT Written Opinion of the International Searching Authority for application PCT/US2013/030521 dated May 14, 2013.
PCT Written Opinion of the International Searching Authority for application PCT/US2015/017559 dated Jun. 5, 2015.
PCT Written Opinion of the International Searching Authority for application PCT/US2015/040911 dated Nov. 2, 2015.
Supplementary European Search Report for European Application No. 11863004.5 dated Nov. 10, 2015.
Supplementary European Search Report for European Application No. 12758350.8 dated Aug. 14, 2014.
Supplementary European Search Report for European Application No. 12824212.0 dated Jun. 3, 2015.
WIPO Application No. PCT/US2009/044538, PCT International Search Report dated Aug. 14, 2009.
WIPO Application No. PCT/US2012/028757, PCT International Search Report dated Aug. 27, 2012.
WIPO Application No. PCT/US2015/017559, PCT International Search Report dated Jun. 5, 2015.

\* cited by examiner

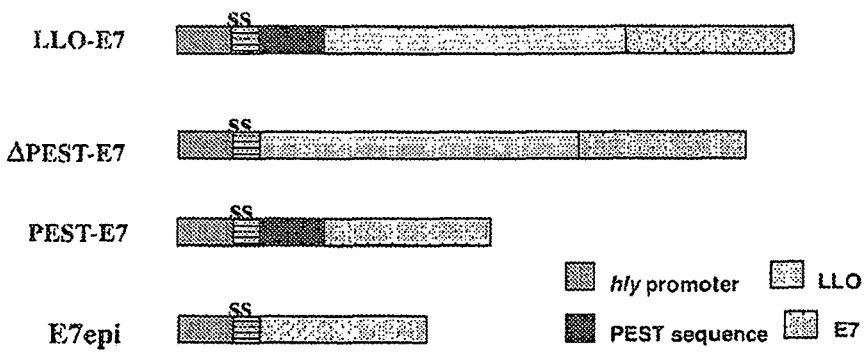
Figure 6A
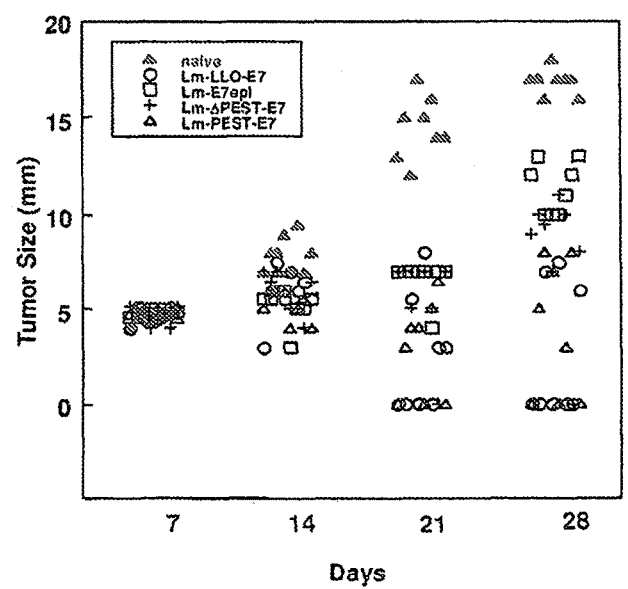
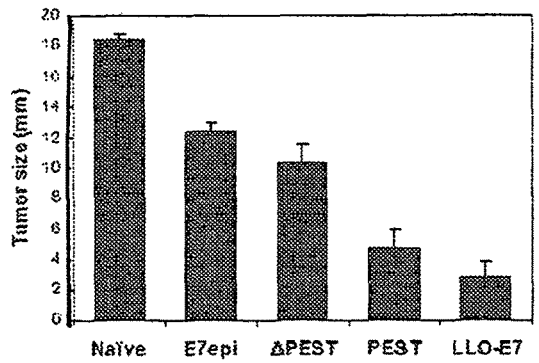
Figure 6B atggcgcgggatggtatactatacaagcgtatggttcaaaaagatactttgaattaagaagt
acaataaagttaacttcattagacaaaaagaaaaaacaaggaagaatagtacatagttataa
atacttggagagtgaggtgtaatatgggggcagctgattttgggggtttcatatatgtagtt
tcaagattagccattgttgcggcagtagtttacttcttatacttattgagaaaaattgcaaa
taaatagaaaaaagccttgtcaaacgaggcttttttatgcaaaaaatacgacgaatgaag
ccatgtgagacaattggaatagcagacaacaaggaaggtagaacatgttttgaaaaatta
ctgattttcgattattattaacgcttgttaatttaaacatctcttattttgctaacatata
agtatacaaagggacataaaaaggttaacagcgtttgttaaataggaagtatatgaaaatcc
tcttttgtgtttctaaatttattttaaggagtggagaatgttgaaaaaaaataattggtta
caaaatgcagtaatagcaatgctagtgttaattgtaggtctgtgcattaatatgggttctgg
aacaaaagtacaagctgagagtattcaacgaccaacgcctattaaccaagtttttccagatc
ccggcctagcgaatgcagtgaaacaaaatttagggaagcaaagtgttacagaccttgtatca
caaaaggaactatctggagtacaaaatttcaatggagataatagcaacattcaatctcttgc
gggaatgcaattttttcactaatttaaaagaacttcatctatcccataatcaaataagtgacc
ttagtcctttaaaggatctaactaagttagaagagctatctgtgaatagaaacagactgaaa
aatttaaacggaattccaagtgcttgtttatctcgcttgttttttagataacaacgaactcag
agatactgactcgcttattcatttgaaaaatctagaaatcttatctattcgtaataataagt
taaaaagtattgtgatgcttggttttttatcaaaactagaggtattagatttgcatggtaat
gaaataacaaatacaggtggactaactagattgaagaaagttaactggatagatttaactgg
tcagaaatgtgtgaatgaaccagtaaaataccaaccagaattgtatataacaaatactgtca
aagacccagatggaagatggatatctccatattacatcagtaatggtgggagttatgtagat
ggttgtgtcctgtgggaattgccagtttatacagatgaagtaagctataagtttagcgaata
tataaacgttggggagactgaggctatatttgatggaacagttacacaacctatcaagaatt
aggacttgtgcacacctgtatactttgagctctcgtataatcacgagagcttttttaaatatg
taagtcttaattatctcttgacaaaaagaacgtttattcgtataaggttaccaagagatgaa
gaaactattttatttacaattcaccttgacaccaaaaactccatatgatatagtaaataagg
ttattaaacaagaaagaagaagcaacccgcttctcgcctcgttaacacgaacgttttcaggc
aaaaaattcaaactttcgtcgcgtagcttacgcgattttgaatgtgcgggattgctgaaaag
cagcccgtttttttatggcctccgaacgaatgagttagcaggccgcagatttgaacagctat
tttctatcttgttgtaacaaaattaagtggaggtggctcaccattagcaaagacatgttggt
aaacgatgggattcgtgcacgtgaagtaagattgatcgaccaagacggtgaacaattaggcg
tgaagagtaaaatcgatgcgcttcaaattgctgaaaaggctaatcttgatctagtgcttgtt
gctccaacagcgaaaccgccagtagctcgta

Figure 10

GAATTCatggcgcgggatggtatactatacaagcgtatggttcaaaaagatactttgaattaa
gaagtacaataaagttaacttcattagacaaaagaaaaaacaaggaagaatagtacatagtt
ataaatacttggagagtgaggtgtaatatgggggcagctgattttgggtttcatatatgta
gtttcaagattagccattgttgcggcagtagtttacttcttatacttattgagaaaaattgca
aataaatagaaaaaagccttgtcaaacgaggcttttttatgcaaaaaatacgacgaatgaa
gccatgtgagacaatttggaatagcagacaacaaggaaggtagaacatgttttgaaaaattta
ctgattttcgattattattaacgcttgttaatttaaacatctcttattttgctaacatataa
gtatacaaagggacataaaaaggttaacagcgtttgttaaataggaagtatatgaaaatcctc
ttttgtgtttctaaatttattttaaggagtggagaGGATCCggacttgtgcacacctgtata
cttgagctctcgtataatcacgagagcttttttaaatatgtaagtcttaattatctcttgaca
aaagaacgtttattcgtataaggttaccaagagatgaagaaactattttatttacaattcac
cttgacaccaaaaactccatatgatatagtaaataaggttattaaacaagaaagaagaagcaa
cccgcttctcgcctcgttaacacgaacgttttcaggcaaaaaattcaaactttcgtcgcgtag
cttacgcgatttgaatgtgcgggattgctgaaaagcagcccgttttttatggcctccgaac
gaatgagttagcaggccgcagatttgaacagctatttctatcttgttgtaacaaaattaagt
ggaggtggctcaccattagcaaagacatgttggtaaacgatgggattcgtgcacgtgaagtaa
gattgatcgaccaagacggtgaacaattaggcgtgaagagtaaaatcgatgcgcttcaaattg
ctgaaaaggctaatcttgatctagtgcttgttgctccaacagcgaaaccgccagtagctcgta
CTGCAG

Figure 11 gcgccaaatcattggttgattggtgaggatgtctgtgtgcgtgggtcgcgagatgggcgaataagaagcattaaagatcctgacaaatat
aatcaagcggctcatatgaaagattacgaatcgcttccactcacagaggaaggcgactggggcggagttcattataatagtggtatccc
gaataaagcagcctataatactatcactaaacttggaaaagaaaaaacagaacagctttatttcgcgccttaaagtactatttaacgaaaa
aatcccagtttaccgatgcgaaaaaagcgcttcaacaagcagcgaaagatttatatggtgaagatgcttctaaaaaagttgctgaagctt
gggaagcagttggggttaactgattaacaaatgttagagaaaaattaattctccaagtgatattcttaaaataattcatgaatattttttcttata
ttagctaattaagaagataactaactgctaatccaattttaacggaacaaattagtgaaaatgaaggccgaattccttgttctaaaaaggt
tgtattagcgtatcacgaggagggagtataa*gtgggattaaacagatttatgcgtgcgatgatggtggttttcattactgccaattgcatt
acgattaaccccgacgtcgacccatacgacgttaattcttgcaatgttagctattggcgtgttctctttaggggcgtttatcaaaattatt
caattaagaaaaaataattaa*aaaacacagaacgaaagaaaaagtgaggtgaatgatatgaaattcaaaaaggtggttctaggtatgtg
cttgatcgcaagtgttctagtcttccggtaacgataaaagcaaatgcctgttgtgatgaatacttacaaacacccgcagctccgcatgata
ttgacagcaaattaccacataaacttagttggtccgcggataacccgacaaatactgacgtaaatacgcactattggcttttaaacaagc
ggaaaaaatactagctaaagatgtaaatcatatgcgagctaatttaatgaatgaacttaaaaaattcgataaacaaatagctcaaggaata
tatgatgcggatcataaaaatccatattatgatactagtacattttatctcattttataatcctgatagagataatacttatttgccgggtttgc
taatgcgaaaataacaggagcaaagtatttcaatcaatcggtgactgattaccgagaagggaa

Figure 13

1- Negative *Lm*-control
2- *Lm*-LLO-ChHer2
3- ADXS31-164

Spleens
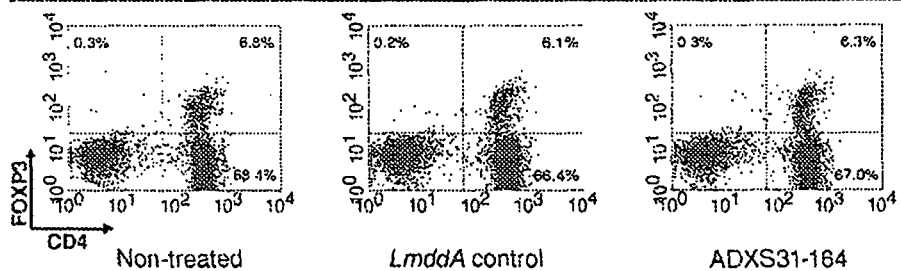
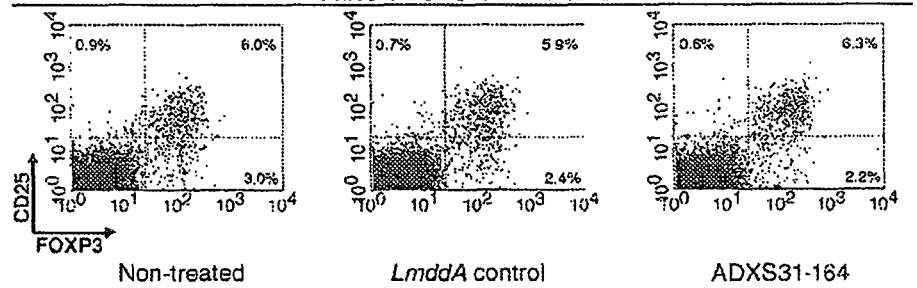
Figure 18

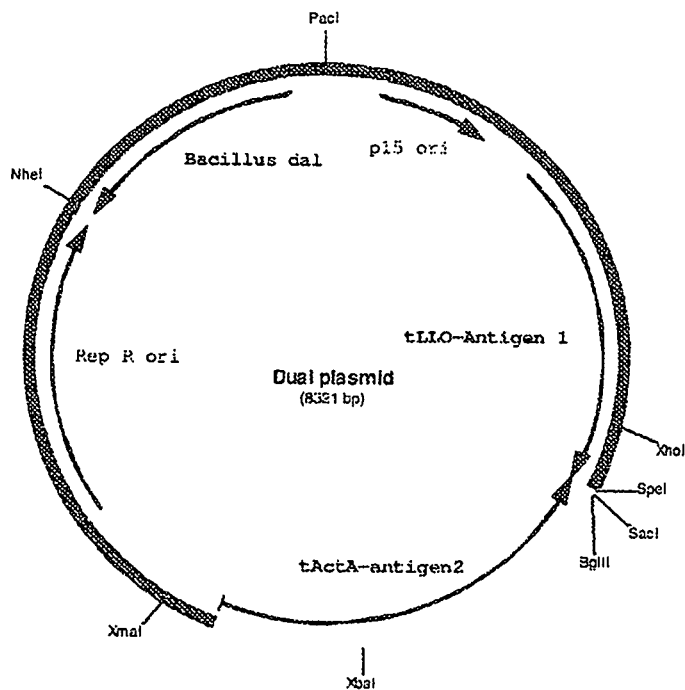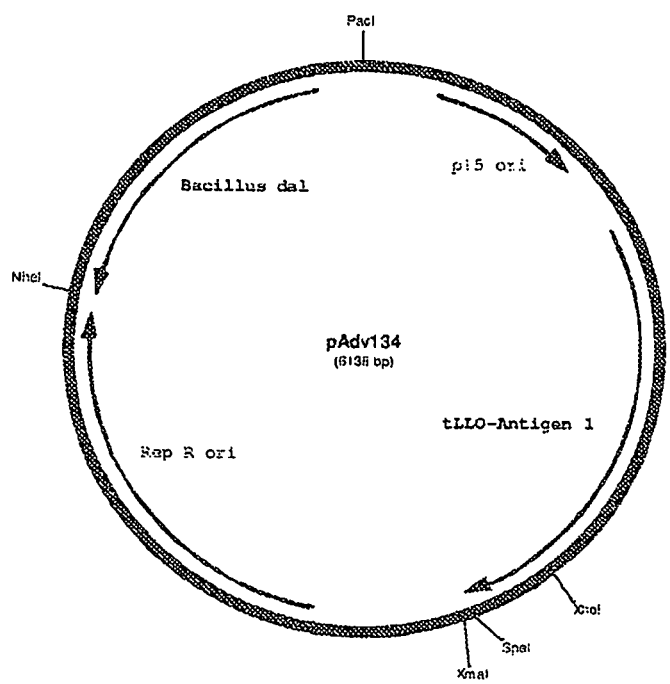
Figure 20

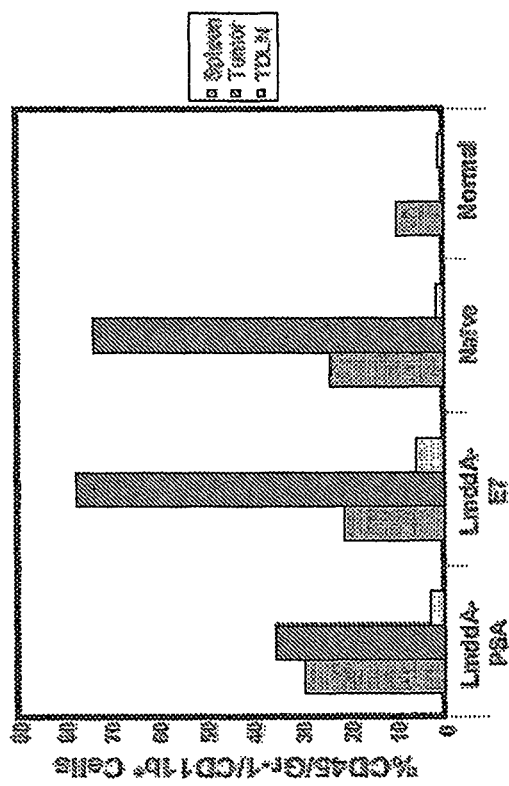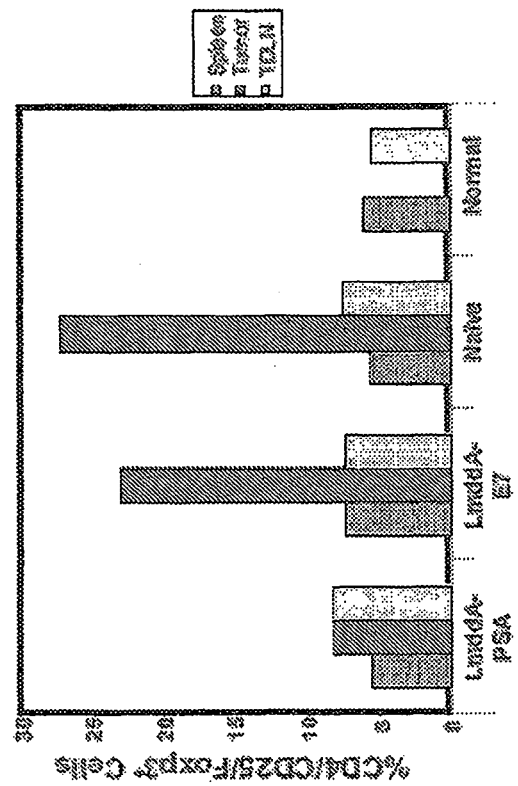
Figure 21

Tumor Treg

Spleen Treg

Tumor Tcon

SUPPRESSOR CELL FUNCTION INHIBITION FOLLOWING *LISTERIA* VACCINE TREATMENT

This application is a National Phase Application of PCT International Application No. PCT/US13/030521, International Filing Date Mar. 12, 2013; which claims priority to U.S. Provisional Patent Application 61/609,627; all of which are incorporated by reference herein in their entirety.

FIELD OF INVENTION

This invention provides methods and compositions for using a live attenuated *Listeria* for inhibiting cell-mediated suppression of anti-disease infiltrating T lymphocytes in a subject having the disease.

BACKGROUND OF THE INVENTION

*Listeria monocytogenes* (Lm) is an intracellular pathogen that primarily infects antigen presenting cells and has adapted for life in the cytoplasm of these cells. *Listeria monocytogenes* and a protein it produces named listeriolysin O (LLO) have strong adjuvant properties that unlike the majority of adjuvants used for cellular based immunotherapies, can be administered after providing an antigen specific treatment.

Tregs play a critical role in the maintenance of peripheral self-tolerance. Naturally occurring $CD4^+CD25^{hi}$ Tregs are produced in the thymus and express FoxP3, a transcriptional factor required for establishment and maintenance of Treg lineage identity and suppressor function. Tregs can accumulate at a disease site, where they suppress the effector function of disease specific T cells. When this occurs it can result in an increase in disease despite the presence of appropriate antigens or T cells activated to attack those antigens. Increased densities of tumor-infiltrating $FoxP3^+$ Tregs have been associated with poor prognosis in various solid tumors, including pancreatic, ovarian, and hepatocellular carcinoma. Depletion of Tregs results in enhanced antitumor immunity and tumor rejection in murine models but may also result in the development of autoimmune diseases.

Myeloid-derived suppressor cells (MDSCs) are a heterogeneous population of early myeloid progenitors, immature granulocytes, macrophages, and dendritic cells at different stages of differentiation. These cells are of great interest because they have the capacity to suppress both the cytotoxic activities of natural killer (NK) and NKT cells, and the adaptive immune response mediated by $CD8^+$ T cells. While the mechanism of NK cell inhibition is currently not well-understood, multiple pathways are responsible for MDSC-mediated T cell suppression including: 1) production of arginase 1/ARG1 and 2) upregulation of nitric oxide synthase 2 (NOS2). ARG1 and NOS2 metabolize L-arginine and either together, or separately, block translation of the T cell CD3 zeta chain, inhibit T cell proliferation, and promote T cell apoptosis. Additionally, MDSCs secrete immunosuppressive cytokines and induce regulatory T cell development. In mice, MDSCs are broadly defined as $CD11b^+Gr$-$1/Ly$-$6G^+$ cells, but the relative expression levels of Ly-6G and Ly-6C identify two specific subsets. Human MDSCs commonly express Siglec-3/CD33 and lack lineage markers and HLA-DR, but heterogeneous expression of CD14 and CD15 suggest that multiple subsets exist.

MDSCs are induced by pro-inflammatory cytokines and are found in increased numbers in infectious and inflammatory pathological conditions. They accumulate in the blood, bone marrow, and secondary lymphoid organs of tumor-bearing mice and their presence in the tumor microenvironment has been suggested to have a causative role in promoting tumor-associated immune suppression. Although it is now evident that MDSCs may serve as a target for preventing tumor progression, further characterization is necessary to determine effective mechanisms by which they can be inhibited.

The invention provides an effective mechanism of inhibiting suppressor cells such as Tregs and MDSCs by providing *Listeria* vaccines that once administered to tumor-bearing subject, proceed to suppress Tregs and MDSC function, thereby allowing anti-tumor T cells to replicate and inhibit tumor growth.

SUMMARY OF THE INVENTION

In one embodiment, the invention relates to a method of increasing a T infiltrating lymphocytes/suppressor cell ratio in a subject having a disease or in a disease site within the subject, the method comprising the step of administering to the subject a composition comprising a live attenuated *Listeria* vaccine strain.

In another embodiment, the invention relates to a method of reducing the percentage of suppressor cells in a disease in a subject, the method comprising the step of administering a live attenuated *Listeria* vaccine strain to said subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 1A shows that Lm-E7 was generated by introducing a gene cassette into the orfZ domain of the *L. monocytogenes* genome. The hly promoter drives expression of the hly signal sequence and the first five amino acids (AA) of LLO followed by HPV-16 E7. FIG. 1B shows that Lm-LLO-E7 was generated by transforming the prfA-strain XFL-7 with the plasmid pGG-55. pGG-55 has the hly promoter driving expression of a nonhemolytic fusion of LLO-E7. pGG-55 also contains the prfA gene to select for retention of the plasmid by XFL-7 in vivo.

Figure 3:
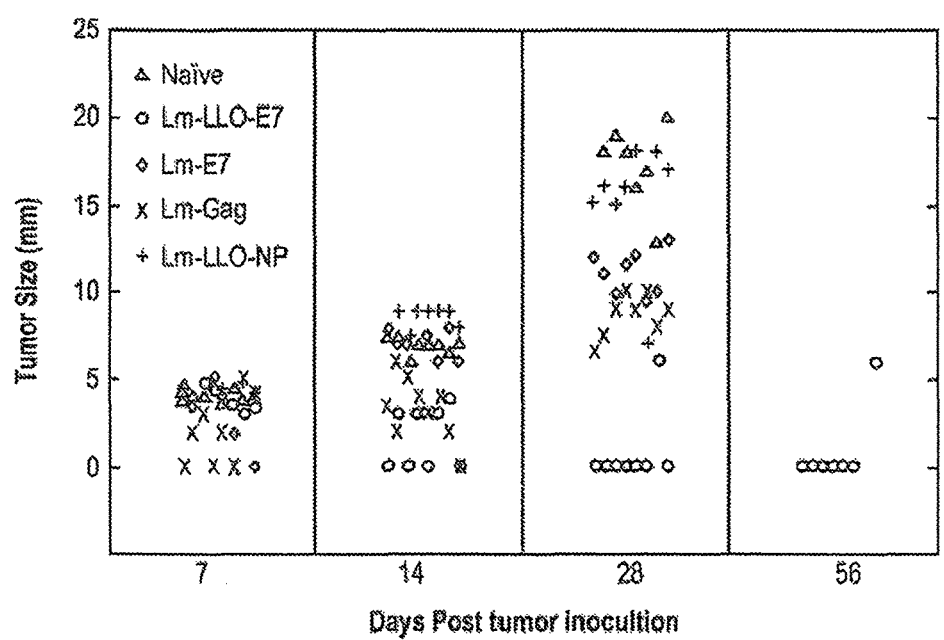

FIG. 3 shows that tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles.

Figure 4:
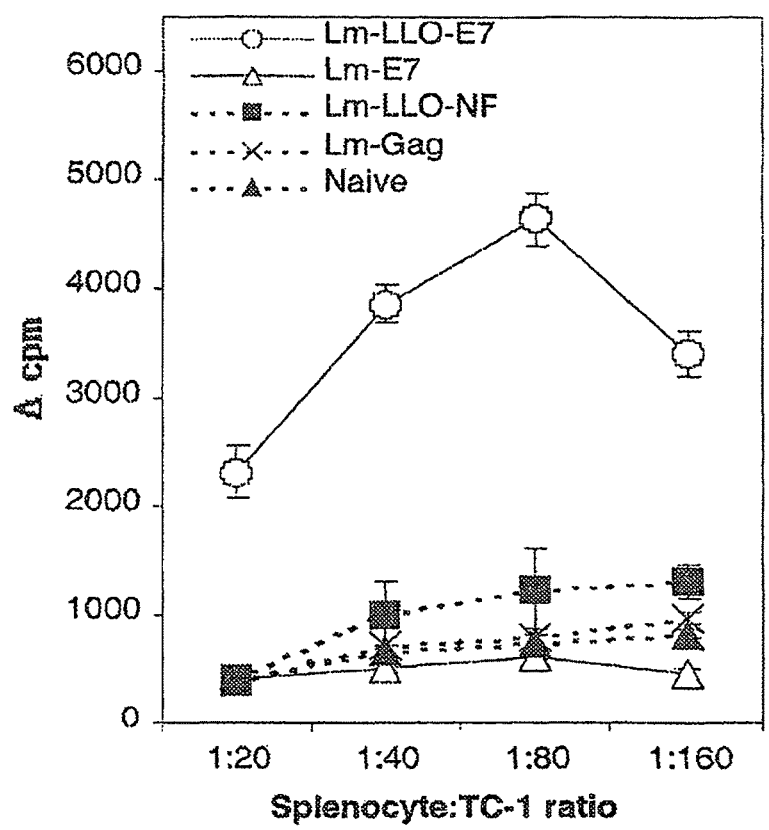

FIG. 4 shows that splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)–(no-TC-1 control).

Figure 5A:
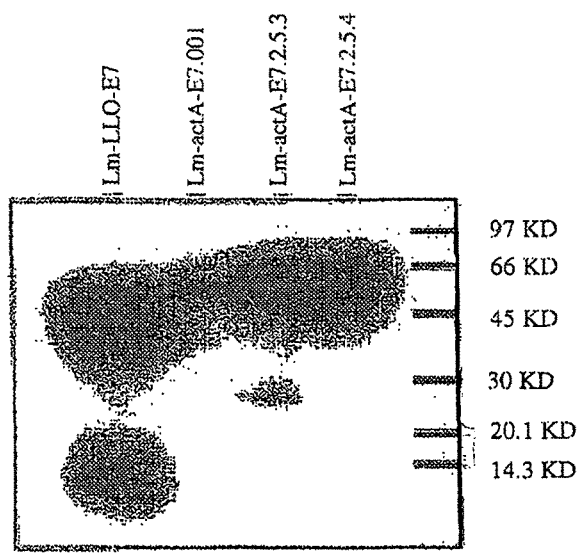
Figure 5B:
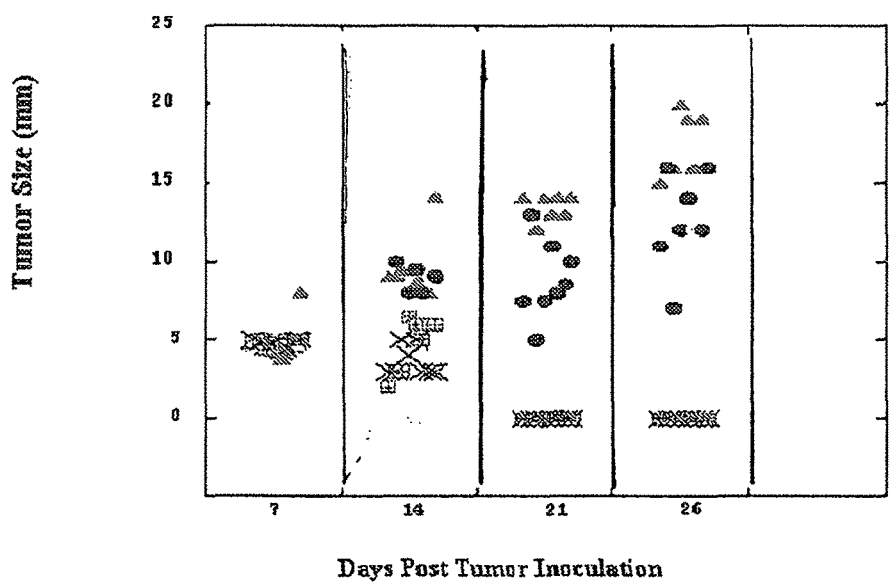

FIGS. 5A and 5B. FIG. 5A shows Western blot demonstrating that Lm-ActA-E7 secretes E7. Lane 1: Lm-LLO-E7; lane 2: Lm-ActA-E7.001; lane 3; Lm-ActA-E7-2.5.3; lane 4: Lm-ActA-E7-2.5.4. FIG. 5B shows Tumor size in mice administered Lm-ActA-E7 (rectangles), Lm-E7 (ovals), Lm-LLO-E7 (X), and naive mice (non-vaccinated; solid triangles).

Figure 6C:
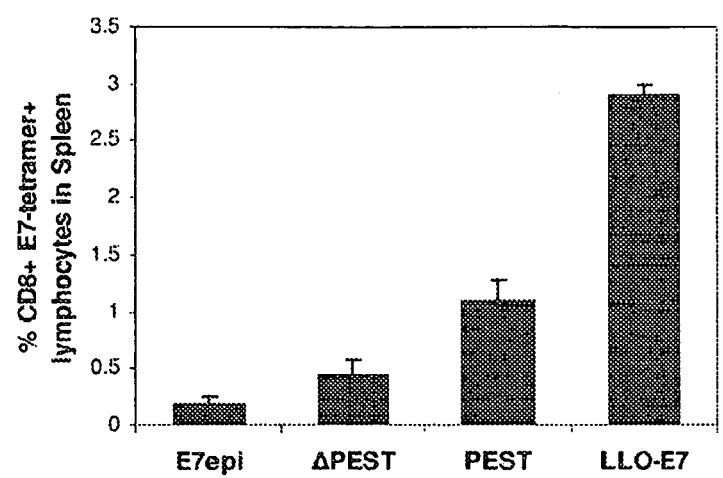

FIGS. 6A-6C. FIG. 6A shows schematic representation of the plasmid inserts used to create 4 LM vaccines. Lm-LLO-E7 insert contains all of the *Listeria* genes used. It contains the hly promoter, the first 1.3 kb of the hly gene (which encodes the protein LLO), and the HPV-16 E7 gene. The first 1.3 kb of hly includes the signal sequence (ss) and the PEST region. Lm-PEST-E7 includes the hly promoter, the signal sequence, and PEST and E7 sequences but excludes the remainder of the truncated LLO gene. Lm-APEST-E7 excludes the PEST region, but contains the hly promoter, the signal sequence, E7, and the remainder of the truncated LLO. Lm-E7epi has only the hly promoter, the signal sequence, and E7. FIG. 6B Top panel: *Listeria* constructs containing PEST regions induce tumor regression. Bottom panel: Average tumor sizes at day 28 post-tumor challenge in 2 separate experiments. FIG. 6C demonstrates *Listeria* constructs containing PEST regions induce a higher percentage of E7-specific lymphocytes in the spleen. Average and SE of data from 3 experiments are depicted.

Figure 7A:
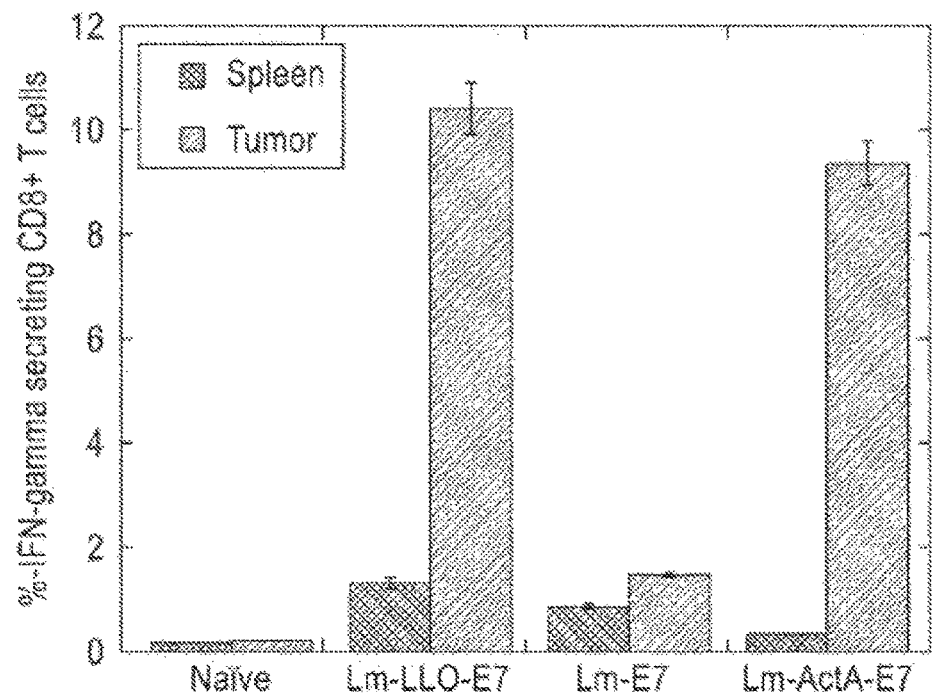
Figure 7B:
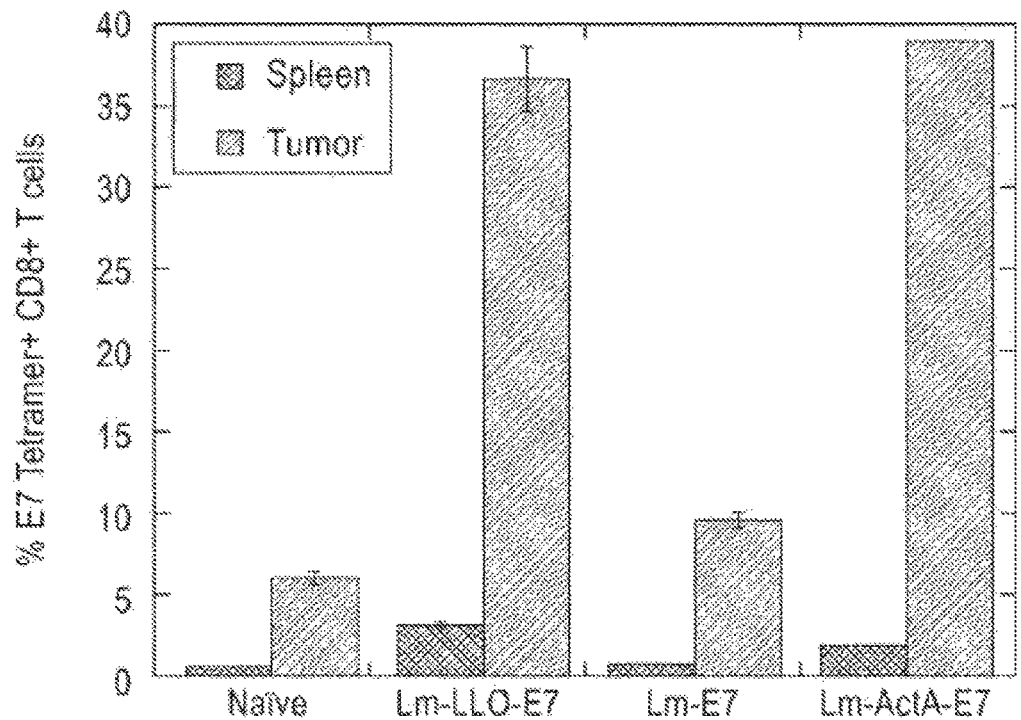

FIGS. 7A and 7B. FIG. 7A shows induction of E7-specific IFN-gamma-secreting CD8$^+$ T cells in the spleens and the numbers penetrating the tumors, in mice administered TC-1 tumor cells and subsequently administered Lm-E7, Lm-LLO-E7, Lm-ActA-E7, or no vaccine (naive). FIG. 7B shows induction and penetration of E7 specific CD8$^+$ cells in the spleens and tumors of the mice described for 7A.

Figure 8A:
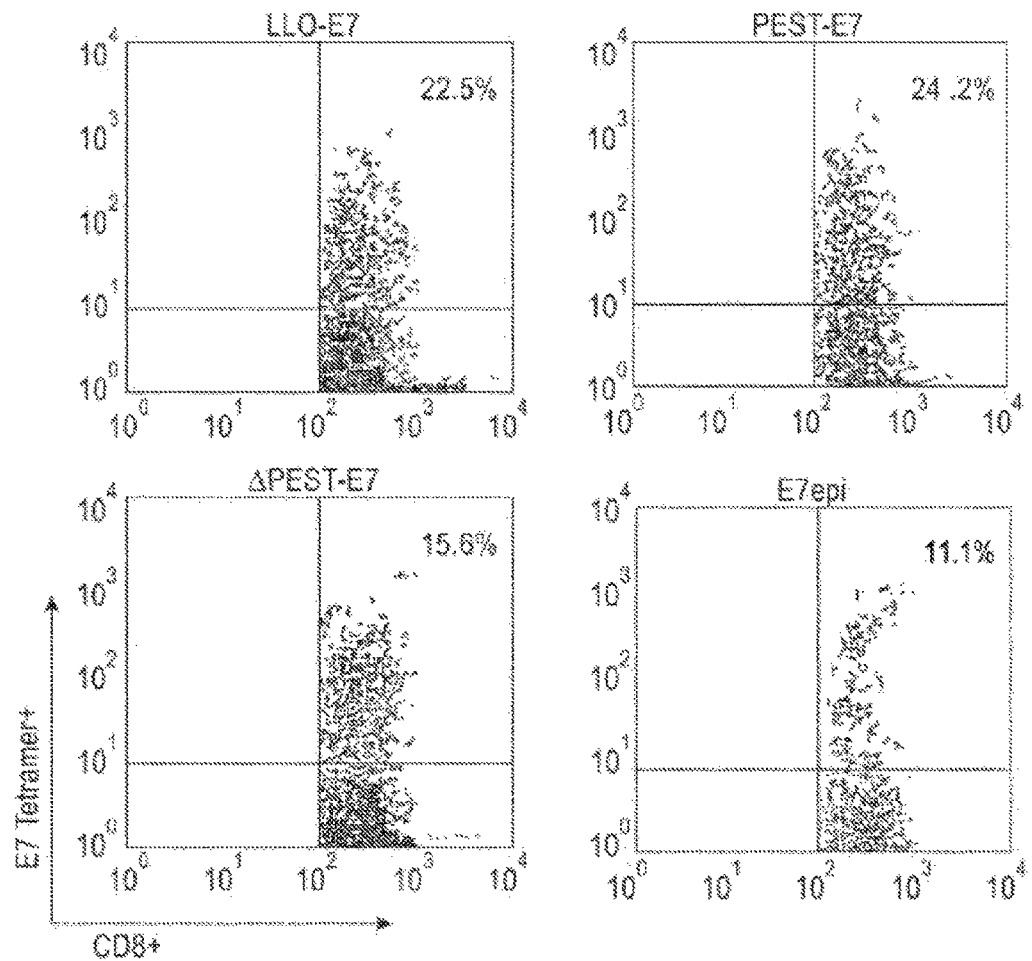
Figure 8B:
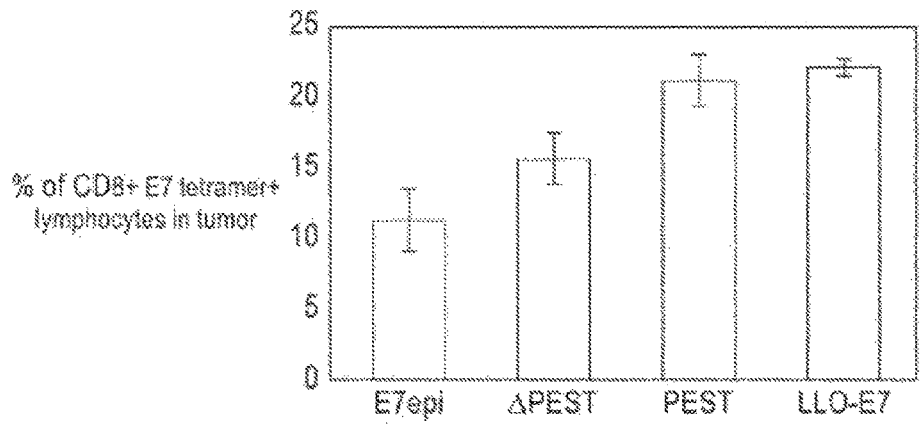

FIGS. 8A and 8b. FIG. 8A shows *Listeria* constructs containing PEST regions induce a higher percentage of E7-specific lymphocytes within the tumor. Data is representative from 1 experiment. FIG. 8B shows average and SE of data from all 3 experiments.

Figure 9A:
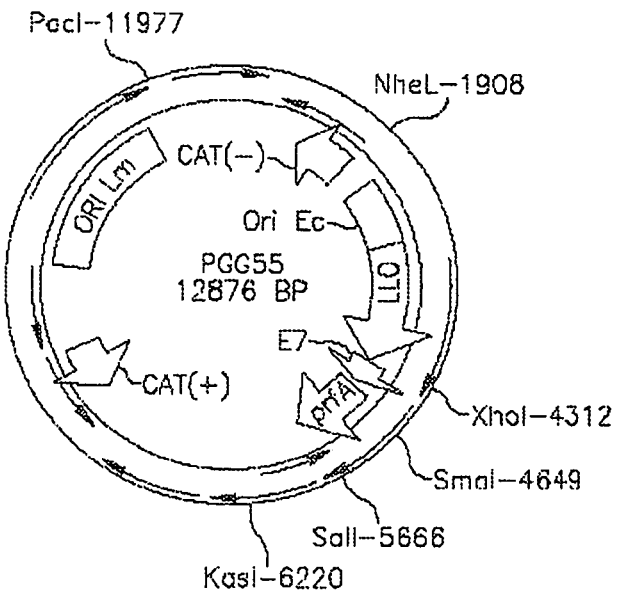
Figure 9B:
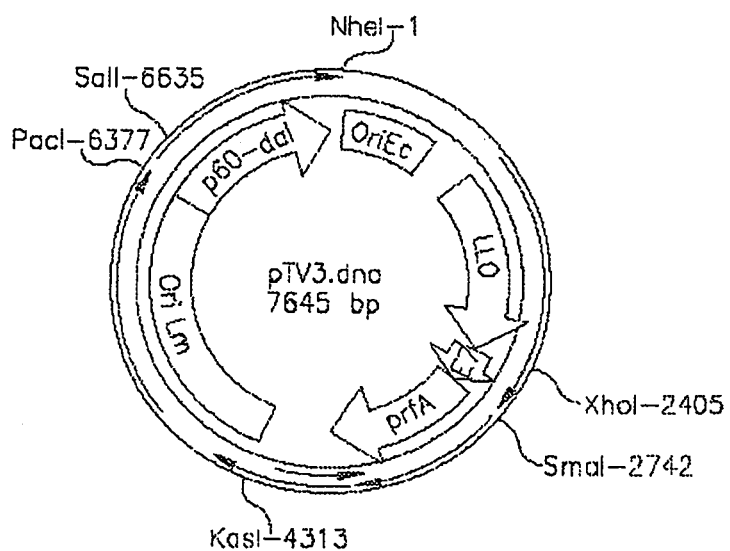

FIGS. 9A and 9B. FIG. 9A shows a schematic map of *E. coli-Listeria* shuttle plasmids pGG55 and FIG. 9B shows a schematic map of pTV3. CAT(–): *E. coli* chloramphenicol transferase; CAT(+): *Listeria* chloramphenicol transferase; Ori Lm: replication origin for *Listeria*; Ori Ec: p15 origin of replication for *E. coli*; prfA: *Listeria* pathogenicity regulating factor A; LLO: C-terminally truncated listeriolysin O, including its promoter; E7: HPV E7; p60-dal; expression cassette of p60 promoter and *Listeria* dal gene. Selected restriction sites are also depicted.

FIG. 10 shows the DNA sequence (SEQ ID NO: 81) present upstream and downstream of the inlC region on the genome of *Listeria* strain EGD. DNA-up (red), inlC gene (blue) and DNA-down (black).

FIG. 11 shows the sequence of DNA (SEQ ID NO: 82) that is cloned in the temperature sensitive plasmid, pKSV7 to create inl C deletion mutant. The restriction enzyme sites used for cloning of these regions are indicated in caps and underlined. GAATTC-EcoRI, GGATCC-BamHI and CTGCAg-PstI. The EcoRI-PstI insert is cloned in the vector, pKSV7.

Figure 12:
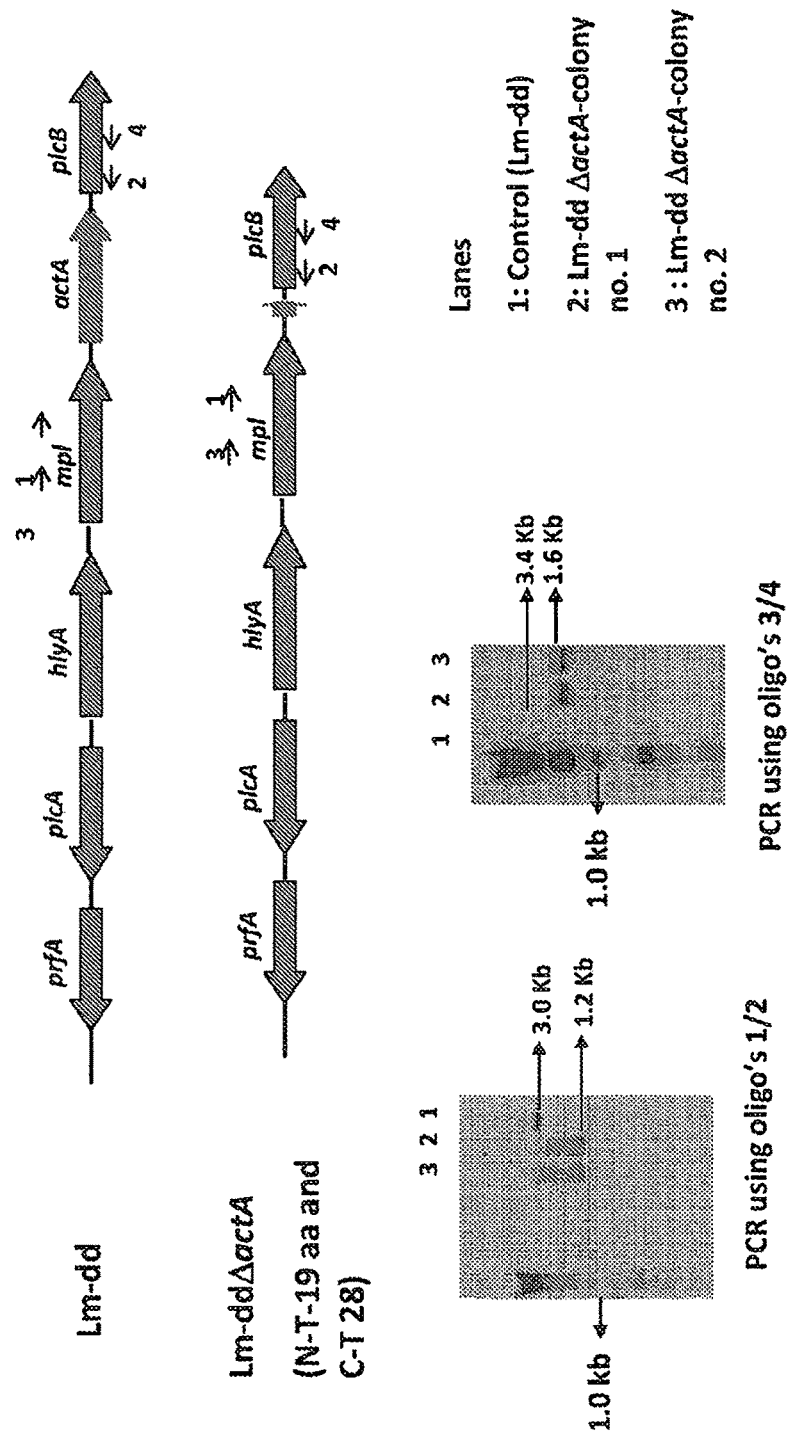

FIG. 12 shows a Schematic representation of the Lm-dd and Lm-ddD actA strains. The gel showing the size of PCR products using oligo's 1/2 and oligo's 3/4 obtained using e chromosomal DNA of the strains, Lm-dd and Lm-ddΔactA as template.

FIG. 13 shows the DNA sequence (SEQ ID NO: 83) present upstream and downstream of the actA gene in the *Listeria* chromosome. The region in italics contains the residual actA sequence element that is present in the LmddΔactA strain. The underlined sequence gtcgac represent the restriction site of XhoI, which is the junction between the N-T and C-T region of actA.

Figure 14:
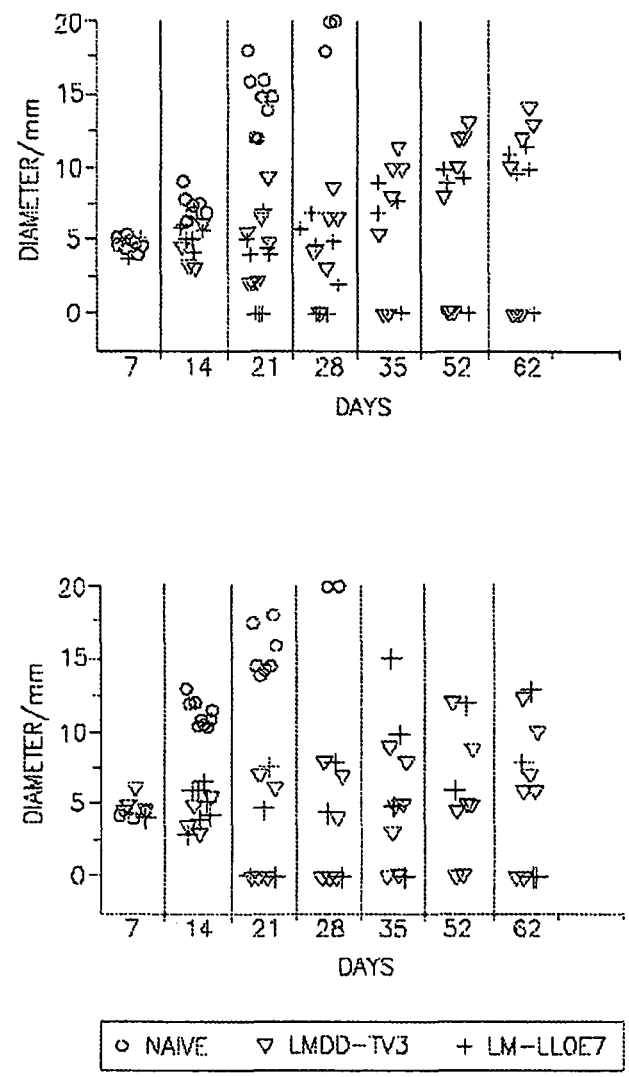

FIG. 14 depicts tumor regression in response to administration of LM vaccine strains (A). Circles represent naive mice, inverted triangles represent mice administered Lmdd-TV3, and crosses represent mice administered Lm-LLOE7.

Figure 15A:
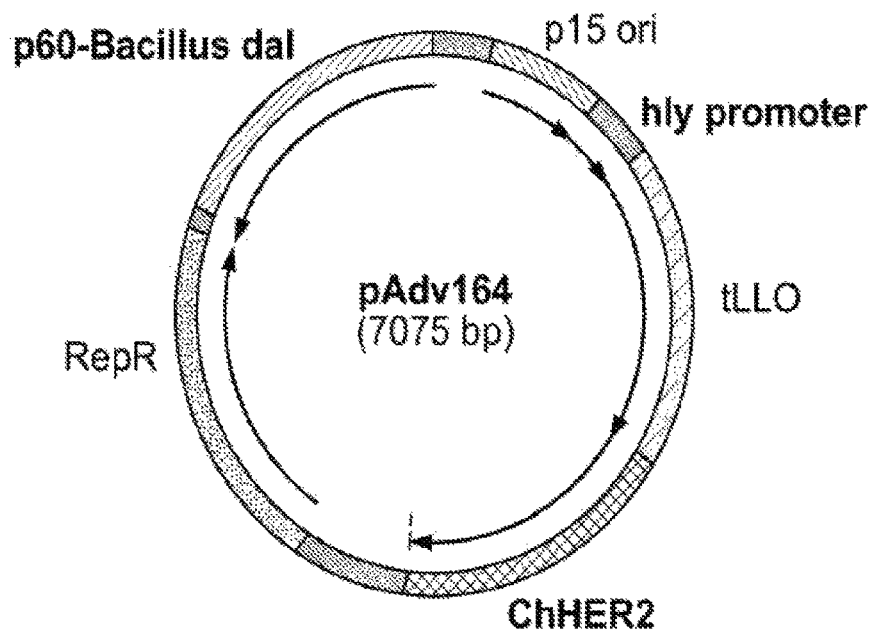
Figure 15B:
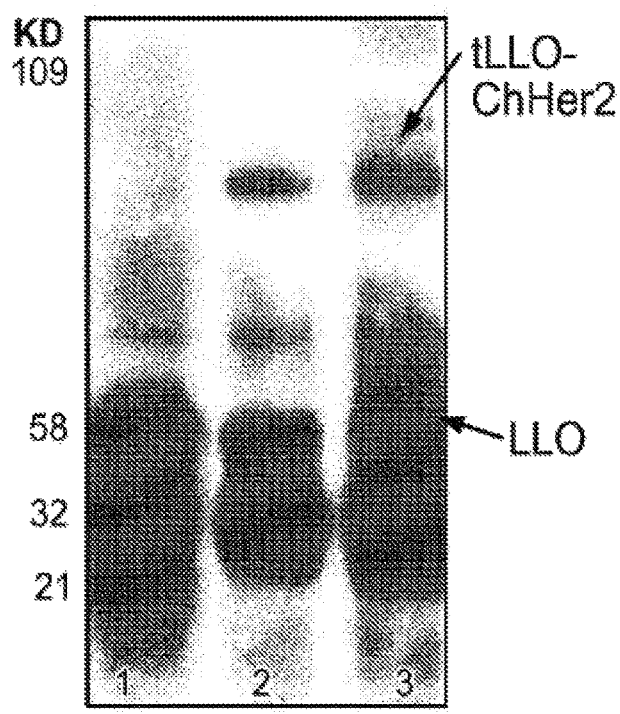

FIGS. 15A and 15B. FIG. 15A shows Plasmid map of pAdv164, which harbors *bacillus subtilis* dal gene under the control of constitutive *Listeria* p60 promoter for complementation of the chromosomal dal-dat deletion in LmddA strain. It also contains the fusion of truncated LLO$_{(1-441)}$ to the chimeric human Her2/neu gene, which was constructed by the direct fusion of 3 fragments the Her2/neu: EC1 (aa 40-170), EC2 (aa 359-518) and ICI (aa 679-808). FIG. 15B shows expression and secretion of tLLO-ChHer2 was detected in Lm-LLO-ChHer2 (Lm-LLO-138) and LmddA-LLO-ChHer2 (ADXS31-164) by western blot analysis of the TCA precipitated cell culture supernatants blotted with anti-LLO antibody. A differential band of ~104 KD corresponds to tLLO-ChHer2. The endogenous LLO is detected as a 58 KD band. *Listeria* control lacked ChHer2 expression.

Figures 16A, 16B, 16C:
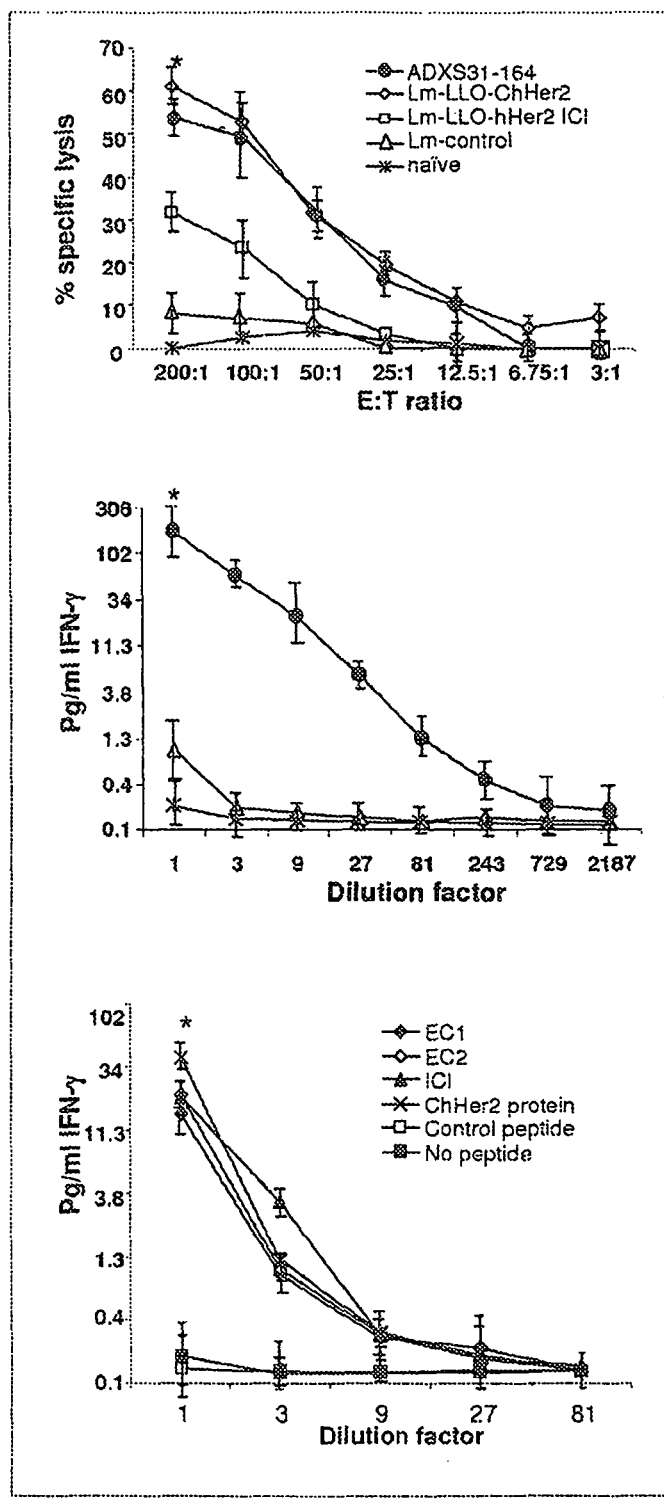

FIGS. 16A-16C. FIG. 16A cytotoxic T cell responses elicited by Her2/neu *Listeria*-based vaccines in splenocytes from immunized mice were tested using NT-2 cells as stimulators and 3T3/neu cells as targets. Lm-control was based on the LmddA background that was identical in all ways but expressed an irrelevant antigen (HPV16-E7). FIG. 16B shows IFN-γ secreted by the splenocytes from immunized FVB/N mice into the cell culture medium, measured by ELISA (enzyme linked immunosorbent assays), after 24 hours of in vitro stimulation with mitomycin C treated NT-2 cells. FIG. 16C shows IFN-γ secretion by splenocytes from HLA-A2 transgenic mice immunized with the chimeric vaccine, in response to in vitro incubation with peptides from different regions of the protein. A recombinant ChHer2 protein was used as positive control and an irrelevant peptide or no peptide groups constituted the negative controls as listed in the figure legend. IFN-γ secretion was detected by an ELISA assay using cell culture supernatants harvested after 72 hours of co-incubation. Each data point was an average of triplicate data+/−standard error. * P value<0.001.

Figure 17:
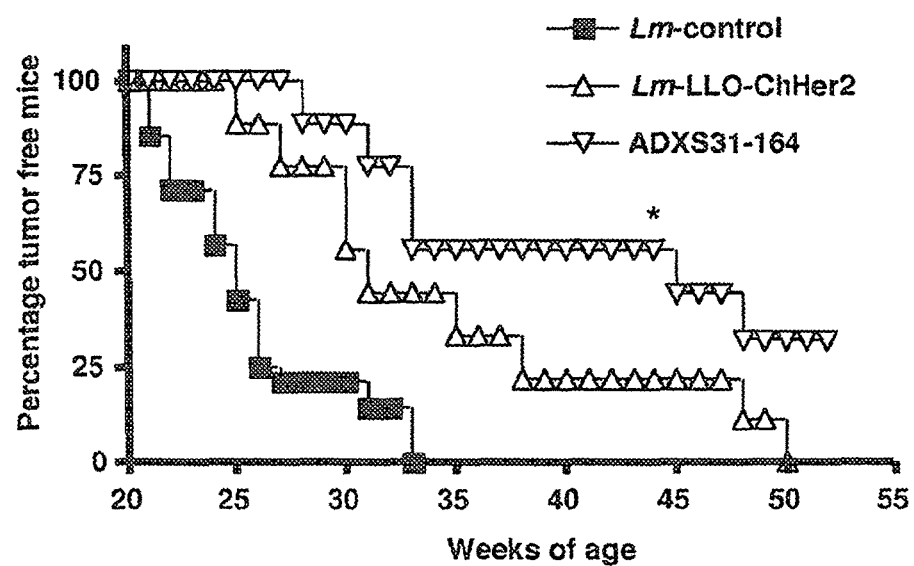

FIG. 17 represents results from Her2/neu transgenic mice that were injected six times with each recombinant *Listeria*-ChHer2 or a control *Listeria* vaccine. Immunizations started at 6 weeks of age and continued every three weeks until week 21. Appearance of tumors was monitored on a weekly basis and expressed as percentage of tumor free mice. *p<0.05, N=9 per group.

FIG. 18 shows FVB/N mice were inoculated s.c. with $1\times10^6$ NT-2 cells and immunized three times with each vaccine at one week intervals. Spleens were harvested 7 days after the second immunization. After isolation of the immune cells, they were stained for detection of Tregs by anti CD3, CD4, CD25 and FoxP3 antibodies. dot-plots of the Tregs from a representative experiment showing the frequency of $CD25^+/FoxP3^+$ T cells, expressed as percentages of the total $CD3^+$ or $CD3^+CD4^+$ T cells across the different treatment groups.

Figure 19A:
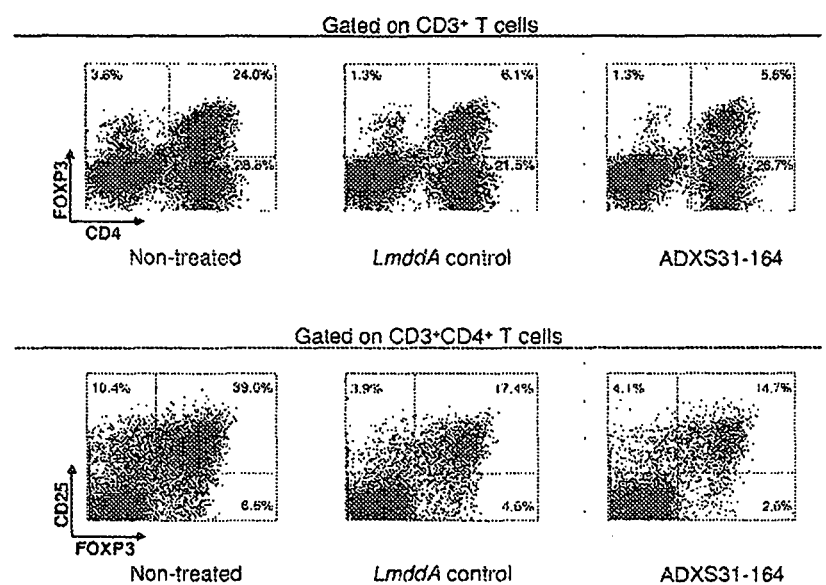
Figure 19B:
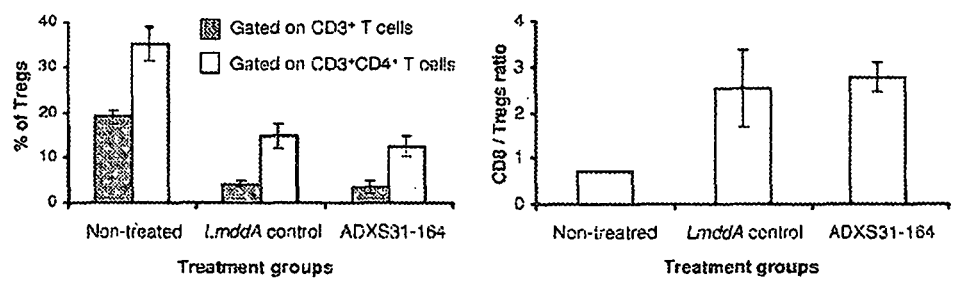

FIGS. 19A and 19B show FVB/N mice were inoculated s.c. with $1\times10^6$ NT-2 cells and immunized three times with each vaccine at one week intervals. Tumors were harvested 7 days after the second immunization. After isolation of the immune cells, they were stained for detection of Tregs by anti CD3, CD4, CD25 and FoxP3 antibodies. FIG. 19A shows dot-plots of the Tregs from a representative experiment. FIG. 19B shows frequency of $CD25^+/FoxP3^+$ T cells, expressed as percentages of the total $CD3^+$ or $CD3^+CD4^+$ T cells (left panel) and intratumoral CD8/Tregs ratio (right panel) across the different treatment groups. Data is shown as mean±SEM obtained from 2 independent experiments.

FIG. 20 shows a schematic representation of pAdv134 plasmid and dual plasmid. The restriction sites that will be used for cloning of antigen 1 (Xho I and SpeI) and antigen 2 (XbaI and SacI or BglII) genes are indicated. The black arrow represents the direction of transcription. p15 on and RepR refer to *Listeria* and *E. coli* origin of replication. tLLO is truncated Listeriolysin 0 protein (1-441 aa) and tActA is truncated ActA (1-233 aa) protein. *Bacillus*-dal gene codes for D-alanine racemase which complements for the synthesis of D-alanine in LmΔdal dat strain.

FIG. 21 shows a decrease in MDSCs and Tregs in tumors. The number of MDSCs (right-hand panel) and Tregs (left-hand panel) following Lm vaccination (LmddAPSA and LmddAE7).

Figure 22:
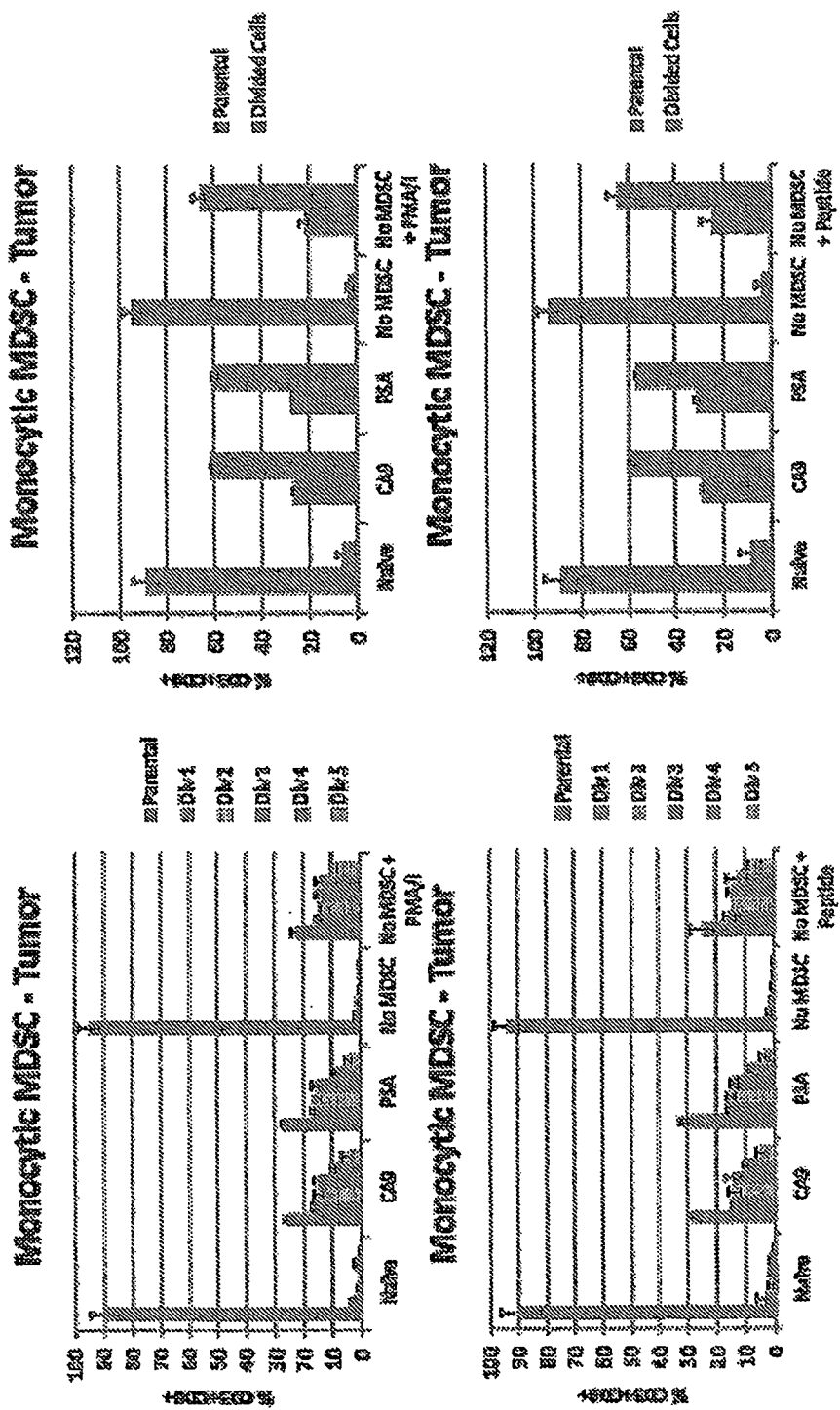

FIG. 22 shows suppressor assay data demonstrating that monocytic MDSCs from TPSA23 tumors are less suppressive after *Listeria* vaccination. This change in the suppressive ability of the MDSCs is not antigen specific as the same decrease in suppression is seen with PSA-antigen specific T cells and also with non-specifically stimulated T cells. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

Figure 23:
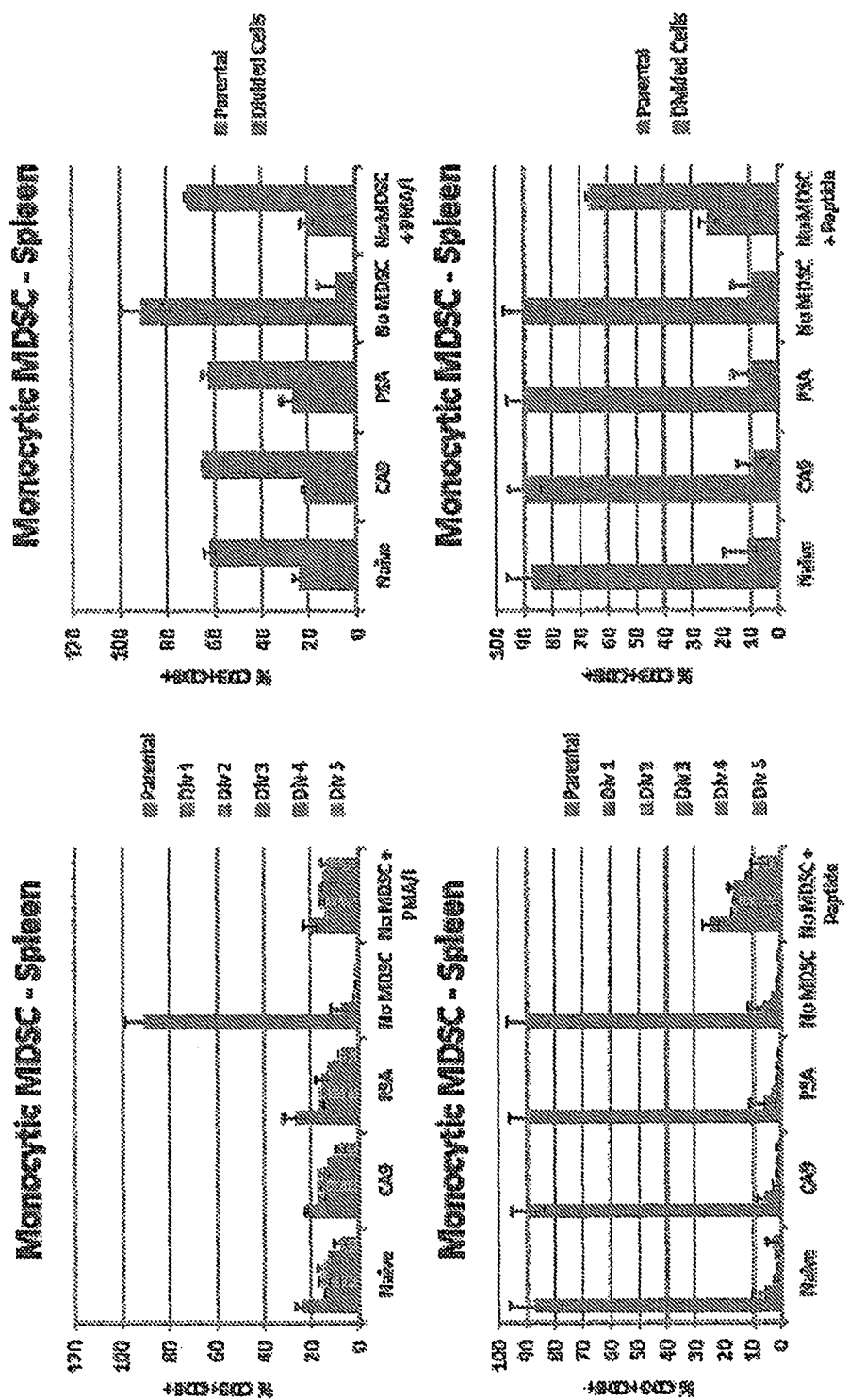

FIG. 23 shows suppressor assay data demonstrating that *Listeria* has no effect on splenic monocytic MDSCs and they are only suppressive in an antigen-specific manner. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

Figure 24:
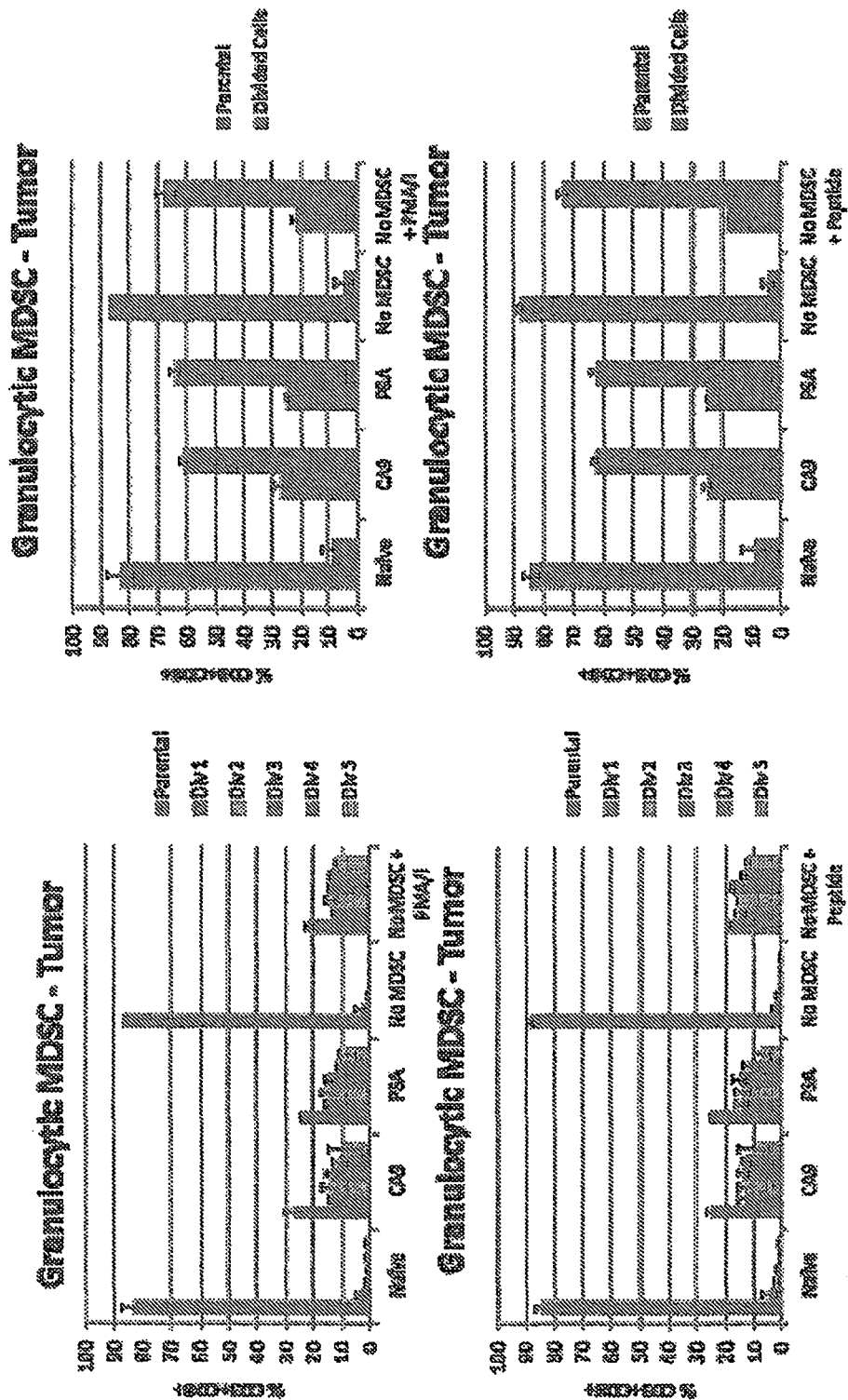

FIG. 24 shows suppressor assay data demonstrating that granulocytic MDSCs from tumors have a reduced ability to suppress T cells after *Listeria* vaccination. This change in the suppressive ability of the MDSCs is not antigen specific as the same decrease in suppression is seen with PSA-antigen specific T cells and also with non-specifically stimulated T cells. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

Figure 25:
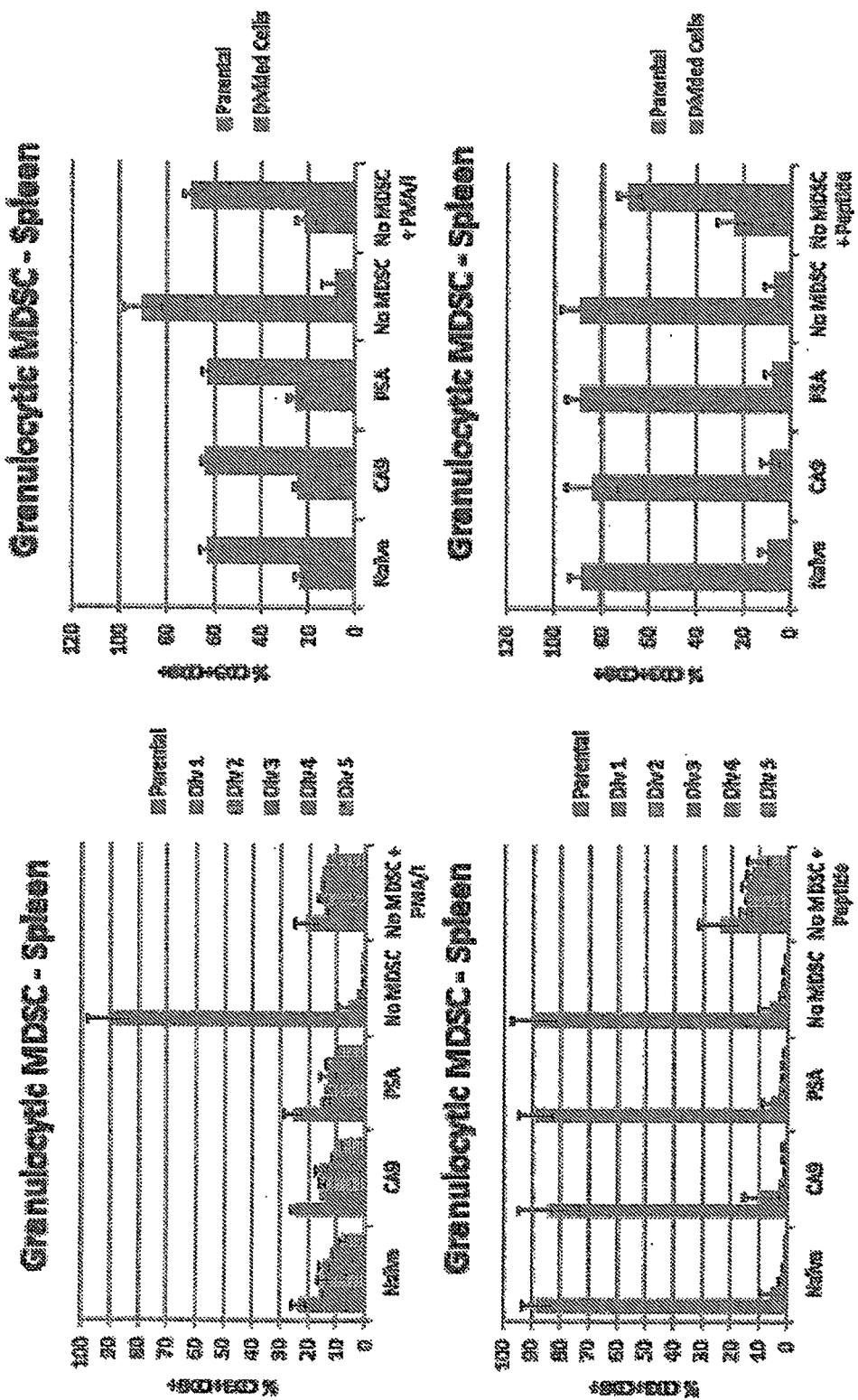

FIG. 25 shows suppressor assay data demonstrating that *Listeria* has no effect on splenic granulocytic MDSCs and they are only suppressive in an antigen-specific manner. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

Figure 26:
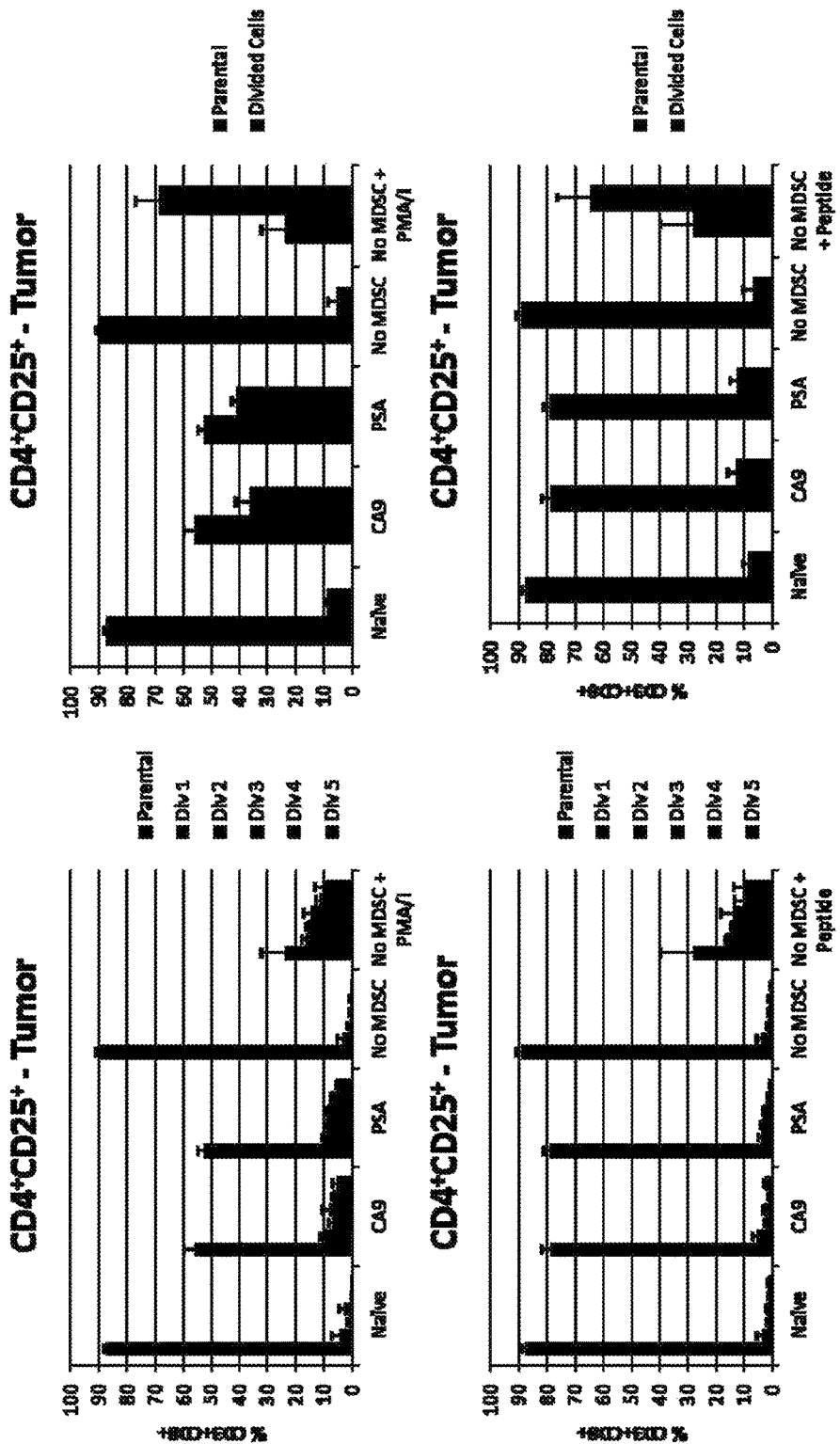

FIG. 26 shows suppressor assay data demonstrating that Tregs from tumors are still suppressive. There is a slight decrease in the suppressive ability of Tregs in a non-antigen specific manner, in this tumor model. The No Treg group shows the lack of division of the responder T cells when they are left unstimulated and the last group shows the division of stimulated cells with no Tregs added to suppress division. Left-hand panels show individual cell division cycles for each group. Right-hand panels show pooled division cycles.

Figure 27:
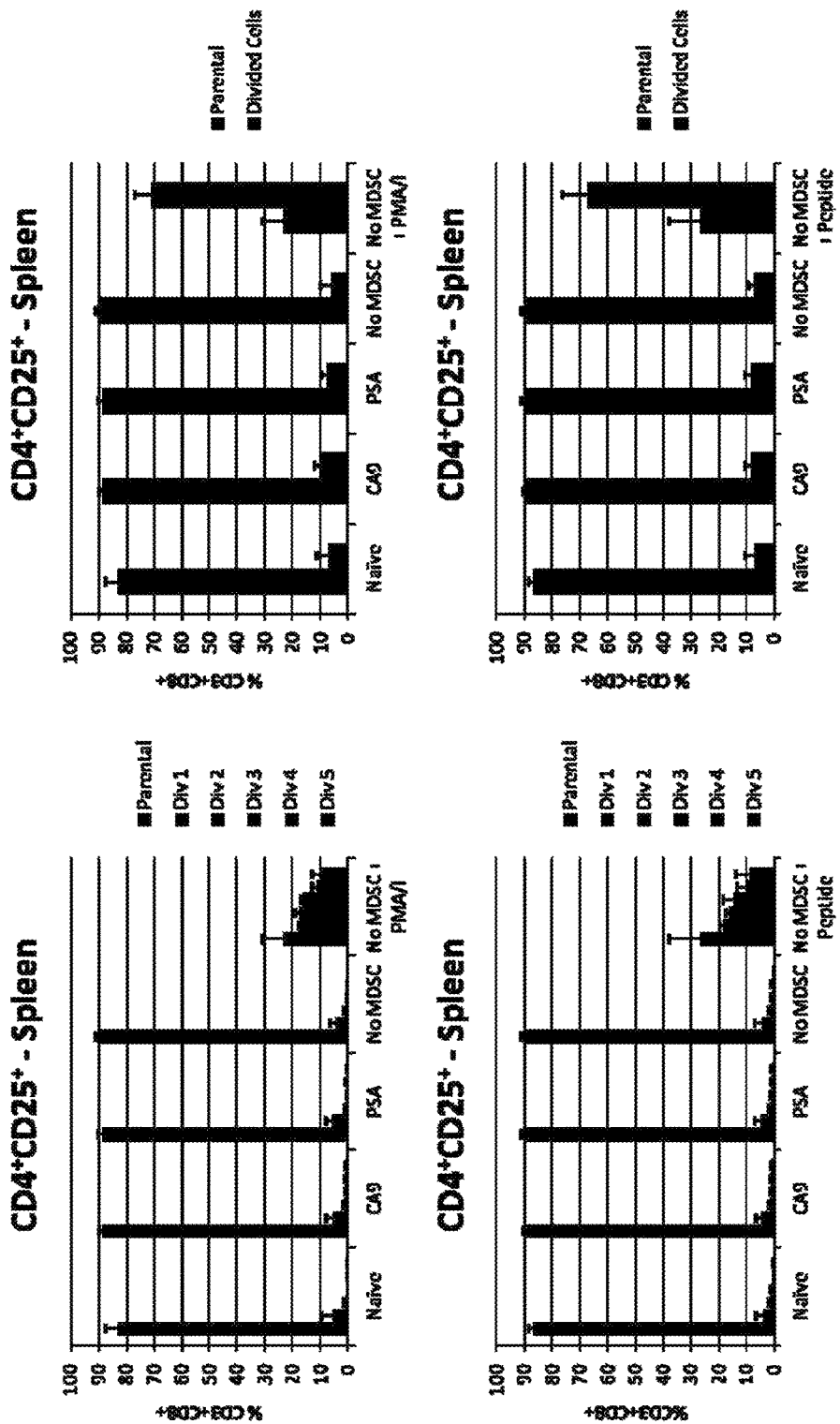

FIG. 27 shows suppressor assay data demonstrating that splenic Tregs are still suppressive. The No Treg group shows the lack of division of the responder T cells when they are left unstimulated and the last group shows the division of stimulated cells with no Tregs added to suppress division. Left-hand panels show individual cell division cycles for each group. Right-hand panels show pooled division cycles.

Figure 28:
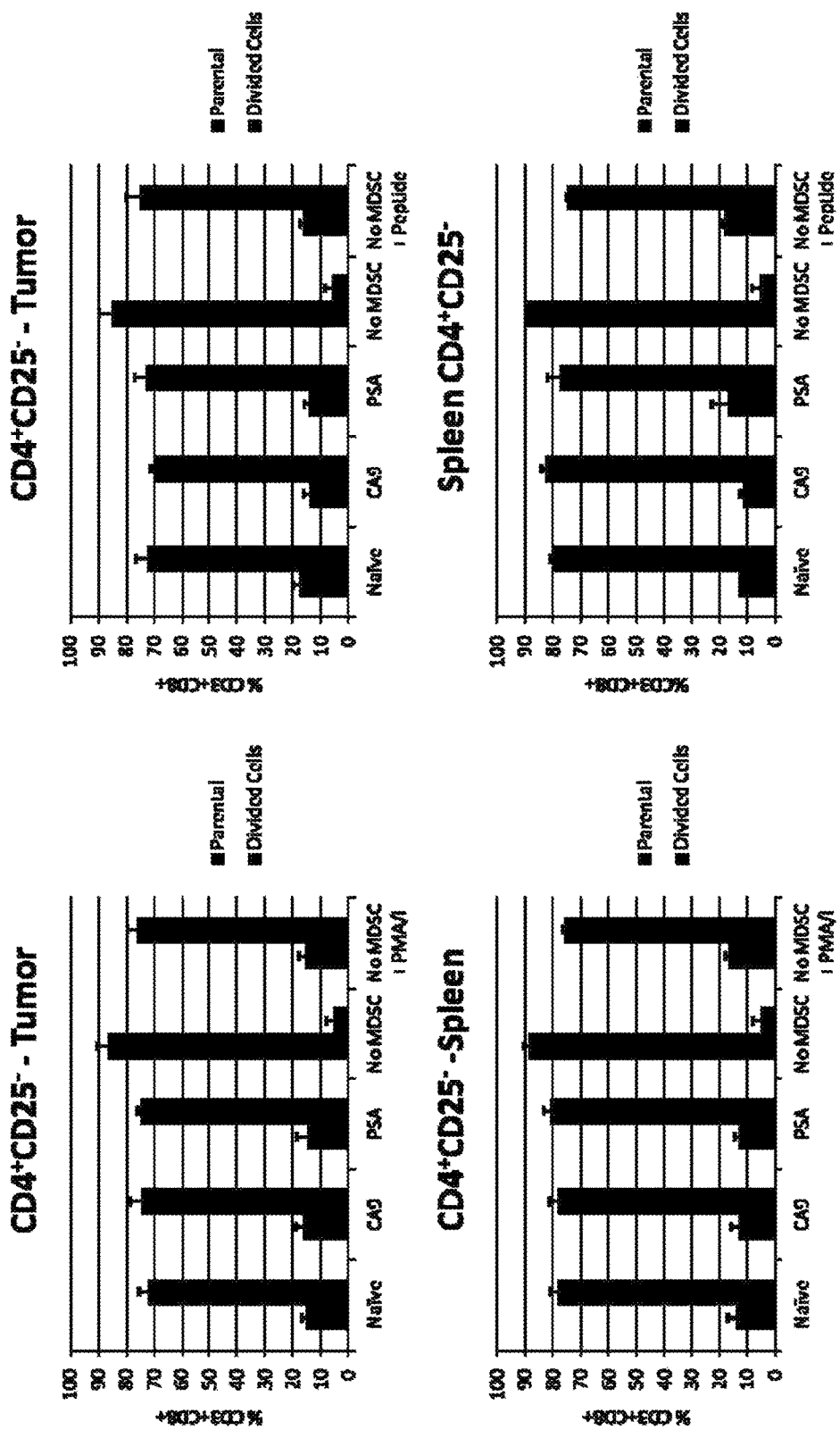

FIG. 28 shows suppressor assay data demonstrating that conventional CD4+ T cells have no effect on cell division regardless of whether they are found in the tumors or spleens of mice. Left-hand and Right-hand panels show pooled division cycles.

Figure 29:
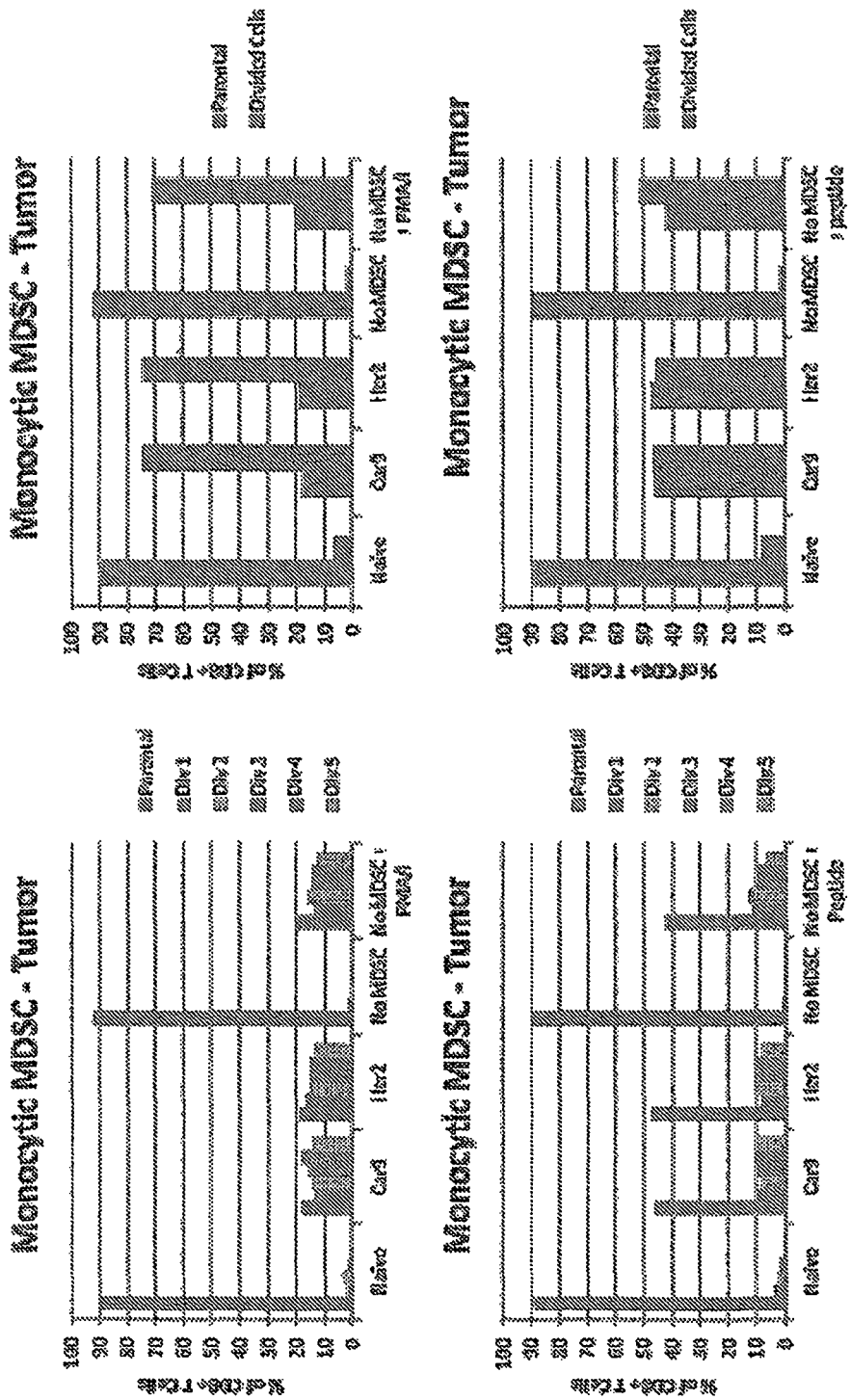

FIG. 29 shows suppressor assay data demonstrating that monocytic MDSCs from 4T1 tumors have decreased suppressive ability after *Listeria* vaccination. This change in the suppressive ability of the MDSCs is not antigen specific as the same decrease in suppression is seen with Her2/neu-antigen specific T cells and also with non-specifically stimulated T cells. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

Figure 30:
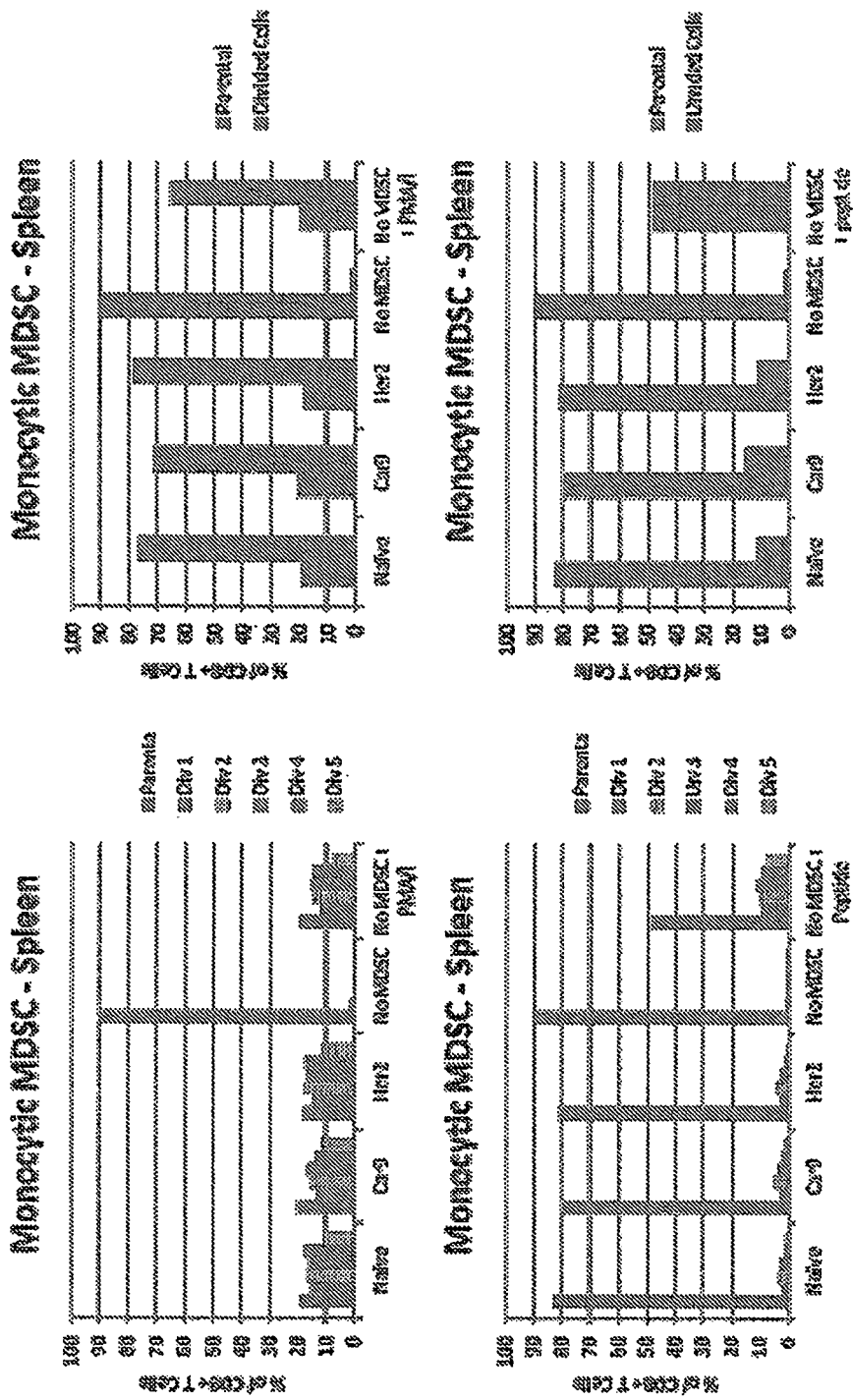

FIG. 30 shows suppressor assay data demonstrating that there is no *Listeria*-specific effect on splenic monocytic MDSCs. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

Figure 31:
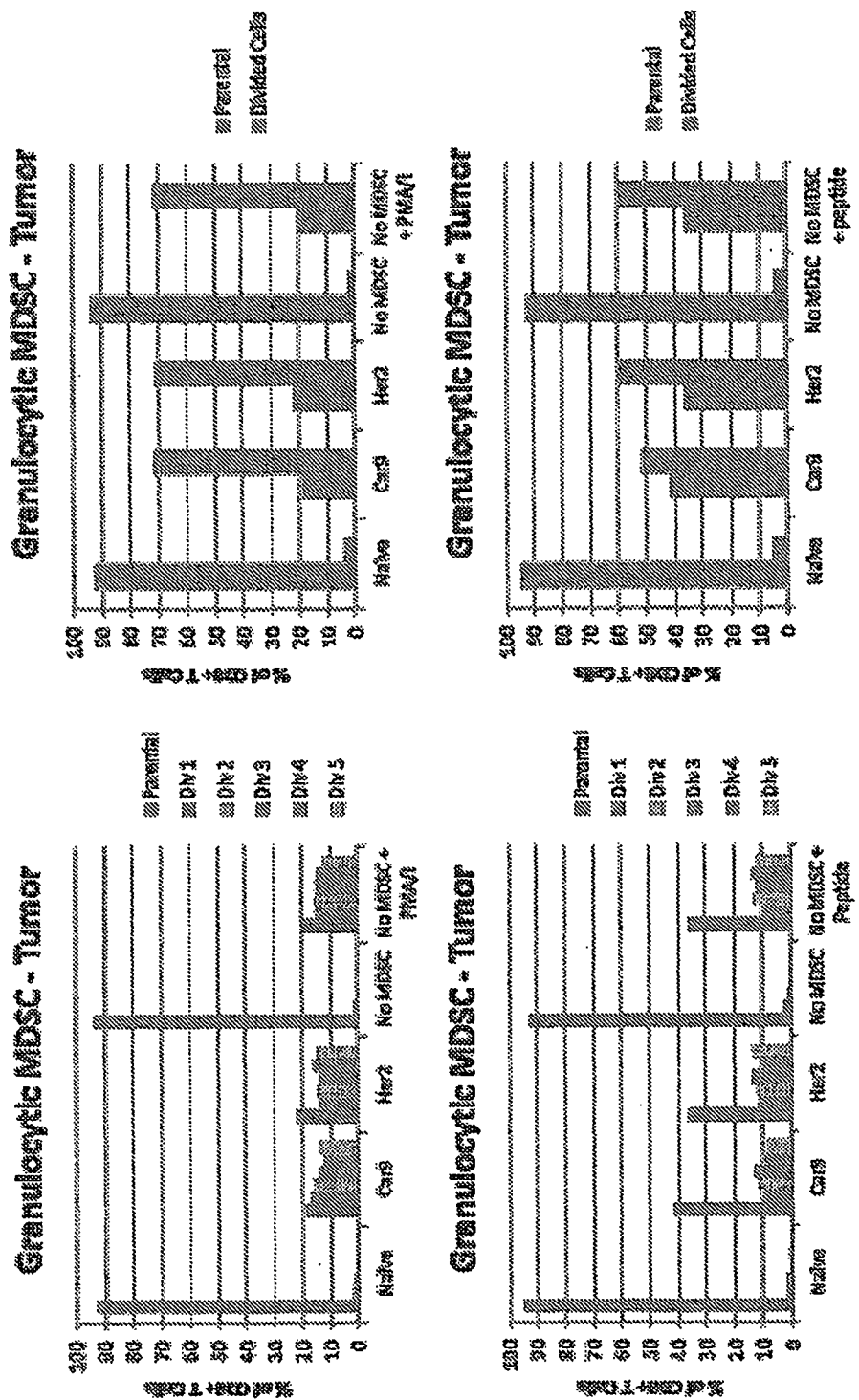

FIG. 31 shows suppressor assay data demonstrating that granulocytic MDSCs from 4T1 tumors have decreased suppressive ability after *Listeria* vaccination. This change in the suppressive ability of the MDSCs is not antigen specific as the same decrease in suppression is seen with Her2/neu-antigen specific T cells and also with non-specifically stimulated T cells. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

Figure 32:
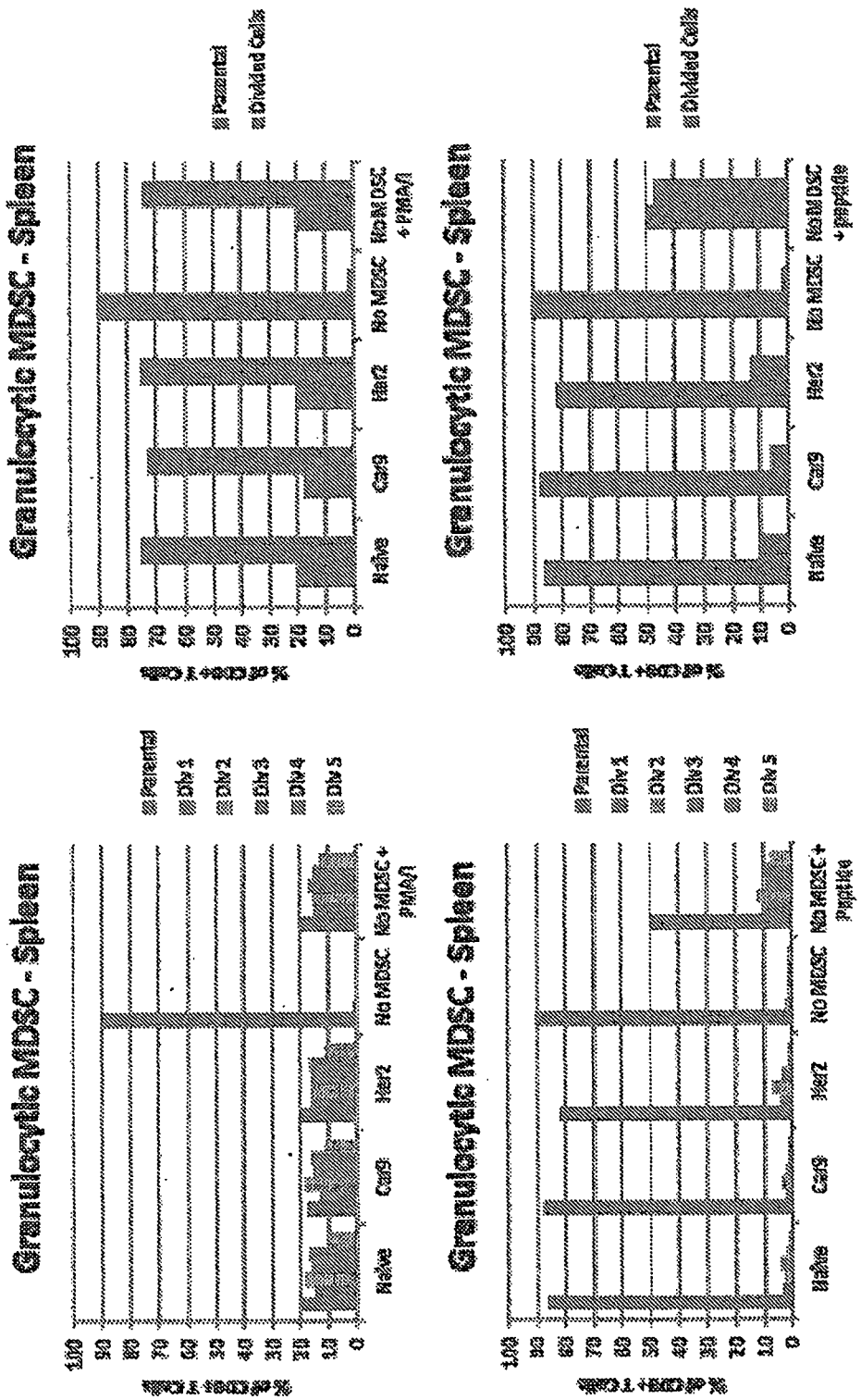

FIG. 32 shows suppressor assay data demonstrating that there is no *Listeria*-specific effect on splenic granulocytic MDSCs. The No MDSC group shows the lack of division of the responder T cells when they are left unstimulated and the last group shows the division of stimulated cells with no MDSCs added to suppress division. Left-hand panels show individual cell division cycles for each group. Right-hand panels show pooled division cycles.

Figure 33:
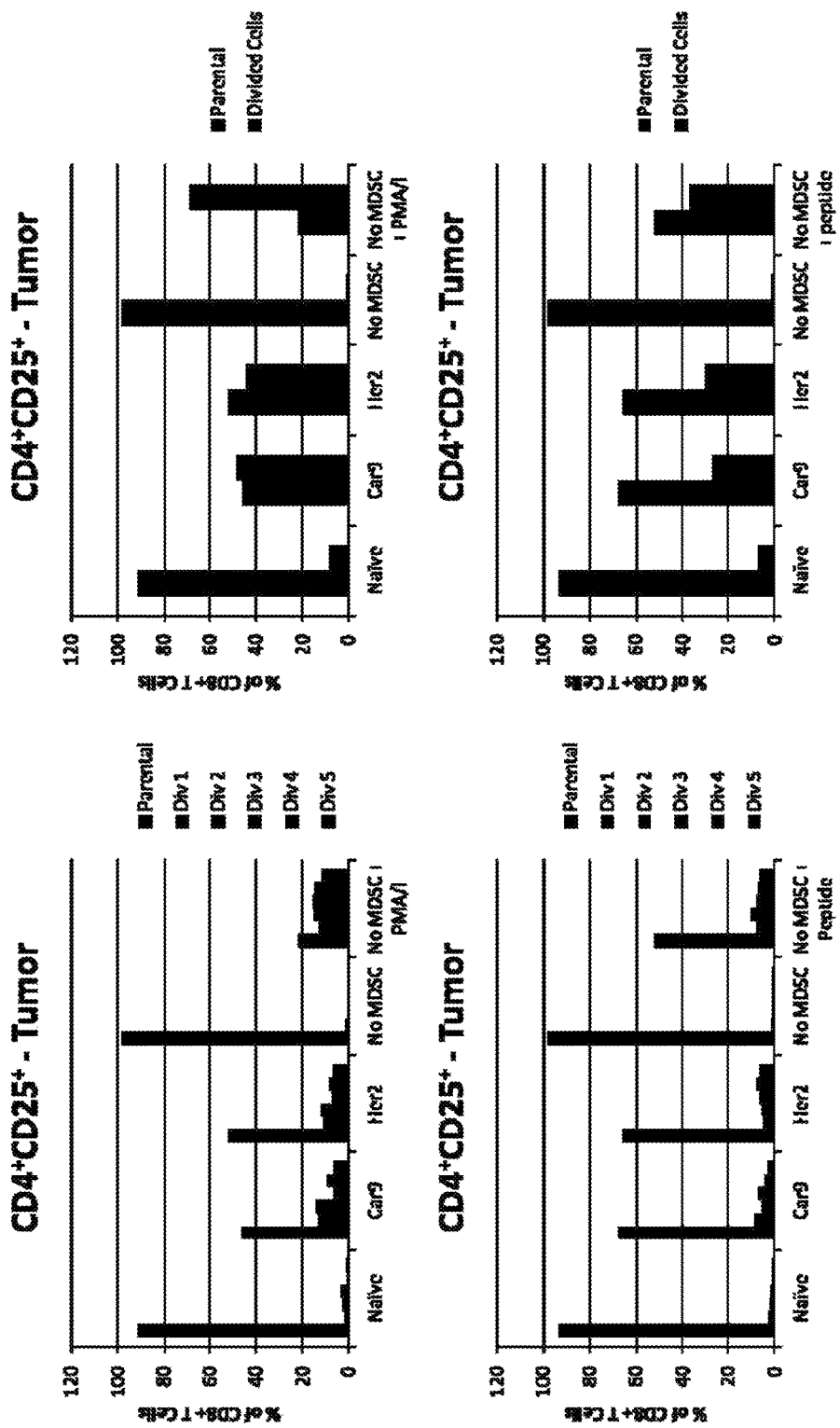

FIG. 33 shows suppressor assay data demonstrating that decrease in the suppressive ability of Tregs from 4T1 tumors after *Listeria* vaccination. This decrease is not antigen specific, as the change in Treg suppressive ability is seen with both Her2/neu-specific and non-specific responder T cells. Left-hand panels show individual cell division cycles for each group. Right-hand panels show pooled division cycles.

Figure 34:
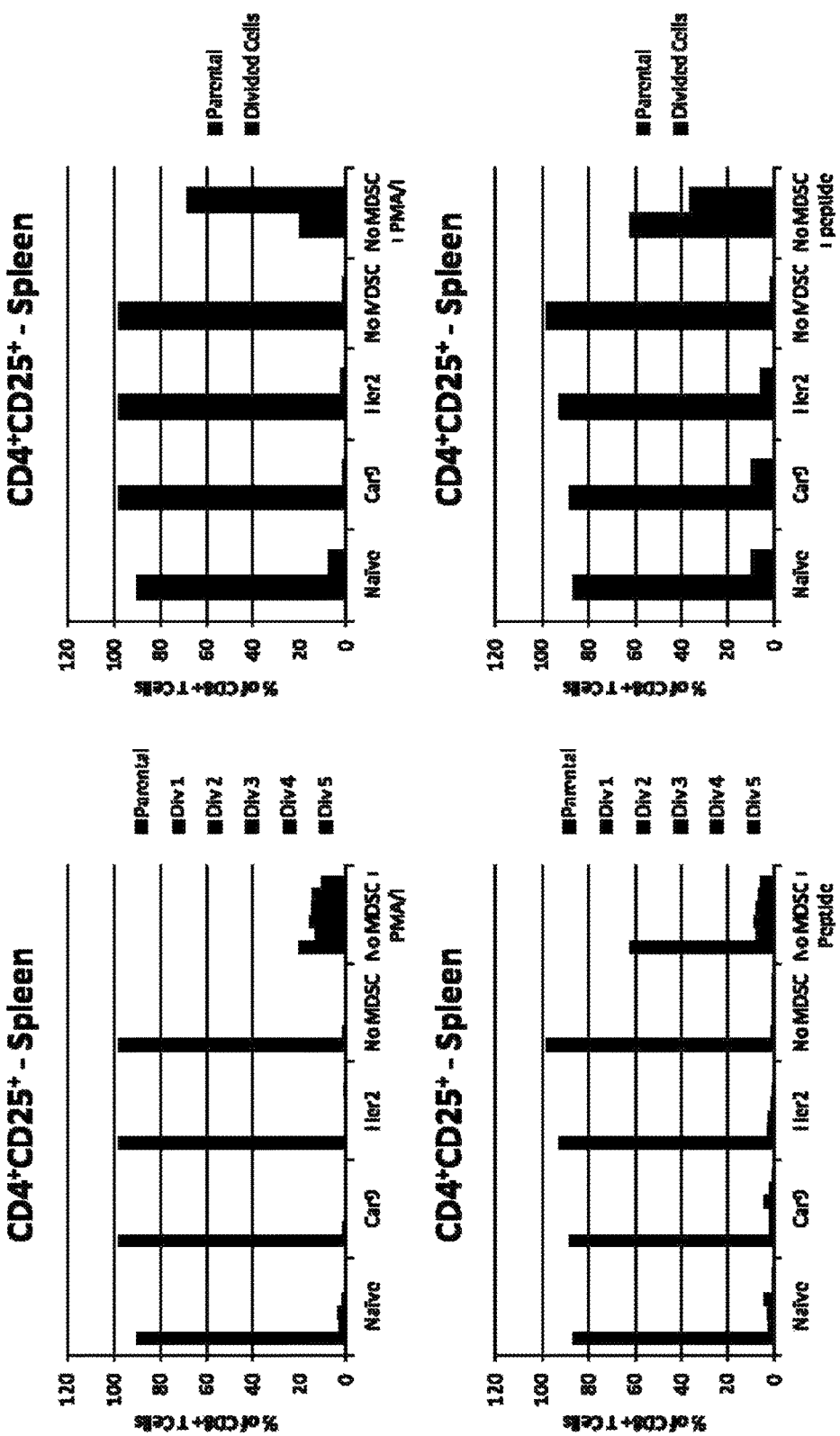
Figure 35A:
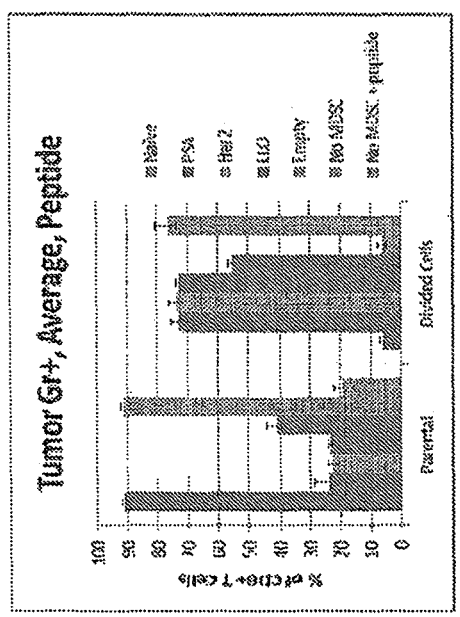
Figure 35B:
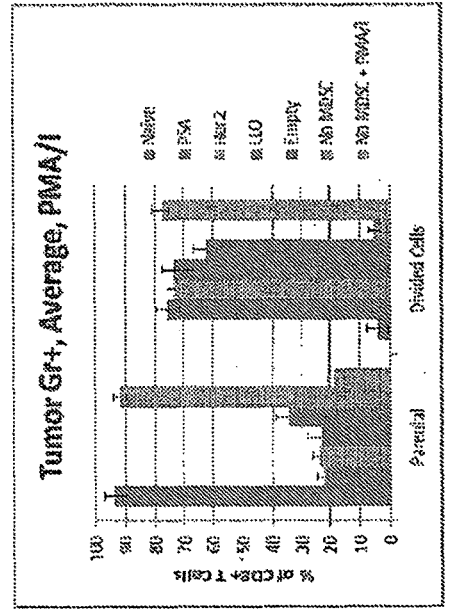
Figure 35C:
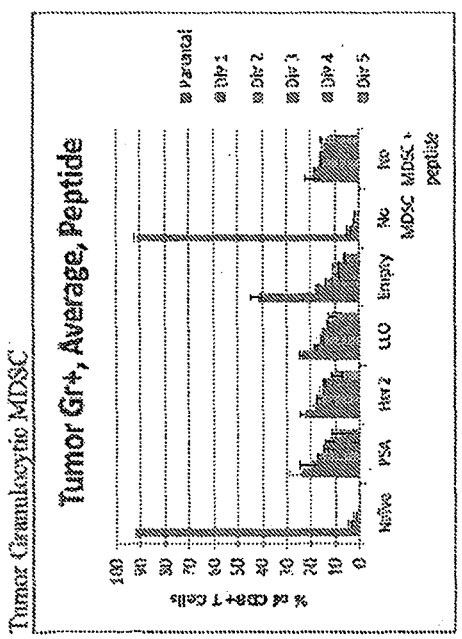
Figure 35D:
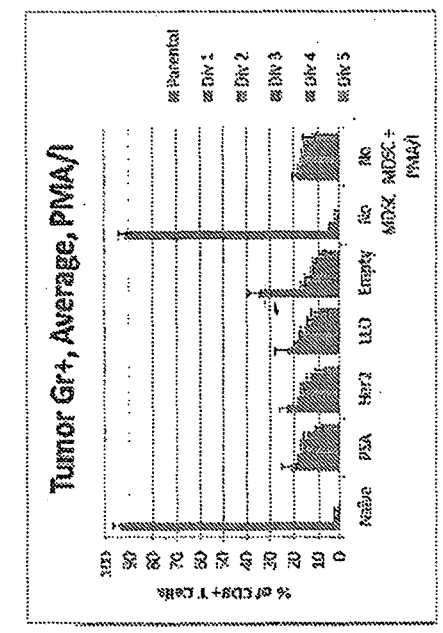
Figure 36A:
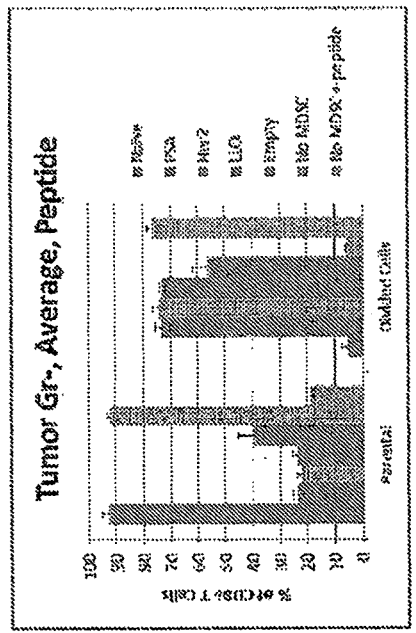
Figure 36B:
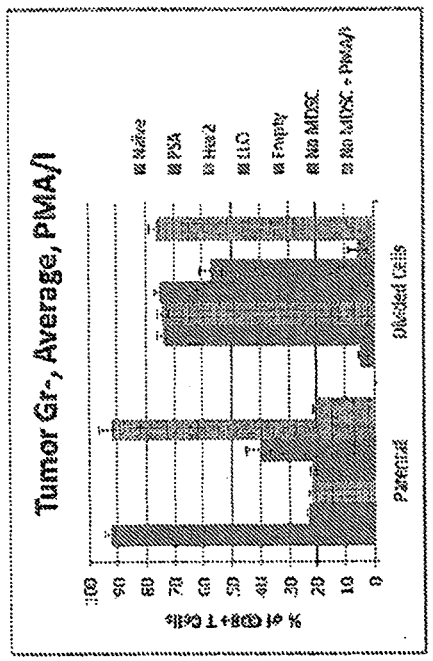
Figure 36C:
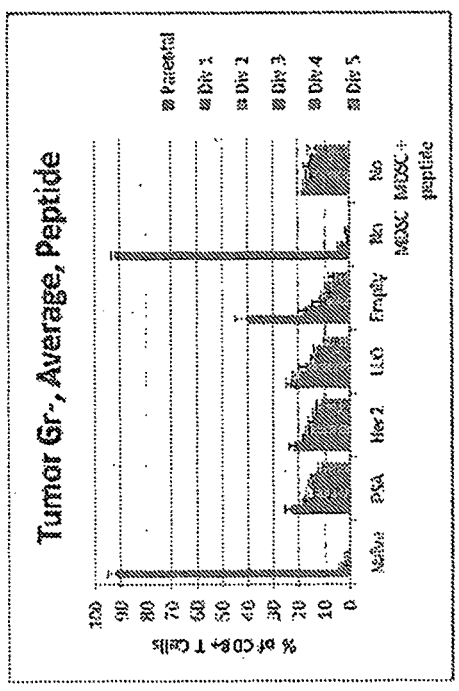
Figure 36D:
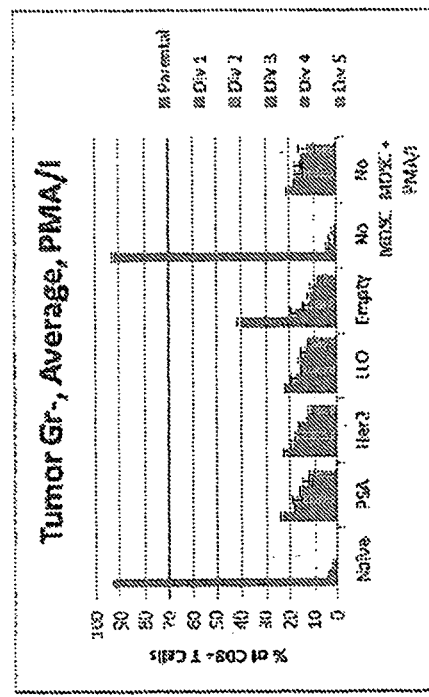

FIG. 34 shows suppressor assay data demonstrating that there is no *Listeria*-specific effect on splenic Tregs. The responder T cells are all capable of dividing, regardless of the whether or not they are antigen specific. Left-hand panels show individual cell division cycles for each group. Right-hand panels show pooled division cycles.

FIGS. 35A-35D show suppressor assay data demonstrating that suppressive ability of the granulocytic MDSC is due to the overexpression of tLLO and is independent of the partnering fusion antigen. Left-hand panels show individual cell division cycles for each group. Right-hand panels show pooled division cycles.

FIGS. 36A-36D show suppressor assay data also demonstrating that suppressive ability of the monocytic MDSC is due to the overexpression of tLLO and is independent of the partnering fusion antigen. Left-hand panels show individual cell division cycles for each group. Right-hand panels show pooled division cycles.

Figure 37A:
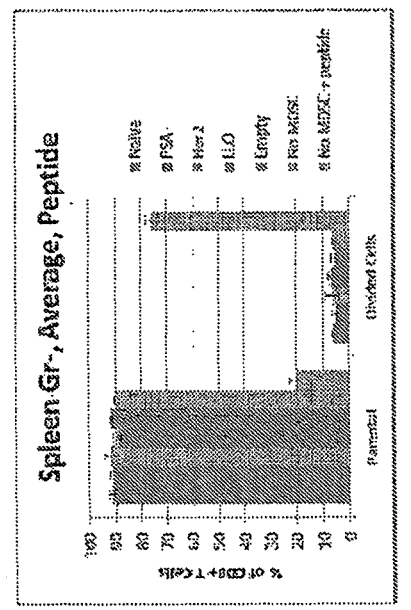
Figure 37B:
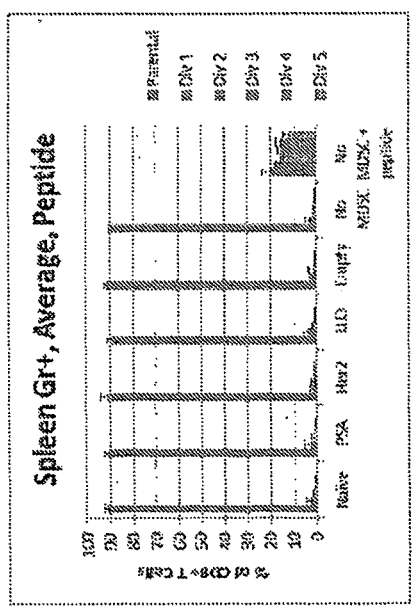
Figure 37C:
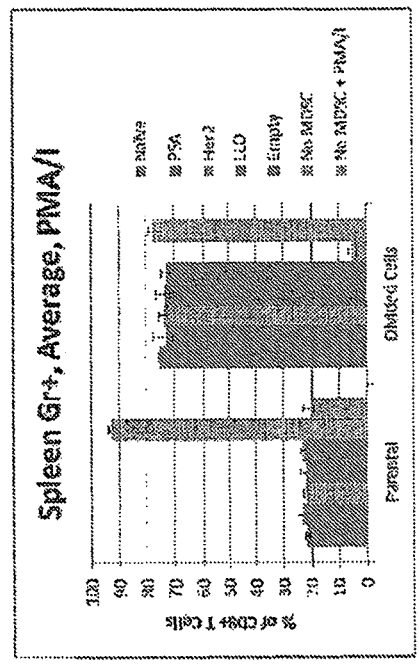
Figure 37D:
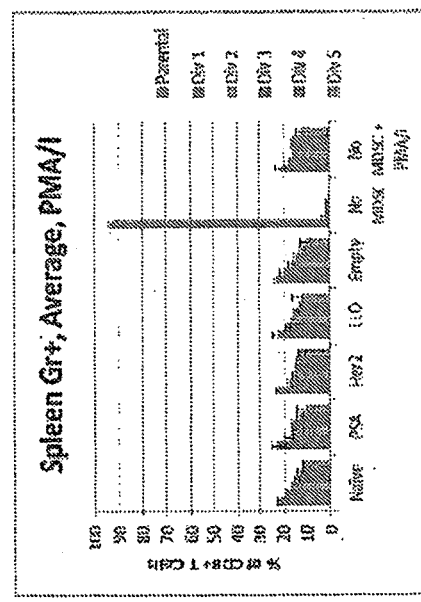

FIGS. 37A-37D show suppressor assay data demonstrating that granulocytic MDSC purified from the spleen retain their ability to suppress the division of the antigen-specific responder T cells after Lm vaccination (FIGS. 37A and 37B). However, after non-specific stimulation, activated T cells (with PMA/ionomycin) are still capable of dividing (FIGS. 37C and 37D). Left-hand panels show individual cell division cycles for each group. Right-hand panels show pooled division cycles.

Figure 38B:
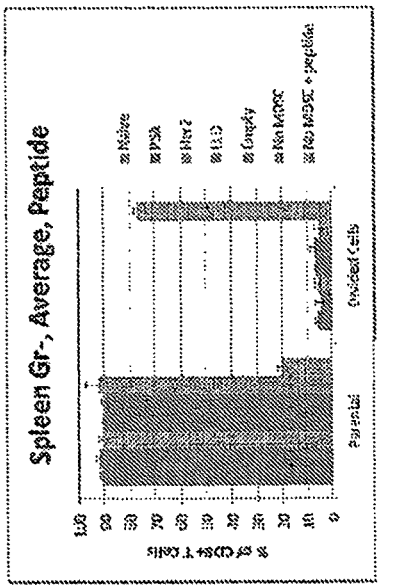
Figure 38D:
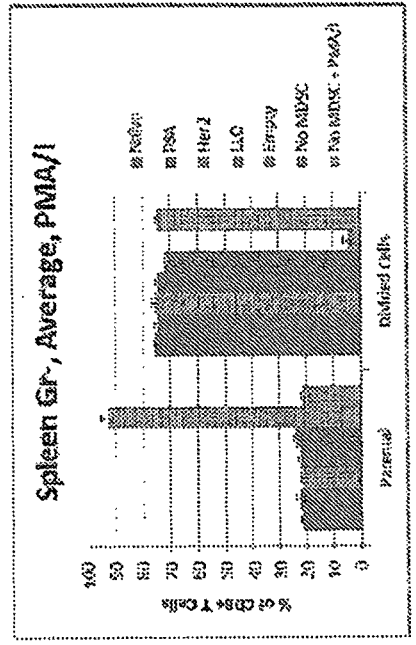
Figure 38A:
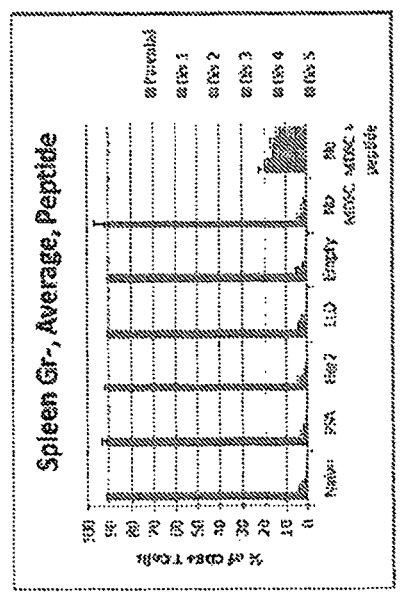
Figure 38C:
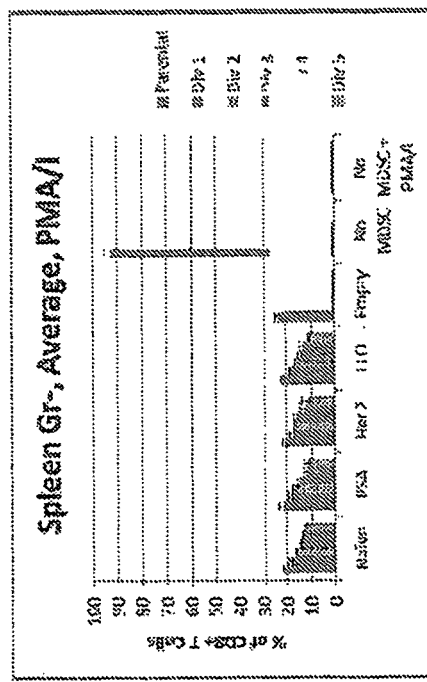
Figure 39A:
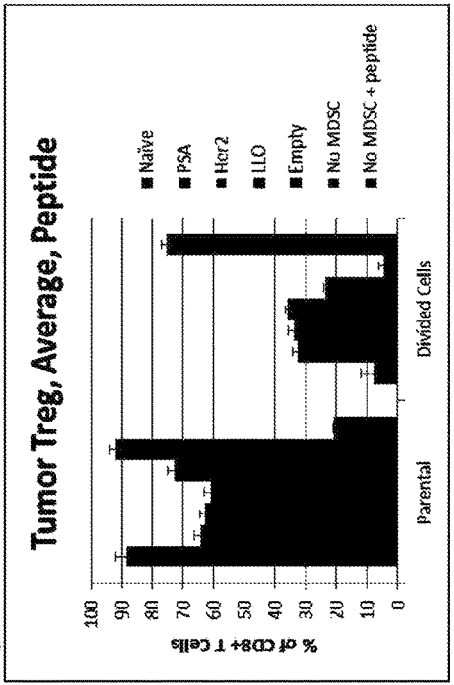
Figure 39B:
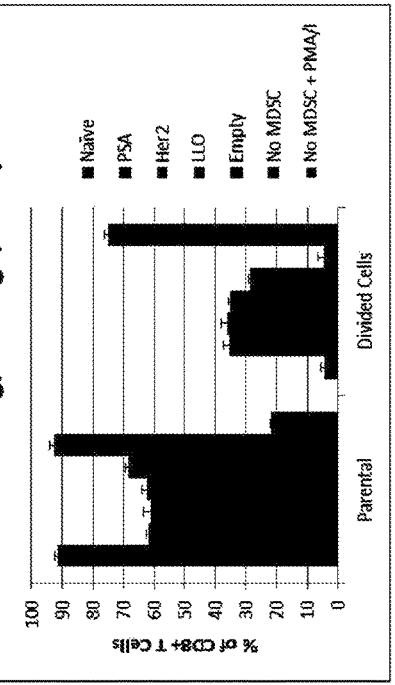
Figure 39C:
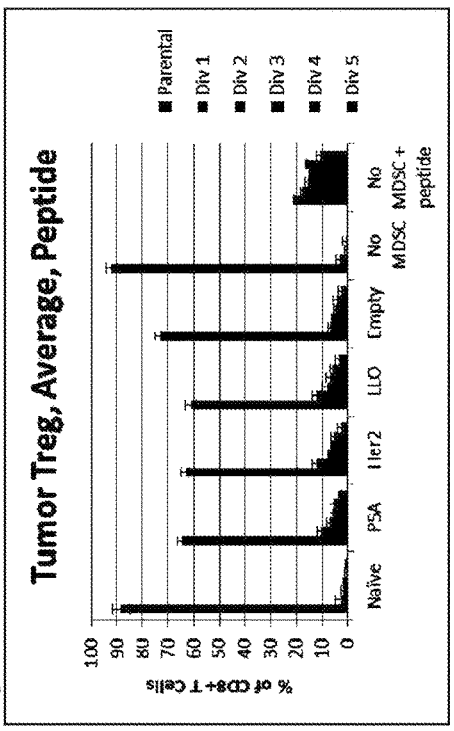
Figure 39D:
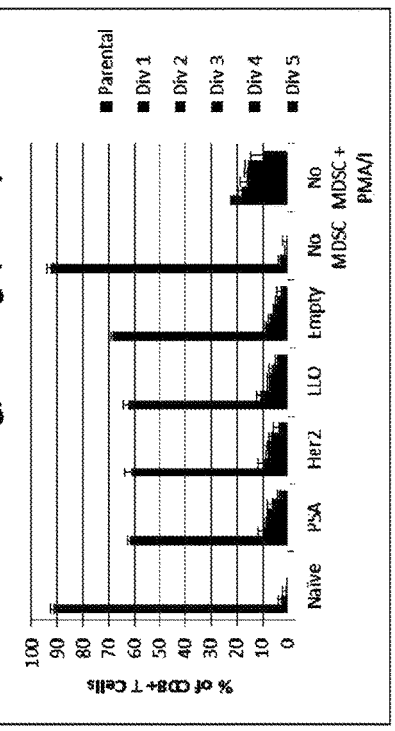
Figure 40A:
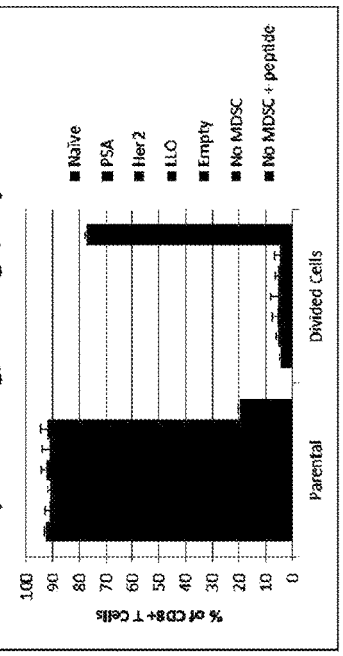
Figure 40B:
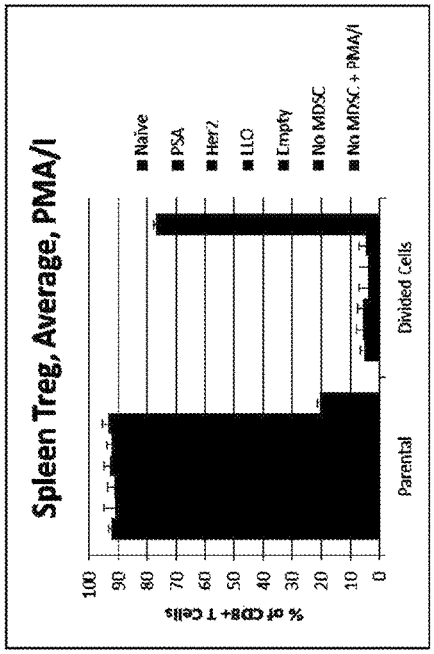
Figure 40C:
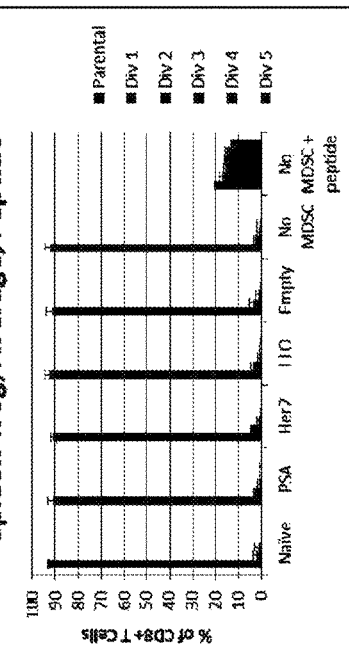
Figure 40D:
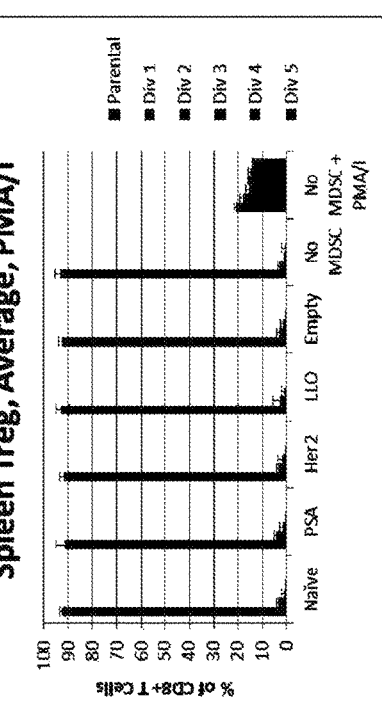
Figure 41A:
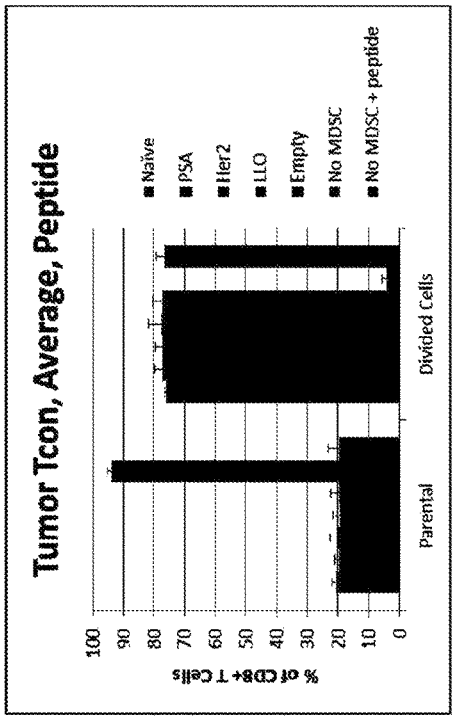
Figure 41B:
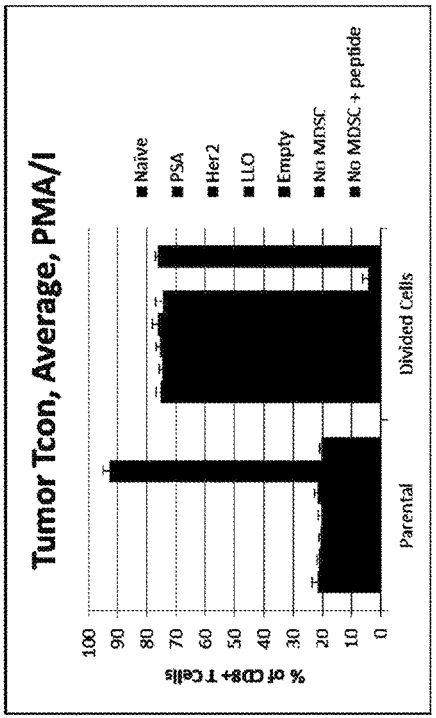
Figure 41C:
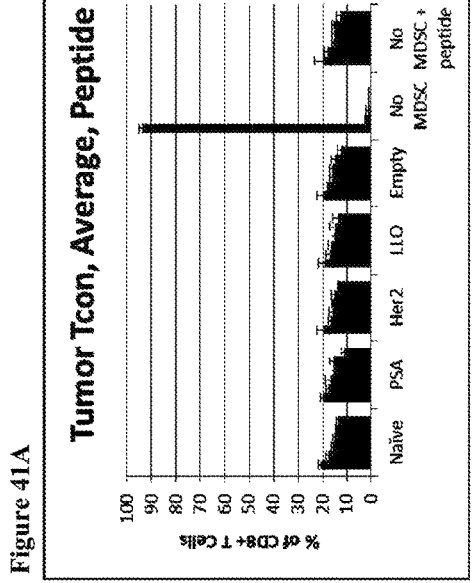
Figure 41D:
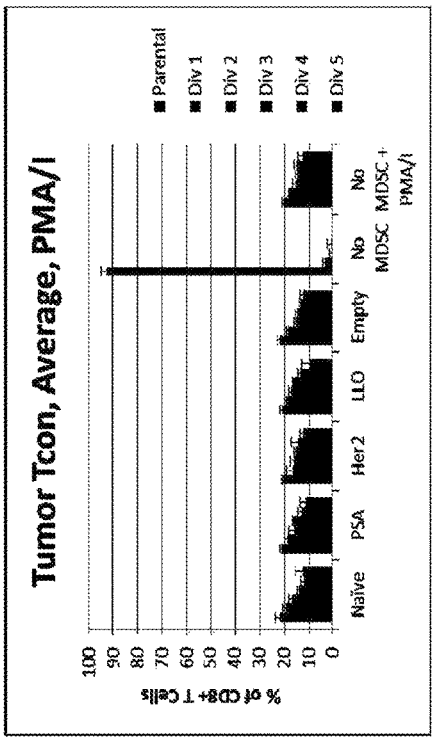
Figure 42B:
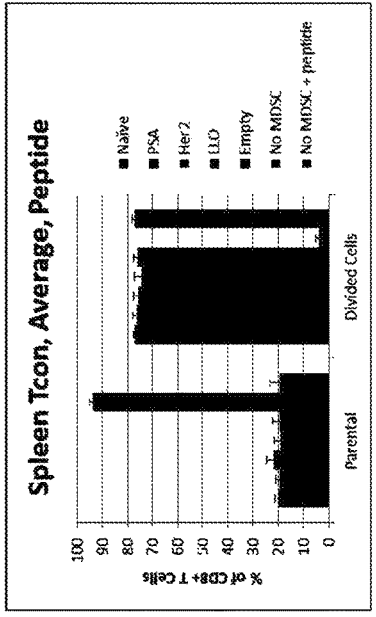
Figure 42D:
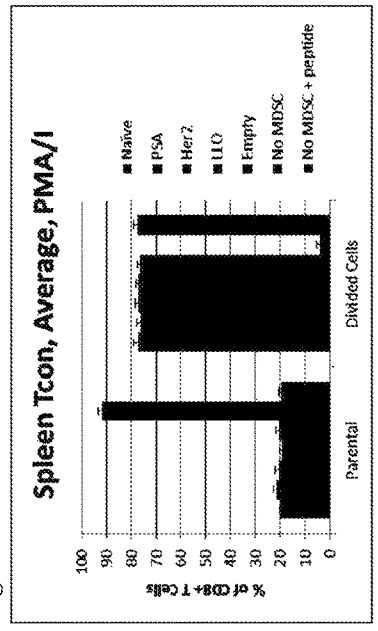
Figure 42A:
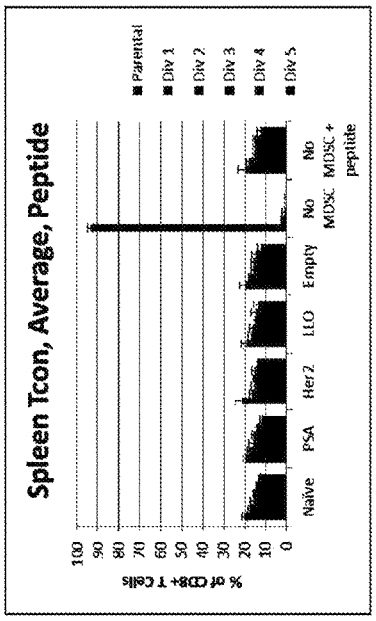
Figure 42C:
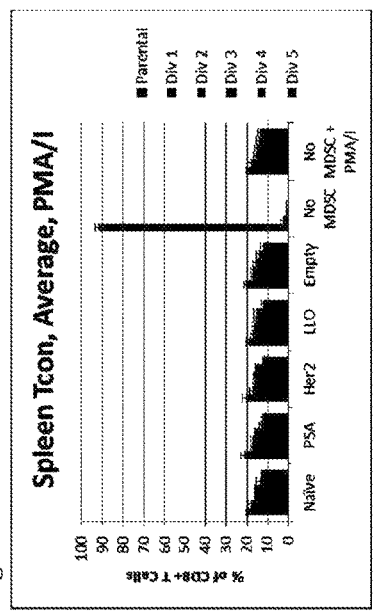

FIGS. 38A-38D show suppressor assay data demonstrating that monocytic MDSC purified from the spleen retain their ability to suppress the division of the antigen-specific responder T cells after Lm vaccination (FIGS. 38A and 38B). However, after non-specific activation (stimulated by PMA/ionomycin), T cells are still capable of dividing (FIGS. 38C and 38D). Left-hand panels show individual cell division cycles for each group. Right-hand panels show pooled division cycles.

FIG. 39 shows suppressor assay data demonstrating that Tregs purified from the tumors of any of the Lm-treated groups have a slightly diminished ability to suppress the division of the responder T cells, regardless of whether the responder cells are antigen specific (A, B) or non-specifically (C, D) activated. Left-hand panels show individual cell division cycles for each group. Right-hand panels show pooled division cycles.

FIG. 40 shows suppressor assay data demonstrating that Tregs purified from the spleen are still capable of suppressing the division of both antigen specific (A, B) and non-specifically (C, D) activated responder T cells.

FIG. 41 shows suppressor assay data demonstrating that tumor Tcon cells are not capable of suppressing the division of T cells regardless of whether the responder cells are antigens specific (A, B) or non-specifically activated (C, D).

FIG. 42 shows suppressor assay data demonstrating that spleen Tcon cells are not capable of suppressing the division of T cells regardless of whether the responder cells are antigens specific (A, B) or non-specifically activated (C, D).

DETAILED DESCRIPTION OF THE INVENTION

In one embodiment, provided herein is a method of increasing the infiltrating T lymphocytes/suppressor cells ratio in a subject having a disease or in a disease site within the subject. In another embodiment, provided herein is a method of increasing the ratio of CD8+ T cells/suppressor cells in a subject having a disease or in a disease site within the subject. In another embodiment, the method of increasing the infiltrating T lymphocyte/suppressor cells or CD8+ T cells/suppressor cells ratio comprises the step of administering to the subject a composition comprising a live attenuated *Listeria*, or recombinant *Listeria* strain of the present invention.

In one embodiment, provided herein is a method of increasing the infiltrating T lymphocyte/T regulatory cell ratio in a subject having a disease or in a disease site within the subject. In another embodiment, provided herein is a method of increasing the ratio of CD8+ T cells/T regulatory cells in a subject having a disease or in a disease site within the subject. In another embodiment, the method of increasing the infiltrating T lymphocyte/T regulatory cells or CD8+ T cell/T regulatory cell ratio comprises the step of administering to the subject a composition comprising a live attenuated *Listeria*, or recombinant *Listeria* strain of the present invention.

In one embodiment, provided herein is a method of increasing the infiltrating T lymphocyte/Myeloid-derived suppressor cell (MDSC) ratio in a subject having a disease or in a disease site within the subject. In another embodiment, provided herein is a method of increasing the ratio of CD8+ T cells/Myeloid-derived suppressor cells (MDSC) in a subject having a disease or in a disease site within the subject. In another embodiment, the method of increasing the infiltrating T lymphocyte/Myeloid-derived suppressor cells (MDSC) or CD8+ T cell/Myeloid-derived suppressor cell (MDSC) ratio comprises the step of administering to the subject a composition comprising a live attenuated *Listeria*, or recombinant *Listeria* strain of the present invention.

In one embodiment, the infiltrating T lymphocyte is a Tumor infiltrating T lymphocyte (TIL).

In one embodiment, provided herein is a method of reducing the amount of cells that suppress an immune response against a disease. In another embodiment, the cells that suppress the immune response are suppressive cells. In another embodiment, the suppressive cells are myeloid-derived suppressor cells (MDSC). In another embodiment, the suppressive cells are T regulatory cells (Tregs).

Common plasma markers in human MDSCs include CD33, CD11b, CD15, CD14 negative, MHC class II negative, HLA DR$^{low\ or\ -}$. Common intracellular markers include arginase, and iNOS. Further, human MDSCs' suppressive activity or mechanism includes use of nitric oxide (NO), arginase, or nitrotyrosine. In mice, myeloid-derived suppressor cells (MDSC) are CD11b and Gr-1 double positive and have also been described as F4/80$^{int}$, CD11c$^{low}$, MHCII–/$^{low}$, Ly6C+. CD11b+/Gr-1+ cells that have immunosuppressive ability have been described to produce IFN-g. MDSCs can be monocytic and granulocytic as well.

In one embodiment, tumor MDSCs can unexpectedly inhibit both, the function of antigen-specific and non-specific T cell function, while spleen MDSCs can only inhibit the function of antigen-specific T cells. As demonstrated in the Examples below (see Examples 17-20), the live attenuated *Listeria* provided herein reduces the percent of suppressor cells in a disease compared to the population of tumor infiltrating lymphocytes (TILs) at the disease site, for example, a tumor site.

Lm or sublytic doses of LLO in human epithelial Caco-2 cells induce the expression of IL-6 that reduces bacterial intracellular growth and causes over expression of inducible nitric oxide synthase (NOS). Nitric oxide appears to be an essential component of the innate immune response to Lm, having an important role in listericidal activity of neutrophils and macrophages, with a deficiency of inducible NO synthase (iNOS) causing susceptibility to Lm infection.

Lm infection also results in the generation of robust MHC Class 2 restricted CD4$^+$ T cell responses, and shifts the phenotype of CD4$^+$ T cells to Th-1. Further, CD4$^+$ T cell help is required for the generation and maintenance of functional CD8$^+$ T cell memory against Lm. Moreover, it has been reported infection of mice intraperitoneally with Lm caused a local induction of CD4$^+$ T$_{\gamma\delta}$ cells associated with IL-17 secretion in the peritoneal cavity however no changes were observed in the splenic or lymph node T cell populations after these injections. In addition, *Listeria* infection also involves other systems not essentially a part of the immune system but which support immune function to affect a therapeutic outcome, such as myelopoesis and vascular endothelial cell function.

Lm infected macrophages produce TNF-α, IL-18 and IL-12, all of which are important in inducing the production of IFN-γ and subsequent killing and degradation of Lm in the phagosome. IL-12 deficiency results in an increased susceptibility to listeriosis, which can be reversed through administration of IFN-γ. NK cells are the major source of IFN-γ in early infection. Upon reinfection memory CD8$^+$ T cells have the ability to produce IFN-γ in response to IL-12 and IL-18 in the absence of the cognate antigen. CD8$^+$ T cells co-localize with the macrophages and Lm in the T cell area of the spleen where they produce IFN-γ independent of antigen. IFN-γ production by CD8$^+$ T cells depends partially on the expression of LLO.

IFN-γ plays an important role in anti-tumor responses obtained by Lm-based vaccines. Although produced initially by NK cells, IFN-γ levels are subsequently maintained by CD4$^+$ T-helper cells for a longer period. Lm vaccines require IFN-γ for effective tumor regression, and IFN-γ is specifically required for tumor infiltration of lymphocytes. IFN-γ also inhibits angiogenesis at the tumor site in the early effector phase following vaccination.

In one embodiment, LLO has an ability to induce epigenetic modifications affecting control of DNA expression. Extracellular LLO induces a dephosphorylation of the histone protein H3 and a similar deacetylation of the histone H4 in early phases of *Listeria* infection. This epigenetic effect results in reduced transcription of certain genes involved in immune function, thus providing a mechanism by which LLO may regulate the expression of gene products required for immune responses. In another embodiment, another genomic effect of LLO is its ability to increase NF-κβ translocation in association with the expression of ICAM and E-selectin, and the secretion of IL-8 and MCP-1. In another embodiment, another signaling cascade affected by LLO is the Mitogen Activated Protein Kinase (MAPK) pathway, resulting in increase of Ca$^{2+}$ influx across the cell membrane, which facilitates the entry of *Listeria* into endothelial cells and their subsequent infection.

In one embodiment, LLO is a potent inducer of inflammatory cytokines such as IL-6, IL-8, IL-12, IL-18, TNF-α, and IFN-γ, GM-CSF as well as NO, chemokines, and costimulatory molecules that are important for innate and adaptive immune responses. In one embodiment, macrophages in the presence of LLO release IL-1α, TNF-α, IL-12 and IL-18, which in turn activate NK cells to release IFN-γ resulting in enhanced macrophage activation.

In one embodiment, LLO secreted by cytosolic Lm causes specific gene upregulation in macrophages resulting in significant IFN-γ transcription and secretion. In another embodiment, cytosolic LLO activates a potent type I interferon response to invasive Lm independent of Toll-like receptors (TLR) without detectable activation of NF-KB and MAPK.

In one embodiment, the *Listeria* (Lm) vaccine strains provided herein reduce the percentage of Tregs and MDSCs at sites of disease, with a corresponding shift in the ratio of effector to suppressor cells at sites of disease. In another embodiment, Lm vaccines provided herein are useful for improving immune responses by reducing the percentage of Tregs and MDSCs and the absolute number of MDSC at a specific site of disease in a subject. Such a site can be an inflammation site due to allergy, trauma, infection, disease or the site can be a tumor site.

In another embodiment, both monocytic and granulocytic MDSCs purified from the tumors of *Listeria*-treated mice are less able to suppress the division of CD8+ T cells than MDSCs purified from the tumors of untreated mice, whereas monocytic and granulocytic MDSCs purified from the spleens of these same tumor-bearing mice show no change in their function after vaccination with *Listeria* (See Examples 17-20 herein). In one embodiment, this effect is seen because splenic MDSCs are only suppressive in an antigen-specific manner. Hence, treatment with *Listeria* has the distinct advantage that it allows for tumor-specific inhibition of tumor suppressive cells such as Tregs and MDSCs. Another unexpected advantage provided by the live attenuated *Listeria* of the methods and compositions provided herein is that there are lower amount of Tregs in the tumor, and the ones that persist lose the ability to suppress T cell replication.

In another embodiment, both monocytic and granulocytic MDSCs purified from the tumors of truncated LLO-expressing *Listeria*-treated mice are less able to suppress the division of CD8+ T cells than MDSCs purified from the tumors of untreated mice, whereas monocytic and granulocytic MDSCs purified from the spleens of these same tumor-bearing mice show no change in their function after vaccination with truncated LLO-expressing *Listeria* (See Example 21 herein). In one embodiment, this effect is seen because splenic MDSCs are only suppressive in an antigen-specific manner. Hence, treatment with truncated LLO-expressing *Listeria* has the distinct advantage that it allows for tumor-specific inhibition of tumor suppressive cells such as Tregs and MDSCs. Another unexpected advantage provided by the truncated LLO-expressing live attenuated *Listeria* of the methods and compositions provided herein is that there are lower amount of Tregs and MDSCs in the tumor, and the ones that persist lose the ability to suppress T cell replication, and this effect is observed even in the absence of an LLO fusion partner, such as a heterologous antigen.

In another embodiment, administering a truncated LLO-expressing live attenuated *Listeria* vaccine enhances an anti-tumor T cell response by suppressing Treg- and MDSC-mediated T cell suppression (see Example 21 herein).

In one embodiment, provided herein is a method of reducing the percentage of suppressor cells in a disease site in a subject, the method comprising the step of administering a live attenuated *Listeria* vaccine strain to the subject.

In another embodiment, provided herein is a method of reducing suppressor cells' ability to suppress T cell replication in a disease site in a subject, the method comprising the step of administering a live attenuated *Listeria* vaccine strain to said subject.

In one embodiment, reducing the number of the suppressor cells at a disease site effectively treats the disease. In another embodiment, reducing the number of the suppressor cells at the disease site enhances an anti-disease immune response in the subject having the disease at the disease site. In another embodiment, the immune response is a cell-mediated immune response. In another embodiment, the immune response is a tumor infiltrating T-lymphocytes (TILs) immune response.

In one embodiment, provided herein is a method of reducing the percentage of suppressor cells in a disease in a subject and enhancing a therapeutic response against the disease in the subject, the method comprising the step of administering a live attenuated *Listeria* vaccine strain to the subject, thereby reducing the percentage of suppressor cells in the disease and enhancing a therapeutic response against the disease in the subject.

In another embodiment, provided herein is a method of reducing suppressor cells' ability to suppress replication of T cells in a disease in a subject and enhancing a therapeutic response against the disease in the subject, the method comprising the step of administering a live attenuated *Listeria* vaccine strain to the subject.

In one embodiment, provided herein is a method of reducing the number of myeloid-derived suppressor cells in a disease in a subject, the method comprising the step of administering a live attenuated *Listeria* vaccine strain to said subject.

In one embodiment, the term "reducing the percentage of" is representative of the amount suppressor cells, either Tregs or MDSCs whose presence at a disease site is diminished or reduced in relation to the presence of T infiltrating cells as in an assay or in an immune response.

In another embodiment, the term "reducing the number of" refers to the absolute number of suppressor cells, either Tregs, or MDSCs who's absolute numbers have been diminished or reduced as a result of administration of the live attenuated *Listeria* provided herein or another reagents that achieve a similar effect, also described elsewhere herein.

In one embodiment, the suppressor cells provided herein are T regulatory cells (Tregs). In another embodiment, the suppressor cells are myeloid-derived suppressor cells (MDSCs).

In another embodiment, the live attenuated *Listeria* provided herein comprises a recombinant nucleic acid sequence comprising a first and at least a second open reading frame each encoding a first and at least a second polypeptide, wherein the first and the second polypeptide each comprise a heterologous antigen or a functional fragment thereof fused to an endogenous PEST-containing polypeptide.

In one embodiment, the heterologous antigen or functional fragments thereof and the endogenous PEST-containing polypeptide provided herein are translated in a single open reading frame. In another embodiment each heterologous antigenic polypeptides and the endogenous PEST-containing polypeptide provided herein are fused after being translated separately.

In another embodiment, the recombinant nucleic acid provided herein further comprises a third open reading frame encoding a third polypeptide, wherein the third polypeptide comprises a heterologous antigen or a functional fragment thereof fused to an endogenous PEST-containing polypeptide.

In another embodiment, the PEST-containing polypeptide is an N-terminal truncated LLO polypeptide, an N-terminal ActA polypeptide, or PEST-peptide, or a functional fragment thereof.

In another embodiment the first, the second or the third heterologous antigen or functional fragment thereof is expressed by or derived from an infectious pathogen, or a tumor cell.

In one embodiment, the first, the second or the third antigen is associated with the local tissue environment that is further associated with the development or metastasis of cancer, or is associated with tumor evasion or resistance to cancer, or is an angiogenic antigen.

In another embodiment, the heterologous antigen is an allergen that causes an allergic, inflammatory reaction in a host.

In another embodiment, the disease provided herein is a localized disease, i.e., to a specific disease site or is a systemic disease.

In another embodiment, the disease is an infectious disease, a respiratory or inflammatory disease, or a cancer or tumor.

In another embodiment, the infectious disease is one caused by, but not limited to, any one of the following pathogens: BCG/Tuberculosis, Malaria, *Plasmodium falciparum, plasmodium malariae, plasmodium vivax*, Rotavirus, Cholera, Diptheria-Tetanus, Pertussis, *Haemophilus influenzae*, Hepatitis B, Human papilloma virus, Influenza seasonal), Influenza A (H1N1) Pandemic, Measles and *Rubella*, Mumps, Meningococcus A+C, Oral Polio Vaccines, mono, bi and trivalent, Pneumococcal, Rabies, Tetanus Toxoid, Yellow Fever, *Bacillus anthracis* (anthrax), *Clostridium botulinum* toxin (botulism), *Yersinia pestis* (plague), Variola major (smallpox) and other related pox viruses, *Francisella tularensis* (tularemia), Viral hemorrhagic fevers, Arenaviruses (LCM, Junin virus, Machupo virus, Guanarito virus, Lassa Fever), Bunyaviruses (Hantaviruses, Rift Valley Fever), Flaviruses (Dengue), Filoviruses (Ebola, Marburg), *Burkholderia pseudomallei, Coxiella burnetii* (Q fever), *Brucella* species (brucellosis), *Burkholderia mallei* (glanders), *Chlamydia psittaci* (Psittacosis), Ricin toxin (from *Ricinus communis*), Epsilon toxin of *Clostridium perfringens, Staphylococcus* enterotoxin B, Typhus fever (*Rickettsia prowazekii*), other Rickettsias, Food- and Waterborne Pathogens, Bacteria (Diarrheagenic *E. coli*, Pathogenic Vibrios, *Shigella* species, *Salmonella* BCG/, *Campylobacter jejuni, Yersinia enterocolitica*), Viruses (Caliciviruses, Hepatitis A, West Nile Virus, LaCrosse, California encephalitis, VEE, EEE, WEE, Japanese Encephalitis Virus, Kyasanur Forest Virus, Nipah virus, hantaviruses, Tickborne hemorrhagic fever viruses, Chikungunya virus, Crimean-Congo Hemorrhagic fever virus, Tickborne encephalitis viruses, Hepatitis B virus, Hepatitis C virus, Herpes Simplex virus (HSV), Human immunodeficiency virus (HIV), Human papillomavirus (HPV)), Protozoa (*Cryptosporidium parvum, Cyclospora* cayatanensis, *Giardia lamblia, Entamoeba histolytica, Toxoplasma*), Fungi (Microsporidia), Yellow fever, Tuberculosis, including drug-resistant TB, Rabies, Prions, Severe acute respiratory syndrome associated coronavirus (SARS-CoV), *Coccidioides posadasii, Coccidioides immitis*, Bacterial vaginosis, *Chlamydia trachomatis*, Cytomegalovirus, Granuloma inguinale, *Hemophilus ducreyi, Neisseria gonorrhea, Treponema pallidum, Trichomonas vaginalis*, or any other infectious disease known in the art that is not listed herein.

In another embodiment, the infectious disease is a livestock infectious disease. In another embodiment, livestock diseases can be transmitted to man and are called "zoonotic diseases." In another embodiment, these diseases include, but are not limited to, Foot and mouth disease, West Nile Virus, rabies, canine parvovirus, feline leukemia virus, equine influenza virus, infectious bovine rhinotracheitis (IBR), pseudorabies, classical swine fever (CSF), IBR, caused by bovine herpesvirus type 1 (BHV-1) infection of cattle, and pseudorabies (Aujeszky's disease) in pigs, toxoplasmosis, anthrax, vesicular stomatitis virus, rhodococcus equi, Tularemia, Plague (*Yersinia pestis*), *trichomonas*.

In another embodiment, the respiratory or inflammatory disease is asthma.

The live attenuated *Listeria* strains are capable of alleviating asthma symptoms without co-administration of other therapeutic agents, such as anti-inflammatory agents or bronchodilators. In another embodiment, the methods provided herein further comprise the step of co-administering to a subject the live attenuated *Listeria* strain and one or more therapeutic agents. In another embodiment, the therapeutic agent is an anti-asthmatic agent. In another embodiment, the agent is an anti-inflammatory agent, a non-steroidal anti-inflammatory agent, an antibiotic, an antichlolinerginc agent, a bronchodilator, a corticosteroid, a short-acting beta-agonist, a long-acting beta-agonist, combination inhalers, an antihistamine, or combinations thereof.

In another embodiment, the present pharmaceutical composition may contain both the live attenuated *Listeria* strain and the co-administered therapeutic agents. The live attenuated *Listeria* strain and the co-administered therapeutic agents may also be in different pharmaceutical compositions.

In another embodiment, the agent includes inhaled corticosteroids, which include fluticasone (FLOVENT DISKUS (fluticasone propionate), FLOVENT HFA (fluticasone propionate in propellant HFA-134a (1,1,1,2-tetrafluoroethane)), budesonide (PULMICORT FLEXHALER (Budesonide Inhalation Powder)), mometasone (ASMANEX), flunisolide (AEROBID), beclomethasone (QVAR (beclomethasone dipropionate HFA)) and others. They are the most commonly prescribed type of long-term asthma medication. Unlike oral corticosteroids, these corticosteroid medications have a relatively low risk of side effects and are generally safe for long-term use.

The agent can be a Leukotriene modifier. These oral medications include montelukast (SINGULAIR (a leukotriene inhibitor)), zafirlukast (ACCOLATE (a leukotriene inhibitor)) and zileuton (ZYFLO, ZYFLO CR (leukotriene inhibitors)). They help prevent asthma symptoms for up to 24 hours.

Moreover, the agent can be long-acting beta agonists (LABAs). These inhaled medications include salmeterol (SEREVENT DISKUS (bronchodilator)) and formoterol (FORADIL AEROLIZER (bronchodilator)). LABAs open the airways and reduce inflammation. However, they've been linked to severe asthma attacks. LABAs should be taken only in combination with an inhaled corticosteroid.

In one embodiment, the cancer treated by a method of the present invention is breast cancer. In another embodiment, the cancer is a cervix cancer. In another embodiment, the cancer is an Her2 containing cancer. In another embodiment, the cancer is a melanoma. In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, it is a glioblastoma multiforme. In another embodiment, it is a hypoxic solid tumor. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non-small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma. Each possibility represents a separate embodiment of the present invention.

In one embodiment, the heterologous antigen provided herein is HPV-E7. In another embodiment, the antigen is HPV-E6. In another embodiment, the antigen is Her-2/neu. In another embodiment, the antigen is NY-ESO-1. In another embodiment, the antigen is telomerase (TERT). In another embodiment, the antigen is SCCE. In another embodiment, the antigen is CEA. In another embodiment, the antigen is LMP-1. In another embodiment, the antigen is p53. In another embodiment, the antigen is carboxic anhydrase IX (CAIX). In another embodiment, the antigen is PSMA. In another embodiment, the antigen is prostate stem cell antigen (PSCA). In another embodiment, the antigen is HMW-MAA. In another embodiment, the antigen is WT-1. In another embodiment, the antigen is HIV-1 Gag. In another embodiment, the antigen is Proteinase 3. In another embodiment, the antigen is Tyrosinase related protein 2. In another embodiment, the antigen is PSA (prostate-specific antigen). In another embodiment, the antigen is selected from HPV-E7, HPV-E6, Her-2, NY-ESO-1, telomerase (TERT), SCCE, HMW-MAA, WT-1, HIV-1 Gag, CEA, LMP-1, p53, PSMA, PSCA, Proteinase 3, Tyrosinase related protein 2, Muc1, PSA (prostate-specific antigen), or a combination thereof.

In another embodiment, the heterologous antigen provided herein is a tumor-associated antigen, which in one embodiment, is one of the following tumor antigens: a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers; the HPV 16/18 antigens associated with cervical cancers, KLH antigen associated with breast carcinoma, CEA (carcinoembryonic antigen) associated with colorectal cancer, gp100, a MART1 antigen associated with melanoma, or the PSA antigen associated with prostate cancer. In another embodiment, the antigen for the compositions and methods provided herein are melanoma-associated antigens, which in one embodiment are TRP-2, MAGE-1, MAGE-3, gp-100, tyrosinase, HSP-70, beta-HCG, or a combination thereof. It is to be understood that a skilled artisan would be able to use any heterologous antigen not mentioned herein but known in the art for use in the methods and compositions provided herein.

In one embodiment, the nucleic acid molecule provided herein further comprises a second open reading frame encoding a metabolic enzyme. In another embodiment, the metabolic enzyme complements an endogenous gene that is lacking in the chromosome of the recombinant *Listeria* strain. In another embodiment, the metabolic enzyme encoded by the second open reading frame is an alanine racemase enzyme. In one embodiment, the *Listeria* further comprises a third open reading frame encoding an additional metabolic enzyme. In another embodiment, the metabolic enzyme encoded by the third open reading frame is a D-amino acid transferase enzyme. In another embodiment, the nucleic acid molecule comprises a fourth reading frame encoding a heterologous antigen or fragment thereof.

In one embodiment, the nucleic acid molecule is integrated into the *Listeria* genome. In another embodiment, the nucleic acid molecule is in a plasmid in the recombinant *Listeria* vaccine strain. In another embodiment, the plasmid is stably maintained in the recombinant *Listeria* vaccine strain in the absence of antibiotic selection. In another embodiment, the plasmid does not confer antibiotic resistance upon the recombinant *Listeria*.

In one embodiment, provided herein is a nucleic acid molecule that is used to transform the *Listeria* in order to arrive at a recombinant *Listeria*. In another embodiment, the nucleic acid provided herein used to transform *Listeria* lacks a virulence gene. In another embodiment, the nucleic acid molecule is integrated into the *Listeria* genome and carries a non-functional virulence gene. In another embodiment, the virulence gene is mutated in the recombinant *Listeria*. In yet another embodiment, the nucleic acid molecule is used to inactivate the endogenous gene present in the *Listeria* genome. In yet another embodiment, the virulence gene is an ActA gene, an inlA gene, and inlB gene, an inlC gene, inlJ gene, a PlbC gene or a PrfA gene. It is to be understood by a skilled artisan, the virulence gene can be any gene known in the art to be associated with virulence in the recombinant *Listeria*.

In one embodiment, the metabolic gene, the virulence gene, etc. is lacking in a chromosome of the *Listeria* strain. In another embodiment, the metabolic gene, virulence gene, etc. is lacking in the chromosome and in any episomal genetic element of the *Listeria* strain. In another embodiment, the metabolic gene, virulence gene, etc. is lacking in the genome of the virulence strain. In one embodiment, the virulence gene is mutated in the chromosome. In another embodiment, the virulence gene is deleted from the chromosome. Each possibility represents a separate embodiment of the present invention.

In one embodiment, the term "nucleic acid molecule" refers, in another embodiment, to a plasmid. In another embodiment, the term refers to an integration vector. In another embodiment, the term refers to a plasmid comprising an integration vector. In another embodiment, the integration vector is a site-specific integration vector. In another embodiment, a nucleic acid molecule of methods and compositions of the present invention are composed of any type of nucleotide known in the art. Each possibility represents a separate embodiment of the present invention.

In another embodiment, the construct or nucleic acid molecule is integrated into the Listerial chromosome using homologous recombination. Techniques for homologous recombination are well known in the art, and are described, for example, in Baloglu S, Boyle S M, et al. (Immune responses of mice to vaccinia virus recombinants expressing either *Listeria monocytogenes* partial listeriolysin or *Brucella abortus* ribosomal L7/L12 protein. Vet Microbiol 2005, 109(1-2): 11-7); and Jiang L L, Song H H, et al., (Characterization of a mutant *Listeria monocytogenes* strain expressing green fluorescent protein. Acta Biochim Biophys Sin (Shanghai) 2005, 37(1): 19-24). In another embodiment, homologous recombination is performed as described in U.S. Pat. No. 6,855,320. In this case, a recombinant Lm strain that expresses E7 was made by chromosomal integration of the E7 gene under the control of the hly promoter and with the inclusion of the hly signal sequence to ensure secretion of the gene product, yielding the recombinant referred to as Lm-AZ/E7. In another embodiment, a temperature sensitive plasmid is used to select the recombinants. Each technique represents a separate embodiment of the present invention.

In another embodiment, the construct or nucleic acid molecule is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed but the disadvantage that the position in the genome where the foreign gene has been inserted is unknown.

In another embodiment, the construct or nucleic acid molecule is integrated into the Listerial chromosome using phage integration sites (Lauer P, Chow M Y et al, Construction, characterization, and use of two *Listeria monocytogenes* site-specific phage integration vectors. J Bacteriol 2002; 184(15): 4177-86). In certain embodiments of this method, an integrase gene and attachment site of a bacteriophage (e.g. U153 or PSA listeriophage) is used to insert the heterologous gene into the corresponding attachment site, which may be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. In another embodiment, the present invention further comprises a phage based chromosomal integration system for clinical applications, where a host strain that is auxotrophic for essential enzymes, including, but not limited to, d-alanine racemase can be used, for example Lmdal(−) dat(−). In another embodiment, in order to avoid a "phage curing step," a phage integration system based on PSA is used. This requires, in another embodiment, continuous selection by antibiotics to maintain the integrated gene. Thus, in another embodiment, the current invention enables the establishment of a phage based chromosomal integration system that does not require selection with antibiotics. Instead, an auxotrophic host strain can be complemented. Each possibility represents a separate embodiment of the present invention.

In another embodiment, the construct or nucleic acid molecule is expressed from an episomal vector, with an endogenous nucleic acid sequence encoding an LLO, PEST or ActA sequence or functional fragments thereof. In another embodiment, the construct or nucleic acid molecule comprises a first and at least a second open reading frame each encoding a first and at least a second polypeptide, wherein the first and the at least second polypeptide each comprise a heterologous antigen or a functional fragment thereof fused to an endogenous PEST-containing polypeptide.

In another embodiment, provided herein is a recombinant *Listeria* strain comprising an episomal recombinant nucleic acid molecule, the nucleic acid molecule comprising a first and at least a second open reading frame each encoding a first and at least a second polypeptide, wherein the first and the at least second polypeptide each comprise a heterologous antigen or a functional fragment thereof fused to an endogenous PEST-containing polypeptide, wherein the nucleic acid further comprises an open reading frame encoding a plasmid replication control region.

In one embodiment, the present invention provides a method of producing a recombinant *Listeria* strain comprising an episomal expression plasmid comprising a first and at least a second nucleic acid encoding a first and at least a second polypeptide, wherein the first and the second polypeptide each comprise a heterologous antigen fused to an endogenous PEST-containing polypeptide, the method comprising the steps of a) recombinantly fusing in the plasmid the first and the second nucleic acid encoding the first and the second polypeptide each comprising a first and a second heterologous antigen fused to an endogenous PEST-containing polypeptide; b) transforming the recombinant *Listeria* with the episomal expression plasmid; and, c) expressing the first, and the at least second antigens under conditions conducive to antigenic expression in the recombinant *Listeria* strain.

In one embodiment, provided herein is a method of producing a recombinant *Listeria* strain comprising an episomal expression plasmid comprising a first, a second and a third nucleic acid encoding a first a second and a third polypeptide, wherein the first, the second and the third polypeptide each comprise a heterologous antigen fused to an endogenous PEST-containing polypeptide, the method comprising the steps of: a) recombinantly fusing in the plasmid the first, the second and the third nucleic acid encoding the first, the second and the third polypeptide each comprising a first, a second and a third heterologous antigen fused to an endogenous PEST-containing polypeptide; b) transforming the recombinant *Listeria* with the episomal expression plasmid; and, c) expressing the first, the second and the third antigens under conditions conducive to antigenic expression in the recombinant *Listeria* strain.

In another embodiment, the present invention provides a recombinant *Listeria* strain comprising at least one episomal recombinant nucleic acid molecule, the nucleic acid molecules comprising a first and at least a second open reading frame each encoding a first and at least a second polypeptide, wherein the first and the at least second polypeptide each comprise a heterologous antigen or a functional fragment thereof fused to an endogenous PEST-containing polypeptide, wherein the nucleic acids further comprise an open reading frame encoding a plasmid replication control region. In another embodiment, the plasmid control region regulates replication of the episomal recombinant nucleic acid molecule.

In another embodiment, the plasmid control region comprises an open reading frame encoding a transcription repressor that represses heterologous antigen expression from the first or at least second nucleic acid molecule. In another embodiment, the plasmid control region comprises an open reading frame encoding transcription inducer that induces heterologous antigen expression from the first or at least second nucleic acid molecule. In another embodiment, the plasmid control region comprises an open reading frame encoding a transcription repressor that represses heterologous antigen expression from the first, second or third nucleic acid molecule. In another embodiment, the plasmid control region comprises an open reading frame encoding a transcription inducer that induces heterologous antigen expression from the first, second or third nucleic acid molecule.

In one embodiment, there are different types of transcription regulation, these include "negative control" and "positive control". In negative control, a regulatory protein or repressor protein binds to the operator and prevents RNA polymerase from binding properly to the promoter sequence. Alternatively, the repressor protein can be synthesized in an inactive form in that it cannot block RNA polymerase binding to the promoter, the repressor is then activated to prevent RNA polymerase binding to the promoter by the binding of a corepressor. This type of control is seen most often in anabolic pathways (e.g., arginine biosynthesis), where the corepressor is often the end product of the anabolic pathway. Alternatively, the repressor protein is synthesized in an active form, binds to the operator and prevents RNA polymerase from binding to promoter. When an inducer binds to the repressor, the repressor becomes inactive, therefore RNA polymerase is now free to initiate transcription. This type of control is seen most often in catabolic pathways (e.g., lactose catabolism). The inducer is often a form of the substrate that will be degraded. In positive control, a regulatory protein, called an activator protein, binds to the operator and the activator molecular stabilizes RNA polymerase binding to the promoter region. An example of this includes the arabinose catabolism. Regulatory proteins (for both positive and negative regulation) are encoded by regulatory genes and can be synthesized continuously at low levels. They can be made to be self-regulated whereby high concentrations of the regulatory protein (associated with high plasmid production) binds to its own operator and represses RNA polymerase from binding to the promoter sequence. This stops transcription until its level drops. Several examples of these types of regulation include the lactose operon, the arginine operon, the diphtheria toxin gene regulation system, etc. Transcription repressors and methods of use thereof are readily known in the art and are contemplated for use in the present invention.

In another embodiment, the plasmid replication regulation region enables the regulation of expression of exogenous heterologous antigen from each of the first or the at least second nucleic acid molecule. In another embodiment, the plasmid replication regulation region enables the regulation of expression of exogenous heterologous antigen from each of the first, second or third nucleic acid molecules.

In one embodiment, measuring metabolic burden is accomplished by any means know in the art at the time of the invention which include but are not limited to, measuring growth rates of the vaccine strain, optical density readings, colony forming unit (CFU) plating, and the like. In another embodiment, the metabolic burden on the bacterial cell is determined by measuring the viability of the bacterial cell. Methods of measuring bacteria viability are readily known and available in the art, some of which include but are not limited to, bacteria plating for viability count, measuring ATP, and flow cytometry. In ATP staining, detection is based on using the luciferase reaction to measure the amount of ATP from viable cells, wherein the amount of ATP in cells correlates with cell viability. As to flow cytometry, this method can be used in various ways, also known in the art, for example after employing the use of viability dyes which are excluded by live bacterial cells and are absorbed or adsorbed by a dead bacterial cells. A skilled artisan would readily understand that these and any other methods known in the art for measuring bacterial viability can be used in the present invention. It is to be understood that a skilled artisan would be able to implement the knowledge available in the art at the time of the invention for measuring growth rates of the vaccine strain or expression of marker genes by the vaccine strain that enable determining the metabolic burden of the vaccine strain expressing multiple heterologous antigens or functional fragments thereof.

In another embodiment, the "functional fragment" is an immunogenic fragment and elicits an immune response when administered to a subject alone or in a vaccine composition provided herein. In another embodiment, a functional fragment has biological activity as will be understood by a skilled artisan and as further provided herein.

In one embodiment, the term "at least second nucleic acid molecule" refers to two or more nucleic acid molecules, alternatively it refers to three, four, five, and so on nucleic acid molecules.

In another embodiment, the recombinant nucleic acid molecule further comprises a third open reading frame encoding a third polypeptide, wherein said third polypeptide comprises a heterologous antigen or a functional fragment thereof fused to an endogenous PEST-containing polypeptide.

In one embodiment, provided herein is a multivalent plasmid that delivers at least two antigens. In another embodiment, the plasmid is a dual plasmid. In another embodiment, provided herein is an episomal recombinant nucleic acid encoding the multivalent plasmid. In another embodiment, the episomal recombinant nucleic acid backbone is encoded by the sequence comprising SEQ ID NO: 1. In another embodiment, the episomal recombinant nucleic acid provided herein is encoded by the sequence consisting of SEQ ID NO: 1. In another embodiment, the episomal recombinant nucleic acid provided herein is encoded by the sequence set forth in SEQ ID NO: 1.

(SEQ ID NO: 1)

```
ggagtgtatactggcttactatgttggcactgatgagggtgtcagtgaagtgcttcatgtggcaggagaaaaaaggctgcaccggtgcgtca
gcagaatatgtgatacaggatatattccgcttcctcgctcactgactcgctacgctcggtcgttcgactgcggcgagcggaaatggcttacga
acggggcggagatttcctggaagatgccaggaagatacttaacagggaagtgagagggccgcggcaaagccgtttttccataggctccgc
ccccctgacaagcatcacgaaatctgacgctcaaatcagtggtggcgaaacccgacaggactataaagataccaggcgtttccccctggcg
gctccctcgtgcgctctcctgttcctgcctttcggtttaccggtgtcattccgctgttatggccgcgtttgtctcattccacgcctgacactcagttc
cgggtaggcagttcgctccaagctggactgtatgcacgaaccccccgttcagtccgaccgctgcgccttatccggtaactatcgtcttgagtc
caacccggaaagacatgcaaaagcaccactggcagcagccactggtaattgatttagaggagttagtcttgaagtcatgcgccggttaagg
ctaaactgaaaggacaagttttggtgactgcgctcctccaagccagttacctcggttcaaagagttggtagctcagagaaccttcgaaaaacc
gccctgcaaggcggttttttcgttttcagagcaagagattacgcgcagaccaaaacgatctcaagaagatcatcttattaatcagataaaatattt
ctagccctcctttgattagtatattcctatcttaaagttacttttatgtggaggcattaacatttgttaatgacgtcaaaaggatagcaagactagaat
aaagctataaagcaagcatataatattgcgtttcatcttagaagcgaatttcgccaatattataattatcaaaagagaggggtggcaaacggta
tttggcattattaggttaaaaaatgtagaaggagagtgaaacccatgaaaaaaataatgctagtttttattacacttatattagttagtctaccaatt
gcgcaacaaactgaagcaaaggatgcatctgcattcaataaagaaaattcaatttcatccatggcaccaccagcatctccgcctgcaagtcct
aagacgccaatcgaaagaaacacgcggatgaaatcgataagtatatacaaggattggattacaataaaaacaatgtattagtataccacgg
agatgcagtgacaaatgtgccgccaagaaaaggttacaaagatggaaatgaatatattgttgtgaaaaaagaagaaatccatcaatcaaa
ataatgcagacattcaagttgtgaatgcaatttcgagcctaacctatccaggtgctctcgtaaaagcgaattcggaattagtagaaaatcaacc
agatgttctccctgtaaaacgtgattcattaacactcagcattgatttgccaggtatgactaatcaagacaataaaatagttgtaaaaaatgccac
taaatcaaacgttaacaacgcagtaaatacattagtggaaagatggaatgaaaaatatgctcaagcttatccaaatgtaagtgcaaaaattgatt
atgatgacgaaatggcttacagtgaatcacaattaattgcgaaatttggtacagcatttaaagctgtaaataatagcttgaatgtaaacttcggcg
caatcagtgaagggaaaatgcaagaagaagtcattagttttaaacaaatttactataacgtgaatgttaatgaacctacaagaccttccagattttt
tcggcaaagctgttactaaagagcagttgcaagcgcttggagtgaatgcagaaaatcctcctgcatatatctcaagtgtggcgtatggccgtc
aagtttatttgaaattatcaactaattcccatagtactaaagtaaaagctgcttttgatgctgccgtaagcggaaaatctgtctcaggtgatgtaga
actaacaaatatcatcaaaaattcttccttcaaagccgtaatttacggaggttccgcaaaagatgaagttcaaatcatcgacggcaacctcgga
gacttacgcgatattttgaaaaaaggcgctactttttaatcgagaaacaccaggagttcccattgcttatacaacaaacttcctaaaagacaatga
attagctgttattaaaaacaactcagaatatattgaaacaacttcaaaagcttatacagatggaaaaattaacatcgatcactctggaggatacgt
tgctcaattcaacatttcttgggatgaagtaaattatgatctcgagactagtctagatttatcacgtacccatttccccgcatcttttattttttaaat
actttagggaaaaatggttttgatttgcttttaaaggttgtggtgtagactcgtctgctgactgcatgctagaatctaagtcactttcagaagcatc
cacaactgactcttcgccacttttctcttatttgcttttgttggtttatctggataagtaaggctttcaagctcactatccgacgacgctatggcttttc
ttctttttttaatttccgctgcgctatccgatgacagacctggatgacgacgctccacttgcagagttggtcggtcgactcctgaagcctcttcatt
tatagccacatttcctgtttgctcaccgttgttattattgttattcggacctttctctgcttttgctttcaacattgctattaggtctgctttgttcgtatt
tttcactttattcgattttctagttcctcaatatcacgtgaacttacttcacgtgcagtttcgtatcttggtcccgtatttacctgcttggctgctcttc
tgttttttcttcttcccattcatctgtgtttagactggaatcttcgctatctgtcgctgcaaatattatgtcggggttaatcgtaatgcagttggcagta
```

-continued

```
atgaaaactaccatcatcgcacgcataaatctgtttaatcccacttatactccctcctcgtgatacgctaatacaaccttttagaacaaggaaaattcg
gccttcattttcactaatttgttccgttaaaaattggattagcagttagttatcttcttaattagctaatataagaaaaaatattcatgaattattttaaga
atatcacttggagaattaattttctctaacatttgttaatcagttaaccccaactgcttcccaagcttcacccgggccactaactcaacgctagta
gtggatttaatcccaaatgagccaacagaaccagaaccagaaacagaacaagtaacattggagttagaaatggaagaagaaaaaagcaat
gatttcgtgtgaataatgcacgaaatcattgcttattttttaaaaagcgatatactagatataacgaaacaacgaactgaataaagaatacaaaa
aaagagccacgaccagttaaagcctgagaaactttaactgcgagcccttaattgattaccaccaatcaattaaagaagtcgagacccaaaattt
ggtaaagtatttaattactttattaatcagatacttaaatatctgtaaaccccattatatcgggttttttgagggggatttcaagtctttaagaagatacca
ggcaatcaattaagaaaaacttagttgattgccttttttgttgtgattcaactttgatcgtagcttctaactaattaatttcgtaagaaaggagaaca
gctgaatgaatatcccttttgttgtagaaactgtgcttcatgacggcttgttaaagtacaaatttaaaaatagtaaaattcgctcaatcactaccaa
gccaggtaaaagtaaagggggctattttttgcgtatcgctcaaaaaaaagcatgattggcggacgtggcgttgttctgacttccgaagaagcgat
tcacgaaaatcaagatacatttacgcattggacaccaaacgtttatcgttatggtacgtatgcagacgaaaaccgttcatacactaaaggacatt
ctgaaaacaatttaagacaaatcaataccttctttattgattttgatattcacacggaaaaagaaactatttcagcaagcgatattttaacaacagct
attgatttaggttttatgcctacgttaattatcaaatctgataaaggttatcaagcatattttgttttagaaacgccagtctatgtgacttcaaaatcag
aatttaaatctgtcaaagcagccaaaataatctcgcaaaatatccgagaatattttggaaagtctttgccagttgatctaacgtgcaatcatttgg
gattgctcgtataccaagaacggacaatgtagaatttttttgatcccaattaccgttattctttcaaagaatggcaagattggtctttcaaacaaaca
gataataagggctttactcgttcaagtctaacggttttaagcggtacagaaggcaaaaaacaagtagatgaaccctggtttaatctcttattgca
cgaaacgaaattttcaggagaaaagggtttagtagggcgcaatagcgttatgtttaccctctctttagcctactttagttcaggctattcaatcga
aacgtgcgaatataatatgtttgagtttaataatcgattagatcaacccttagaagaaaagaagtaatcaaaattgttagaagtgcctattcaga
aaactatcaaggggctaatagggaatacattaccattctttgcaaagcttgggtatcaagtgatttaaccagtaaagatttatttgtccgtcaagg
gtggtttaaattcaagaaaaaagaagcgaacgtcaacgtgttcatttgtcagaatggaaagaagatttaatggcttatattagcgaaaaaagc
gatgtatacaagccttatttagcgacgaccaaaaaagagattagagaagtgctaggcattcctgaacggacattagataaattgctgaaggta
ctgaaggcgaatcaggaaattttcttttaagattaaaccaggaagaaatggtggcattcaacttgctagtgttaaatcattgttgctatcgatcatta
aattaaaaaagaagaacgagaaagctatataaaggcgctgacagcttcgtttaatttagaacgtacatttattcaagaaactctaaacaaattg
gcagaacgccccaaaacggacccacaactcgatttgtttagctacgatacaggctgaaaataaaacccgcactatgccattacatttatatcta
tgatacgtgtttgttttcttttgctggctagcttaattgcttatatttacctgcaataaaggatttcttacttccattatactcccatttttccaaaaaca
tacggggaacacgggaacttattgtacaggccacctcatagttaatggtttcgagccttcctgcaatctcatccatggaaatatattcatcccctgc
cggcctattaatgtgacttttgtgccggcggatattcctgatccagctccaccataaattggtccatgcaaattcggccggcaattttcaggcg
ttttcccttcacaaggatgtcggtcccttcaattttcggagccagccgtccgcatagcctacaggcaccgtcccgatccatgtgtcttttccgct
gtgtactcggctccgtagctgacgctctcgccttttctgatcagtttgacatgtgacagtgtcgaatgcagggtaaatgccggacgcagctgaa
acggtatctcgtccgacatgtcagcagacgggcgaaggccatacatgccgatgccgaatctgactgcattaaaaaagccttttttcagccgg
agtccagcggcgctgttcgcgcagtggaccattagattcttttaacgcagcggagcaatcagctctttaaagcgctcaaactgcattaagaaa
tagcctctttctttttcatccgctgtcgcaaaatgggtaaatacccctttgcactttaaacgaggggttgcggtcaagaattgccatcacgttctgaa
cttcttcctctgtttttacaccaagtctgttcatccccgtatcgaccttcagatgaaaatgaagagaaccttttttcgtgtggcgggctgcctcctga
agccattcaacagaataacctgttaaggtcacgtcatactcagcagcgattgccacatactccgggggaaccgcgccaagcaccaatatag
gcgccttcaatccctttttgcgcagtgaaatcgcttcatccaaaatggccacggccaagcatgaagcacctgcgtcaagagcagcctttgctg
tttctgcatcaccatgcccgtaggcgtttgctttcacaactgccatcaagtggacatgttcaccgatatgtttttttcatattgctgacattttcctttat
cacggacaagtcaatttccgcccacgtatctctgtaaaaaggttttgtgctcatggaaaactcctctctttttttcagaaaatcccagtacgtaatta
agtatttgagaattaattttatattgattaatactaagttttacccagttttcacctaaaaaacaaatgatgagataatagctccaaaggctaaagag
gactataccaactatttgttaat.
```

In one embodiment, the multivalent plasmid backbone comprises at least two nucleic acid sequences encoding at least two antigens. In another embodiment, the recombinant episomal nucleic acid encodes a plasmid backbone sequence and at least two antigens. In another embodiment, the antigens are heterologous antigens to the bacteria host carrying the plasmid. In another embodiment, the antigens are heterologous antigens to the *Listeria* host carrying the plasmid. In another embodiment, the recombinant episomal nucleic acid sequence encoding the plasmid backbone and at least two heterologous antigens comprises SEQ ID NO: 2. In another embodiment, the recombinant episomal nucleic acid sequence encoding the plasmid backbone and at least two heterologous antigens consists of SEQ ID NO: 2.

(SEQ ID NO: 2)

```
ggagtgtatactggcttactatgttggcactgatgagggtgtcagtgaagtgcttcatgtggcaggagaaaaaaggctgcaccggtgcgtca
gcagaatatgtgatacaggatatattccgcttcctcgctcactgactcgctacgctcggtcgttcgactgcggcgagcggaaatggcttacga
acggggcggagatttcctggaagatgccaggaagatacttaacagggaagtgagagggccgcggcaaagccgttttccataggctccgc
cccctgacaagcatcacgaaatctgacgctcaaatcagtggtggcgaaacccgacaggactataaagataccaggcgtttccccctggcg
gctccctcgtgcgctctcctgttcctgcctttcggtttaccggtgtcattccgctgttatggccgcgtttgtctcattccacgcctgacactcagttc
cgggtaggcagttcgctccaagctggactgtatgcacgaaccccccgttcagtccgaccgctgcgccttatccggtaactatcgtcttgagtc
caacccggaaagacatgcaaaagcaccactggcagcagccactggtaattgatttagaggagttagtcttgaagtcatgcgccggttaagg
ctaaactgaaaggacaagttttggtgactgcgctcctccaagccagttacctcggttcaaagagttggtagctcagagaaccttcgaaaaacc
gccctgcaaggcggttttttcgttttcagagcaagagattacgcgcagaccaaaacgatctcaagaagatcatcttattaatcagataaaatattt
ctagcctcctttgattagtatattcctatcttaaagttacttttatgtggaggcattaacatttgttaatgacgtcaaaaggatagcaagactagaat
aaagctataaagcaagcatataatattgcgtttcatcttagaagcgaatttcgccaatattataattatcaaagagaggggtggcaaacggta
tttggcattattaggttaaaaaatgtagaaggagagtgaaacccatgaaaaaaataatgctagttttattacacttatattagttagtctaccaatt
gcgcaacaaactgaagcaaaggatgcatctgcattcaataaagaaaattcaatttcatccatggcaccaccagcatctccgcctgcaagtcct
aagacgccaatcgaaaagaaacacgcggatgaaatcgataagtatatacaaggattggattacaataaaaacaatgtattagtataccacgg
agatgcagtgacaaatgtgccgccaagaaaaggttacaaagatggaaatgaatatattgttgtggagaaaaagaagaaatccatcaatcaaa
ataatgcagacattcaagttgtgaatgcaatttcgagcctaacctatccaggtgctctcgtaaaagcgaattcggaattagtagaaaatcaacc
agatgttctccctgtaaaacgtgattcattaacactcagcattgatttgccaggtatgactaatcaagacaataaaatagttgtaaaaaatgccac
taaatcaaacgttaacaacgcagtaaatacattagtggaaagatggaatgaaaaatatgctcaagcttatccaaatgtaagtgcaaaaattgatt
atgatgacgaaatggcttacagtgaatcacaattaattgcgaaatttggtacagcatttaaagctgtaaataatagcttgaatgtaaacttcggcg
caatcagtgaagggaaaatgcaagaagaagtcattagttttaaacaaatttactataacgtgaatgttaatgaacctacaagaccttccagattttt
tcggcaaagctgttactaaagagcagttgcaagcgcttggagtgaatgcagaaaatcctcctgcatatatctcaagtgtggcgtatggccgtc
aagtttatttgaaattatcaactaattcccatagtactaaagtaaaagctgcttttgatgctgccgtaagcggaaaatctgtctcaggtgatgtaga
actaacaaatatcatcaaaaattcttccttcaaagccgtaatttacggaggttccgcaaaagatgaagttcaaatcatcgacggcaacctcgga
gacttacgcgatattttgaaaaaaggcgctacttttaatcgagaaacaccaggagttcccattgcttatacaacaaacttcctaaaagacaatga
attagctgttattaaaaacaactcagaatatattgaaacaacttcaaaagcttatacagatggaaaaattaacatcgatcactctggaggatacgt
tgctcaattcaacatttcttgggatgaagtaaattatgatctcgagcatggagatacacctacattgcatgaatatatgttagatttgcaacc
agagacaactgatctctactgttatgagcaattaaatgacagctcagaggaggaggatgaaatagatggtccagctggacaagca
gaaccggacagagcccattacaatattgtaaccttttgttgcaagtgtgactctacgcttcggttgtgcgtacaaagcacacacgtag
acattcgtactttggaagacctgttaatgggcacactaggaattgtgtgccccatctgttctcagaaaccataaactagtctagtggtg
atggtgatgatggagctcagatctgtctaagaggcagccatagggcataagctgtgtcaccagctgcaccgtggatgtcaggcagatg
cccagaaggcgggagacatatggggagcccacaccagccatcacgtatgcttcgtctaagatttctttgttggctttgggggatgtgttttc
cctcaacactttgatggccactggaattttcacattctccccatcagggatccagatgcccttgtagactgtgccaaaagcgccagatcca
agcaccttcaccttcctcagctccgtctctttcaggatccgcatctgcgcctggttgggcatcgctccgctaggtgtcagcggctccaccag
ctccgtttcctgcagcagtctccgcatcgtgtacttccggatcttctgctgccctcgggcgcacagctggtggcaggccaggccctcgccc
acacactcgtcctctggccggttggcagtgtggagcagagcttggtgcgggttccgaaagagctggtcccagggcaccgtgtgcacga
agcagaggtgggtgttatggtggatgagggccagtccactgcccagttccctcagtgagcgcagcccagccagctgatgcccagccc
ttgcagggtcagcgagtaggcgccattgtgcagaattcgtccccggattacttgcaggttctggaagacgctgaggtcaggcaggctgtc
```

-continued

```
cggccatgctgagatgtataggtaacctgtgatctcttccagagtctcaaacacttggagctgctctggctggagcggggcagtgttgga ggctgggtccccatcaaagctctccggcagaaatgccaggctcccaaagatcttcttgcagccagcaaactcctggatattcttccacaa aatcgtgtcctggtagcagagctgggggttccgctggatcaagacccctcctttcaagatctctgtgaggcttcgaagctgcagctcccgc aggcctcctggggaggcccctgtgacaggggtggtattgttcagcgggtctccattgtctagcacggccagggcatagttgtcctcaaag agctgggtgcctcgcacaatccgcagcctctgcagtgggacctgcctcacttggttgtgagcgatgagcacgtagccctgcacctcctgg atatcctgcaggaaggacaggctggcattggtgggcaggtaggtgagttccaggtttccctgcaccacctggcagccctggtagaggtg gcggagcatgtccaggtgggttctagatttatcacgtacccatttccccgcatcttttattttttaaatactttagggaaaaatggttttttgatttgct tttaaaggttgtggtgtagactcgtctgctgactgcatgctagaatctaagtcacttttcagaagcatccacaactgactctttcgccacttttctctt atttgcttttgttggtttatctggataagtaaggctttcaagctcactatccgacgacgctatggcttttcttcttttttaatttccgctgcgctatccg atgacagacctggatgacgacgctccacttgcagagttggtcggtcgactcctgaagcctcttcatttatagccacatttcctgtttgctcaccgt tgttattattgttattcggacctttctctgcttttgctttcaacattgctattaggtctgctttgttcgtattttttcactttattcgattttttctagttcc tcaatatcacgtgaacttacttcacgtgcagtttcgtatcttggtcccgtatttacctcgcttggctgctcttctgtttttttcttcttcccattcatcgt gtttagactggaatcttcgctatctgtcgctgcaaatattatgtcggggttaatcgtaatgcagttggcagtaatgaaaactaccatcatcgcacgcataa atctgtttaatcccacttatactccctcctcgtgatacgctaatacaaccttttttagaacaaggaaaattcggccttcattttcactaatttgttccgttaa aaattggattagcagttagttatcttcttaattagctaatataagaaaaaatattcatgaattattttaagaatatcacttggagaattaattttttctctaa catttgttaatcagttaaccccaactgcttcccaagcttcacccgggccactaactcaacgctagtagtggatttaatcccaaatgagccaaca gaaccagaaccagaaacagaacaagtaacattggagttagaaatggaagaagaaaaaagcaatgatttcgtgtgaataatgcacgaaatca ttgcttatttttttaaaaagcgatatactagatataacgaaacaacgaactgaataaagaatacaaaaaaagagccacgaccagttaaagcctg agaaactttaactgcgagccttaattgattaccaccaatcaattaaagaagtcgagacccaaaatttggtaaagtatttaattactttattaatcag atacttaaatatctgtaaaccattatatcgggttttttgaggggatttcaagtctttaagaagataccaggcaatcaattaagaaaaacttagttgat tgccttttttgttgtgattcaactttgatcgtagcttctaactaattaatttttcgtaagaaaggagaacagctgaatgaatatccctttttgttgtagaaa ctgtgcttcatgacggcttgttaaagtacaaatttaaaaatagtaaaattcgctcaatcactaccaagccaggtaaaagtaaaggggctatttttg cgtatcgctcaaaaaaaagcatgattggcggacgtggcgttgttctgacttccgaagaagcgattcacgaaaatcaagatacatttacgcattg gacaccaaacgtttatcgttatggtacgtatgcagacgaaaaccgttcatacactaaaggacattctgaaaacaatttaagacaaatcaatacct tctttattgattttgatattcacacggaaaaagaaactatttcagcaagcgatattttaacaacagctattgatttaggttttatgcctacgttaattat caaatctgataaaggttatcaagcatattttgttttagaaacgccagtctatgtgacttcaaaatcagaatttaaatctgtcaaagcagccaaataa tctcgcaaaatatccgagaatattttggaaagtctttgccagttgatctaacgtgcaatcattttgggattgctcgtataccaagaacggacaatg tagaatttttttgatcccaattaccgttattctttcaaagaatggcaagattggtctttcaaacaaacagataataagggctttactcgttcaagtctaa cggttttaagcggtacagaaggcaaaaaacaagtagatgaaccctggtttaatctcttattgcacgaaacgaaatttttcaggagaaaagggttt agtagggcgcaatagcgttatgtttaccctctctttagcctactttagttcaggctattcaatcgaaacgtgcgaatataatatgtttgagtttaata atcgattagatcaacccttagaagaaaagaagtaatcaaaattgttagaagtgccattcagaaaactatcaaggggctaatagggaatacat taccattctttgcaaagcttgggtatcaagtgatttaaccagtaaagatttatttgtccgtcaagggtggtttaaattcaagaaaaaagaagcga acgtcaacgtgttcattgtcagaatggaaagaagatttaatggcttatattagcgaaaaagcgatgtatacaagcctatttagcgacgacca aaaagagattagagaagtgctaggcattcctgaacggacattagataaattgctgaaggtactgaaggcgaatcaggaaattttctttaagat taaaccaggaagaaatggtggcattcaacttgctagtgttaaatcattgttgctatcgatcattaaattaaaaaagaagaacgagaaagctata taaaggcgctgacagcttcgtttaatttagaacgtacatttattcaagaaactctaaacaaattggcagaacgccccaaaacggacccacaact cgatttgtttagctacgatacaggctgaaaataaaacccgcactatgccattacatttatatctatgatacgtgtttgtttttcttttgctggctagctta attgcttatatttacctgcaataaaggattttcttacttccattatactcccattttccaaaaacatacggggaacacgggaacttattgtacaggca cctcatagttaatggtttcgagccttcctgcaatctcatccatggaaatatattcatcccctgccggcctattaatgtgacttttgtgccggcgg atattcctgatccagctccaccataaaattggtccatgcaaattcggccggcaattttcaggcgttttcccttcacaaggatgtcggtccctttcaat
```

-continued

```
tttcggagccagccgtccgcatagcctacaggcaccgtcccgatccatgtgtcttttccgctgtgtactcggctccgtagctgacgctctcgc cttttctgatcagtttgacatgtgacagtgtcgaatgcagggtaaatgccggacgcagctgaaacggtatctcgtccgacatgtcagcagacg ggcgaaggccatacatgccgatgccgaatctgactgcattaaaaaagccttttttcagccggagtccagcggcgctgttcgcgcagtggacc attagattcttttaacggcagcggagcaatcagctctttaaagcgctcaaactgcattaagaaatagcctctttcttttttcatccgctgtcgcaaat gggtaaataccccttttgcactttaaacgagggttgcggtcaagaattgccatcacgttctgaacttcttcctctgtttttacaccaagtctgttcatc cccgtatcgaccttcagatgaaaatgaagagaaccttttttcgtgtggcgggctgcctcctgaagccattcaacagaataacctgttaaggtca cgtcatactcagcagcgattgccacatactccgggggaaccgcgccaagcaccaatataggcgccttcaatccctttttgcgcagtgaaatc gcttcatccaaaatggccacggccaagcatgaagcacctgcgtcaagagcagcctttgctgtttctgcatcaccatgcccgtaggcgtttgctt tcacaactgccatcaagtggacatgttcaccgatatgtttttcatattgctgacattttcctttatcacggacaagtcaatttccgcccacgtatctc tgtaaaaggttttgtgctcatggaaaactcctctctttttttcagaaaatcccagtacgtaattaagtatttgagaattaattttatattgattaatacta agtttacccagttttcacctaaaaaacaaatgatgagataatagctccaaaggctaaagaggactataccaactatttgttaat.
```

In another embodiment, one of the antigens encoded by a sequence within SEQ ID NO: 2 is E7 (bolded in SEQ ID NO:2). In another embodiment, the E7 sequence is set forth in SEQ ID NO: 3

```
                                          (SEQ ID NO: 3)
Ctcgagcatggagatacacctacattgcatgaatatatgttagatttgc aaccagagacaactgatctctactgttatgagcaattaaatgacagctc agaggaggaggatgaaatagatggtccagctggacaagcagaaccggac agagcccattacaatattgtaaccttttgttgcaagtgtgactctacgc ttcggttgtgcgtacaaagcacacacgtagacattcgtactttggaaga cctgttaatgggcacactaggaattgtgtgccccatctgttctcagaaa ccataaactagt.
```

In one embodiment, one of the antigens encoded by a sequence within SEQ ID NO: 2 is a chimeric Her2-neu antigen (italicized in SEQ ID NO: 2). In another embodiment, the chimeric Her2-neu sequence is set forth in SEQ ID NO: 4.

```
                                          (SEQ ID NO: 4)
ctagtggtgatggtgatgatggagctcagatctgtctaagaggcagcca tagggcataagctgtgtcaccagctgcaccgtggatgtcaggcagatgc ccagaaggcgggagacatatggggagcccacaccagccatcacgtatgc ttcgtctaagatttcttttgttggctttggggatgtgttttccctcaac actttgatggccactggaattttcacattctccccatcagggatccaga tgcccttgtagactgtgccaaaagcgccagatccaagcaccttcacctt cctcagctccgtctctttcaggatccgcatctgcgcctggttgggcatc gctccgctaggtgtcagcggctccaccagctccgtttcctgcagcagtc tccgcatcgtgtacttccggatcttctgctgccctcgggcgcacagctg gtggcaggccaggccctcgcccacacactcgtcctctggccggttggca gtgtggagcagagcttggtgcgggttccgaaagagctggtcccagggca ccgtgtgcacgaagcagaggtgggtgttatggtggatgagggccagtcc actgcccagttccctcagtgagcgcagccccagccagctgatgcccagc ccttgcagggtcagcgagtaggcgccattgtgcagaattcgtcccgga ttacttgcaggttctggaagacgctgaggtcaggcaggctgtccggcca tgctgagatgtataggtaacctgtgatctcttccagagtctcaaacact tggagctgctctggctggagcggggcagtgttggaggctgggtccccat caaagctctccggcagaaatgccaggctcccaaagatcttcttgcagcc agcaaactcctggatattcttccacaaaatcgtgtcctggtagcagagc tgggggttccgctggatcaagacccctcctttcaagatctctgtgaggc ttcgaagctgcagctcccgcaggcctcctggggaggcccctgtgacagg ggtggtattgttcagcgggtctccattgtctagcacggccagggcatag ttgtcctcaaagagctgggtgcctcgcacaatccgcagcctctgcagtg ggacctgcctcacttggttgtgagcgatgagcacgtagccctgcacctc ctggatatcctgcaggaaggacaggctggcattggtgggcaggtaggtg agttccaggtttccctgcaccacctggcagccctggtagaggtggcgga gcatgtccaggtgggttctagat.
```

"Metabolic enzyme" refers, in another embodiment, to an enzyme involved in synthesis of a nutrient required by the host bacteria. In another embodiment, the term refers to an enzyme required for synthesis of a nutrient required by the host bacteria. In another embodiment, the term refers to an enzyme involved in synthesis of a nutrient utilized by the host bacteria. In another embodiment, the term refers to an enzyme involved in synthesis of a nutrient required for sustained growth of the host bacteria. In another embodiment, the enzyme is required for synthesis of the nutrient. Each possibility represents a separate embodiment of the present invention.

"Stably maintained" refers, in another embodiment, to maintenance of a nucleic acid molecule or plasmid in the absence of selection (e.g. antibiotic selection) for 10 generations, without detectable loss. In another embodiment, the period is 15 generations. In another embodiment, the period is 20 generations. In another embodiment, the period is 25 generations. In another embodiment, the period is 30 generations. In another embodiment, the period is 40 generations. In another embodiment, the period is 50 generations. In another embodiment, the period is 60 generations. In another embodiment, the period is 80 generations. In another embodiment, the period is 100 generations. In another embodiment, the period is 150 generations. In another embodiment, the period is 200 generations. In another embodiment, the period is 300 generations. In another embodiment, the period is 500 generations. In another embodiment, the period is more than generations. In another embodiment, the nucleic acid molecule or plasmid is maintained stably in vitro (e.g. in culture). In another embodiment, the nucleic acid molecule or plasmid is maintained stably in vivo. In another embodiment, the nucleic acid molecule or plasmid is maintained stably both in vitro and in vitro. Each possibility represents a separate embodiment of the present invention.

In another embodiment, the metabolic enzyme of the methods and compositions provided herein is an amino acid metabolism enzyme, where, in another embodiment, the metabolic enzyme is an alanine racemase enzyme. In another embodiment, the metabolic enzyme is a D-amino acid transferase enzyme. In another embodiment, the metabolic enzyme catalyzes a formation of an amino acid used for a cell wall synthesis in the recombinant Listeria strain, where in another embodiment the metabolic enzyme is an alanine racemase enzyme.

In another embodiment, the gene encoding the metabolic enzyme is expressed under the control of the Listeria p60 promoter. In another embodiment, the inlA (encodes internalin) promoter is used. In another embodiment, the hly promoter is used. In another embodiment, the ActA promoter is used. In another embodiment, the integrase gene is expressed under the control of any other gram positive promoter. In another embodiment, the gene encoding the metabolic enzyme is expressed under the control of any other promoter that functions in Listeria. The skilled artisan will appreciate that other promoters or polycistronic expression cassettes may be used to drive the expression of the gene. Each possibility represents a separate embodiment of the present invention.

In one embodiment, the live attenuated Listeria is a recombinant Listeria. In another embodiment, the recombinant Listeria comprises a mutation or a deletion of a genomic internalin C (inlC) gene, an ActA gene, a PlcA gene, PrfA gene or a PlcB gene. In another embodiment, the recombinant Listeria comprises a mutation or a deletion of a genomic actA gene and a genomic internalin C gene.

In one embodiment, the recombinant Listeria strain has been passaged through an animal host. In another embodiment, the animal host is a non-human animal host. In another embodiment, the passaging maximizes efficacy of the strain as a vaccine vector. In another embodiment, the passaging stabilizes the immunogenicity of the Listeria strain. In another embodiment, the passaging stabilizes the virulence of the Listeria strain. In another embodiment, the passaging increases the immunogenicity of the Listeria strain. In another embodiment, the passaging increases the virulence of the Listeria strain. In another embodiment, the passaging removes unstable sub-strains of the Listeria strain. In another embodiment, the passaging reduces the prevalence of unstable sub-strains of the Listeria strain. In another embodiment, the passaging attenuates the strain, or in another embodiment, makes the strain less virulent. Methods for passaging a recombinant Listeria strain through an animal host are well known in the art, and are described, for example, in U.S. patent application Ser. No. 10/541,614. Each possibility represents a separate embodiment of the methods and composition provided herein.

In one embodiment, this invention provides methods and compositions for preventing disease, treating disease and vaccinating a human subject.

In another embodiment, the present invention is directed to enhancing an anti-tumor immune response of a human. In another embodiment, the methods of enhancing an anti-tumor response in a subject by administering the compositions provided herein can be combined with other known anti-tumor or anti-cancer therapies. In another embodiment, Lm-LLO can be used alone, or in combination with any therapy in which an adjuvant is appropriate, and may have utility in settings where no adjuvant has been commonly used, such as chemotherapy or radiotherapy.

In another embodiment, the Listeria strain provided herein further comprises a third open reading frame encoding a metabolic enzyme.

In one embodiment, the metabolic enzyme is an amino acid metabolism enzyme. In another embodiment, the metabolic enzyme encoded by the second open reading frame is an alanine racemase enzyme or a D-amino acid transferase enzyme. In another embodiment, the metabolic enzyme encoded by the third open reading frame is an alanine racemase enzyme or a D-amino acid transferase enzyme. In another embodiment, the metabolic enzyme is encoded dal gene, where in another embodiment the dal gene is from B. subtilis. In another embodiment, the metabolic enzyme is encoded by the dat gene.

In another embodiment, the recombinant Listeria is an attenuated auxotrophic strain.

In one embodiment the attenuated strain is Lm dal(−)dat(−) (Lmdd). In another embodiment, the attenuated strains is Lm dal(−)dat(−)ΔactA (LmddA). LmddA is based on a Listeria vaccine vector which is attenuated due to the deletion of virulence gene actA and retains the plasmid for a desired heterologous antigen or truncated LLO expression in vivo and in vitro by complementation of dal gene.

In another embodiment the attenuated strain is Lmdda. In another embodiment, the attenuated strain is LmΔactA. In another embodiment, the attenuated strain is LmΔPrfA. In another embodiment, the attenuated strain is LmΔPlcB. In another embodiment, the attenuated strain is LmΔPlcA. In another embodiment, the strain is the double mutant or triple mutant of any of the above-mentioned strains. In another embodiment, this strain exerts a strong adjuvant effect which is an inherent property of Listeria-based vaccines. In another embodiment, this strain is constructed from the EGD Listeria backbone. In another embodiment, the strain used in the invention is a Listeria strain that expresses a non-hemolytic LLO. In yet another embodiment the Listeria strain is a prfA mutant, ActA mutant, a plcB deletion mutant, or a double mutant lacking both plcA and plcB. All these Listeria strain are contemplated for use in the methods provided herein. Each possibility represents a separate embodiment of the present invention.

In one embodiment, translocation of Listeria to adjacent cells is inhibited by the deletion of the actA gene and/or the inlC gene, which are involved in the process, thereby resulting in unexpectedly high levels of attenuation with increased immunogenicity and utility as a vaccine backbone.

In one embodiment, the recombinant Listeria strain provided herein is attenuated. In another embodiment, the recombinant Listeria lacks the ActA virulence gene. In another embodiment, the recombinant Listeria lacks the PrfA virulence gene.

In another embodiment, the recombinant Listeria vaccine strain comprises an adjuvant, wherein the adjuvant is listeriolysin O. In another embodiment, the recombinant Listeria vaccine strain comprises an adjuvant, wherein the adjuvant is ActA. In another embodiment, the recombinant Listeria vaccine strain comprises an adjuvant, wherein the adjuvant is a PEST amino acid sequence.

In another embodiment, the methods provided herein further provide methods of overcoming or "breaking" tolerance toward a heterologous antigen that is a self-antigen. Such antigens may be aberrantly expressed by various tumors which are subject to treatment or prophylaxis under the scope of the present invention by using the methods and compositions provided herein.

In one embodiment, the immune response induced by the methods and compositions provided herein is a therapeutic one. In another embodiment it is a prophylactic immune response. In another embodiment, it is an enhanced immune response over methods available in the art for inducing an immune response in a subject afflicted with the conditions provided herein. In another embodiment, the immune response leads to clearance of a tumor provided herein that is afflicting the subject.

In one embodiment, recombinant attenuated, *Listeria* expressing truncated listeriolysin O in combination with other therapeutic modalities are useful for enhancing an immune response, and for preventing, and treating a disease including cancer or solid tumors. In one embodiment, recombinant attenuated, *Listeria* expressing truncated ActA in combination with other therapeutic modalities are useful for enhancing an immune response, and for preventing, and treating a disease including cancer or solid tumors. In one embodiment, recombinant attenuated, *Listeria* expressing PEST amino acid sequence in combination with other therapeutic modalities are useful for enhancing an immune response, and for preventing, and treating a disease including cancer or solid tumors.

In another embodiment, provided herein is a method of improving the immunogenicity of a therapeutic vaccine, the method comprising co-administering the vaccine and a live attenuated *Listeria* to a subject, wherein the live attenuated *Listeria* enhances the immunogenicity of the vaccine, thereby improving the immunogenicity of the vaccine. In another embodiment, the live attenuated *Listeria* is a recombinant *Listeria*. In one embodiment, the method enables the treatment of a tumor for which the vaccine is specific against.

In one embodiment, provided herein is a method of enhancing an immune response against a disease in an antigen-independent manner, the method comprising administering a live attenuated *Listeria* or recombinant *Listeria* to a subject.

In another embodiment, the live attenuated or recombinant *Listeria* provided herein expresses an LLO protein or a non-hemolytic fragment thereof. In another embodiment, *Listeria* provided herein is used alone or is combined with an additional adjuvant. In another embodiment, the additional adjuvant utilized in methods and compositions of the present invention is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21 (a purified fraction of Saponin extracted from *Quillarja Saponaria*). In another embodiment, the adjuvant is monophosphoryl lipid A. In another embodiment, the adjuvant comprises monophosphoryl lipid A. In another embodiment, the adjuvant is SBAS2 (SB SMITHKLINE BEECHAM adjuvant system 2, Monophosphoryl Lipid A (MPL), QS21, and a proprietary oil in water emulsion based adjuvant). In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. In another embodiment, the adjuvant is or comprises any other adjuvant known in the art. Each possibility represents a separate embodiment of the present invention.

The LLO utilized in the methods and compositions provided herein is, in one embodiment, a *Listeria* LLO. In one embodiment, the *Listeria* from which the LLO is derived is *Listeria monocytogenes* (Lm). In another embodiment, the *Listeria* is *Listeria ivanovii*. In another embodiment, the *Listeria* is *Listeria* welshimeri. In another embodiment, the *Listeria* is *Listeria seeligeri*.

In one embodiment, the LLO protein is encoded by the following nucleic acid sequence set forth in (SEQ ID NO: 5).

```
                                                  (SEQ ID NO: 5)
atgaaaaaaataatgctagttttttattacacttatattagttagtctac caattgcgcaacaaactgaagcaaaggatgcatctgcattcaataaaga aaattcaatttcatccatggcaccaccagcatctccgcctgcaagtcct aagacgccaatcgaaaagaaacacgcggatgaaatcgataagtatatac aaggattggattacaataaaaacaatgtattagtataccacggagatgc agtgacaaatgtgccgccaagaaaaggttacaaagatggaaatgaatat attgttgtggagaaaagaagaaatccatcaatcaaaataatgcagaca ttcaagttgtgaatgcaatttcgagcctaacctatccaggtgctctcgt aaaagcgaattcggaattagtagaaaatcaaccagatgttctccctgta aaacgtgattcattaacactcagcattgatttgccaggtatgactaatc aagacaataaaatagttgtaaaaaatgccactaaatcaaacgttaacaa cgcagtaaatacattagtggaaagatggaatgaaaaatatgctcaagct tatccaaatgtaagtgcaaaaattgattatgatgacgaaatggcttaca gtgaatcacaattaattgcgaaatttggtacagcatttaaagctgtaaa taatagcttgaatgtaaacttcggcgcaatcagtgaagggaaaatgcaa gaagaagtcattagttttaaacaaatttactataacgtgaatgttaatg aacctacaagaccttccagattttttcggcaaagctgttactaaagagca gttgcaagcgcttggagtgaatgcagaaaatcctcctgcatatatctca agtgtggcgtatggccgtcaagtttatttgaaattatcaactaattccc atagtactaaagtaaaagctgcttttgatgctgccgtaagcggaaaatc tgtctcaggtgatgtagaactaacaaatatcatcaaaaattcttccttc
```

-continued
aaagccgtaatttacggaggttccgcaaaagatgaagttcaaatcatcg acggcaacctcggagacttacgcgatattttgaaaaaaggcgctactttt taatcgagaaacaccaggagttcccattgcttatacaacaaacttccta aaagacaatgaattagctgttattaaaaacaactcagaatatattgaaa caacttcaaaagcttatacagatggaaaaattaacatcgatcactctgg aggatacgttgctcaattcaacatttcttgggatgaagtaaattatgat ctcgag.

In another embodiment, the LLO protein has the sequence SEQ ID NO: 6

```
                                     (SEQ ID NO: 6)
M K K I M L V F I T L I L V S L P I A Q Q T E A K

D A S A F N K E N S I S S M A P P A S P P A S P K

T P I E K K H A D E I D K Y I Q G L D Y N K N N V

L V Y H G D A V T N V P P R K G Y K D G N E Y I V

V E K K K K S I N Q N N A D I Q V V N A I S S L T

Y P G A L V K A N S E L V E N Q P D V L P V K R D

S L T L S I D L P G M T N Q D N K I V V K N A T K

S N V N N A V N T L V E R W N E K Y A Q A Y P N V

S A K I D Y D D E M A Y S E S Q L I A K F G T A F

K A V N N S L N V N F G A I S E G K M Q E E V I S

F K Q I Y Y N V N V N E P T R P S R F F G K A V T

K E Q L Q A L G V N A E N P P A Y I S S V A Y G R

Q V Y L K L S T N S H S T K V K A A F D A A V S G

K S V S G D V E L T N I I K N S S F K A V I Y G G

S A K D E V Q I I D G N L G D L R D I L K K G A T

F N R E T P G V P I A Y T T N F L K D N E L A V I

K N N S E Y I E T T S K A Y T D G K I N I D H S G

G Y V A Q F N I S W D E V N Y D L
```

The first 25 amino acids of the proprotein corresponding to this sequence are the signal sequence and are cleaved from LLO when it is secreted by the bacterium. Thus, in this embodiment, the full length active LLO protein is 504 residues long. In another embodiment, the LLO protein has a sequence set forth in GenBank Accession No. DQ054588, DQ054589, AY878649, U25452, or U25452. In another embodiment, the LLO protein is a variant of an LLO protein. In another embodiment, the LLO protein is a homologue of an LLO protein. Each possibility represents a separate embodiment of the present invention.

In another embodiment, "truncated LLO" or "tLLO" refers to a fragment of LLO that comprises the PEST-like domain. In another embodiment, the terms refer to an LLO fragment that does not contain the activation domain at the amino terminus and does not include cystine 484. In another embodiment, the LLO fragment consists of a PEST sequence. In another embodiment, the LLO fragment comprises a PEST sequence. In another embodiment, the LLO fragment consists of about the first 400 to 441 amino acids of the 529 amino acid full-length LLO protein. In another embodiment, the LLO fragment is a non-hemolytic form of the LLO protein.

In one embodiment, the LLO fragment consists of about residues 1-25. In another embodiment, the LLO fragment consists of about residues 1-50. In another embodiment, the LLO fragment consists of about residues 1-75. In another embodiment, the LLO fragment consists of about residues 1-100. In another embodiment, the LLO fragment consists of about residues 1-125. In another embodiment, the LLO fragment consists of about residues 1-150. In another embodiment, the LLO fragment consists of about residues 1175. In another embodiment, the LLO fragment consists of about residues 1-200. In another embodiment, the LLO fragment consists of about residues 1-225. In another embodiment, the LLO fragment consists of about residues 1-250. In another embodiment, the LLO fragment consists of about residues 1-275. In another embodiment, the LLO fragment consists of about residues 1-300. In another embodiment, the LLO fragment consists of about residues 1-325. In another embodiment, the LLO fragment consists of about residues 1-350. In another embodiment, the LLO fragment consists of about residues 1-375. In another embodiment, the LLO fragment consists of about residues 1-400. In another embodiment, the LLO fragment consists of about residues 1-425. Each possibility represents a separate embodiment of the present invention.

In another embodiment, homologues of LLO from other species, including known lysins, such as streptolysin O, perfringolysin O, pneumolysin, etc, or fragments thereof may be used in the invention.

In one embodiment, the live attenuated *Listeria* or recombinant *Listeria* provided herein expresses an ActA protein or a fragment thereof. In another embodiment of the methods and compositions of the present invention, a fragment of an ActA protein is fused to the heterologous antigen or a fragment thereof also provided herein. In another embodiment, the fragment of an ActA protein has the sequence:
MRAMMVVFITANCITINPDIIFAATDSEDSSLNT-DEWEEEKTEEQPSEVNTGPRY ETAREVSSRDIKELEKSNKVRNTNKADLIAMLKEKA-EKGPNINNNNSEQTENAAINEEAS GADRPAIQVER-RHPGLPSDSAAEIKKRRKAIASSDSELESLTYPDKPT-KVNKKKVAKESV ADASESDLDSSMQSADESSPQPLKANQQPFFPKVFK-KIKDAGKWVRDKIDENPEVKKAI VDKSAGLIDQLLT-KKKSEEVNASDFPPPPTDEELRLALPETPMLLGFNA-PATSEPSSFEFPP PPTDEELRLALPETPMLLGFNAPATSEPSSFEFPPPPT-EDELEIIRETASSLDSSFTRGDLAS LRNAINRHSQNF-SDFPPIPTEEELNGRGGRP (SEQ ID No: 7). In another embodiment, an ActA AA sequence of methods and compositions of the present invention comprises the sequence set forth in SEQ ID No: 7. In another embodiment, the ActA AA sequence is a homologue of SEQ ID No: 7. In another embodiment, the ActA AA sequence is a variant of SEQ ID No: 7. In another embodiment, the ActA AA sequence is a fragment of SEQ ID No: 7. In another embodiment, the ActA AA sequence is an isoform of SEQ ID No: 5. Each possibility represents a separate embodiment of the present invention.

In another embodiment, the ActA fragment is encoded by a recombinant nucleotide comprising the sequence: ATGCGTGCGATGATGGTGGTTTTCATTACTGCCAAT-TGCATTACGATTAACCCCGACA TAATATTTGCAGC-GACAGATAGCGAAGATTCTAGTCTAAACACAGAT-GAATGGGAA GAAGAAAAAACAGAAGAGCAACCAAGCGAGG-
TAAATACGGGACCAAGATACGAAA CTGCACGT-
GAAGTAAGTTCACGTGATATTAAAGAACTA-
GAAAAATCGAATAAAGTG
AGAAATACGAACAAAGCAGACCTAATAGCAATGTT-
GAAAGAAAAAGCAGAAAAAG GTCCAAATAT-
CAATAATAACAACAGTGAACAAACTGAGAATGCG-
GCTATAAATGAA
GAGGCTTCAGGAGCCGACCGACCAGCTATA-
CAAGTGGAGCGTCGTCATCCAGGATT GCCATCG-
GATAGCGCAGCGGAAAT-
TAAAAAAAGAAGGAAAGCCATAGCATCATCGG
ATAGTGAGCTTGAAAGCCTTACTTATCCGGA-
TAAACCAACAAAAGTAAATAAGAAA AAAGTGGC-
GAAAGAGTCAGTTGCGGATGCTTCTGAAAGT-
GACTTAGATTCTAGCATG
CAGTCAGCAGATGAGTCTTCACCACAACCTT-TAAAAGCAAACCAACAACCATTTTTC CCTAAAGT-ATTTAAAAAAAATAAAAGATGCGGGGAAATGGG-TACGTGATAAAATCGA CGAAAATCCTGAAGTAAAGAAAGCGATTGTTGA-TAAAAGTGCAGGGTTAATTGACC AATTATTAAC-CAAAAAGAAAAGTGAAGAGGTAAATGCTTCG-GACTTCCCGCCACCA CCTACGGATGAAGAGTTAAGACTTGCTTTGCCAGA-GACACCAATGCTTCTTGGTTTT AATGCTCCTGCTA-CATCAGAACCGAGCTCATTCGAATTTCCACCAC-CACCTACGGAT GAAGAGTTAAGACTTGCTTTGCCAGAGACGC-CAATGCTTCTTGGTTTTAATGCTCCTG CTACATCG-GAACCGAGCTCGTTCGAATTTCCACCGCCTC-CAACAGAAGATGAACTAG AAATCATCCGGGAAACAGCATCCTCGCTAGAT-TCTAGTTTTACAAGAGGGGATTTAG CTAGTTT-GAGAAATGCTATTAATCGCCATAGT-CAAAATTTCTCTGATTTCCCACCAAT CCCAACAGAAGAAGAGTTGAA CGGGAGAGGCGG-TAGACCA (SEQ ID NO: 8). In another embodiment, the recombinant nucleotide has the sequence set forth in SEQ ID NO: 8. In another embodiment, an ActA-encoding nucleotide of methods and compositions of the present invention comprises the sequence set forth in SEQ ID No: 8. In another embodiment, the ActA-encoding nucleotide is a homologue of SEQ ID No: 8. In another embodiment, the ActA-encoding nucleotide is a variant of SEQ ID No: 8. In another embodiment, the ActA-encoding nucleotide is a fragment of SEQ ID No: 8. In another embodiment, the ActA-encoding nucleotide is an isoform of SEQ ID No: 8. Each possibility represents a separate embodiment of the present invention.

In another embodiment, the ActA fragment is encoded by a recombinant nucleotide comprising the sequence:

Tttatcacgtacccatttccccgcatcttttatttttttaaatactt-tagggaaaaatggtttttgatttgcttttaaaggttgtggtgtaga ctcgtctgct-gactgcatgctagaatctaagtcactttcagaagcatccacaactgactctttcgc-cacttttctcttatttgcttttgttggtttatct ggataagtaaggctttcaagctcactatccgacgacgctatggcttttcttctttttt-taatttccgctgcgctatccgatgacagacctggatgac gacgctccacttgca-gagttggtcggtcgactcctgaagcctcttcatttatagccacatttcctgtttgct-caccgttgttattattgttattcgga cctttctctgcttttgctttcaacattgctattaggtctgctttgttcgt-atttttcactttattcgatttttctagttcctcaatatcacgtgaacttacttca cgtgca-gtttcgtatcttggtcccgtatttacctcgcttggctgctcttctgtttttcttcttc-ccattcatctgtgtttagactggaatcttcgctatct gtcgctgcaaatattatgtcggggttaatcgtaatgcagttggcagtaatgaaaac-taccatcatcgcacgcat (SEQ ID NO: 9). In another embodiment, the recombinant nucleotide has the sequence set forth in SEQ ID NO: 9. In another embodiment, an ActA-encoding nucleotide of methods and compositions of the present invention comprises the sequence set forth in SEQ ID No: 9. In another embodiment, the ActA-encoding nucleotide is a homologue of SEQ ID No: 9. In another embodiment, the ActA-encoding nucleotide is a variant of SEQ ID No: 9. In another embodiment, the ActA-encoding nucleotide is a fragment of SEQ ID No: 9. In another embodiment, the ActA-encoding nucleotide is an isoform of SEQ ID No: 9. In another embodiment SEQ ID NO: 9 is used to arrive at the construct of SEQ ID NO: 2, also provided herein. Each possibility represents a separate embodiment of the present invention.

In another embodiment of methods and compositions of the present invention, a fragment of an ActA protein is fused to a heterologous antigen or fragment thereof. In another embodiment, the fragment of an ActA protein has the sequence as set forth in Genbank Accession No. AAF04762. In another embodiment, an ActA AA sequence of methods and compositions of the present invention comprises the sequence set forth in Genbank Accession No. AAF04762. In another embodiment, the ActA AA sequence is a homologue of Genbank Accession No. AAF04762. In another embodiment, the ActA AA sequence is a variant of Genbank Accession No. AAF04762. In another embodiment, the ActA AA sequence is a fragment of Genbank Accession No. AAF04762. In another embodiment, the ActA AA sequence is an isoform of Genbank Accession No. AAF04762. Each possibility represents a separate embodiment of the present invention.

An N-terminal fragment of an ActA protein utilized in methods and compositions of the present invention has, in another embodiment, the sequence set forth in SEQ ID NO: 10:

MRAMMVVFITANCITINPDIIFAATDSEDSSLNT-DEWEEEKTEEQPSEVNTGPRYETARE VSSRDIKELEKSNKVRNTNKADLIAMLKEKAEKGP-NINNNNSEQTENAAINEEASGADR PAIQVERRH-PGLPSDSAAEIKKRRKAIASSDSELESLTYPDKPTK-VNKKKVAKESVADAS ESDLDSSMQSADESSPQPLKANQQPFFPKVFK-KIKDAGKWVRDKIDENPEVKKAIVDKS AGLIDQLLT-KKKSEEVNASDFPPPPTDEELRLALPETPMLLGFNA-PATSEPSSFEFPPPPTD EELRLALPETPMLLGFNAPATSEPSSFEFPPPPT-EDELEIIRETASSLDSSFTRGDLASLRNA INRHSQNF-SDFPPIPTEEELNGRGGRP. In another embodiment, the ActA fragment comprises the sequence set forth in SEQ ID NO: 10. In another embodiment, the ActA fragment is any other ActA fragment known in the art. Each possibility represents a separate embodiment of the present invention.

In another embodiment, the recombinant nucleotide encoding a fragment of an ActA protein comprises the sequence set forth in SEQ ID NO: 11:

Atgcgtgcgatgatggtggttttcattactgccaattgcattacgattaaccccga-cataatatttgcagcgacagatagcgaagattctagtct aaacacagat-gaatgggaagaagaaaaaacagaagagcaaccaagcgaggtaaatacgggac-caagatacgaaactgcacgtgaagta agttcacgtgatattaaagaactagaaaaatcgaataaagtgagaaatac-gaacaaagcagacctaatagcaatgttgaaagaaaaagcaga aaaaggtc-caaatatcaataataacaacagtgaacaaactgagaatgcggctataaat-gaagaggcttcaggagccgaccgaccagctata caagtggagcgtcgtcatccaggattgccatcggatagcgcagcggaaat-taaaaaaagaaggaaagccatagcatcatcggatagtgag cttgaaagccttact-tatccggataaaccaacaaaagtaaataagaaaaaagtggcgaaagagtcagtt-gcggatgcttctgaaagtgactta gattctagcatgcagtcagcagatgagtcttcaccacaacctttaaaagcaaac-caacaaccatttttccctaaagtatttaaaaaaataaaaga tgcggggaaatgggtacgtgataaaatcgacgaaaatcctgaagtaaagaaagcgattgttgataaaagt-
gcagggttaattgaccaattatt
aaccaaaaagaaaagtgaagaggtaaatgcttcggacttcccgccaccac-
ctacggatgaagagttaagacttgctttgccagagacacca atgcttcttggttt-
taatgctcctgctacatcagaaccgagctcattcgaatttccaccaccacctacg-
gatgaagagttaagacttgctttgcca
gagacgccaatgcttcttggttttaatgctcctgctacatcggaaccgagctcgttc-
gaatttccaccgcctccaacagaagatgaactagaaa tcatccgggaaacag-
catcctcgctagattctagttttacaagagggggatttagctagtttgagaaatgctat-
taatcgccatagtcaaaatttctc
tgatttccaccaatcccaacagaagaagagttgaacgggagaggcggta-
gacca. In another embodiment, the recombinant nucleotide
has the sequence set forth in SEQ ID NO: 11. In another
embodiment, the recombinant nucleotide comprises any
other sequence that encodes a fragment of an ActA protein.
Each possibility represents a separate embodiment of the
present invention.

In another embodiment, the ActA fragment is encoded by
a recombinant nucleotide comprising the sequence as set
forth in Genbank Accession No. AF103807. In another
embodiment, the recombinant nucleotide has the sequence
set forth in Genbank Accession No. AF103807. In another
embodiment, an ActA-encoding nucleotide of methods and
compositions of the present invention comprises the
sequence set forth in Genbank Accession No. AF103807. In
another embodiment, the ActA-encoding nucleotide is a
homologue of Genbank Accession No. AF103807. In
another embodiment, the ActA-encoding nucleotide is a
variant of Genbank Accession No. AF103807. In another
embodiment, the ActA-encoding nucleotide is a fragment of
Genbank Accession No. AF103807. In another embodiment,
the ActA-encoding nucleotide is an isoform of Genbank
Accession No. AF103807. Each possibility represents a
separate embodiment of the present invention.

In another embodiment, the ActA fragment is any other
ActA fragment known in the art. In another embodiment, a
recombinant nucleotide of the present invention comprises
any other sequence that encodes a fragment of an ActA
protein. In another embodiment, the recombinant nucleotide
comprises any other sequence that encodes an entire ActA
protein. Each possibility represents a separate embodiment
of the present invention.

In one embodiment, the live attenuated Listeria or recom-
binant Listeria provided herein expresses a PEST sequence
peptide. In another embodiment of methods and composi-
tions of the present invention, a PEST AA sequence is fused
to the heterologous antigen or fragment. In another embodi-
ment, the PEST AA sequence is KENSISSMAPPASPPASP-
KTPIEKKHADEIDK (SEQ ID NO: 12). In another embodi-
ment, the PEST sequence is KENSISSMAPPASPPASPK
(SEQ ID No: 13). In another embodiment, fusion of an
antigen to any LLO sequence that includes one of the PEST
AA sequences enumerated herein can enhance cell mediated
immunity against HMW-MAA.

In another embodiment, the PEST AA sequence is a PEST
sequence from a Listeria ActA protein. In another embodi-
ment, the PEST sequence is KTEEQPSEVNTGPR (SEQ ID
NO: 14), KASVTDTSEGDLDSSMQSADESTPQPLK
(SEQ ID NO: 15), KNEEVNASDFPPPPTDEELR (SEQ ID
NO: 16), or RGGIPTSEEFSSLNSGDFTDDENSETTEEE-
IDR (SEQ ID NO: 17). In another embodiment, the PEST-
like sequence is a variant of the PEST sequence described
hereinabove, which in one embodiment, is KESVVDASE
SDLDSSMQSADESTPQPLK (SEQ ID NO: 18), K
SEEVNASDFPPPPTDEELR (SEQ ID NO: 19), or RGG
RPTSEEFSSLNSGDFTDDENSETTEEEIDR (SEQ ID
NO: 20), as would be understood by a skilled artisan. In
another embodiment, the PEST-like sequence is from List-
eria seeligeri cytolysin, encoded by the lso gene. In another
embodiment, the PEST sequence is RSEVTISPAETPESP-
PATP (SEQ ID NO: 21). In another embodiment, the PEST
sequence is from Streptolysin O protein of Streptococcus sp.
In another embodiment, the PEST sequence is from Strep-
tococcus pyogenes Streptolysin O, e.g. KQN-
TASTETTTTNEQPK (SEQ ID NO: 22) at AA 35-51. In
another embodiment, the PEST-like sequence is from Strep-
tococcus equisimilis Streptolysin O, e.g. KQNTAN-
TETTTTNEQPK (SEQ ID NO: 23) at AA 38-54. In another
embodiment, the PEST-like sequence has a sequence
selected from SEQ ID NO: 14-20. In another embodiment,
the PEST-like sequence has a sequence selected from SEQ
ID NO: 14-23. In another embodiment, the PEST sequence
is another PEST AA sequence derived from a prokaryotic
organism.

Identification of Proline, Glutamic acid, Serine and
Threonine (PEST) sequences is well known in the art, and
is described, for example in Rogers S et al (Amino acid
sequences common to rapidly degraded proteins: the PEST
hypothesis. Science 1986; 234(4774):364-8) and Rech-
steiner M et al (PEST sequences and regulation by proteoly-
sis. Trends Biochem Sci 1996; 21(7):267-71). "PEST
sequence" refers, in another embodiment, to a region rich in
proline (P), glutamic acid (E), serine (S), and threonine (T)
residues. In another embodiment, the PEST sequence is
flanked by one or more clusters containing several positively
charged amino acids. In another embodiment, the PEST
sequence mediates rapid intracellular degradation of pro-
teins containing it. In another embodiment, the PEST
sequence fits an algorithm disclosed in Rogers et al. In
another embodiment, the PEST sequence fits an algorithm
disclosed in Rechsteiner et al. In another embodiment, the
PEST sequence contains one or more internal phosphory-
lation sites, and phosphorylation at these sites precedes
protein degradation.

In one embodiment, PEST sequences of prokaryotic
organisms are identified in accordance with methods such as
described by, for example Rechsteiner and Rogers (1996,
Trends Biochem. Sci. 21:267-271) for LM and in Rogers S
et al (Science 1986; 234(4774):364-8). Alternatively, PEST
AA sequences from other prokaryotic organisms can also be
identified based on this method. Other prokaryotic organ-
isms wherein PEST AA sequences would be expected to
include, but are not limited to, other Listeria species. In one
embodiment, the PEST sequence fits an algorithm disclosed
in Rogers et al. In another embodiment, the PEST sequence
fits an algorithm disclosed in Rechsteiner et al. In another
embodiment, the PEST sequence is identified using the
PEST-find program.

In another embodiment, identification of PEST motifs is
achieved by an initial scan for positively charged AA R, H,
and K within the specified protein sequence. All AA between
the positively charged flanks are counted and only those
motifs are considered further, which contain a number of AA
equal to or higher than the window-size parameter. In
another embodiment, a PEST-like sequence must contain at
least 1 P, 1 D or E, and at least 1 S or T.

In another embodiment, the quality of a PEST motif is
refined by means of a scoring parameter based on the local
enrichment of critical AA as well as the motifs hydropho-
bicity. Enrichment of D, E, P, S and T is expressed in mass
percent (w/w) and corrected for 1 equivalent of D or E, 1 of
P and 1 of S or T. In another embodiment, calculation of hydrophobicity follows in principle the method of J. Kyte and R. F. Doolittle (Kyte, J and Doolittle, R F. J. Mol. Biol. 157, 105 (1982).

In another embodiment, a potential PEST motif's hydrophobicity is calculated as the sum over the products of mole percent and hydrophobicity index for each AA species. The desired PEST score is obtained as combination of local enrichment term and hydrophobicity term as expressed by the following equation:

PEST score=0.55*DEPST−0.5*hydrophobicity index.

It will be appreciated that the terms "PEST sequence", "PEST-like sequence" or "PEST-like sequence peptide" can encompass peptides having a score of at least +5, using the above algorithm. In another embodiment, the term refers to a peptide having a score of at least 6. In another embodiment, the peptide has a score of at least 7. In another embodiment, the score is at least 8. In another embodiment, the score is at least 9. In another embodiment, the score is at least 10. In another embodiment, the score is at least 11. In another embodiment, the score is at least 12. In another embodiment, the score is at least 13. In another embodiment, the score is at least 14. In another embodiment, the score is at least 15. In another embodiment, the score is at least 16. In another embodiment, the score is at least 17. In another embodiment, the score is at least 18. In another embodiment, the score is at least 19. In another embodiment, the score is at least 20. In another embodiment, the score is at least 21. In another embodiment, the score is at least 22. In another embodiment, the score is at least 22. In another embodiment, the score is at least 24. In another embodiment, the score is at least 24. In another embodiment, the score is at least 25. In another embodiment, the score is at least 26. In another embodiment, the score is at least 27. In another embodiment, the score is at least 28. In another embodiment, the score is at least 29. In another embodiment, the score is at least 30. In another embodiment, the score is at least 32. In another embodiment, the score is at least 35. In another embodiment, the score is at least 38. In another embodiment, the score is at least 40. In another embodiment, the score is at least 45. Each possibility represents a separate embodiment of the present invention.

In another embodiment, the PEST sequence is identified using any other method or algorithm known in the art, e.g the CASPREDICTOR (Garay-Malpartida H M, Occhiucci J M, Alves J, Belizario J E. Bioinformatics. 2005 June; 21 Suppl 1:i169-76). In another embodiment, the following method is used.

A PEST index is calculated for each stretch of appropriate length (e.g. a 30-35 AA stretch) by assigning a value of 1 to the AA Ser, Thr, Pro, Glu, Asp, Asn, or Gln. The coefficient value (CV) for each of the PEST residue is 1 and for each of the other AA (non-PEST) is 0.

Each method for identifying a PEST-like sequence represents a separate embodiment of the present invention.

In another embodiment, the PEST sequence is any other PEST sequence known in the art. Each PEST sequence and type thereof represents a separate embodiment of the present invention.

It will be appreciated that the term "Fusion to a PEST sequence" encompass fusion to a protein fragment comprising a PEST sequence. In another embodiment, the term includes cases wherein the protein fragment comprises surrounding sequence other than the PEST sequence. In another embodiment, the protein fragment consists of the PEST sequence. It will also be appreciated that the term "fusion" encompasses fusion to two peptides or protein fragments either linked together at their respective ends or embedded one within the other.

In another embodiment, provided herein is a vaccine comprising a recombinant form of *Listeria* of the present invention.

In another embodiment, provided herein, is a culture of a recombinant form of *Listeria* of the present invention.

In another embodiment, the *Listeria* of methods and compositions of the present invention is *Listeria monocytogenes*. In another embodiment, the *Listeria* is *Listeria ivanovii*. In another embodiment, the *Listeria* is *Listeria welshimeri*. In another embodiment, the *Listeria* is *Listeria seeligeri*. Each type of *Listeria* represents a separate embodiment of the present invention.

In one embodiment, attenuated *Listeria* strains, such as LM ΔactA mutant, *L. monocytogenes* ΔplcA, or ΔActA, ΔINL-b, ΔINL-c are used in the present invention. In another embodiment, attenuated *Listeria* strains are constructed by introducing one or more attenuating mutations, as will be understood by one of average skill in the art when equipped with the disclosure herein. Examples of such strains include, but are not limited to *Listeria* strains auxotrophic for aromatic amino acids and mutant for the formation of lipoteichoic acids and those attenuated by a lack of a virulence gene (see examples herein).

In another embodiment, the nucleic acid molecule of methods and compositions of the present invention is operably linked to a promoter/regulatory sequence. In another embodiment, the first open reading frame of methods and compositions of the present invention is operably linked to a promoter/regulatory sequence. In another embodiment, the second open reading frame of methods and compositions of the present invention is operably linked to a promoter/regulatory sequence. In another embodiment, each of the open reading frames are operably linked to a promoter/regulatory sequence. Each possibility represents a separate embodiment of the present invention.

The skilled artisan, when equipped with the present disclosure and the methods provided herein, will readily understand that different transcriptional promoters, terminators, carrier vectors or specific gene sequences (e.g. those in commercially available cloning vectors) can be used successfully in methods and compositions of the present invention. As is contemplated in the present invention, these functionalities are provided in, for example, the commercially available vectors known as the PUC (plasmid cloning vectors) series. In another embodiment, non-essential DNA sequences (e.g. antibiotic resistance genes) are removed. Each possibility represents a separate embodiment of the present invention. In another embodiment, a commercially available plasmid is used in the present invention. Such plasmids are available from a variety of sources, for example, INVITROGEN (La Jolla, Calif.), STRATAGENE (La Jolla, Calif.), CLONTECH (Palo Alto, Calif.), or can be constructed using methods well known in the art.

Another embodiment is a plasmid such as PCR2.1 (INVITROGEN, La Jolla, Calif.), which is a prokaryotic expression vector with a prokaryotic origin of replication and promoter/regulatory elements to facilitate expression in a prokaryotic organism. In another embodiment, extraneous nucleotide sequences are removed to decrease the size of the plasmid and increase the size of the cassette that can be placed therein.

Such methods are well known in the art, and are described in, for example, Sambrook et al. (1989, Molecular Cloning: A Laboratory Manual, Cold Spring Harbor Laboratory Press, New York) and Ausubei et al. (1997, Current Protocols in Molecular Biology, Green & Wiley, New York).

Antibiotic resistance genes are used in the conventional selection and cloning processes commonly employed in molecular biology and vaccine preparation. Antibiotic resistance genes contemplated in the present invention include, but are not limited to, gene products that confer resistance to ampicillin, penicillin, methicillin, streptomycin, erythromycin, kanamycin, tetracycline, cloramphenicol (CAT), neomycin, hygromycin, gentamicin and others well known in the art. Each gene represents a separate embodiment of the present invention.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the Listeria vaccine strain of the present invention is transformed by electroporation. Each method represents a separate embodiment of the present invention.

In another embodiment, conjugation is used to introduce genetic material and/or plasmids into bacteria. Methods for conjugation are well known in the art, and are described, for example, in Nikodinovic J et al. (A second generation snp-derived Escherichia coli-Streptomyces shuttle expression vector that is generally transferable by conjugation. Plasmid. 2006 November; 56(3):223-7) and Auchtung J M et al (Regulation of a Bacillus subtilis mobile genetic element by intercellular signaling and the global DNA damage response. Proc Natl Acad Sci USA. 2005 Aug. 30; 102 (35):12554-9). Each method represents a separate embodiment of the present invention.

It will be appreciated that the term "transforming," can be used identically with the term "transfecting," and refers to engineering a bacterial cell to take up a plasmid or other heterologous DNA molecule. It is also to be understood that the term "transforming" can refer to engineering a bacterial cell to express a gene of a plasmid or other heterologous DNA molecule.

Plasmids and other expression vectors useful in the present invention are described elsewhere herein, and can include such features as a promoter/regulatory sequence, an origin of replication for gram negative and gram positive bacteria, an isolated nucleic acid encoding a fusion protein and an isolated nucleic acid encoding an amino acid metabolism gene. Further, an isolated nucleic acid encoding a fusion protein and an amino acid metabolism gene will have a promoter suitable for driving expression of such an isolated nucleic acid. Promoters useful for driving expression in a bacterial system are well known in the art, and include bacteriophage lambda, the bla promoter of the beta-lactamase gene of PBR322 (plasmid cloning vector), and the CAT promoter of the chloramphenicol acetyl transferase gene of PBR325 (plasmid cloning vector). Further examples of prokaryotic promoters include the major right and left promoters of 5 bacteriophage lambda (PL and PR), the trp, recA, lacZ, lad, and gal promoters of E. coli, the alpha-amylase (Ulmanen et al, 1985. J. Bacteriol. 162: 176-182) and the S28-specific promoters of B. subtilis (Gilman et al, 1984 Gene 32: 11-20), the promoters of the bacteriophages of Bacillus (Gryczan, 1982, In: The Molecular Biology of the Bacilli, Academic Press, Inc., New York), and Streptomyces promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the Listerial prfA promoter, the Listerial hly promoter, the Listerial p60 promoter and the Listerial ActA promoter (GenBank Acc. No. NC_003210) or fragments thereof.

In one embodiment, DNA encoding the recombinant non-hemolytic LLO is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid. Each method represents a separate embodiment of the present invention.

Recombinant proteins of the present invention are synthesized, in another embodiment, using recombinant DNA methodology. This involves, in one embodiment, creating a DNA sequence, placing the DNA in an expression cassette, such as the plasmid of the present invention, under the control of a particular promoter/regulatory element, and expressing the protein. DNA encoding the protein (e.g. non-hemolytic LLO) of the present invention is prepared, in another embodiment, by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 15 1859-1862); and the solid support method of U.S. Pat. No. 4,458,066.

In another embodiment, chemical synthesis is used to produce a single stranded oligonucleotide. This single stranded oligonucleotide is converted, in various embodiments, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences can be obtained by the ligation of shorter sequences. In another embodiment, subsequences are cloned and the appropriate subsequences cleaved using appropriate restriction enzymes. The fragments are then be ligated to produce the desired DNA sequence.

In another embodiment, DNA encoding the recombinant protein of the present invention is cloned using DNA amplification methods such as polymerase chain reaction (PCR). Thus, the gene for non-hemolytic LLO is PCR amplified, using a sense primer comprising a suitable restriction site and an antisense primer comprising another restriction site, e.g. a non-identical restriction site to facilitate cloning.

In another embodiment, the recombinant fusion protein gene is operably linked to appropriate expression control sequences for each host. Promoter/regulatory sequences are described in detail elsewhere herein. In another embodiment, the plasmid further comprises additional promoter regulatory elements, as well as a ribosome binding site and a transcription termination signal. For eukaryotic cells, the control sequences will include a promoter and an enhancer derived from e.g. immunoglobulin genes, SV40, cytomegalovirus, etc., and a polyadenylation sequence. In another embodiment, the sequences include splice donor and acceptor sequences.

In one embodiment, the term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

In another embodiment, in order to select for an auxotrophic bacteria comprising the plasmid, transformed auxotrophic bacteria are grown on a media that will select for expression of the amino acid metabolism gene. In another embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacterium auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, BD, Franklin Lakes, N.J.). Each method represents a separate embodiment of the present invention.

In another embodiment, once the auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the Listeria vaccine vector by adjusting the volume of the media in which the auxotrophic bacteria comprising the plasmid are growing.

The skilled artisan will appreciate that, in another embodiment, other auxotroph strains and complementation systems are adopted for the use with this invention.

In one embodiment, provided herein is a method of administering the composition of the present invention. In another embodiment, provided herein is a method of administering the vaccine of the present invention. In another embodiment, provided herein is a method of administering the attenuated recombinant form of Listeria of the present invention.

In another embodiment, the methods of the present invention comprise the step of administering a recombinant Listeria monocytogenes, in any form or embodiment as described herein. In one embodiment, the methods of the present invention consist of the step of administering a recombinant Listeria monocytogenes of the present invention, in any form or embodiment as described herein. In another embodiment, the methods of the present invention consist essentially of the step of administering a recombinant Listeria monocytogenes of the present invention, in any form or embodiment as described herein. In one embodiment, the term "comprise" refers to the inclusion of the step of administering a recombinant Listeria monocytogenes in the methods, as well as inclusion of other methods or treatments that may be known in the art. In another embodiment, the term "consisting essentially of" refers to a method, whose functional component is the administration of recombinant Listeria monocytogenes, however, other steps of the methods may be included that are not involved directly in the therapeutic effect of the methods and may, for example, refer to steps which facilitate the effect of the administration of recombinant Listeria monocytogenes. In one embodiment, the term "consisting" refers to a method of administering recombinant Listeria monocytogenes with no additional steps.

In another embodiment, the immune response elicited by methods and compositions of the present invention comprises a $CD8^+$ T cell-mediated response. In another embodiment, the immune response consists primarily of a $CD8^+$ T cell-mediated response. In another embodiment, the only detectable component of the immune response is a $CD8^+$ T cell-mediated response.

In another embodiment, the immune response elicited by methods and compositions of the present invention comprises a $CD4^+$ T cell-mediated response. In another embodiment, the immune response consists primarily of a $CD4^+$ T cell-mediated response. In another embodiment, the only detectable component of the immune response is a $CD4^+$ T cell-mediated response.

In another embodiment, the immune response elicited by methods and compositions of the present invention comprises an innate immune response. In another embodiment, the immune response consists primarily of an innate immune response. In another embodiment, the only detectable component of the immune response is a innate immune response. It is to be understood that the activation of an innate immune response involves the activation of macrophages such as M1 macrophages and also of dendritic cells (DC).

In another embodiment, the present invention provides a method of reducing an incidence of cancer or infectious disease or allergy, comprising administering a composition of the present invention. In another embodiment, the present invention provides a method of ameliorating cancer or infectious disease or allergy, comprising administering a composition of the present invention. Each possibility represents a separate embodiment of the present invention.

In one embodiment, the recombinant Listeria monocytogenes for use in the present invention secretes a heterologous peptide. In another embodiment, the recombinant Listeria monocytogenes for use in the present invention expresses a heterologous peptide. In another embodiment, the recombinant Listeria monocytogenes for use in the present invention expresses and secretes a non-hemolytic LLO, as described herein.

In one embodiment, a treatment protocol of the present invention is therapeutic. In another embodiment, the protocol is prophylactic. In another embodiment, the vaccines of the present invention are used to protect people at risk for cancer such as breast cancer or other types of tumors because of familial genetics or other circumstances that predispose them to these types of ailments as will be understood by a skilled artisan. In another embodiment, the vaccines of the present invention are used to treat people having cancer such as breast cancer or other types of tumors because of familial genetics or other circumstances that predispose them to these types of ailments as will be understood by a skilled artisan. In another embodiment, the vaccines of the present invention are used prior to an alternative treatment in people having cancer such as breast cancer or other types of tumors because of familial genetics or other circumstances that predispose them to these types of ailments as will be understood by a skilled artisan. In another embodiment, such treatments include chemotherapy, surgery, radiation, and the like. Prior to such treatments, the vaccines of the present invention are administered so that the CTL response to the tumor antigen of the vaccine destroys remaining metastases and prolongs remission from the cancer. In another embodiment, vaccines of the present invention are used to effect the growth of previously established tumors and to kill existing tumor cells. Each possibility represents a separate embodiment of the present invention.

In another embodiment, the vaccines and immunogenic compositions utilized in any of the methods described above have any of the characteristics of vaccines and immunogenic compositions of the present invention. Each characteristic represents a separate embodiment of the present invention.

Various embodiments of dosage ranges are contemplated by this invention. In one embodiment, in the case of vaccine vectors, the dosage is in the range of 0.4 $LD_{50}$/dose. In another embodiment, the dosage is from about 0.4-4.9 $LD_{50}$/dose. In another embodiment the dosage is from about 0.5-0.59 $LD_{50}$/dose. In another embodiment the dosage is from about 0.6-0.69 $LD_{50}$/dose. In another embodiment the dosage is from about 0.7-0.79 $LD_{50}$/dose. In another embodiment the dosage is about 0.8 $LD_{50}$/dose. In another embodiment, the dosage is 0.4 $LD_{50}$/dose to 0.8 of the $LD_{50}$/dose.

In another embodiment, the dosage is $10^7$ bacteria/dose. In another embodiment, the dosage is $1.5 \times 10^7$ bacteria/dose. In another embodiment, the dosage is $2 \times 10^7$ bacteria/dose. In another embodiment, the dosage is $3 \times 10^7$ bacteria/dose. In another embodiment, the dosage is $4 \times 10^7$ bacteria/dose. In another embodiment, the dosage is $6 \times 10^7$ bacteria/dose. In another embodiment, the dosage is $8 \times 10^7$ bacteria/dose. In another embodiment, the dosage is $1 \times 10^8$ bacteria/dose. In another embodiment, the dosage is $1.5 \times 10^8$ bacteria/dose. In another embodiment, the dosage is $2 \times 10^8$ bacteria/dose. In another embodiment, the dosage is $3 \times 10^8$ bacteria/dose. In another embodiment, the dosage is $4 \times 10^8$ bacteria/dose. In another embodiment, the dosage is $6 \times 10^8$ bacteria/dose. In another embodiment, the dosage is $8 \times 10^8$ bacteria/dose. In another embodiment, the dosage is $1 \times 10^9$ bacteria/dose. In another embodiment, the dosage is $1.5 \times 10^9$ bacteria/dose. In another embodiment, the dosage is $2 \times 10^9$ bacteria/dose. In another embodiment, the dosage is $3 \times 10^9$ bacteria/dose. In another embodiment, the dosage is $5 \times 10^9$ bacteria/dose. In another embodiment, the dosage is $6 \times 10^9$ bacteria/dose. In another embodiment, the dosage is $8 \times 10^9$ bacteria/dose. In another embodiment, the dosage is $1 \times 10^{10}$ bacteria/dose. In another embodiment, the dosage is $1.5 \times 10^{10}$ bacteria/dose. In another embodiment, the dosage is $2 \times 10^{10}$ bacteria/dose. In another embodiment, the dosage is $3 \times 10^{10}$ bacteria/dose. In another embodiment, the dosage is $5 \times 10^{10}$ bacteria/dose. In another embodiment, the dosage is $6 \times 10^{10}$ bacteria/dose. In another embodiment, the dosage is $8 \times 10^{10}$ bacteria/dose. In another embodiment, the dosage is $8 \times 10^9$ bacteria/dose. In another embodiment, the dosage is $1 \times 10^{11}$ bacteria/dose. In another embodiment, the dosage is $1.5 \times 10^{11}$ bacteria/dose. In another embodiment, the dosage is $2 \times 10^{11}$ bacteria/dose. In another embodiment, the dosage is $3 \times 10^{11}$ bacteria/dose. In another embodiment, the dosage is $5 \times 10^{11}$ bacteria/dose. In another embodiment, the dosage is $6 \times 10^{11}$ bacteria/dose. In another embodiment, the dosage is $8 \times 10^{11}$ bacteria/dose. Each possibility represents a separate embodiment of the present invention.

In another embodiment, the methods of the present invention further comprise the step of administering to the subject a booster vaccination. In one embodiment, the booster vaccination follows a single priming vaccination. In another embodiment, a single booster vaccination is administered after the priming vaccinations. In another embodiment, two booster vaccinations are administered after the priming vaccinations. In another embodiment, three booster vaccinations are administered after the priming vaccinations. In one embodiment, the period between a prime and a boost vaccine is experimentally determined by the skilled artisan. In another embodiment, the period between a prime and a boost vaccine is 1 week, in another embodiment it is 2 weeks, in another embodiment, it is 3 weeks, in another embodiment, it is 4 weeks, in another embodiment, it is 5 weeks, in another embodiment it is 6-8 weeks, in yet another embodiment, the boost vaccine is administered 8-10 weeks after the prime vaccine.

In one embodiment, a vaccine or immunogenic composition of the present invention is administered alone to a subject. In another embodiment, the vaccine or immunogenic composition is administered together with another therapy. The additional therapy can be antibiotic-mediated therapy for infectious diseases, or chemotherapy, immunotherapy, radiation, or surgery for cancer, or any other type of disease therapy available in the art as will be understood by a skilled artisan. Each possibility represents a separate embodiment of the present invention.

In another embodiment, one of various promoters is used to express protein containing same. In one embodiment, an LM promoter is used, e.g. promoters for the genes hly, actA, plcA, plcB and mpl, which encode the Listerial proteins hemolysin, actA, phosphotidylinositol-specific phospholipase, phospholipase C, and metalloprotease, respectively. Each possibility represents a separate embodiment of the present invention.

In another embodiment, methods and compositions of the present invention utilize a homologue of a heterologous antigen or LLO sequence of the present invention. The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-76 of greater than 60%. In another embodiment, "homology" refers to identity to a sequence selected from SEQ ID No: 1-76 of greater than 70%. In another embodiment, the identity is greater than 75%. In another embodiment, the identity is greater than 78%. In another embodiment, the identity is greater than 80%. In another embodiment, the identity is greater than 82%. In another embodiment, the identity is greater than 83%. In another embodiment, the identity is greater than 85%. In another embodiment, the identity is greater than 87%. In another embodiment, the identity is greater than 88%. In another embodiment, the identity is greater than 90%. In another embodiment, the identity is greater than 92%. In another embodiment, the identity is greater than 93%. In another embodiment, the identity is greater than 95%. In another embodiment, the identity is greater than 96%. In another embodiment, the identity is greater than 97%. In another embodiment, the identity is greater than 98%. In another embodiment, the identity is greater than 99%. In another embodiment, the identity is 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7. 6), 5×Denhardt's solution, 10% dextran sulfate, and 20 µg/ml denatured, sheared salmon sperm DNA.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPSRCH or SCANP5 DNA and/or protein sequence alignment and analysis software packages, and may employ the use of the Smith and Waterman algorithms, and/or global/local or BLOCKS alignments (a system for protein classification) for analysis, for example. Each method of determining homology represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

It will be well appreciated that the terms "contacting" or "administering," can encompass directly contacting the cancer cell, tumor, or site of disease with a composition of the present invention. In another embodiment, the terms refer to indirectly contacting the cancer cell, tumor, or site of disease with a composition of the present invention. In another embodiment, methods of the present invention include methods in which the subject is contacted with a composition of the present invention after which the composition is brought in contact with the cancer cell, tumor, or site of disease by diffusion or any other active transport or passive transport process known in the art by which compounds circulate within the body. Each possibility represents a separate embodiment of the present invention.

In another embodiment, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals or organisms. This can be readily carried out by using hybridization probes to identify the same genetic locus in a variety of individuals or organisms. Any and all such nucleotide variations and resulting amino acid polymorphisms or variations that are the result of natural allelic variation and that do not alter the functional activity are intended to be within the scope of the invention.

The pharmaceutical compositions containing vaccines and compositions of the present invention are, in another embodiment, administered to a subject by any method known to a person skilled in the art, such as parenterally, paracancerally, transmucosally, transdermally, intramuscularly, intravenously, intra-dermally, subcutaneously, intraperitonealy, intra-ventricularly, intra-cranially, intra-vaginally or intra-tumorally.

In another embodiment of the methods and compositions provided herein, the vaccines or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a gelatin capsule.

In another embodiment, the vaccines or compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intra-muscular administration.

It will be appreciated that the term "treating" can encompass curing a disease, preventing a disease, reducing the incidence of a disease, ameliorating symptoms of a disease, inducing remission of a disease, slowing the progression of a disease. The terms "reducing", "suppressing" and "inhibiting" refer in another embodiment to lessening or decreasing.

It will be well appreciated that the term "therapeutically effective dose" or "therapeutic effective amount" can encompass a dose that produces the desired effect for which it is administered. The exact dose will be ascertainable by one skilled in the art using known techniques.

It will be well appreciated that the term "about" can encompass in quantitative terms plus or minus 5%, or in another embodiment plus or minus 10%, or in another embodiment plus or minus 15%, or in another embodiment plus or minus 20%.

It will be well appreciated that the term "subject" can encompass a mammal including a human in need of therapy for, or susceptible to, a condition or its sequelae, and also may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Example 1: LLO-Antigen Fusions Induce Anti-Tumor Immunity

Materials and Experimental Methods (Examples 1-2)

Cell Lines

The C57BL/6 syngeneic TC-1 tumor was immortalized with HPV-16 E6 and E7 and transformed with the c-Ha-ras oncogene. TC-1, provided by T. C. Wu (Johns Hopkins University School of Medicine, Baltimore, Md.) is a highly tumorigenic lung epithelial cell expressing low levels of with HPV-16 E6 and E7 and transformed with the c-Ha-ras oncogene. TC-1 was grown in RPMI 1640 (cell media utilizing a bicarbonate buffering system), 10% FCS, 2 mM L-glutamine, 100 U/ml penicillin, 100 µg/ml streptomycin, 100 µM nonessential amino acids, 1 mM sodium pyruvate, 50 micromolar (mcM) 2-ME, 400 microgram (mcg)/ml G418 (GENETICIN, aminoglycoside antibiotic), and 10% National Collection Type Culture-109 medium at 37° with 10% CO2. C3 is a mouse embryo cell from C57BL/6 mice immortalized with the complete genome of HPV 16 and transformed with pEJ-ras. EL-4/E7 is the thymoma EL-4 retrovirally transduced with E7.

*L. monocytogenes* Strains and Propagation

Figures 1A, 1B:
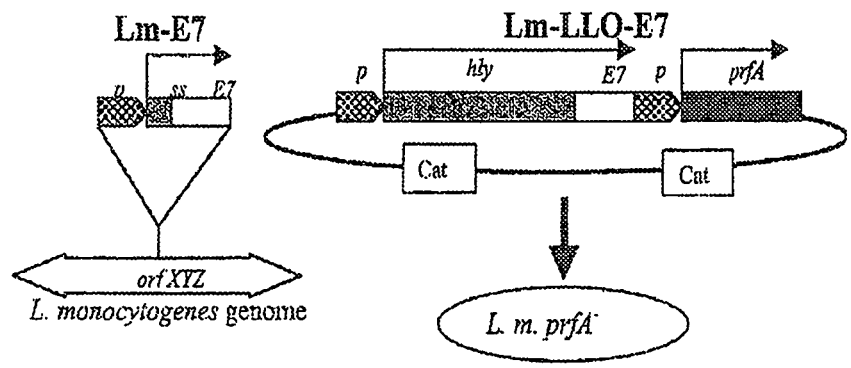
FIGS. 1A and 1B show that Lm-E7 and Lm-LLO-E7 use different expression systems to express and secrete E7.
Figure 2:
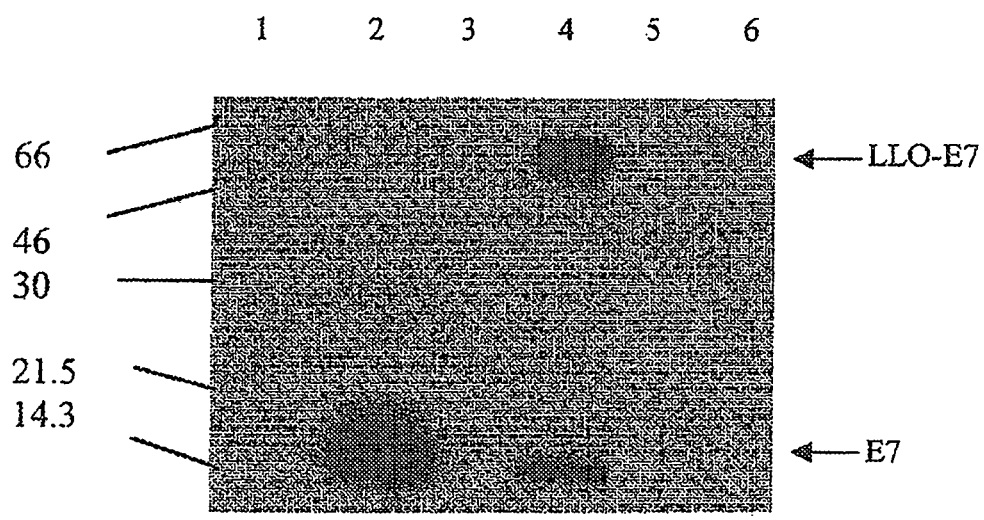
FIG. 2 shows that Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (AMERSHAM), and then developed using ECL detection reagents.

*Listeria* strains used were Lm-LLO-E7 (hly-E7 fusion gene in an episomal expression system; FIG. 1A), Lm-E7 (single-copy E7 gene cassette integrated into *Listeria* genome), Lm-LLO-NP ("DP-L2028"; hly-NP fusion gene in an episomal expression system), and Lm-Gag ("ZY-18"; single-copy HIV-1 Gag gene cassette integrated into the chromosome). E7 was amplified by PCR using the primers 5'-GGCTCGAGCATGGAGATACACC-3' (SEQ ID No: 24; XhoI site is underlined) and 5'-GGGGACTAGTTTATG-GTTTCTGAGAACA-3' (SEQ ID No: 25; SpeI site is underlined) and ligated into PCR2.1 (TA cloning vector, INVITROGEN, San Diego, Calif.). E7 was excised from PCR2.1 by XhoI/SpeI digestion and ligated into pGG-55. The hly-E7 fusion gene and the pluripotential transcription factor prfA were cloned into pAM401, a multicopy shuttle plasmid (Wirth R et al, J Bacteriol, 165: 831, 1986), generating pGG-55. The hly promoter drives the expression of the first 441 AA of the hly gene product, (lacking the hemolytic C-terminus, referred to below as "ΔLLO"), which is joined by the XhoI site to the E7 gene, yielding a hly-E7 fusion gene that is transcribed and secreted as LLO-E7. Transformation of a prfA negative strain of *Listeria*, XFL-7 (provided by Dr. Hao Shen, University of Pennsylvania), with pGG-55 selected for the retention of the plasmid in vivo (FIGS. 1A-B). The hly promoter and gene fragment were generated using primers 5'-GGGGGCTAGCCCTCCTTT-GATTAGTATATTC-3' (SEQ ID No: 26; NheI site is underlined) and 5'-CTCCCTCGAGATCATAATTTACTTCATC-3' (SEQ ID No: 27; XhoI site is underlined). The prfA gene was PCR amplified using primers 5'-GACTACAAGGAC-GATGACCGACAAGTGATAAC-CCGGGATCTAAATAAATCCGTT T-3' (SEQ ID No: 28; XbaI site is underlined) and 5'-CCCGTCGACCAGCTCT-TCTTGGTGAAG-3' (SEQ ID No: 29; SalI site is underlined). Lm-E7 was generated by introducing an expression cassette containing the hly promoter and signal sequence driving the expression and secretion of E7 into the orfZ domain of the LM genome. E7 was amplified by PCR using the primers 5'-GCGGATCCCATGGAGATACACCTAC-3' (SEQ ID No: 30; BamHI site is underlined) and 5'-GCTCTAGATTATGGTTTCTGAG-3' (SEQ ID No: 31; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the orfX, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 µg/ml). Bacteria were frozen in aliquots at −80° C. Expression was verified by Western blotting (FIG. 2).

Western Blotting

*Listeria* strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an anti-E7 monoclonal antibody (mAb) (ZYMED Laboratories, South San Francisco, Calif.), then incubated with HRP-conjugated anti-mouse secondary Ab (AMERSHAM Pharmacia Biotech, Little Chalfont, U.K.), developed with AMERSHAM ECL detection reagents (chemiluminescent detection reagents), and exposed to HYPERFILM (chemiluminescent detection film, AMERSHAM Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm. Tumor measurements for each time point are shown only for surviving mice.

Effects of Listeria Recombinants on Established Tumor Growth

Six- to 8-wk-old C57BL/6 mice (CHARLES RIVER) received $2\times10^5$ TC-1 cells s.c. on the left flank. One week following tumor inoculation, the tumors had reached a palpable size of 4-5 mm in diameter. Groups of eight mice were then treated with 0.1 LD50 i.p. Lm-LLO-E7 ($10^7$ CFU), Lm-E7 ($10^6$ CFU), Lm-LLO-NP ($10^7$ CFU), or Lm-Gag ($5\times10^5$ CFU) on days 7 and 14.

$^{51}$Cr Release Assay

C57BL/6 mice, 6-8 wk old, were immunized i.p. with $0.1LD_{50}$ Lm-LLO-E7, Lm-E7, Lm-LLO-NP, or Lm-Gag. Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7 H-2b peptide (RAHYNIVTF) (SEQ ID NO:32). E:T cell ratios, performed in triplicate, were 80:1, 40:1, 20:1, 10:1, 5:1, and 2.5:1. Following a 4-h incubation at 37° C., cells were pelleted, and 50 μl supernatant was removed from each well. Samples were assayed with a Wallac 1450 scintillation counter (Gaithersburg, Md.). The percent specific lysis was determined as [(experimental counts per minute (cpm)−spontaneous cpm)/(total cpm−spontaneous cpm)]×100.

TC-1-Specific Proliferation

C57BL/6 mice were immunized with 0.1 LD50 and boosted by i.p. injection 20 days later with 1 LD50 Lm-LLO-E7, Lm-E7, Lm-LLO-NP, or Lm-Gag. Six days after boosting, spleens were harvested from immunized and naive mice. Splenocytes were established in culture at $5\times10^5$/well in flat-bottom 96-well plates with $2.5\times10^4$, $1.25\times10^4$, $6\times10^3$, or $3\times10^3$ irradiated TC-1 cells/well as a source of E7 Ag, or without TC-1 cells or with 10 μg/ml Con A. Cells were pulsed 45 h later with 0.5 μCi [3H]thymidine/well. Plates were harvested 18 h later using a TOMTEC HARVESTER 96 (cell harvester, Orange, Conn.), and proliferation was assessed with a Wallac 1450 scintillation counter. The change in cpm was calculated as experimental cpm—no Ag cpm.

Flow Cytometric Analysis

C57BL/6 mice were immunized intravenously (i.v.) with 0.1 LD50 Lm-LLO-E7 or Lm-E7 and boosted 30 days later. Three-color flow cytometry for CD8 (53-6.7, PE conjugated), CD62 ligand (CD62L; MEL-14, APC conjugated), and E7 H-2Db tetramer was performed using a FACSCALIBUR® flow cytometer with CELLQUEST® software (Flow and Image Cytometry Analysis Software, Becton Dickinson, Mountain View, Calif.). Splenocytes harvested 5 days after the boost were stained at room temperature (rt) with H-2Db tetramers loaded with the E7 peptide (RAHYNIVTF) (SEQ ID NO:32) or a control (HIV-Gag) peptide. Tetramers were used at a 1/200 dilution and were provided by Dr. Larry R. Pease (Mayo Clinic, Rochester, Minn.) and by the NIAID Tetramer Core Facility and the NIH AIDS Research and Reference Reagent Program. Tetramer+, CD8+, CD62Llow cells were analyzed.

B16F0-Ova Experiment

24 C57BL/6 mice were inoculated with $5\times10^5$ B16F0-Ova cells. On days 3, 10 and 17, groups of 8 mice were immunized with 0.1 $LD_{50}$ Lm-OVA ($10^6$ cfu), Lm-LLO-OVA ($10^8$ cfu) and eight animals were left untreated.

Statistics

For comparisons of tumor diameters, mean and SD of tumor size for each group were determined, and statistical significance was determined by Student's t test. $p \leq 0.05$ was considered significant.

Results

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm). Mice were vaccinated on days 7 and 14 with 0.1 $LD_{50}$ Lm-E7, Lm-LLO-E7, or, as controls, Lm-Gag and Lm-LLO-NP. Lm-LLO-E7 induced complete regression of 75% of established TC-1 tumors, while tumor growth was controlled in the other 2 mice in the group (FIG. 3). By contrast, immunization with Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with 2 other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively. Animals immunized with Lm-LLO-E7 remained tumor free until termination of the experiment (day 124 in the case of TC-1 and day 54 for EL-4/E7).

Thus, expression of an antigen as a fusion protein with ALLO enhances the immunogenicity of the antigen.

Example 2: Lm-LLO-E7 Treatment Elicits TC-1 Specific Splenocyte Proliferation

To measure induction of T cells by Lm-E7 with Lm-LLO-E7, E7-specific proliferative responses, a measure of antigen-specific immunocompetence, were measured in immunized mice. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control-immunized mice exhibited only background levels of proliferation.

Example 3: ActA-E7 and PEST-E7 Fusions Confer Anti-Tumor Immunity

Materials and Experimental Methods

Construction of Lm-ActA-E7

Lm-ActA-E7 is a recombinant strain of LM, comprising a plasmid that expresses the E7 protein fused to a truncated version of the actA protein. Lm-actA-E7 was generated by introducing a plasmid vector pDD-1, constructed by modifying pDP-2028, into Listeria. pDD-1 comprises an expression cassette expressing a copy of the 310 bp hly promoter and the hly signal sequence (ss), which drives the expression and secretion of ActA-E7; 1170 bp of the actA gene that comprises four PEST sequences (SEQ ID NO: 11) (the truncated ActA polypeptide consists of the first 390 AA of the molecule, SEQ ID NO: 10); the 300 bp HPV E7 gene; the 1019 bp prfA gene (controls expression of the virulence genes); and the CAT gene (chloramphenicol resistance gene)

for selection of transformed bacteria clones (Sewell et al. (2004), Arch. Otolaryngol. Head Neck Surg., 130: 92-97).

The hly promoter (pHly) and gene fragment were PCR amplified from pGG55 (Example 1) using primer 5'-GGGG TCTAGACCTCCTTTGATTAGTATATTC-3' (Xba I site is underlined; SEQ ID NO: 33) and primer 5'-ATCTTCGC-TATCTGTCGC CGCGGCGCGTGCTTCAGTTTGTTGCGC-'3 (Not I site is underlined. The first 18 nucleotides are the ActA gene overlap; SEQ ID NO: 34). The actA gene was PCR amplified from the LM 10403s wildtype genome using primer 5'-GCGCAACAAACTGAAGCAGC GGCCGCGGCGACAGATAGCGAAGAT-3' (NotI site is underlined; SEQ ID NO: 35) and primer 5'-TGTAGGTG-TATCTCCATGCTCGAGAGCTAGGCGATCAATTTC-3' (XhoI site is underlined; SEQ ID NO: 36). The E7 gene was PCR amplified from pGG55 (pLLO-E7) using primer 5'-GGAATTGATCGCCTAGCT CTCGAGCATGGAGATACACCTACA-3' (XhoI site is underlined; SEQ ID NO: 37) and primer 5'-AAACGGATT-TATTTAGATCCCGGGTTATGGTTTCTGAGAACA-3' (XmaI site is underlined; SEQ ID NO: 38). The prfA gene was PCR amplified from the LM 10403s wild-type genome using primer 5'-TGTTCTCAGAAACCATAA CCCGGGATCTAAATAAATCCGTTT-3' (XmaI site is underlined; SEQ ID NO: 39) and primer 5'-GGGGG TCGACCAGCTCTTCTTGGTGAAG-3' (SalI site is underlined; SEQ ID NO: 40). The hly promoter-actA gene fusion (pHly-actA) was PCR generated and amplified from purified pHly DNA and purified actA DNA using the upstream pHly primer (SEQ ID NO: 33) and downstream actA primer (SEQ ID NO: 36).

The E7 gene fused to the prfA gene (E7-prfA) was PCR generated and amplified from purified E7 DNA and purified prfA DNA using the upstream E7 primer (SEQ ID NO: 37) and downstream prfA gene primer (SEQ ID NO: 40).

The pHly-actA fusion product fused to the E7-prfA fusion product was PCR generated and amplified from purified fused pHly-actA DNA product and purified fused E7-prfA DNA product using the upstream pHly primer (SEQ ID NO: 33) and downstream prfA gene primer (SEQ ID NO: 40) and ligated into PCRII (TA cloning vector, INVITROGEN, La Jolla, Calif.). Competent E. coli (TOP10F' chemically competent E. coli, INVITROGEN, La Jolla, Calif.) were transformed with pCRII-ActAE7. After lysis and isolation, the plasmid was screened by restriction analysis using BamHI (expected fragment sizes 770 bp and 6400 bp (or when the insert was reversed into the vector: 2500 bp and 4100 bp)) and BstXI (expected fragment sizes 2800 bp and 3900 bp) and also screened with PCR analysis using the upstream pHly primer (SEQ ID NO: 33) and the downstream prfA gene primer (SEQ ID NO: 40).

The pHly-actA-E7-prfA DNA insert was excised from pCRII by double digestion with Xba I and Sal I and ligated into pDP-2028 also digested with Xba I and Sal I. After transforming TOP10F' (chemically competent E. coli) (INVITROGEN, La Jolla, Calif.) with expression system pAc-tAE7, chloramphenicol resistant clones were screened by PCR analysis using the upstream pHly primer (SEQ ID NO: 33) and the downstream PrfA gene primer (SEQ ID NO: 40). A clone comprising pActAE7 was grown in brain heart infusion medium (with chloramphenicol (20 mcg (microgram)/ml (milliliter), Difco, Detroit, Mich.) and pActAE7 was isolated from the bacteria cell using a Midiprep DNA purification system kit (PROMEGA, Madison, Wis.). A prfA-negative strain of penicillin-treated Listeria (strain XFL-7) was transformed with expression system pActAE7, as described in Ikonomidis et al. (1994, J. Exp. Med. 180: 2209-2218) and clones were selected for the retention of the plasmid in vivo. Clones were grown in brain heart infusion with chloramphenicol (20 mcg/ml) at 37° C. Bacteria were frozen in aliquots at –80° C.

Immunoblot Verification of Antigen Expression

To verify that Lm-ActA-E7 secretes ActA-E7, (about 64 kD), Listeria strains were grown in Luria-Bertoni (LB) medium at 37° C. Protein was precipitated from the culture supernatant with trichloroacetic acid (TCA) and resuspended in 1× sample buffer with 0.1N sodium hydroxide. Identical amounts of each TCA precipitated supernatant were loaded on 4% to 20% Tris-glycine sodium dodecyl sulfatepolyacrylamide gels (NOVEX, San Diego, Calif.). Gels were transferred to polyvinylidene difluoride membranes and probed with 1:2500 anti-E7 monoclonal antibody (ZYMED Laboratories, South San Francisco, Calif.), then with 1:5000 horseradish peroxidaseconjugated anti-mouse IgG (AMERS HAM Pharmacia Biotech, Little Chalfont, England). Blots were developed with AMERSHAM Enhanced Chemiluminescence (ECL) detection reagents (luminol-based detection) and exposed to autoradiography film (AMERSHAM) (FIG. 5A).

Construction of Lm-PEST-E7, Lm-ΔPEST-E7, and Lm-E7epi (FIG. 6A)

Lm-PEST-E7 is identical to Lm-LLO-E7, except that it contains only the promoter and PEST sequence of the hly gene, specifically the first 50 AA of LLO. To construct Lm-PEST-E7, the hly promoter and PEST regions were fused to the full-length E7 gene using the SOE (gene splicing by overlap extension) PCR technique. The E7 gene and the hly-PEST gene fragment were amplified from the plasmid pGG-55, which contains the first 441 AA of LLO, and spliced together by conventional PCR techniques. To create a final plasmid, pVS 16.5, the hly-PEST-E7 fragment and the prfA gene were subcloned into the plasmid pAM401, which includes a chloramphenicol resistance gene for selection in vitro, and the resultant plasmid was used to transform XFL-7.

Lm-ΔPEST-E7 is a recombinant Listeria strain that is identical to Lm-LLO-E7 except that it lacks the PEST sequence. It was made essentially as described for Lm-PEST-E7, except that the episomal expression system was constructed using primers designed to remove the PEST-containing region (bp 333-387) from the hly-E7 fusion gene. Lm-E7epi is a recombinant strain that secretes E7 without the PEST region or LLO. The plasmid used to transform this strain contains a gene fragment of the hly promoter and signal sequence fused to the E7 gene. This construct differs from the original Lm-E7, which expressed a single copy of the E7 gene integrated into the chromosome. Lm-E7epi is completely isogenic to Lm-LLO-E7, Lm-PEST-E7, and Lm-ΔPEST-E7 except for the form of the E7 antigen expressed.

Results

To compare the anti-tumor immunity induced by Lm-ActA-E7 versus Lm-LLO-E7, $2 \times 10^5$ TC-1 tumor cells were implanted subcutaneously in mice and allowed to grow to a palpable size (approximately 5 millimeters [mm]). Mice were immunized i.p. with one $LD_{50}$ of either Lm-ActA-E7 ($5 \times 10^8$ CFU), (crosses) Lm-LLO-E7 ($10^8$ CFU) (squares) or Lm-E7 ($10^6$ CFU) (circles) on days 7 and 14. By day 26, all of the animals in the Lm-LLO-E7 and Lm-ActA-E7 were tumor free and remained so, whereas all of the naive animals (triangles) and the animals immunized with Lm-E7 grew large tumors (FIG. 5B). Thus, vaccination with ActA-E7 fusions causes tumor regression.

In addition, Lm-LLO-E7, Lm-PEST-E7, Lm-ΔPEST-E7, and Lm-E7epi were compared for their ability to cause regression of E7-expressing tumors. S.c. TC-1 tumors were established on the left flank of 40 C57BL/6 mice. After tumors had reached 4-5 mm, mice were divided into 5 groups of 8 mice. Each groups was treated with 1 of 4 recombinant LM vaccines, and 1 group was left untreated. Lm-LLO-E7 and Lm-PEST-E7 induced regression of established tumors in 5/8 and 3/8 cases, respectively. There was no statistical difference between the average tumor size of mice treated with Lm-PEST-E7 or Lm-LLO-E7 at any time point. However, the vaccines that expressed E7 without the PEST sequences, Lm-ΔPEST-E7 and Lm-E7epi, failed to cause tumor regression in all mice except one (FIG. 6B, top panel). This was representative of 2 experiments, wherein a statistically significant difference in mean tumor sizes at day 28 was observed between tumors treated with Lm-LLO-E7 or Lm-PEST-E7 and those treated with Lm-E7epi or Lm-ΔPEST-E7; P<0.001, Student's t test; FIG. 6B, bottom panel). In addition, increased percentages of tetramer-positive splenocytes were seen reproducibly over 3 experiments in the spleens of mice vaccinated with PEST-containing vaccines (FIG. 6C). Thus, vaccination with PEST-E7 fusions causes tumor regression.

Example 4: Fusion of E7 to LLO, Acta, or a Pest-Like Sequence Enhances E7-Specific Immunity and Generates Tumor-Infiltrating E7-Specific CD8+ Cells Materials and Experimental Methods 500 mcl (microliter) of MATRIGEL® (extracellular matrix (ECM)-based hydrogel), comprising 100 mcl of $2 \times 10^5$ TC-1 tumor cells in phosphate buffered saline (PBS) plus 400 mcl of MATRIGEL® (extracellular matrix (ECM)-based hydrogel, BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor MATRIGELs (extracellular matrix (ECM)-based hydrogel) were removed from the mice and incubated at 4° C. overnight in tubes containing 2 milliliters (ml) of RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of NaN3 in PBS for tetramer and IFN-gamma staining.

Splenocytes and tumor cells were incubated with 1 micromole (mcm) E7 peptide for 5 hours in the presence of brefeldin A at $10^7$ cells/ml. Cells were washed twice and incubated in 50 mcl of anti-mouse Fc receptor supernatant (2.4 G2) for 1 hour or overnight at 4° C. Cells were stained for surface molecules CD8 and CD62L, permeabilized, fixed using the permeabilization kit GOLGI-STOP® or GOLGI-PLUG® (Protein Transport Inhibitor, PHARMINGEN, San Diego, Calif.), and stained for IFN-gamma. 500,000 events were acquired using two-laser flow cytometer FACSCALIBUR and analyzed using CELLQUEST Software (Flow and Image Cytometry Analysis Software, Becton Dickinson, Franklin Lakes, N.J.). Percentages of IFN-gamma secreting cells within the activated (CD62Llow) CD8+ T cells were calculated.

For tetramer staining, H-2D$^b$ tetramer was loaded with phycoerythrin (PE)-conjugated E7 peptide (RAHYNIVTF, SEQ ID NO: 32), stained at rt for 1 hour, and stained with anti-allophycocyanin (APC) conjugated MEL-14 (CD62L) and FITC-conjugated CD8β at 4° C. for 30 min. Cells were analyzed comparing tetramer+CD8+ CD62L$^{low}$ cells in the spleen and in the tumor.

Results

To analyze the ability of Lm-ActA-E7 to enhance antigen specific immunity, mice were implanted with TC-1 tumor cells and immunized with either Lm-LLO-E7 ($1 \times 10^7$ CFU), Lm-E7 ($1 \times 10^6$ CFU), or Lm-ActA-E7 ($2 \times 10^8$ CFU), or were untreated (naïve). Tumors of mice from the Lm-LLO-E7 and Lm-ActA-E7 groups contained a higher percentage of IFN-gamma-secreting CD8+ T cells (FIG. 7A) and tetramer-specific CD8+ cells (FIG. 7B) than in Lm-E7 or naive mice.

In another experiment, tumor-bearing mice were administered Lm-LLO-E7, Lm-PEST-E7, Lm-ΔPEST-E7, or Lm-E7epi, and levels of E7-specific lymphocytes within the tumor were measured. Mice were treated on days 7 and 14 with 0.1 LD$_{50}$ of the 4 vaccines. Tumors were harvested on day 21 and stained with antibodies to CD62L, CD8, and with the E7/Db tetramer. An increased percentage of tetramer-positive lymphocytes within the tumor were seen in mice vaccinated with Lm-LLO-E7 and Lm-PEST-E7 (FIG. 8A). This result was reproducible over three experiments (FIG. 8B).

Thus, Lm-LLO-E7, Lm-ActA-E7, and Lm-PEST-E7 are each efficacious at induction of tumor-infiltrating CD8+ T cells and tumor regression.

Materials and Experimental Methods (See Examples 5-10)

Bacterial Strains, Transformation and Selection

E. coli strain MB2159 was used for transformations, using standard protocols. Bacterial cells were prepared for electroporation by washing with H$_2$O.

E. coli strain MB2159 (Strych U et al, FEMS Microbiol Lett. 2001 Mar. 15; 196(2):93-8) is an alr (−)/dadX (−) deficient mutant that is not able to synthesize D-alanine racemase. Listeria strain Lm dal(−)/dat(−) (Lmdd) similarly is not able to synthesize D-alanine racemase due to partial deletions of the dal and the dat genes.

Plasmid Constructions

Using the published sequence of the plcA gene (Mengaud et al., Infect. Immun. 1989 57, 3695-3701), PCR was used to amplify the gene from chromosomal DNA. The amplified product was then ligated into pAM401 using SalI- and XbaI-generated DNA ends to generate pDP1462.

Plasmid pDP1500, containing prfA alone, was constructed by deleting the plcA gene, bases 429 to 1349 (Mengaud et al., supra), from pDP1462 after restriction with XbaI and PstI, treatment of the DNA ends with T4 DNA polymerase to make them blunt, and intramolecular ligation.

Plasmid pDP1499, containing the plcA promoter and a portion of the 3' end of plcA, was constructed by deleting a plcA internal fragment, bases 428 to 882 (Mengaud et al., Infect. Immun. 1989 57, 3695-3701), from pDP1339 after restriction with PstI and NsiI and intramolecular ligation.

pDP1526 (pKSV7::4plcA) was constructed by a single three-part ligation of pKSV7 restricted with BAMHI and XbaI, the 468 bp XbaI and NsiI-generated fragment from pAM401::plcA containing the 5' end of plcA (bases 882 to 1351; Mengaud et al., supra) and, the 501 bp PstI- and BamHI-generated fragment from pAM401::plcA prfA containing the 3' end of plcA (bases 77 to 429; Mengaud et al., supra).

The prfA promoter, bases 1-429 (Mengaud et al., supra), was isolated by EcoRI and PstI double digestion of pDP1462 and the fragment was subsequently ligated into EcoRI- and PstI-restricted pKSV7 to generate pDP1498. Two random HindIII-generated 10403S chromosomal DNA fragments, approximately 3 kb in length, were ligated into HindIII-restricted pKSV7, to generate the random integration control plasmids pDP1519 and pDP1521.

Construction of L. monocytogenes Mutant Strains

L. monocytogenes strain DP-L1387 was isolated as a mutant with reduced lecithinase (PC-PLC) from a Tn917-LTV3 bank of SLCC 5764, constructed as previously described (Camilli et al., J. Bacteriol. 1990, 172, 3738-3744). The site of Tn917-LTV3 insertion was determined by sequencing one transposon-chromosomal DNA junction as previously described (Sun et al., Infect. Immun. 1990 58, 3770-3778). L. monocytogenes was transformed with plasmid DNA as previously described (Camilli et al., supra). Selective pressure for maintenance of pAM401, pKSV7, and their derivatives in L. monocytogenes was exerted in the presence of 10 µg of chloramphenicol per ml of media. In addition, maintenance of pKSV7 derivatives required growth at 30° C., a permissive temperature for plasmid replication in Gram-positive bacteria.

Integration of pKSV7 derivatives into the L. monocytogenes chromosome occurred by homologous recombination between L. monocytogenes DNA sequences on the plasmids and their corresponding chromosomal alleles. Integration mutants were enriched by growth for approximately 30 generations at 40° C., a non-permissive temperature for pKSV7 replication, in Brain Heart Infusion (BHI) broth containing 10 µg chloramphenicol per ml of media. Each integration strain was subsequently colony purified on BHI agar containing 10 µg chloramphenicol per ml of media and incubated at 40° C. Southern blot analyses of chromosomal DNA isolated from each integration strain confirmed the presence of the integrated plasmid.

Construction of DP-L1552 is achieved by integration of the pKSV7 derivative, pDP1526, to generate a merodiploid intermediate as described above. Spontaneous excision of the integrated plasmid, through intramolecular homologous recombination, occurred at a low frequency. Bacteria in which the plasmid had excised from the chromosome were enriched by growth at 30° C. in BHI broth for approximately 50 generations. The nature of the selective pressure during this step was not known but may be due to a slight growth defect of strains containing integrated temperature-sensitive plasmids. Approximately 50% of excision events, i.e., those resulting from homologous recombination between sequences 3' of the deletion, resulted in allelic exchange of ΔplcA for the wild-type allele on the chromosome.

The excised plasmids were cured by growing the bacteria at 40° C. in BHI for approximately 30 generations. Bacteria cured of the plasmid retaining the ΔplcA allele on the chromosome were identified by their failure to produce a zone of turbidity surrounding colonies after growth on BHI agar plates containing a 5 ml overlay of BHI agar/2.5% egg yolk/2.5% phosphate-buffered saline (PBS) (BHI/egg yolk agar). The turbid zones resulted from PI-PLC hydrolysis of PI in the egg yolk, giving an insoluble diacylglycerol precipitate. The correct plcA deletion on the L. monocytogenes chromosome was confirmed by amplifying the deleted allele using PCR and sequencing across the deletion.

Thus, PI-PLC negative mutants (plcA deletion mutants) may be used according to the present invention to generate attenuated L. monocytogenes vaccines. Other mutants were made using the same method, namely, an actA deletion mutant, a plcB deletion mutant, and a double mutant lacking both plcA and plcB, all of which may also be used according to the present disclosure to generate attenuated *L. monocytogenes* vaccines. Given the present disclosure, one skilled in the art would be able to create other attenuated mutants in addition to those mentioned above.

Construction of Lmdd

The dal gene was initially inactivated by means of a double-allelic exchange between the chromosomal gene and the temperature-sensitive shuttle plasmid pKSV7 (Smith K et al, Biochimie. 1992 July-August; 74(7-8):705-11) carrying an erythromycin resistance gene between a 450-bp fragment from the 5' end of the original 850-bp dal gene PCR product and a 450-bp fragment from the 3' end of the dal gene PCR product. Subsequently, a dal deletion mutant covering 82% of the gene was constructed by a similar exchange reaction with pKSV7 carrying homology regions from the 5' and 3' ends of the intact gene (including sequences upstream and downstream of the gene) surrounding the desired deletion. PCR analysis was used to confirm the structure of this chromosomal deletion.

The chromosomal dat gene was inactivated by a similar allelic exchange reaction. pKSV7 was modified to carry 450-bp fragments derived by PCR from both the 5' and 3' ends of the intact dat gene (including sequences upstream and downstream of the gene). These two fragments were ligated by appropriate PCR. Exchange of this construct into the chromosome resulted in the deletion of 30% of the central bases of the dat gene, which was confirmed by PCR analysis.

Bacterial Culture and In Vivo Passaging of *Listeria*

*E. coli* were cultured following standard methods. *Listeria* were grown at 37° C., 250 rpm shaking in LB media (DIFCO, Detroit, Mich.)+50 μg/ml streptomycin, and harvested during exponential growth phase. For Lm-LLOE7, 37 μg/ml chloramphenicol was added to the media. For growth kinetics determinations, bacteria were grown for 16 hours in 10 ml of LB+antibiotics. The OD600 nm was measured and culture densities were normalized between the strains. The culture was diluted 1:50 into LB+suitable antibiotics and D-alanine if applicable.

Passaging of LM in Mice $1\times10^8$ CFU were injected intraperitoneally (i.p.) into C57BL/6 mice. On day three, spleens were isolated and homogenized in PBS. An aliquot of the spleen suspension was plated on LB plates with antibiotics as applicable. Several colonies were expanded and mixed to establish an injection stock.

Construction of Antibiotic Resistance Factor Free Plasmid pTV3

Construction of p60-Dal Cassette.

The first step in the construction of the antibiotic resistance gene-free vector was construction of a fusion of a truncated p60 promoter to the dal gene. The LM alanine racemase (dal) gene (forward primer: 5'-CCA TGG TGA CAG GCT GGC ATC-3'; SEQ ID NO: 41) (reverse primer: 5'-GCT AGC CTA ATG GAT GTA TTT TCT AGG-3'; SEQ ID NO: 42) and a minimal p60 promoter sequence (forward primer: 5'-TTA ATT AAC AAA TAG TTG GTA TAG TCC-3'; SEQ ID No: 43) (reverse primer: 5'-GAC GAT GCC AGC CTG TCA CCA TGG AAA ACT CCT CTC-3'; SEQ ID No: 44) were isolated by PCR amplification from the genome of LM strain 10403S. The primers introduced a PacI site upstream of the p60 sequence, an NheI site downstream of the dal sequence (restriction sites in bold type), and an overlapping dal sequence (the first 18 bp) downstream of the p60 promoter for subsequent fusion of p60 and dal by splice overlap extension (SOE)-PCR. The sequence of the truncated p60 promoter was: CAAATAGT-TGGTATAGTCCTCTTTAGCCTTTGGAGTATTATCT-CATCATTTGTTTTTA GGTGAAAACTGGGTAAACT-TAGTATTATCAATATAAAATTAATTCTCAAATACTTAA TTACGTACTGGGATTTTCTGAAAAAAGAGAG-GAGTTTTCC (SEQ ID NO: 45) (Kohler et al, J Bacteriol 173: 4668-74, 1991). Using SOE-PCR, the p60 and dal PCR products were fused and cloned into cloning vector pCR2.1 (Invitrogen, La Jolla, Calif.).

Removal of Antibiotic Resistance Genes from pGG55.

The subsequent cloning strategy for removing the Chloramphenicol acetyltransferase (CAT) genes from pGG55 and introducing the p60-dal cassette also intermittently resulted in the removal of the gram-positive replication region (oriRep; Brantl et al, Nucleic Acid Res 18: 4783-4790, 1990). In order to re-introduce the gram-positive oriRep, the oriRep was PCR-amplified from pGG55, using a 5'-primer that added a NarI/EheI site upstream of the sequence (GGCGCCACTAACTCAACGCTAGTAG, SEQ ID NO: 46) and a 3'-primer that added a NheI site downstream of the sequence (GCTAGCCAG-CAAAGAAAAACAAACACG, SEQ ID NO: 47). The PCR product was cloned into cloning vector pCR2.1 and sequence verified.

In order to incorporate the p60-dal sequence into the pGG55 vector, the p60-dal expression cassette was excised from pCR-p60dal by PacI/NheI double digestion. The replication region for gram-positive bacteria in pGG55 was amplified from pCR-oriRep by PCR (primer 1, 5'-GTC GAC GGT CAC CGG CGC CAC TAA CTC AAC GCT AGT AG-3'; SEQ ID No: 48); (primer 2, 5'-TTA ATT AAG CTA GCC AGC AAA GAA AAA CAA ACA CG-3'; SEQ ID No: 49) to introduce additional restriction sites for EheI and NheI. The PCR product was ligated into PCR2.1-TOPO (TA cloning vector, INVITROGEN, Carlsbad, Calif.), and the sequence was verified. The replication region was excised by EheI/NheI digestion, and vector pGG55 was double digested with EheI and NheI, removing both CAT genes from the plasmid simultaneously. The two inserts, p60-dal and oriRep, and the pGG55 fragment were ligated together, yielding pTV3 (FIG. 9). pTV3 also contains a prfA (pathogenicity regulating factor A) gene. This gene is not necessary for the function of pTV3, but can be used in situations wherein an additional selected marker is required or desired.

Preparation of DNA for Real-Time PCR

Total *Listeria* DNA was prepared using the MASTER-PURE® Total DNA kit (DNA and RNA Purification Kit, EPICENTRE, Madison, Wis.). *Listeria* were cultured for 24 hours at 37° C. and shaken at 250 rpm in 25 ml of Luria-Bertoni broth (LB). Bacterial cells were pelleted by centrifugation, resuspended in PBS supplemented with 5 mg/ml of lysozyme and incubated for 20 minutes at 37° C., after which DNA was isolated.

In order to obtain standard target DNA for real-time PCR, the LLO-E7 gene was PCR amplified from pGG55 (5'-ATGAAAAAAATAATGCTAGTTTTTATTAC-3' (SEQ ID NO: 50); 5'-GCGGCCGCTTAATGATGATGATGAT-GTGGTTTCTG AGAACAGATG-3' (SEQ ID NO: 51)) and cloned into vector PETBLUE1 (plasmid vector, NOVAGEN, San Diego, Calif.). Similarly, the plcA amplicon was cloned into PCR2.1. (TA cloning vector) *E. coli* were transformed with pET-LLOE7 and pCR-plcA, respectively, and purified plasmid DNA was prepared for use in real-time PCR.

Real-Time PCR

TAQMAN primer-probe sets (real-time PCR (qPCR) assay probes, APPLIED BIOSYSTEMS, Foster City, Calif.) were designed using the ABI PRIMER EXPRESS software (software for designing primers and probes for real-time PCR, APPLIED BIOSYSTEMS) with E7 as a plasmid target, using the following primers: 5'-GCAAGTGT-GACTCTACGCTTCG-3' (SEQ ID NO: 52); 5'-TGCCCAT-TAACAGGTCTTCCA-3' (SEQ ID NO: 53); 5'-FAM-TGCGTA CAAAGCACACACGTAGACATTCGTAC-TAMRA-3' (SEQ ID NO: 54) and the one-copy gene plcA (TGACATCGTTTGTGTTTGAGCTAG-3' (SEQ ID NO: 55), 5'-GCAGCGCTCTCTATACCAGGTAC-3' (SEQ ID NO: 56); 5'-TET-TTAATGTCCATGTTA TGTCTCCGT-TATAGCTCATCGTA-TAMRA-3'; SEQ ID NO: 57) as a *Listeria* genome target.

0.4 µM primer and 0.05 mM probe were mixed with PURE TAQ RTG PCR beads (beads comprising PCR mix AMERSHHAM, Piscataway, N.J.) as recommended by the manufacturer. Standard curves were prepared for each target with purified plasmid DNA, pET-LLOE7 and pCR-plcA (internal standard) and used to calculate gene copy numbers in unknown samples. Mean ratios of E7 copies/plcA copies were calculated based on the standard curves and calibrated by dividing the results for Lmdd-TV3 and Lm-LLOE7 with the results from Lm-E7, a *Listeria* strain with a single copy of the E7 gene integrated into the genome. All samples were run in triplicate in each qPCR assay which was repeated three times. Variation between samples was analyzed by Two-Way ANOVA using the KyPlot software. Results were deemed statistically significant if $p<0.05$.

Growth Measurements

Bacteria were grown at 37° C., 250 rpm shaking in Luria Bertani (LB) Medium+/−100 micrograms (µg)/ml D-alanine and/or 37 µg/ml chloramphenicol. The starting inoculum was adjusted based on $OD_{600}$ nm measurements to be the same for all strains.

Hemolytic Lysis Assay $4 \times 10^9$ CFU of *Listeria* were thawed, pelleted by centrifugation (1 minute, 14000 rpm) and resuspended in 100 µl PBS, pH 5.5 with 1 M cysteine. Bacteria were serially diluted 1:2 and incubated for 45 minutes at 37° C. in order to activate secreted LLO. Defibrinated total sheep blood (CEDARLANE, Hornby, Ontario, Canada) was washed twice with 5 volumes of PBS and three to four times with 6 volumes of PBS-Cysteine until the supernatant remained clear, pelleting cells at 3000×g for 8 minutes between wash steps, then resuspended to a final concentration of 10% (v/v) in PBS-Cysteine. 100 µl of 10% washed blood cells were mixed with 100 µl of *Listeria* suspension and incubated for additional 45 minutes at 37° C. Un-lysed blood cells were then pelleted by centrifugation (10 minutes, 1000×g). 100 µl of supernatant was transferred into a new plate and the OD 530 nm was determined and plotted against the sample dilution.

Therapeutic Efficacy of Lmdd-Tv3

$10^5$ TC-1 (ATCC, Manassas, Va.) were implanted subcutaneously in C57BL/6 mice (n=8) and allowed to grow for about 7 days, after which tumors were palpable. TC-1 is a C57BL/6 epithelial cell line that was immortalized with HPV E6 and E7 and transformed with activated ras, which forms tumors upon subcutaneous implantation. Mice were immunized with 0.1 $LD_{50}$ of the appropriate *Listeria* strain on days 7 and 14 following implantation of tumor cells. A non-immunized control group (naïve) was also included. Tumor growth was measured with electronic calipers.

Generation of an ActA Deletion Mutant

The strain Lm dal dat (Lmdd) was attenuated by the irreversible deletion of the virulence factor, ActA. An in frame deletion of actA in the Lmdaldat (Lmdd) background was constructed to avoid any polar effects on the expression of downstream genes. The Lm dal dat ΔactA contains the first 19 amino acids at the N-terminal and 28 amino acid residues of the C-terminal with a deletion of 591 amino acids of ActA. The deletion of the gene into the chromosomal spot was verified using primers that anneal external to the actA deletion region. These are primers 3 (Adv 305-tgggatggc-caagaaattc) (SEQ ID NO: 58) and 4 (Adv304-ctaccatgtcttc-cgttgcttg) (SEQ ID NO: 59) as shown in the FIG. 12. The PCR analysis was performed on the chromosomal DNA isolated from Lmdd and Lm-ddΔactA. The sizes of the DNA fragments after amplification with two different set of primer pairs 1, 2 and 3, 4 in Lm-dd chromosomal DNA was expected to be 3.0 Kb and 3.4 Kb. However, for the Lm-ddΔactA the expected sizes of PCR using the primer pairs 1, 2 and 3, 4 was 1.2 Kb and 1.6 Kb. Thus, PCR analysis in FIG. 12 confirms that 1.8 kb region of actA was deleted in the strain, Lm-ddΔactA. DNA sequencing was also performed on PCR products to confirm the deletion of actA containing region in the strain, Lm-ddΔactA (FIG. 13).

```
                                              (SEQ ID NO: 60)
gcgccaaatcattggttgattggtgaggatgtctgtgtgcgtgggtcgc gagatgggcgaataagaagcattaaagatcctgacaaatataatcaagc ggctcatatgaaagattacgaatcgcttccactcacagaggaaggcgac tggggcggagttcattataatagtggtatcccgaataaagcagcctata atactatcactaaacttggaaaagaaaaacagaacagctttattttcg cgccttaaagtactatttaacgaaaaaatcccagtttaccgatgcgaaa aaagcgcttcaacaagcagcgaaagatttatatggtgaagatgcttcta aaaaagttgctgaagcttgggaagcagttggggttaactgattaacaaa tgttagagaaaaattaattctccaagtgatattcttaaaataattcatg aatattttttcttatattagctaattaagaagataactaactgctaatc caattttttaacggaacaaattagtgaaaatgaaggccgaattttccttg ttctaaaaaggttgtattagcgtatcacgaggagggagtataagtggga ttaaacagatttatgcgtgcgatgatggtggttttcattactgccaatt gcattacgattaacccgacgtcgaccatacgacgttaattcttgca atgttagctattggcgtgttctctttaggggcgtttatcaaaattattc aattaagaaaaataattaaaaacacagaacgaaagaaaaagtgaggtg aatgatatgaaattcaaaaaggtggttctaggtatgtgcttgatcgcaa gtgttctagtctttccggtaacgataaaagcaaatgcctgttgtgatga atacttacaaacacccgcagctccgcatgatattgacagcaaattacca cataaacttagttggtccgcggataacccgacaaatactgacgtaaata cgcactattggcttttttaaacaagcggaaaaaatactagctaaagatgt aaatcatatgcgagctaatttaatgaatgaacttaaaaaattcgataaa caaatagctcaaggaatatatgatgcggatcataaaaatccatattatg
```

-continued
```
atactagtacatttttatctcatttttataatcctgatagagataatac ttatttgccgggttttgctaatgcgaaaataacaggagcaaagtatttc aatcaatcggtgactgattaccgagaagggaa.
```

Production of Inflammatory Cytokines:

Macrophages such as RAW 264.7 are infected with different Listeria backbones such as Lm prfA-(pGG55), Lm dal dat, Lm dal dat actA, Lm dal dat actA Δ inlC and Lm dal dat Δ inlC and supernatant is harvested at different time points to quantify the level of various cytokines using different ELISA based kits. The cytokines that are quantified include IFN-γ, TNF-α and IL-6.

In Vivo Cytokine Production:

To measure the in vivo cytokine production and recruitment of neutrophils, C57BL/6 mice are injected intraperitoneally with different $10^8$ CFU of Lm prfA-(pGG55), Lm dal dat, Lm dal dat actA, Lm dal dat actA Δ inlC and Lm dal dat Δ inlC, Listeria control or an equivalent volume of saline. After 12 h mice are killed and peritoneal cavities are washed with 2 mL of PBS. The peritoneal washes are examined for bacterial load after plating on growth medium and analysis of proinflammatory cytokines such as MIP-1α, KC, MCP etc. Using flow cytometry the number of neutrophils and macrophages is determine after staining with markers such as Gr-1, CD11b and F4/80 and further these populations are quantified using CELLQUEST software (Flow and Image Cytometry Analysis Software).

Transwell Migration Assay:

This assay is done to determine if there is an increase in the migration of neutrophils following infection of bone marrow derived macrophages or dendritic cells with the inlC deletion strain. Bone marrow-derived macrophages or dendritic cells are isolated from mice such as C57BL/6 and are infected with the inlC deletion mutants or control Listeria. Using infected cells the transwell assay is set up using corning costar Transwell plates. The assay is initially standardized using 3, 5, or 8 micron pore transwell plates. To test neutrophil migration, plate the infected APCs in the bottom of the plate and the neutrophils in the top of the well in the chamber. At different time points the cells are counted to determine the number of neutrophils that have migrated to the bottom.

Therapeutic efficacy of the Lm dal dat actA Δ inlC Mutant:

To determine the therapeutic efficacy of inlC mutant, human Prostate specific antigen (PSA) is used as tumor antigen as proof of concept. The backbone Lm dal dat actA inlC are transformed with the plasmid, pAdv142 that contains expression cassette for human PSA resulting in Lmd-dAinlC142. The strain LmddAinlC142 is characterized for the expression and secretion of fusion protein, tLLO-PSA. Further the strain LmddAinlC142 are passaged twice in vivo in mice and the colonies obtained after two in vivo passages are examined for the expression and secretion of fusion protein, tLLO-PSA. The vaccine working stock are prepared from the colonies obtained after second in vivo passage and this are used for the assessment of therapeutic effects and immunogenicity.

Impact on Tumor Microenvironment:

The ability of LmddA, LmddAΔactA, LmddAΔPlcA, LmddAΔPlcB, LmddAΔprfA, LmddAinlC142, LmddA142 and other control strains to cause infiltration of immune cells in the tumor microenvironment are determined. In this study mice are inoculated with $1\times10^6$ TPSA23 tumor cells on day 0 and are vaccinated on day 7, 14 and 21 with $10^8$ CFU of LmddAinlC142, LmddA142 and other control strains.

Tumors are harvested on day 28 and processed for further staining with different cell surface markers such as Gr-1, CD11b, CD3, CD4, CD8, CD25, Foxp3, NK1.1 and CD62L. Using these markers different cell populations that are examined include macrophages (CD11b$^+$), NK cells (NK1.1$^+$), neutrophils (Gr-1$^+$ CD11b$^+$), myeloid derived suppressor cells (MDSCs) (Gr-1$^+$CD11b$^+$), regulatory T cells (CD4$^+$ CD25$^+$ Foxp3$^+$) and effector T cells (CD8$^+$ CD3$^+$ CD62L$^{low}$). Further effector T cells are characterized for their functional ability to produce effector cytokines such as IFN-γ, TNF-α and IL-2. The intratumoral regulatory T cells and MDSCs are tested for their ability to cause suppression of T cell proliferation.

Results

Example 5: A Plasmid Containing an Amino Acid Metabolism Enzyme Instead of an Antibiotic Resistance Gene is Retained in E. coli and LM Both In Vitro and In Vivo An auxotroph complementation system based on D-alanine racemase was utilized to mediate plasmid retention in LM without the use of an antibiotic resistance gene. E. coli strain MB2159 is an alr (−)/dadX (−) deficient mutant that is not able to synthesize D-alanine racemase. Listeria strain Lm dal(−)/dat(−) (Lmdd) similarly is not able to synthesize D-alanine racemase due to partial deletions of the dal and the dat genes. Plasmid pGG55, which is based on E. coli-Listeria shuttle vector pAM401, was modified by removing both CAT genes and replacing them with a p60-dal expression cassette under control of the Listeria p60 promoter to generate pTV3 (FIG. 9). DNA was purified from several colonies.

Example 6: Plasmids Containing a Metabolic Enzyme do not Increase the Virulence of Bacteria As virulence is linked to LLO function, the hemolytic lysis activity between Lmdd-TV3 and Lm-LLOE7 was compared. This assay tests LLO function by lysis of red blood cells and can be performed with culture supernatant, purified LLO or bacterial cells. Lmdd-TV3 displayed higher hemolytic lysis activity than Lm-LLOE7.

In vivo virulence was also measured by determining LD$_{50}$ values, a more direct, and therefore accurate, means of measuring virulence. The LD$_{50}$ of Lmdd-TV3 (0.75×10$^9$) was very close to that of Lm-LLOE7 (1×10$^9$), showing that plasmids containing a metabolic enzyme do not increase the virulence of bacteria.

Example 7: Induction of Anti-Tumor Immunity by Plasmids Containing a Metabolic Enzyme Efficacy of the metabolic enzyme-containing plasmid as a cancer vaccine was determined in a tumor regression model. The TC-1 cell line model, which is well characterized for HPV vaccine development and which allowed for a controlled comparison of the regression of established tumors of similar size after immunization with Lmdd-TV3 or Lm-LLOE7, was used. In two separate experiments, immunization of mice with Lmdd-TV3 and Lm-LLOE7 resulted in similar tumor regression (FIG. 14) with no statistically significant difference (p<0.05) between vaccinated groups. All immunized mice were still alive after 63 days, whereas non-immunized mice had to be sacrificed when their tumors reached 20 mm diameter. Cured mice remained tumor-free until the termination of the experiment.

Thus, metabolic enzyme-containing plasmids are efficacious as a therapeutic cancer vaccine. Because immune responses required for a therapeutic cancer vaccine are stronger than those required for a prophylactic cancer vaccine, these results demonstrate utility as well for a prophylactic cancer vaccine.

Example 8: inlC-Deletion Mutant Generate Significantly High Levels of the Chemokines and Cytokines inlC deletion mutant generates significantly high levels of the chemokines such as MIP-1α, KC (mouse homolog of IL-8), MCP resulting in infiltration of neutrophils and leukocytes towards the site of infection. Thus when different Listeria strains are administered intraperitoneally, the inlC mutant demonstrate an increase production of these cytokines and chemokines, which attract neutrophils and macrophages in the peritoneal fluid obtained 12 h after injection. Further, inlC deletion mutant generate significantly high levels of the inflammatory cytokines when compared to control strains.

Example 9: inlC-Deletion Mutants Induce Neutrophil Migration

The macrophages infected with inlC deletion mutant show significant increase in the migration of neutrophils at different time points when compared to other control strains. The results of this experiment strongly support the ability of this strain to attract immune cells such as neutrophils during infection.

Example 10: inlC-Deletion Mutants Effect a Therapeutic Anti-Tumor Response

The results of anti-tumor studies using both LmddA142 and LmddAinlC142 are very comparable to each other and therapeutic regression of tumors is observed. Further, two doses of LmddAinlC142 are comparable to three doses of the strain LmddA142 because of its ability to generate high levels of innate responses and increased secretion of proinflammatory cytokines.

Materials and Methods (Examples 11-16)

Oligonucleotides were synthesized by INVITROGEN (Carlsbad, Calif.) and DNA sequencing was done by GENEWIZ Inc, South Plainfield, N.J. Flow cytometry reagents were purchased from Becton Dickinson Biosciences (BD, San Diego, Calif.). Cell culture media, supplements and all other reagents, unless indicated, were from SIGMA-ALDRICH (St. Louise, Mo.). Her2/neu HLA-A2 peptides were synthesized by EZBIOLABS (Westfield, Ind.). Complete RPMI 1640 (C-RPMI) medium contained 2 mM glutamine, 0.1 mM non-essential amino acids, and 1 mM sodium pyruvate, 10% fetal bovine serum, penicillin/streptomycin, Hepes (25 mM). The polyclonal anti-LLO antibody was described previously and anti-Her2/neu antibody was purchased from SIGMA-ALDRICH.

Mice and Cell Lines

All animal experiments were performed according to approved protocols by IACUC at the University of Pennsylvania or Rutgers University. FVB/N mice were purchased from Jackson laboratories (Bar Harbor, Me.). The FVB/N Her2/neu transgenic mice, which overexpress the rat Her2/neu onco-protein were housed and bred at the animal core facility at the University of Pennsylvania. The NT-2 tumor cell line expresses high levels of rat Her2/neu protein, was derived from a spontaneous mammary tumor in these mice and grown as described previously. DHFR-G8 (3T3/neu) cells were obtained from ATCC and were grown according to the ATCC recommendations. The EMT6-Luc cell line was a generous gift from Dr. John Ohlfest (University of Minnesota, Minn.) and was grown in complete C-RPMI medium. Bioluminescent work was conducted under guidance by the Small Animal Imaging Facility (SAIF) at the University of Pennsylvania (Philadelphia, Pa.).

Listeria Constructs and Antigen Expression

Her2/neu-pGEM7Z was kindly provided by Dr. Mark Greene at the University of Pennsylvania and contained the full-length human Her2/neu (hHer2) gene cloned into the pGEM7Z plasmid (PROMEGA, Madison Wis.). This plasmid was used as a template to amplify three segments of hHer-2/neu, namely, EC1, EC2, and IC1, by PCR using PFX DNA polymerase (hot start high fidelity DNA polimerase INVITROGEN) and the oligos indicated in Table 1.

TABLE 1

Primers for cloning of Human her-2-Chimera

| | DNA sequence | Base pair region | Amino acid region or junctions |
|---|---|---|---|
| Her-2-Chimera (F) | TGATCTCGAGACCCAC CTGGACATGCTC (SEQ ID NO: 61) | 120-510 | 40-170 |
| HerEC1-EC2F (Junction) | CTACCAGGACACGATT TTGTGGAAG-AATATC CAGGAGTTTGCTGGCT GC (SEQ ID NO: 62) | 510/1077 | 170/359 |
| HerEC1-EC2R (Junction) | GCAGCCAGCAAACTCC TGGATATT-CTTCCAC AAAATCGTGTCCTGGT AG (SEQ ID NO: 63) | | |
| HerEC2-IC1F (Junction) | CTGCCACCAGCTGTGC GCCCGAGGG-CAGCAG AAGATCCGGAAGTACA CGA (SEQ ID NO: 64) | 1554/2034 | 518/679 |
| HerEC2-IC1R (Junction) | TCGTGTACTTCCGGAT CTTCTGCTGCCCTCGG GC GCACAGCTGGTGG CAG (SEQ ID NO: 65) | | |
| Her-2-Chimera (R) | GTGGCCCGGGTCTAGA TTAGTCTAAGAGGCAG CCATAGG (SEQ ID NO: 66) | 2034-2424 | 679-808 |

The Her-2/neu chimera construct was generated by direct fusion by the SOEing PCR method and each separate hHer-2/neu segment as templates. Primers are shown in Table 2.

Sequence of primers for amplification of different segments human Her2 regions.

| DNA sequence | | Base pair region | Amino acid region |
|---|---|---|---|
| Her-2-EC1(F) | CCGCCTCGAGGCCGCG AGCACCCAAGTG (SEQ ID NO: 67) | 58-979 | 20-326 |
| Her-2-EC1(R) | CGCGACTAGTTTAATC CTCTGCTGTCACCTC (SEQ ID NO: 68) | | |
| Her-2-EC2(F) | CCGCCTCGAGTACCTT TCTACGGACGTG (SEQ ID NO: 69) | 907-1504 | 303-501 |
| Her-2-EC2(R) | CGCGACTAGTTTACTC TGGCCGGTTGGCAG (SEQ ID NO: 70) | | |
| Her-2-IC1(F) | CCGCCTCGAGCAGCAG AAGATCCGGAAGTAC (SEQ ID NO: 71) | 2034-3243 | 679-1081 |
| Her-2-IC1(R) | CGCGACTAGTTTAAGC CCCTTCGGAGGGTG (SEQ ID NO: 72) | | |

Sequence of primers for amplification of different segments human Her2 regions.

ChHer2 gene was excised from pAdv138 using XhoI and SpeI restriction enzymes, and cloned in frame with a truncated, non-hemolytic fragment of LLO in the Lmdd shuttle vector, pAdv134. The sequences of the insert, LLO and hly promoter were confirmed by DNA sequencing analysis. This plasmid was electroporated into electro-competent actA, dal, dat mutant Listeria monocytogenes strain, LmddA and positive clones were selected on Brain Heart infusion (BHI) agar plates containing streptomycin (250 µg/ml). In some experiments similar Listeria strains expressing hHer2/neu (Lm-hHer2) fragments were used for comparative purposes. These have been previously described. In all studies, an irrelevant Listeria construct (Lm-control) was included to account for the antigen independent effects of Listeria on the immune system. Lm-controls were based on the same Listeria platform as ADXS31-164, but expressed a different antigen such as HPV16-E7 or NY-ESO-1. Expression and secretion of fusion proteins from Listeria were tested. Each construct was passaged twice in vivo.

Cytotoxicity Assay

Groups of 3-5 FVB/N mice were immunized three times with one week intervals with $1 \times 10^8$ colony forming units (CFU) of Lm-LLO-ChHer2, ADXS31-164, Lm-hHer2 ICI or Lm-control (expressing an irrelevant antigen) or were left naïve. NT-2 cells were grown in vitro, detached by trypsin and treated with mitomycin C (250 µg/ml in serum free C-RPMI medium) at 37° C. for 45 minutes. After 5 washes, they were co-incubated with splenocytes harvested from immunized or naive animals at a ratio of 1:5 (Stimulator: Responder) for 5 days at 37° C. and 5% CO2. A standard cytotoxicity assay was performed using europium labeled 3T3/neu (DHFR-G8) cells as targets according to the method previously described. Released europium from killed target cells was measured after 4 hour incubation using a spectrophotometer (PERKIN ELMER, VICTOR2, multitask plate reader) at 590 nm. Percent specific lysis was defined as (lysis in experimental group-spontaneous lysis)/ (Maximum lysis-spontaneous lysis).

Interferon-γ Secretion by Splenocytes from Immunized Mice

Groups of 3-5 FVB/N or HLA-A2 transgenic mice were immunized three times with one week intervals with $1 \times 10^8$ CFU of ADXS31-164, a negative Listeria control (expressing an irrelevant antigen) or were left naïve. Splenocytes from FVB/N mice were isolated one week after the last immunization and co-cultured in 24 well plates at 5×10⁶ cells/well in the presence of mitomycin C treated NT-2 cells in C-RPMI medium. Splenocytes from the HLA-A2 transgenic mice were incubated in the presence of 1 μM of HLA-A2 specific peptides or 1 μg/ml of a recombinant His-tagged ChHer2 protein, produced in E. coli and purified by a nickel based affinity chromatography system. Samples from supernatants were obtained 24 or 72 hours later and tested for the presence of interferon-γ (IFN-γ) using mouse IFN-γ Enzyme-linked immunosorbent assay (ELISA) kit according to manufacturer's recommendations.

Tumor Studies in her2 Transgenic Animals

Six weeks old FVB/N rat Her2/neu transgenic mice (9-14/group) were immunized 6 times with 5×10⁸ CFU of Lm-LLO-ChHer2, ADXS31-164 or Lm-control. They were observed twice a week for the emergence of spontaneous mammary tumors, which were measured using an electronic caliper, for up to 52 weeks. Escaped tumors were excised when they reached a size 1 cm² in average diameter and preserved in RNALATER (tissue storage reagent that permeates tissues to stabilize and protect cellular RNA) at −20° C. In order to determine the effect of mutations in the Her2/neu protein on the escape of these tumors, genomic DNA was extracted using a genomic DNA isolation kit, and sequenced.

Effect of ADXS31-164 on Regulatory T Cells in Spleens and Tumors

Mice were implanted subcutaneously (s.c.) with 1×10⁶ NT-2 cells. On days 7, 14 and 21, they were immunized with 1×10⁸ CFUs of ADXS31-164, LmddA-control or left naïve. Tumors and spleens were extracted on day 28 and tested for the presence of CD3+/CD4+/FoxP3+ Tregs by FACS analysis. Briefly, splenocytes were isolated by homogenizing the spleens between two glass slides in C-RPMI medium. Tumors were minced using a sterile razor blade and digested with a buffer containing DNase (12 U/ml), and collagenase (2 mg/ml) in PBS. After 60 min incubation at RT with agitation, cells were separated by vigorous pipetting. Red blood cells were lysed by RBC lysis buffer followed by several washes with complete RPMI-1640 medium containing 10% FBS. After filtration through a nylon mesh, tumor cells and splenocytes were resuspended in FACS buffer (2% FBS/PBS) and stained with anti-CD3-PerCP-Cy5.5, CD4-FITC, CD25-APC antibodies followed by permeabilization and staining with anti-Foxp3-PE. Flow cytometry analysis was performed using 4-color FACSCALIBUR (cell analysis and cell sorter, BD) and data were analyzed using CELL QUEST software (Flow and Image Cytometry Analysis Software, BD).

Statistical Analysis

The log-rank Chi-Squared test was used for survival data and student's t-test for the CTL and ELISA assays, which were done in triplicates. A p-value of less than 0.05 (marked as *) was considered statistically significant in these analyzes. All statistical analysis was done with either PRISM software, V. 4.0a (2006) or SPSS software, V. 15.0 (2006) (statistical analysis software). For all FVB/N rat Her2/neu transgenic studies we used 8-14 mice per group, for all wild-type FVB/N studies we used at least 8 mice per group unless otherwise stated. All studies were repeated at least once except for the long term tumor study in Her2/neu transgenic mouse model.

Results

Example 11: Generation of L. monocytogenes Strains that Secrete LLO Fragments Fused to Her-2 Fragments: Construction of ADXS31-164

Construction of the chimeric Her2/neu gene (ChHer2) was described previously. Briefly, ChHer2 gene was generated by direct fusion of two extracellular (aa 40-170 and aa 359-433) and one intracellular fragment (aa 678-808) of the Her2/neu protein by SOEing PCR method. The chimeric protein harbors most of the known human MHC class I epitopes of the protein. ChHer2 gene was excised from the plasmid, pAdv138 (which was used to construct Lm-LLO-ChHer2) and cloned into LmddA shuttle plasmid, resulting in the plasmid pAdv164 (FIG. 15A). There are two major differences between these two plasmid backbones. 1) Whereas pAdv138 uses the chloramphenicol resistance marker (cat) for in vitro selection of recombinant bacteria, pAdv164 harbors the D-alanine racemase gene (dal) from bacillus subtilis, which uses a metabolic complementation pathway for in vitro selection and in vivo plasmid retention in LmddA strain which lacks the dal-dat genes. This vaccine platform was designed and developed to address FDA concerns about the antibiotic resistance of the engineered Listeria vaccine strains. 2) Unlike pAdv138, pAdv164 does not harbor a copy of the prfA gene in the plasmid (see sequence below and FIG. 15A), as this is not necessary for in vivo complementation of the Lmdd strain. The LmddA vaccine strain also lacks the actA gene (responsible for the intracellular movement and cell-to-cell spread of Listeria) so the recombinant vaccine strains derived from this backbone are 100 times less virulent than those derived from the Lmdd, its parent strain. LmddA-based vaccines are also cleared much faster (in less than 48 hours) than the Lmdd-based vaccines from the spleens of the immunized mice. The expression and secretion of the fusion protein tLLO-ChHer2 from this strain was comparable to that of the Lm-LLO-ChHer2 in TCA precipitated cell culture supernatants after 8 hours of in vitro growth (FIG. 15B) as a band of ~104 KD was detected by an anti-LLO antibody using Western Blot analysis. The Listeria backbone strain expressing only tLLO was used as negative control.

pAdv164 sequence (7075 base pairs) (see FIG. 15):

(SEQ ID NO: 73)

```
cggagtgtatactggcttactatgttggcactgatgagggtgtcagtgaagtgcttcatgtggcaggagaaaaaggctgcaccggtgcgtca gcagaatatgtgatacaggatatattccgcttcctcgctcactgactcgctacgctcggtcgttcgactgcggcgagcggaaatggcttacga acggggcggagatttcctggaagatgccaggaagatacttaacagggaagtgagagggccgcggcaaagccgttttccataggctccgc cccctgacaagcatcacgaaatctgacgctcaaatcagtggtggcgaaacccgacaggactataaagataccaggcgtttcccctggcg gctccctcgtgcgctctcctgttcctgcctttcggtttaccggtgtcattccgctgttatggccgcgtttgtctcattccacgcctgacactcagttc cgggtaggcagttcgctccaagctggactgtatgcacgaaccccccgttcagtccgaccgctgcgccttatccggtaactatcgtcttgagtc caacccggaaagacatgcaaaagcaccactggcagcagccactggtaattgatttagaggagttagtcttgaagtcatgcgccggttaaggc
```

-continued

```
taaactgaaaggacaagttttggtgactgcgctcctccaagccagttacctcggttcaaagagttggtagctcagagaaccttcgaaaaaccg ccctgcaaggcggttttttcgttttcagagcaagagattacgcgcagaccaaaacgatctcaagaagatcatcttattaatcagataaaatatttc tagccctcctttgattagtatattcctatcttaaagttacttttatgtggaggcattaacatttgttaatgacgtcaaaaggatagcaagactagaata aagctataaagcaagcatataatattgcgtttcatctttagaagcgaatttcgccaatattataattatcaaaagagaggggtggcaaacggtatt tggcattattaggttaaaaaatgtagaaggagagtgaaacccatgaaaaaaataatgctagttttattacacttatattagttagtctaccaattgc gcaacaaactgaagcaaaggatgcatctgcattcaataaagaaaattcaatttcatccatggcaccaccagcatctccgcctgcaagtcctaa gacgccaatcgaaaagaaacacgcggatgaaatcgataagtatatacaaggattggattacaataaaaacaatgtattagtataccacggag atgcagtgacaaatgtgccgccaagaaaaggttacaaagatggaaatgaatatattgttgtggagaaaagaagaaatccatcaatcaaaata atgcagacattcaagttgtgaatgcaatttcgagcctaacctatccaggtgctctcgtaaaagcgaattcggaattagtagaaaatcaaccagat gttctccctgtaaaacgtgattcattaacactcagcattgatttgccaggtatgactaatcaagacaataaaatagttgtaaaaaatgccactaaat caaacgttaacaacgcagtaaatacattagtggaaagatggaatgaaaaatatgctcaagcttatccaaatgtaagtgcaaaaattgattatgat gacgaaatggcttacagtgaatcacaattaattgcgaaatttggtacagcatttaaagctgtaaataatagcttgaatgtaaacttcggcgcaatc agtgaagggaaaatgcaagaagaagtcattagttttaaacaaatttactataacgtgaatgttaatgaacctacaagaccttccagattttcggc aaagctgttactaaagagcagttgcaagcgcttggagtgaatgcagaaaatcctcctgcatatatctcaagtgtggcgtatggccgtcaagttt atttgaaattatcaactaattcccatagtactaaagtaaaagctgcttttgatgctgccgtaagcggaaaatctgtctcaggtgatgtagaactaac aaatatcatcaaaaattcttccttcaaagccgtaatttacggaggttccgcaaaagatgaagttcaaatcatcgacggcaacctcggagacttac gcgatattttgaaaaaaggcgctacttttaatcgagaaacaccaggagttcccattgcttatacaacaaacttcctaaaagacaatgaattagct gttattaaaaacaactcagaatatattgaaacaacttcaaaagcttatacagatggaaaaattaacatcgatcactctggaggatacgttgctcaa ttcaacatttcttgggatgaagtaaattatgatctcgagacccacctggacatgctccgccacctctaccagggctgccaggtggtgcaggga aacctggaactcacctacctgcccaccaatgccagcctgtccttcctgcaggatatccaggaggtgcagggctacgtgctcatcgctcacaa ccaagtgaggcaggtcccactgcagaggctgcggattgtgcgaggcacccagctctttgaggacaactatgccctggccgtgctagacaat ggagaccgctgaacaataccacccctgtcacagggggcctcccaggaggcctgcgggagctgcagcttcgaagcctcacagagatcttg aaaggaggggtcttgatccagcggaaccccagctctgctaccaggacacgattttgtggaagaatatccaggagtttgctggctgcaagaa gatctttgggagcctggcatttctgccggagagctttgatggggacccagcctccaacactgccccgctccagccagagcagctccaagtgt ttgagactctggaagagatcacaggttacctatacatctcagcatggccggacagcctgcctgacctcagcgtcttccagaacctgcaagtaa tccggggacgaattctgcacaatggcgcctactcgctgaccctgcaagggctgggcatcagctggctggggctgcgctcactgagggaac tgggcagtggactggccctcatccaccataacacccacctctgcttcgtgcacacggtgccctgggaccagctctttcggaacccgcaccaa gctctgctccacactgccaaccggccagaggacgagtgtgtgggcgagggcctggcctgccaccagctgtgcgcccgagggcagaga agatccggaagtacacgatgcggagactgctgcaggaaacggagctggtggagccgctgacacctagcggagcgatgcccaaccaggc gcagatgcggatcctgaaagagacggagctgaggaaggtgaaggtgcttggatctggcgcttttggcacagtctacaagggcatctggatc cctgatggggagaatgtgaaaattccagtggccatcaaagtgttgagggaaaacacatcccccaaagccaacaaagaaatcttagacgaag catacgtgatggctggtgtgggctccccatatgtctcccgccttctgggcatctgcctgacatccacggtgcagctggtgacacagcttatgcc ctatggctgcctcttagactaatctagacccgggccactaactcaacgctagtagtggatttaatcccaaatgagccaacagaaccagaacca gaaacagaacaagtaacattggagttagaaatggaagaagaaaaaagcaatgatttcgtgtgaataatgcacgaaatcattgcttattttttaa aaagcgatatactagatataacgaaacaacgaactgaataaagaatacaaaaaagagccacgaccagttaaagcctgagaaactttaactg cgagccttaattgattaccaccaatcaattaaagaagtcgagacccaaaatttggtaaagtatttaattactttattaatcagatacttaaatatctgt aaacccattatatcgggttttgaggggatttcaagtcttaagaagataccaggcaatcaattaagaaaaacttagttgattgccttttttgttgtga ttcaactttgatcgtagcttctaactaattaattttcgtaagaaaggagaacagctgaatgaatatccctttgttgtagaaactgtgcttcatgacg gcttgtaaagtacaaatttaaaaatagtaaaattcgctcaatcactaccaagccaggtaaaagtaaggggctattttgcgtatcgctcaaaaa aaagcatgattggcggacgtggcgttgttctgacttccgaagaagcgattcacgaaaatcaagatacatttacgcattggacaccaaacgttta
```

-continued

```
tcgttatggtacgtatgcagacgaaaaccgttcatacactaaaggacattctgaaaacaatttaagacaaatcaataccttctttattgattttgata ttcacacggaaaaagaaactatttcagcaagcgatattttaacaacagctattgatttaggttttatgcctacgttaattatcaaatctgataaggt tatcaagcatattttgttttagaaacgccagtctatgtgacttcaaaatcagaatttaaatctgtcaaagcagccaaaataatctcgcaaaatatcc gagaatattttggaaagtctttgccagttgatctaacgtgcaatcattttgggattgctcgtataccaagaacggacaatgtagaattttttgatccc aattaccgttattctttcaaagaatggcaagattggtctttcaaacaaacagataataagggctttactcgttcaagtctaacggttttaagcggta cagaaggcaaaaaacaagtagatgaaccctggtttaatctcttattgcacgaaacgaattttcaggagaaaagggtttagtagggcgcaata gcgttatgtttaccctctctttagcctactttagttcaggctattcaatcgaaacgtgcgaatataatatgtttgagtttaataatcgattagatcaacc cttagaagaaaagaagtaatcaaaattgttagaagtgcctattcagaaaactatcaagggctaatagggaatacattaccattctttgcaaag cttgggtatcaagtgatttaaccagtaaagatttatttgtccgtcaagggtggtttaaattcaagaaaaaaagaagcgaacgtcaacgtgttcattt gtcagaatggaaagaagatttaatggcttatattagcgaaaaaagcgatgtatacaagccttatttagcgacgaccaaaaaagagattagaga agtgctaggcattcctgaacggacattagataaattgctgaaggtactgaaggcgaatcaggaaattttctttaagattaaaccaggaagaaat ggtggcattcaacttgctagtgttaaatcattgttgctatcgatcattaaattaaaaaaagaagaacgagaaagctatataaaggcgctgacagc ttcgtttaatttagaacgtacatttattcaagaaactctaaacaaattggcagaacgccccaaaacggacccacaactcgatttgtttagctacga tacaggctgaaaataaaacccgcactatgccattacatttatatctatgatacgtgtttgttttctttgctggctagcttaattgcttatatttacctgc aataaaggatttcttacttccattatactcccattttccaaaaacatacggggaacacgggaacttattgtacaggccacctcatagttaatggttt cgagccttcctgcaatctcatccatggaaatatattcatcccctgccggcctattaatgtgacttttgtgcccggcggatattcctgatccagctc caccataaattggtccatgcaaattcggccggcaattttcaggcgttttcccttcacaaggatgtcggtcccttcaattttcggagccagccgtc cgcatagcctacaggcaccgtcccgatccatgtgtcttttccgctgtgtactcggctccgtagctgacgctctcgccttttctgatcagtttgaca tgtgacagtgtcgaatgcagggtaaatgccggacgcagctgaaacggtatctcgtccgacatgtcagcagacgggcgaaggccatacatg ccgatgccgaatctgactgcattaaaaaagccttttttcagccggagtccagcggcgctgttcgcgcagtggaccattagattctttaacggca gcggagcaatcagctctttaaagcgctcaaactgcattaagaaatagcctctttctttttcatccgctgtcgcaaaatgggtaaatacccctttgc actttaaacgagggttgcggtcaagaattgccatcacgttctgaacttcttcctctgtttttacaccaagtctgttcatcccgtatcgaccttcaga tgaaaatgaagagaaccttttttcgtgtggcgggctgcctcctgaagccattcaacagaataacctgttaaggtcacgtcatactcagcagcga ttgccacatactccggggaaccgcgccaagcaccaatataggcgccttcaatcccttttttgcgcagtgaaatcgcttcatccaaaatggcca cggccaagcatgaagcacctgcgtcaagagcagcctttgctgtttctgcatcaccatgcccgtaggcgtttgctttcacaactgccatcaagtg gacatgttcaccgatatgttttttcatattgctgacattttccttttatcgcggacaagtcaatttccgcccacgtatctctgtaaaaaggttttgtgctc atggaaaactcctctctttttttcagaaaatcccagtacgtaattaagtatttgagaattaattttatattgattaatactaagtttacccagttttcaccta aaaaacaaatgatgagataatagctccaaaggctaaagaggactataccaactatttgttaattaa
```

Example 12: ADXS31-164 is as Immunogenic as LM-LLO-ChHer2

Immunogenic properties of ADXS31-164 in generating anti-Her2/neu specific cytotoxic T cells were compared to those of the Lm-LLO-ChHer2 vaccine in a standard CTL assay. Both vaccines elicited strong but comparable cytotoxic T cell responses toward Her2/neu antigen expressed by 3T3/neu target cells. Accordingly, mice immunized with a Listeria expressing only an intracellular fragment of Her2-fused to LLO showed lower lytic activity than the chimeras which contain more MHC class I epitopes. No CTL activity was detected in naïve animals or mice injected with the irrelevant Listeria vaccine (FIG. 16A). ADXS31-164 was also able to stimulate the secretion of IFN-γ by the splenocytes from wild type FVB/N mice (FIG. 16B). This was detected in the culture supernatants of these cells that were co-cultured with mitomycin C treated NT-2 cells, which express high levels of Her2/neu antigen (FIG. 19C).

Proper processing and presentation of the human MHC class I epitopes after immunizations with ADXS31-164 was tested in HLA-A2 mice. Splenocytes from immunized HLA-A2 transgenics were co-incubated for 72 hours with peptides corresponding to mapped HLA-A2 restricted epitopes located at the extracellular (HLYQGCQVV SEQ ID NO: 74 or KIFGSLAFL SEQ ID NO: 75) or intracellular (RLLQETELV SEQ ID NO: 76) domains of the Her2/neu molecule (FIG. 16C). A recombinant ChHer2 protein was used as positive control and an irrelevant peptide or no peptide as negative controls. The data from this experiment show that ADXS31-164 is able to elicit anti-Her2/neu specific immune responses to human epitopes that are located at different domains of the targeted antigen.

Example 13: ADXS31-164 was More Efficacious than LM-LLO-ChHER2 in Preventing the Onset of Spontaneous Mammary Tumors Anti-tumor effects of ADXS31-164 were compared to those of Lm-LLO-ChHer2 in Her2/neu transgenic animals which develop slow growing, spontaneous mammary tumors at 20-25 weeks of age. All animals immunized with the irrelevant *Listeria*-control vaccine developed breast tumors within weeks 21-25 and were sacrificed before week 33. In contrast, Liseria-Her2/neu recombinant vaccines caused a significant delay in the formation of the mammary tumors. On week 45, more than 50% o ADXS31-164 vaccinated mice (5 out of 9) were still tumor free, as compared to 25% of mice immunized with Lm-LLO-ChHer2. At week 52, 2 out of 8 mice immunized with ADXS31-164 still remained tumor free, whereas all mice from other experimental groups had already succumbed to their disease (FIG. 17). These results indicate that despite being more attenuated, ADXS31-164 is more efficacious than Lm-LLO-ChHer2 in preventing the onset of spontaneous mammary tumors in Her2/neu transgenic animals.

Example 14: Mutations in Her2/Neu Gene Upon Immunization with ADXS31-164

Mutations in the MHC class I epitopes of Her2/neu have been considered responsible for tumor escape upon immunization with small fragment vaccines or HERCEPTIN TRASTUZUMAB, a monoclonal antibody that targets an epitope in the extracellular domain of Her2/neu. To assess this, genomic material was extracted from the escaped tumors in the transgenic animals and sequenced the corresponding fragments of the neu gene in tumors immunized with the chimeric or control vaccines. Mutations were not observed within the Her-2/neu gene of any vaccinated tumor samples suggesting alternative escape mechanisms (data not shown).

Example 15: ADXS31-164 Causes a Significant Decrease in Intra-Tumoral T Regulatory Cells To elucidate the effect of ADXS31-164 on the frequency of regulatory T cells in spleens and tumors, mice were implanted with NT-2 tumor cells. Splenocytes and intratumoral lymphocytes were isolated after three immunizations and stained for Tregs, which were defined as $CD3^+/CD4^+/CD25^+/FoxP3^+$ cells, although comparable results were obtained with either FoxP3 or CD25 markers when analyzed separately. The results indicated that immunization with ADXS31-164 had no effect on the frequency of Tregs in the spleens, as compared to an irrelevant *Listeria* vaccine or the naïve animals (See FIG. 18). In contrast, immunization with the *Listeria* vaccines caused a considerable impact on the presence of Tregs in the tumors (FIG. 19A). Whereas in average 19.0% of all $CD3^+$ T cells in untreated tumors were Tregs, this frequency was reduced to 4.2% for the irrelevant vaccine and 3.4% for ADXS31-164, a 5-fold reduction in the frequency of intra-tumoral Tregs (FIG. 19B). The decrease in the frequency of intra-tumoral Tregs in mice treated with either of the LmddA vaccines could not be attributed to differences in the sizes of the tumors. In a representative experiment, the tumors from mice immunized with ADXS31-164 were significantly smaller [mean diameter (mm)±SD, 6.71±0.43, n=5] than the tumors from untreated mice (8.69±0.98, n=5, p<0.01) or treated with the irrelevant vaccine (8.41±1.47, n=5, p=0.04), whereas comparison of these last two groups showed no statistically significant difference in tumor size (p=0.73). The lower frequency of Tregs in tumors treated with LmddA vaccines resulted in an increased intratumoral CD8/Tregs ratio, suggesting that a more favorable tumor microenvironment can be obtained after immunization with LmddA vaccines. However, only the vaccine expressing the target antigen HER2/neu (ADXS31-164) was able to reduce tumor growth, indicating that the decrease in Tregs has an effect only in the presence on antigen-specific responses in the tumor.

Example 16: Construction of Dual Plasmid that Concomitantly Delivers Two Heterologous Antigens DNA corresponding to the actA promoter region and 1-233 amino acids of N-terminus of ActA is amplified from *Listeria* genomic DNA by Polymerase Chain Reaction (PCR) using the following primers ActA-F-5'-at cccggg tgaagcttgggaagcagttggg-3' (XmaI) (SEQ ID NO: 77) and ActA-R-at tctaga tttatcacgtacccatttccccgc(XbaI)(SEQ ID NO:78). The restriction sites used for cloning are underlined. XmaI/XbaI segment is cloned in plasmid pNEB 193 to create pNEB193-ActA. Further antigen 2, which is Chimera Her2 is PCR amplified using the primers Ch-Her2-F-5'-at tctaga acccacctggacatgctcgccac-3'(XbaI)(SEQ ID NO: 79) and Ch-Her2-R-5'- gtcgacactagt ctagtggtgatggtgatgatg gagctcagatct gtctaagaggcagccatagggc-3'(RE sites-SalI-SpeI-SacI-BglII)(SEQ ID NO: 80). The XbaI and SalI fragment of Ch-Her2 is cloned in the plasmid pNEB193-ActA to create pNEB193-ActA-Ch-Her2 plasmid. His tag DNA sequence is included in the Ch-Her2 reverse primer sequence between SacI and SpeI restriction site. The XmaI/SpeI fragment corresponding to tActA-Ch-Her2-His from the plasmid pNEB193-ActA-Ch-Her2 is excised for cloning in XmaI/SpeI restricted pAdv134 to create dual plasmid.

A *Listeria*-based plasmid that delivers two recombinant antigens concomitantly as fusion proteins is then generated. The two fusion proteins that are expressed by this plasmid include tLLO-antigen 1 and tActA-antigen 2. The expression and secretion of the antigen 1 is under the control of hly promoter and LLO signal sequence and it is expressed as a fusion to non-hemolytic fragment of Listeriolysin O (truncated LLO or tLLO). The expression and secretion of antigen 2 is under the control of actA promoter and ActA signal sequence and it is expressed as fusion to 1-233 amino acids of ActA (truncated ActA or tActA). The construction of antibiotic-marker free plasmid pAdv134 has been described previously and it contains the gene cassette for the expression of tLLO-antigen 1 fusion protein. The SpeI and Xma I restriction sites present downstream of the tLLO-antigen 1 in pAdv134 are used for the cloning of actA promoter-tActA-antigen 2 DNA segment FIG. 20. The restriction sites XbaI, SacI and BglII are added in the cassette to facilitate cloning of the antigen 2 insert at XbaI/SacI or XbaI/BglII. A DNA sequence coding for His tag is added after SacI site to facilitate the detection of tActA-antigen 2-his fusion protein. The dual plasmid is able to concomitantly express and secrete two different antigens as fusion proteins.

Materials and Methods (Examples 17-21)

MDSC and Treg Function

Tumors were implanted in mice on the flank or a physiological site depending on the tumor model. After 7 days, mice were then vaccinated, the initial vaccination day depends on the tumor model being used. The mice were then administered a booster vaccine one week after the vaccine was given.

Mice were then sacrificed and tumors and spleen were harvested 1 week after the boost or, in the case of an aggressive tumor model, 3-4 days after the boost. Five days before harvesting the tumor, non-tumor bearing mice were vaccinated to use for responder T cells. Splenocytes were prepared using standard methodology.

Briefly, single cell suspensions of both the tumors and the spleens were prepared. Spleens were crushed manually and red blood cells were lysed. Tumors were minced and incubated with collagenase/DNase. Alternatively, the GENTLEMACS™ dissociator was used with the tumor dissociation kit.

MDSCs or Tregs were purified from tumors and spleens using a Miltenyi kit and columns or the AUTOMACs separator (cell separator device and reagents). Cells were then counted.

Single cell suspension was prepared and the red blood cells were lysed. Responder T cells were then labeled with CFSE.

Cells were plated together at a 2:1 ratio of responder T cells (from all division cycle stages) to MDSCs or Tregs at a density of $1 \times 10^5$ T cells per well in 96 well plates. Responder T cells were then stimulated with either the appropriate peptide (PSA OR CA9) or non-specifically with PMA/ionomycin. Cells were incubated in the dark for 2 days at 37° C. with 5% $CO_2$. Two days later, the cells were stained for FACS and analyzed on a FACS machine.

Analysis of T-Cell Responses

For cytokine analysis by ELISA, splenocytes were harvested and plated at 1.5 million cells per well in 48-well plates in the presence of media, SEA or conA (as a positive control). After incubation for 72 hours, supernatants were harvested and analyzed for cytokine level by ELISA (BD). For antigen-specific IFN-γ ELISpot, splenocytes were harvested and plated at 300K and 150K cells per well in IFN-γ ELISpot plates in the presence of media, specific CTL peptide, irrelevant peptide, specific helper peptide or conA (as a positive control). After incubation for 20 hours, ELISpots (BD) were performed and spots counted by the IMMUNOSPOT analyzer (laboratory plate reader for scanning and evaluating a wide range of microtiter plate-based bioassays, C.T.L.). Number of spots per million splenocytes were graphed.

Splenocytes were counted using a COULTER COUNTER, Z1 (Cell and Particle Counter). The frequency of IFN-γ producing CD8+ T cells after re-stimulation with gag-CTL, gag-helper, medium, an irrelevant antigen, and conA (positive control) was determined using a standard IFN-γ-based ELISPOT assay.

Briefly, IFN-γ was detected using the mAb R46-A2 at 5 mg/ml and polyclonal rabbit anti-IFN-γ used at an optimal dilution (kindly provided by Dr. Phillip Scott, University of Pennsylvania, Philadelphia, Pa.). The levels of IFN-γ were calculated by comparison with a standard curve using murine rIFN-γ (LIFE TECHNOLOGIES, Gaithersburg, Md.). Plates were developed using a peroxidase-conjugated goat anti-rabbit IgG Ab (IFN-γ). Plates were then read at 405 nm. The lower limit of detection for the assays was 30 pg/ml.

Results

Example 17: Suppressor Cell Function after Listeria Vaccine Treatment

At day 0 tumors were implanted in mice. At day 7 mice were vaccinated with Lmdda-E7 or LmddA-PSA. At day 14 tumors were harvested and the number and percentages of infiltrating MDSCs and Treg were measured for vaccinated and naïve groups. It was found that there is a decrease in the percentages of both MDSC and Tregs in the tumors of Listeria-treated mice, and the absolute number of MDSC, whereas the same effect is not observed in the spleens or the draining lymph nodes (TLDN) (FIG. 21).

Isolated splenocytes and tumor-infiltrating lymphocytes (TILs) extracted from tumor bearing mice in the above experiment were pooled and stained for CD3, and CD8 to elucidate the effect of immunization with Lm-LLO-E7, Lm-LLO-PSA and Lm-LLO-CA9, Lm-LLO-Her2 (FIG. 22-34) on the presence of MDSCs and Tregs (both splenic and tumoral MDSCs and Tregs) in the tumor. Each column represents the % of T cell population at a particular cell division stage and is subgrouped under a particular treatment group (naïve, peptide-CA9 or PSA-treated, no MDSC/Treg, and no MDSC+PMA/ionomycin) (see FIGS. 22-34).

Blood from tumor-bearing mice was analyzed for the percentages of Tregs and MDSCs present. There is a decrease in both MDSC and Tregs in the blood of mice after Lm vaccination.

Example 18: MDSCs from TPSA23 Tumors but not Spleen are Less Suppressive after Listeria Vaccination Suppressor assays were carried out using monocytic and granulocytic MDSCs isolated from TPSA23 tumors with non-specifically activated naïve murine cells, and specifically activated cells (PSA, CA9, PMA/ionomycyn). Results demonstrated that the MDSCs isolated from tumors from the Lm vaccinated groups have a diminished capacity to suppress the division of activated T cells as compared to MDSC from the tumors of naïve mice. (see Lm-LLO-PSA and Lm-LLO-treated Groups in FIGS. 22 & 24, right-hand panel in figures represents pooled cell division data from left-hand panel). In addition, T responder cells from untreated mice where no MDSCs were present and where the cells were unstimulated/activated, remained in their parental (resting) state (FIGS. 22 & 24), whereas T cells stimulated with PMA or ionomycin were observed to replicate (FIGS. 22 & 24). Further, it was observed that both, the Gr+Ly6G+ and the $Gr_{dim}$Ly6G-MDSCs are less suppressive after treatment with Listeria vaccines. This applies to their decreased abilities to suppress both the division of activated PSA-specific T cells and non-specific (PMA/Ionomycin stimulated) T cells.

Moreover, suppressor assays carried out using MDSCs isolated from TPSA23 tumors with non-specifically activated naïve murine cells demonstrated that the MDSCs isolated from tumors from the Lm vaccinated groups have a diminished capacity to suppress the division of activated T cells as compared to MDSC from the tumors of naïve mice (see FIGS. 22 & 24).

In addition, the observations discussed immediately above relating to FIGS. 22 and 18 were not observed when using splenic MDSCs. In the latter, splenocytes/T cells from the naïve group, the Listeria-treated group (PSA, CA9), and the PMA/ionomycin stimulated group (positive control) all demonstrated the same level of replication (FIGS. 23 & 25). Hence, these results show that Listeria-mediated inhibition of suppressor cells in tumors worked in an antigen-specific and non-specific manner, whereas Listeria has no effect on splenic granulocytic MDSCs as they are only suppressive in an antigen-specific manner.

Example 19: Tumor T Regulatory Cells' Reduced Suppression

Suppressor assays were carried out using Tregs isolated from TPSA23 tumors after Listeria treatment. It was observed that after treatment with *Listeria* there is a reduction of the suppressive ability of Tregs from tumors (FIG. 26), however, it was found that splenic Tregs are still suppressive (FIG. 27).

As a control conventional CD4+ T cells were used in place of MDSCs or Tregs and were found not to have an effect on cell division (FIG. 28).

Example 20: MDSCs and TREGS from 4T1 Tumors but not Spleen are Less Suppressive after *Listeria* Vaccination As in the above, the same experiments were carried out using 4T1 tumors and the same observations were made, namely, that MDSCs are less suppressive after *Listeria* vaccination (FIGS. 29 & 31), that *Listeria* has no specific effect on splenic monocytic MDSCs (FIGS. 30 & 32), that there is a decrease in the suppressive ability of Tregs from 4T1 tumors after *Listeria* vaccination (FIG. 33), and that *Listeria* has no effect on the suppressive ability of splenic Tregs (FIG. 34).

Finally, it was observed that *Listeria* has no effect on the suppressive ability of splenic Tregs.

Example 21: Change in the Suppressive Ability of the Granulocity and Monocytic MDSC is Due to the Overexpression of tLLO The LLO plasmid shows similar results as the *Listeria* vaccines with either the TAA or an irrelevant antigen (FIG. 35). This means that the change in the suppressive ability of the granulocytic MDSC is due to the overexpression of tLLO and is independent of the partnering fusion antigen. The empty plasmid construct alone also led to a change in the suppressive ability of the MDSC, although not to exactly the same level as any of the vaccines that contain the truncated LLO on the plasmid. The average of the 3 independent experiments show that the difference in suppression between the empty plasmid and the other plasmids with tLLO (with and without a tumor antigen) are significant. Reduction in MDSC suppressive ability was identical regardless of the fact if antigen specific or non-specific stimulated responder T cells were used.

Similar to the granulocytic MDSC, the average of the 3 independent experiments shows that the differences observed in the suppressive ability of the monocytic MDSCs purified from the tumors after vaccination with the Lm-empty plasmid vaccine are significant when compared to the other vaccine constructs (FIG. 36).

Similar to the above observations, granulocytic MDSC purified from the spleen retain their ability to suppress the division of the antigen-specific responder T cells after Lm vaccination (FIG. 37). However, after non-specific stimulation, activated T cells (with PMA/ionomycin) are still capable of dividing. None of these results are altered with the use of the LLO only or the empty plasmid vaccines showing that the Lm-based vaccines are not affecting the splenic granulocytic MDSC (FIG. 37).

Similarly, monocytic MDSC purified from the spleen retain their ability to suppress the division of the antigen-specific responder T cells after Lm vaccination. However, after non-specific activation (stimulated by PMA/ionomycin), T cells are still capable of dividing. None of these results are altered with the use of the LLO only or the empty plasmid vaccines showing that the Lm vaccines are not affecting the splenic monocytic MDSC (FIG. 38).

Tregs purified from the tumors of any of the Lm-treated groups have a slightly diminished ability to suppress the division of the responder T cells, regardless of whether the responder cells are antigen specific or non-specifically activated. Especially for the non-specifically activated responder T cells, it looks as though the vaccine with the empty plasmid shows the same results as all the vaccines that contain LLO on the plasmid. Averaging this experiment with the others shows that the differences are not significant (FIG. 39).

Tregs purified from the spleen are still capable of suppressing the division of both antigen specific and non-specifically activated responder T cells. There is no effect of Lm treatment on the suppressive ability of splenic Tregs (FIG. 40).

Tcon cells are not capable of suppressing the division of T cells regardless of whether the responder cells are antigens specific or non-specifically activated, which is consistent with the fact that these cells are non-suppressive. Lm has no effect on these cells and there was no difference if the cells were purified from the tumors or the spleen of mice (FIGS. 41-42).

The preceding examples are presented in order to more fully illustrate the embodiments of the invention. They should in no way be construed, however, as limiting the broad scope of the invention.

SEQUENCE LISTING

```
<160> NUMBER OF SEQ ID NOS: 83

<210> SEQ ID NO 1
<211> LENGTH: 6733
<212> TYPE: DNA
<213> ORGANISM: Artificial Sequence
<220> FEATURE:
<223> OTHER INFORMATION: episomal recombinant nucleic acid backbone

<400> SEQUENCE: 1
ggagtgtata ctggcttact atgttggcac tgatgagggt gtcagtgaag tgcttcatgt      60
ggcaggagaa aaaaggctgc accggtgcgt cagcagaata tgtgatacag gatatattcc     120
gcttcctcgc tcactgactc gctacgctcg gtcgttcgac tgcggcgagc ggaaatggct     180
tacgaacggg gcggagattt cctggaagat gccaggaaga tacttaacag ggaagtgaga     240
gggccgcggc aaagccgttt ttccataggc tccgcccccc tgacaagcat cacgaaatct     300
```

```
gacgctcaaa tcagtggtgg cgaaacccga caggactata aagataccag gcgtttcccc    360
ctggcggctc cctcgtgcgc tctcctgttc ctgcctttcg gtttaccggt gtcattccgc    420
tgttatggcc gcgtttgtct cattccacgc ctgacactca gttccgggta ggcagttcgc    480
tccaagctgg actgtatgca cgaacccccc gttcagtccg accgctgcgc cttatccggt    540
aactatcgtc ttgagtccaa cccggaaaga catgcaaaag caccactggc agcagccact    600
ggtaattgat ttagaggagt tagtcttgaa gtcatgcgcc ggttaaggct aaactgaaag    660
gacaagtttt ggtgactgcg ctcctccaag ccagttacct cggttcaaag agttggtagc    720
tcagagaacc ttcgaaaaac cgccctgcaa ggcggttttt tcgttttcag agcaagagat    780
tacgcgcaga ccaaaacgat ctcaagaaga tcatcttatt aatcagataa aatatttcta    840
gccctccttt gattagtata ttcctatctt aaagttactt ttatgtggag cattaacat    900 ttgttaatga cgtcaaaagg atagcaagac tagaataaag ctataaagca agcatataat    960
attgcgtttc atctttagaa gcgaatttcg ccaatattat aattatcaaa agagaggggt   1020
ggcaaacggt atttggcatt attaggttaa aaatgtaga aggagagtga aacccatgaa    1080
aaaaataatg ctagtttttta ttacacttat attagttagt ctaccaattg cgcaacaaac   1140
tgaagcaaag gatgcatctg cattcaataa agaaaattca atttcatcca tggcaccacc   1200
agcatctccg cctgcaagtc ctaagacgcc aatcgaaaag aaacgcgg atgaaatcga    1260 taagtatata caaggattgg attacaataa aaacaatgta ttagtatacc acggagatgc    1320
agtgacaaat gtgccgccaa gaaaaggtta caagatggaa atgaatata ttgttgtgga    1380 gaaaagaag aaatccatca atcaaaataa tgcagacatt caagttgtga atgcaatttc    1440
gagcctaacc tatccaggtg ctctcgtaaa agcgaattcg gaattagtag aaaatcaacc    1500
agatgttctc cctgtaaaac gtgattcatt aacactcagc attgatttgc caggtatgac    1560
taatcaagac aataaaatag ttgtaaaaaa tgccactaaa tcaaacgtta acaacgcagt    1620
aaatacatta gtggaaagat ggaatgaaaa atatgctcaa gcttatccaa atgtaagtgc    1680
aaaaattgat tatgatgacg aaatggctta cagtgaatca caattaattg cgaaatttgg    1740
tacagcattt aaagctgtaa ataatagctt gaatgtaaac ttcggcgcaa tcagtgaagg    1800
gaaaatgcaa gaagaagtca ttagttttaa acaaatttac tataacgtga atgttaatga    1860
acctacaaga ccttccagat ttttcggcaa agctgttact aaagagcagt tgcaagcgct    1920
tggagtgaat gcagaaaatc ctcctgcata tatctcaagt gtggcgtatg ccgtcaagt    1980 ttatttgaaa ttatcaacta attcccatag tactaaagta aaagctgctt ttgatgctgc    2040
cgtaagcgga aaatctgtct caggtgatgt agaactaaca aatatcatca aaaattcttc    2100
cttcaaagcc gtaatttacg gaggttccgc aaaagatgaa gttcaaatca tcgacggcaa    2160
cctcggagac ttacgcgata ttttgaaaaa aggcgctact tttaatcgag aaacaccagg    2220
agttcccatt gcttatacaa caaacttcct aaaagacaat gaattagctg ttattaaaaa    2280
caactcagaa tatattgaaa caacttcaaa agcttataca gatggaaaaa ttaacatcga    2340
tcactctgga ggatacgttg ctcaattcaa catttcttgg gatgaagtaa attatgatct    2400
cgagactagt tctagattta tcacgtaccc atttccccgc atcttttatt tttttaaata    2460
ctttagggaa aaatggtttt tgatttgctt ttaaaggttg tggtgtagac tcgtctgctg    2520
actgcatgct agaatctaag tcactttcag aagcatccac aactgactct tcgccactt    2580 ttctcttatt tgcttttgtt ggtttatctg gataagtaag gctttcaagc tcactatccg    2640
```

-continued

| | | | | | |
|---|---|---|---|---|---|
| acgacgctat | ggcttttctt | cttttttaa | tttccgctgc | gctatccgat | gacagacctg | 2700 |
| gatgacgacg | ctccacttgc | agagttggtc | ggtcgactcc | tgaagcctct | tcatttatag | 2760 |
| ccacatttcc | tgtttgctca | ccgttgttat | tattgttatt | cggacctttc | tctgcttttg | 2820 |
| ctttcaacat | tgctattagg | tctgcttttgt | tcgtattttt | cactttattc | gattttctta | 2880 |
| gttcctcaat | atcacgtgaa | cttacttcac | gtgcagtttc | gtatcttggt | cccgtattta | 2940 |
| cctcgcttgg | ctgctcttct | gttttttctt | cttcccattc | atctgtgttt | agactggaat | 3000 |
| cttcgctatc | tgtcgctgca | aatattatgt | cggggttaat | cgtaatgcag | ttggcagtaa | 3060 |
| tgaaaactac | catcatcgca | cgcataaatc | tgtttaatcc | cacttatact | ccctcctcgt | 3120 |
| gatacgctaa | tacaacctt | ttagaacaag | gaaaattcgg | ccttcatttt | cactaatttg | 3180 |
| ttccgttaaa | aattggatta | gcagttagtt | atcttcttaa | ttagctaata | taagaaaaaa | 3240 |
| tattcatgaa | ttatttaag | aatatcactt | ggagaattaa | tttttctcta | acatttgtta | 3300 |
| atcagttaac | cccaactgct | tcccaagctt | caccccgggcc | actaactcaa | cgctagtagt | 3360 |
| ggatttaatc | ccaaatgagc | caacagaacc | agaaccagaa | acagaacaag | taacattgga | 3420 |
| gttagaaatg | gaagaagaaa | aaagcaatga | tttcgtgtga | ataatgcacg | aaatcattgc | 3480 |
| ttattttttt | aaaaagcgat | atactagata | taacgaaaca | cgaactgaa | taagaaatac | 3540 |
| aaaaaaagag | ccacgaccag | ttaaagcctg | agaaacttta | actgcgagcc | ttaattgatt | 3600 |
| accaccaatc | aattaaagaa | gtcgagaccc | aaaatttggt | aaagtattta | attacttat | 3660 |
| taatcagata | cttaaatatc | tgtaaaccca | ttatatcggg | ttttgaggg | gatttcaagt | 3720 |
| ctttaagaag | ataccaggca | atcaattaag | aaaaacttag | ttgattgcct | tttttgttgt | 3780 |
| gattcaactt | tgatcgtagc | ttctaactaa | ttaattttcg | taagaaagga | gaacagctga | 3840 |
| atgaatatcc | cttttgttgt | agaaactgtg | cttcatgacg | gcttgttaaa | gtacaaattt | 3900 |
| aaaaatagta | aaattcgctc | aatcactacc | aagccaggta | aaagtaaagg | ggctatttt | 3960 |
| gcgtatcgct | caaaaaaaag | catgattggc | ggacgtggcg | ttgttctgac | ttccgaagaa | 4020 |
| gcgattcacg | aaaatcaaga | tacatttacg | cattggacac | caaacgttta | tcgttatggt | 4080 |
| acgtatgcag | acgaaaaccg | ttcatacact | aaaggacatt | ctgaaaacaa | tttaagacaa | 4140 |
| atcaatacct | tctttattga | ttttgatatt | cacacggaaa | aagaaactat | ttcagcaagc | 4200 |
| gatattttaa | caacagctat | tgatttaggt | tttatgccta | cgttaattat | caatctgat | 4260 |
| aaaggttatc | aagcatattt | tgttttagaa | acgccagtct | atgtgacttc | aaaatcagaa | 4320 |
| tttaaatctg | tcaaagcagc | caaaataatc | tcgcaaaata | tccgagaata | tttttggaaag | 4380 |
| tctttgccag | ttgatctaac | gtgcaatcat | tttgggattg | ctcgtatacc | aagaacggac | 4440 |
| aatgtagaat | ttttgatcc | caattaccgt | tattctttca | aagaatggca | agattggtct | 4500 |
| ttcaaacaaa | cagataataa | gggctttact | cgttcaagtc | taacggtttt | aagcggtaca | 4560 |
| gaaggcaaaa | aacaagtaga | tgaaccctgg | tttaatctct | tattgcacga | aacgaaattt | 4620 |
| tcaggagaaa | agggtttagt | agggcgcaat | agcgttatgt | ttaccctctc | tttagcctac | 4680 |
| tttagttcag | gctattcaat | cgaaacgtgc | gaatataata | tgtttgagtt | taataatcga | 4740 |
| ttagatcaac | ccttagaaga | aaaagaagta | atcaaaattg | ttagaagtgc | ctattcagaa | 4800 |
| aactatcaag | gggctaatag | ggaatacatt | accattcttt | gcaaagcttg | ggtatcaagt | 4860 |
| gatttaacca | gtaaagattt | atttgtccgt | caagggtggt | ttaaattcaa | gaaaaaaga | 4920 |
| agcgaacgtc | aacgtgttca | tttgtcagaa | tggaaagaag | atttaatggc | ttatattagc | 4980 |
| gaaaaaagcg | atgtatacaa | gccttattta | gcgacgacca | aaaagagat | tagagaagtg | 5040 |

```
ctaggcattc ctgaacggac attagataaa ttgctgaagg tactgaaggc gaatcaggaa      5100
attttcttta agattaaacc aggaagaaat ggtggcattc aacttgctag tgttaaatca      5160
ttgttgctat cgatcattaa attaaaaaaa gaagaacgag aaagctatat aaaggcgctg      5220
acagcttcgt ttaatttaga acgtacattt attcaagaaa ctctaaacaa attggcagaa      5280
cgccccaaaa cggacccaca actcgatttg tttagctacg atacaggctg aaaataaaac      5340
ccgcactatg ccattacatt tatatctatg atacgtgttt gtttttcttt gctggctagc      5400
ttaattgctt atatttacct gcaataaagg atttcttact tccattatac tcccattttc      5460
caaaaacata cggggaacac gggaacttat tgtacaggcc acctcatagt taatggtttc      5520
gagccttcct gcaatctcat ccatggaaat atattcatcc ccctgccggc ctattaatgt      5580
gacttttgtg cccggcggat attcctgatc cagctccacc ataaattggt ccatgcaaat      5640
tcggccggca attttcaggc gttttccctt cacaaggatg tcggtccctt tcaattttcg      5700
gagccagccg tccgcatagc ctacaggcac cgtcccgatc catgtgtctt tttccgctgt      5760
gtactcggct ccgtagctga cgctctcgcc ttttctgatc agtttgacat gtgacagtgt      5820
cgaatgcagg gtaaatgccg gacgcagctg aaacggtatc tcgtccgaca tgtcagcaga      5880
cgggcgaagg ccatacatgc cgatgccgaa tctgactgca ttaaaaaagc cttttttcag      5940
ccggagtcca gcgcgctgt tcgcgcagtg gaccattaga ttctttaacg gcagcggagc       6000
aatcagctct ttaaagcgct caaactgcat taagaaatag cctcttttctt tttcatccgc      6060 tgtcgcaaaa tgggtaaata cccctttgca ctttaaacga gggttgcggt caagaattgc      6120
catcacgttc tgaacttctt cctctgtttt tacaccaagt ctgttcatcc ccgtatcgac      6180
cttcagatga aaatgaagag aacctttttt cgtgtggcgg gctgcctcct gaagccattc      6240
aacagaataa cctgttaagg tcacgtcata ctcagcagcg attgccacat actccggggg      6300
aaccgcgcca agcaccaata taggcgcctt caatcccttt ttgcgcagtg aaatcgcttc      6360
atccaaaatg gccacggcca agcatgaagc acctgcgtca agagcagcct ttgctgtttc      6420
tgcatcacca tgcccgtagg cgtttgcttt cacaactgcc atcaagtgga catgttcacc      6480
gatatgtttt ttcatattgc tgacatttc ctttatcacg acaagtcaa tttccgccca       6540 cgtatctctg taaaaggtt ttgtgctcat ggaaaactcc tctcttttt cagaaaatcc        6600 cagtacgtaa ttaagtattt gagaattaat tttatattga ttaatactaa gtttacccag      6660
ttttcaccta aaaacaaat gatgagataa tagctccaaa ggctaaagag gactatacca       6720
actatttgtt aat                                                         6733

<210> SEQ ID NO 2
<211> LENGTH: 8317
<212> TYPE: DNA
<213> ORGANISM: Artificial Sequence
<220> FEATURE:
<223> OTHER INFORMATION: plasmid backbone and E7 and chimeric Her2
      heterologous antigens

<400> SEQUENCE: 2
ggagtgtata ctggcttact atgttggcac tgatgagggt gtcagtgaag tgcttcatgt        60
ggcaggagaa aaaaggctgc accggtgcgt cagcagaata tgtgatacag gatatattcc       120
gcttcctcgc tcactgactc gctacgctcg gtcgttcgac tgcggcgagc ggaaatggct       180
tacgaacggg gcggagattt cctggaagat gccaggaaga tacttaacag ggaagtgaga      240
gggccgcggc aaagccgttt ttccataggc tccgcccccc tgacaagcat cacgaaatct      300
```

```
gacgctcaaa tcagtggtgg cgaaacccga caggactata aagataccag gcgtttcccc    360
ctggcggctc cctcgtgcgc tctcctgttc ctgcctttcg gtttaccggt gtcattccgc    420
tgttatggcc gcgtttgtct cattccacgc ctgacactca gttccgggta ggcagttcgc    480
tccaagctgg actgtatgca cgaaccccccc gttcagtccg accgctgcgc cttatccggt    540
aactatcgtc ttgagtccaa cccggaaaga catgcaaaag caccactggc agcagccact    600
ggtaattgat ttagaggagt tagtcttgaa gtcatgcgcc ggttaaggct aaactgaaag    660
gacaagtttt ggtgactgcg ctcctccaag ccagttacct cggttcaaag agttggtagc    720
tcagagaacc ttcgaaaaac cgccctgcaa ggcggttttt tcgttttcag agcaagagat    780
tacgcgcaga ccaaaacgat ctcaagaaga tcatcttatt aatcagataa aatatttcta    840
gccctccttt gattagtata ttcctatctt aaagttactt ttatgtggag cattaacat    900 ttgttaatga cgtcaaaagg atagcaagac tagaataaag ctataaagca agcatataat    960
attgcgtttc atctttagaa gcgaatttcg ccaatattat aattatcaaa agagaggggt   1020
ggcaaacggt atttggcatt attaggttaa aaatgtaga aggagagtga aacccatgaa   1080
aaaaataatg ctagttttta ttacacttat attagttagt ctaccaattg cgcaacaaac   1140
tgaagcaaag gatgcatctg cattcaataa agaaaattca atttcatcca tggcaccacc   1200
agcatctccg cctgcaagtc ctaagacgcc aatcgaaaag aaaacgcgg atgaaatcga   1260 taagtatata caaggattgg attacaataa aaacaatgta ttagtatacc acggagatgc   1320
agtgacaaat gtgccgccaa gaaaaggtta caagatgga aatgaatata ttgttgtgga   1380 gaaaagaag aaatccatca atcaaaataa tgcagacatt caagttgtga atgcaatttc   1440
gagcctaacc tatccaggtg ctctcgtaaa agcgaattcg gaattagtag aaaatcaacc   1500
agatgttctc cctgtaaaac gtgattcatt aacactcagc attgatttgc caggtatgac   1560
taatcaagac aataaaatag ttgtaaaaaa tgccactaaa tcaaacgtta acaacgcagt   1620
aaatacatta gtggaaagat ggaatgaaaa atatgctcaa gcttatccaa atgtaagtgc   1680
aaaaattgat tatgatgacg aaatggctta cagtgaatca caattaattg cgaaatttgg   1740
tacagcattt aaagctgtaa ataatagctt gaatgtaaac ttcggcgcaa tcagtgaagg   1800
gaaaatgcaa gaagaagtca ttagttttaa acaaatttac tataacgtga atgttaatga   1860
acctacaaga ccttccagat ttttcggcaa agctgttact aaagagcagt tgcaagcgct   1920
tggagtgaat gcagaaaatc ctcctgcata tatctcaagt gtggcgtatg ccgtcaagt   1980 ttatttgaaa ttatcaacta attcccatag tactaaagta aaagctgctt ttgatgctgc   2040
cgtaagcgga aaatctgtct caggtgatgt agaactaaca aatatcatca aaaattcttc   2100
cttcaaagcc gtaatttacg gaggttccgc aaaagatgaa gttcaaatca tcgacggcaa   2160
cctcggagac ttacgcgata ttttgaaaaa aggcgctact tttaatcgag aaacaccagg   2220
agttcccatt gcttatacaa caaacttcct aaaagacaat gaattagctg ttattaaaaa   2280
caactcagaa tatattgaaa caacttcaaa agcttataca gatggaaaaa ttaacatcga   2340
tcactctgga ggatacgttg ctcaattcaa catttcttgg gatgaagtaa attatgatct   2400
cgagcatgga gatacaccta cattgcatga atatatgtta gatttgcaac cagagacaac   2460
tgatctctac tgttatgagc aattaaatga cagctcagag gaggaggatg aaatagatgg   2520
tccagctgga caagcagaac cggacagagc ccattacaat attgtaacct tttgttgcaa   2580
gtgtgactct acgcttcggt tgtgcgtaca aagcacacac gtagacattc gtactttgga   2640
```

```
agacctgtta atgggcacac taggaattgt gtgccccatc tgttctcaga aaccataaac    2700
tagtctagtg gtgatggtga tgatggagct cagatctgtc taagaggcag ccatagggca    2760
taagctgtgt caccagctgc accgtggatg tcaggcagat gcccagaagg cgggagacat    2820
atggggagcc cacaccagcc atcacgtatg cttcgtctaa gatttctttg ttggctttgg    2880
gggatgtgtt ttccctcaac actttgatgg ccactggaat tttcacattc tccccatcag    2940
ggatccagat gcccttgtag actgtgccaa aagcgccaga tccaagcacc ttcaccttcc    3000
tcagctccgt ctctttcagg atccgcatct gcgcctggtt gggcatcgct ccgctaggtg    3060
tcagcggctc caccagctcc gtttcctgca gcagtctccg catcgtgtac ttccggatct    3120
tctgctgccc tcgggcgcac agctggtggc aggccaggcc ctcgcccaca cactcgtcct    3180
ctggccggtt ggcagtgtgg agcagagctt ggtgcgggtt ccgaaagagc tggtcccagg    3240
gcaccgtgtg cacgaagcag aggtgggtgt tatggtggat gagggccagt ccactgccca    3300
gttccctcag tgagcgcagc cccagccagc tgatgcccag cccttgcagg gtcagcgagt    3360
aggcgccatt gtgcagaatt cgtccccgga ttacttgcag gttctggaag acgctgaggt    3420
caggcaggct gtccggccat gctgagatgt ataggtaacc tgtgatctct tccagagtct    3480
caaacacttg gagctgctct ggctggaacg gggcagtgtt ggaggctggg tccccatcaa    3540
agctctccgg cagaaatgcc aggctcccaa agatcttctt gcagccagca aactcctgga    3600
tattcttcca caaaatcgtg tcctggtagc agagctgggg gttccgctgg atcaagaccc    3660
ctcctttcaa gatctctgtg aggcttcgaa gctgcagctc ccgcaggcct cctggggagg    3720
cccctgtgac aggggtggta ttgttcagcg ggtctccatt gtctagcacg gccagggcat    3780
agttgtcctc aaagagctgg gtgcctcgca caatccgcag cctctgcagt gggacctgcc    3840
tcacttggtt gtgagcgatg agcacgtagc cctgcacctc ctggatatcc tgcaggaagg    3900
acaggctggc attggtgggc aggtaggtga gttccaggtt tccctgcacc acctggcagc    3960
cctggtagag gtggcggagc atgtccaggt gggttctaga tttatcacgt acccatttcc    4020
ccgcatcttt tatttttta aatactttag ggaaaaatgg ttttgatt  gcttttaaag     4080
gttgtggtgt agactcgtct gctgactgca tgctagaatc taagtcactt tcagaagcat    4140
ccacaactga ctctttcgcc acttttctct tatttgcttt tgttggttta tctggataag    4200
taaggctttc aagctcacta tccgacgacg ctatggcttt tcttctttt ttaatttccg     4260
ctgcgctatc cgatgacaga cctggatgac gacgctccac ttgcagagtt ggtcggtcga    4320
ctcctgaagc ctcttcattt atagccacat ttcctgtttg ctcaccgttg ttattattgt    4380
tattcggacc tttctctgct tttgctttca acattgctat taggtctgct ttgttcgtat    4440
ttttcacttt attcgatttt tctagttcct caatatcacg tgaacttact tcacgtgcag    4500
tttcgtatct tggtcccgta tttacctcgc ttggctgctc ttctgttttt tcttcttccc    4560
attcatctgt gtttagactg gaatcttcgc tatctgtcgc tgcaaatatt atgtcggggt    4620
taatcgtaat gcagttggca gtaatgaaaa ctaccatcat cgcacgcata aatctgttta    4680
atcccactta tactccctcc tcgtgatacg ctaatacaac cttttagaa caaggaaaat     4740
tcggccttca ttttcactaa tttgttccgt taaaaattgg attagcagtt agttatcttc    4800
ttaattagct aatataagaa aaaatattca tgaattattt taagaatatc acttggagaa    4860
ttaattttc tctaacattt gttaatcagt taacccccaac tgcttcccaa gcttcacccg    4920
ggccactaac tcaacgctag tagtggattt aatcccaaat gagccaacag aaccagaacc    4980
agaaacagaa caagtaacat tggagttaga aatggaagaa gaaaaaagca atgatttcgt    5040
```

```
gtgaataatg cacgaaatca ttgcttattt ttttaaaaag cgatatacta gatataacga    5100
aacaacgaac tgaataaaga atacaaaaaa agagccacga ccagttaaag cctgagaaac    5160
tttaactgcg agccttaatt gattaccacc aatcaattaa agaagtcgag acccaaaatt    5220
tggtaaagta tttaattact ttattaatca gatacttaaa tatctgtaaa cccattatat    5280 cgggttttg aggggatttc aagtctttaa gaagatacca ggcaatcaat taagaaaaac    5340
ttagttgatt gccttttttg ttgtgattca actttgatcg tagcttctaa ctaattaatt    5400
ttcgtaagaa aggagaacag ctgaatgaat atcccttttg ttgtagaaac tgtgcttcat    5460
gacggcttgt taaagtacaa atttaaaaat agtaaaattc gctcaatcac taccaagcca    5520
ggtaaaagta aaggggctat ttttgcgtat cgctcaaaaa aaagcatgat tggcggacgt    5580
ggcgttgttc tgacttccga agaagcgatt cacgaaaatc aagatacatt tacgcattgg    5640
acaccaaacg tttatcgtta tggtacgtat gcagacgaaa accgttcata cactaaagga    5700
cattctgaaa acaatttaag acaaatcaat accttcttta ttgattttga tattcacacg    5760 gaaaagaaa ctatttcagc aagcgatatt ttaacaacag ctattgattt aggttttatg    5820
cctacgttaa ttatcaaatc tgataaaggt tatcaagcat attttgtttt agaaacgcca    5880
gtctatgtga cttcaaaatc agaatttaaa tctgtcaaag cagccaaaat aatctcgcaa    5940
aatatccgag aatattttgg aaagtctttg ccagttgatc taacgtgcaa tcattttggg    6000
attgctcgta taccaagaac ggacaatgta gaatttttg atcccaatta ccgttattct    6060
ttcaaagaat ggcaagattg gtcttttcaaa caaacagata ataagggctt tactcgttca    6120
agtctaacgg ttttaagcgg tacagaaggc aaaaaacaag tagatgaacc ctggtttaat    6180
ctcttattgc acgaaacgaa attttcagga gaaaagggtt tagtagggcg caatagcgtt    6240
atgtttaccc tctctttagc ctactttagt tcaggctatt caatcgaaac gtgcgaatat    6300
aatatgtttg agtttaataa tcgattagat caacccttag aagaaaaaga agtaatcaaa    6360
attgttagaa gtgcctattc agaaaactat caaggggcta tagggaata cattaccatt    6420 ctttgcaaag cttgggtatc aagtgattta accagtaaag atttatttgt ccgtcaaggg    6480
tggtttaaat tcaagaaaaa aagaagcgaa cgtcaacgtg ttcatttgtc agaatggaaa    6540
gaagatttaa tggcttatat tagcgaaaaa agcgatgtat acaagcctta tttagcgacg    6600
accaaaaaag agattagaga agtgctaggc attcctgaac ggacattaga taaattgctg    6660
aaggtactga aggcgaatca ggaaattttc tttaagatta aaccaggaag aaatggtggc    6720
attcaacttg ctagtgttaa atcattgttg ctatcgatca ttaaattaaa aaaagaagaa    6780
cgagaaagct atataaaggc gctgacagct tcgtttaatt tagaacgtac atttattcaa    6840
gaaactctaa acaaattggc agaacgcccc aaaacggacc cacaactcga tttgtttagc    6900
tacgatacag gctgaaaata aaacccgcac tatgccatta catttatatc tatgatacgt    6960
gtttgttttt ctttgctggc tagcttaatt gcttatattt acctgcaata aaggatttct    7020
tacttccatt atactcccat tttccaaaaa catacgggga acacgggaac ttattgtaca    7080
ggccacctca tagttaatgg tttcgagcct cctgcaatc tcatccatgg aaatatattc    7140 atcccctgc cggcctatta atgtgacttt tgtgcccggc ggatattcct gatccagctc    7200
caccataaat tggtccatgc aaattcggcc ggcaatttc aggcgttttc ccttcacaag    7260
gatgtcggtc cctttcaatt ttcggagcca gccgtccgca tagcctacag gcaccgtccc    7320
gatccatgtg tctttttccg ctgtgtactc ggctccgtag ctgacgctct cgccttttct    7380
```

| | |
|---|---|
| gatcagtttg acatgtgaca gtgtcgaatg cagggtaaat gccggacgca gctgaaacgg | 7440 |
| tatctcgtcc gacatgtcag cagacgggcg aaggccatac atgccgatgc cgaatctgac | 7500 |
| tgcattaaaa aagccttttt tcagccggag tccagcggcg ctgttcgcgc agtggaccat | 7560 |
| tagattcttt aacggcagcg gagcaatcag ctctttaaag cgctcaaact gcattaagaa | 7620 |
| atagcctctt tcttttttcat ccgctgtcgc aaaatgggta atatccccctt tgcactttaa | 7680 |
| acgagggttg cggtcaagaa ttgccatcac gttctgaact tcttcctctg ttttttacacc | 7740 |
| aagtctgttc atccccgtat cgaccttcag atgaaaatga agagaacctt ttttcgtgtg | 7800 |
| gcgggctgcc tcctgaagcc attcaacaga ataacctgtt aaggtcacgt catactcagc | 7860 |
| agcgattgcc acatactccg ggggaaccgc gccaagcacc aatataggcg ccttcaatcc | 7920 |
| ctttttgcgc agtgaaatcg cttcatccaa aatggccacg gccaagcatg aagcacctgc | 7980 |
| gtcaagagca gcctttgctg tttctgcatc accatgcccg taggcgtttg ctttcacaac | 8040 |
| tgccatcaag tggacatgtt caccgatatg ttttttcata ttgctgacat tttcctttat | 8100 |
| cacggacaag tcaatttccg cccacgtatc tctgtaaaaa ggttttgtgc tcatggaaaa | 8160 |
| ctcctctctt ttttcagaaa atcccagtac gtaattaagt atttgagaat taattttata | 8220 |
| ttgattaata ctaagtttac ccagttttca cctaaaaaac aaatgatgag ataatagctc | 8280 |
| caaaggctaa agaggactat accaactatt tgttaat | 8317 |

<210> SEQ ID NO 3
<211> LENGTH: 306
<212> TYPE: DNA
<213> ORGANISM: Human papillomavirus type 16

<400> SEQUENCE: 3

| | |
|---|---|
| ctcgagcatg gagatacacc tacattgcat gaatatatgt tagatttgca accagagaca | 60 |
| actgatctct actgttatga gcaattaaat gacagctcag aggaggagga tgaaatagat | 120 |
| ggtccagctg gacaagcaga accggacaga gcccattaca atattgtaac cttttgttgc | 180 |
| aagtgtgact ctacgcttcg gttgtgcgta caaagcacac acgtagacat tcgtactttg | 240 |
| gaagacctgt taatgggcac actaggaatt gtgtgcccca tctgttctca gaaaccataa | 300 |
| actagt | 306 |

<210> SEQ ID NO 4
<211> LENGTH: 1297
<212> TYPE: DNA
<213> ORGANISM: Artificial Sequence
<220> FEATURE:
<223> OTHER INFORMATION: chimeric Her2-neu

<400> SEQUENCE: 4

| | |
|---|---|
| ctagtggtga tggtgatgat ggagctcaga tctgtctaag aggcagccat agggcataag | 60 |
| ctgtgtcacc agctgcaccg tggatgtcag gcagatgccc agaaggcggg agacatatgg | 120 |
| ggagcccaca ccagccatca cgtatgcttc gtctaagatt tctttgttgg ctttggggga | 180 |
| tgtgtttttcc ctcaacactt tgatggccac tggaattttc acattctccc catcagggat | 240 |
| ccagatgccc ttgtagactg tgccaaaagc gccagatcca agcacttca ccttcctcag | 300 |
| ctccgtctct ttcaggatcc gcatctgcgc ctggttgggc atcgctccgc taggtgtcag | 360 |
| cggctccacc agctccgttt cctgcagcag tctccgcatc gtgtacttcc ggatcttctg | 420 |
| ctgccctcgg gcgcacagct ggtggcaggc caggccctcg cccacacact cgtcctctgg | 480 |
| ccggttggca gtgtggagca gagcttggtg cgggttccga aagagctggt cccagggcac | 540 |

```
cgtgtgcacg aagcagaggt gggtgttatg gtggatgagg gccagtccac tgcccagttc      600
cctcagtgag cgcagcccca gccagctgat gcccagccct tgcagggtca gcgagtaggc      660
gccattgtgc agaattcgtc cccggattac ttgcaggttc tggaagacgc tgaggtcagg      720
caggctgtcc ggccatgctg agatgtatag gtaacctgtg atctcttcca gagtctcaaa      780
cacttggagc tgctctggct ggagcggggc agtgttggag gctgggtccc catcaaagct      840
ctccggcaga aatgccaggc tcccaaagat cttcttgcag ccagcaaact cctggatatt      900
cttccacaaa atcgtgtcct ggtagcagag ctggggttc cgctggatca agacccctcc       960
tttcaagatc tctgtgaggc ttcgaagctg cagctcccgc aggcctcctg gggaggcccc     1020
tgtgacaggg gtggtattgt tcagcgggtc tccattgtct agcacggcca gggcatagtt     1080
gtcctcaaag agctgggtgc ctcgcacaat ccgcagcctc tgcagtggga cctgcctcac     1140
ttggttgtga gcgatgagca cgtagccctg cacctcctgg atatcctgca ggaaggacag     1200
gctggcattg gtgggcaggt aggtgagttc caggtttccc tgcaccacct ggcagccctg     1260
gtagaggtgg cggagcatgt ccaggtgggt tctagat                              1297

<210> SEQ ID NO 5
<211> LENGTH: 1329
<212> TYPE: DNA
<213> ORGANISM: Artificial Sequence
<220> FEATURE:
<223> OTHER INFORMATION: Listeriolysin-O

<400> SEQUENCE: 5
atgaaaaaaa taatgctagt ttttattaca cttatattag ttagtctacc aattgcgcaa       60
caaactgaag caaggatgc atctgcattc aataaagaaa attcaatttc atccatggca      120
ccaccagcat ctccgcctgc aagtcctaag acgccaatcg aaaagaaaca cgcggatgaa      180
atcgataagt atatacaagg attggattac aataaaaaca atgtattagt ataccacgga      240
gatgcagtga caaatgtgcc gccaagaaaa ggttacaaag atggaaatga atatattgtt      300
gtggagaaaa agaagaaatc catcaatcaa aataatgcag acattcaagt tgtgaatgca      360
atttcgagcc taacctatcc aggtgctctc gtaaaagcga attcggaatt agtagaaaat      420
caaccagatg ttctcccctgt aaaacgtgat tcattaacac tcagcattga tttgccaggt      480
atgactaatc aagacaataa aatagttgta aaaaatgcca ctaaatcaaa cgttaacaac      540
gcagtaaata cattagtgga agatggaat gaaaaatatg ctcaagctta tccaaatgta      600
agtgcaaaaa ttgattatga tgacgaaatg gcttacagtg aatcacaatt aattgcgaaa      660
tttggtacag catttaaagc tgtaaataat agcttgaatg taaacttcgg cgcaatcagt      720
gaagggaaaa tgcaagaaga agtcattagt tttaaacaaa tttactataa cgtgaatgtt      780
aatgaaccta agaccttca cagattttc ggcaaagctg ttactaaaga gcagttgcaa      840
gcgcttggag tgaatgcaga aaatcctcct gcatatatct caagtgtggc gtatggccgt     900
caagtttatt tgaaattatc aactaattcc catagtacta agtaaaagc tgcttttgat       960 gctgccgtaa gcggaaaatc tgtctcaggt gatgtagaac taacaaatat catcaaaaat     1020
tcttccttca aagccgtaat ttacggaggt tccgcaaaag atgaagttca atcatcgac      1080 ggcaacctcg gagacttacg cgatattttg aaaaaggcg ctactttaa tcgagaaaca     1140 ccaggagttc ccattgctta tacaacaaac ttcctaaaag acaatgaatt agctgttatt     1200
aaaaacaact cagaatatat tgaaacaact tcaaagagtt atacagatgg aaaaattaac     1260
```

```
                                                       -continued atcgatcact ctggaggata cgttgctcaa ttcaacattt cttgggatga agtaaattat    1320
gatctcgag                                                           1329
```

<210> SEQ ID NO 6
<211> LENGTH: 442
<212> TYPE: PRT
<213> ORGANISM: Artificial Sequence
<220> FEATURE:
<223> OTHER INFORMATION: Listeriolysin-O

<400> SEQUENCE: 6

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350
```

```
Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
            405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Leu
            435                 440

<210> SEQ ID NO 7
<211> LENGTH: 390
<212> TYPE: PRT
<213> ORGANISM: Artificial Sequence
<220> FEATURE:
<223> OTHER INFORMATION: actA

<400> SEQUENCE: 7

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Thr Asp Glu Glu Leu Arg Leu Ala Leu
            260                 265                 270
```

```
Pro Glu Thr Pro Met Leu Leu Gly Phe Asn Ala Pro Ala Thr Ser Glu
            275                 280                 285

Pro Ser Ser Phe Glu Phe Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
                340                 345                 350

Thr Arg Gly Asp Leu Ala Ser Leu Arg Asn Ala Ile Asn Arg His Ser
            355                 360                 365

Gln Asn Phe Ser Asp Phe Pro Pro Ile Pro Thr Glu Glu Glu Leu Asn
            370                 375                 380

Gly Arg Gly Gly Arg Pro
385                 390

<210> SEQ ID NO 8
<211> LENGTH: 1170
<212> TYPE: PRT
<213> ORGANISM: Artificial Sequence
<220> FEATURE:
<223> OTHER INFORMATION: actA

<400> SEQUENCE: 8

Ala Thr Gly Cys Gly Thr Gly Cys Gly Ala Thr Gly Ala Thr Gly Gly
1               5                   10                  15

Thr Gly Gly Thr Thr Thr Thr Cys Ala Thr Thr Ala Cys Thr Gly Cys
                20                  25                  30

Cys Ala Ala Thr Thr Gly Cys Ala Thr Thr Ala Cys Gly Ala Thr Thr
            35                  40                  45

Ala Ala Cys Cys Cys Cys Gly Ala Cys Ala Thr Ala Thr Ala Thr Ala
        50                  55                  60

Thr Thr Gly Cys Ala Gly Cys Gly Ala Cys Ala Gly Ala Thr Ala Gly
65              70                  75                  80

Cys Gly Ala Ala Gly Ala Thr Thr Cys Thr Ala Gly Thr Cys Thr Ala
                85                  90                  95

Ala Ala Cys Ala Cys Ala Gly Ala Thr Gly Ala Ala Thr Gly Gly Gly
                100                 105                 110

Ala Ala Gly Ala Ala Gly Ala Ala Ala Ala Cys Ala Gly Ala
            115                 120                 125

Ala Gly Ala Gly Cys Ala Ala Cys Cys Ala Gly Cys Gly Ala Gly
            130                 135                 140

Gly Thr Ala Ala Ala Thr Ala Cys Gly Gly Ala Cys Cys Ala Ala
145                 150                 155                 160

Gly Ala Thr Ala Cys Gly Ala Ala Cys Thr Gly Cys Ala Cys Gly
                165                 170                 175

Thr Gly Ala Ala Gly Thr Ala Ala Gly Thr Thr Cys Ala Cys Gly Thr
                180                 185                 190

Gly Ala Thr Ala Thr Ala Ala Gly Ala Ala Cys Thr Ala Gly
            195                 200                 205

Ala Ala Ala Ala Ala Thr Cys Gly Ala Ala Thr Ala Ala Gly Thr
        210                 215                 220

Gly Ala Gly Ala Ala Ala Thr Ala Cys Gly Ala Ala Cys Ala Ala Ala
225                 230                 235                 240
```

-continued

```
Gly Cys Ala Gly Ala Cys Cys Thr Ala Thr Ala Gly Cys Ala Ala
                245                 250                 255
Thr Gly Thr Thr Gly Ala Ala Gly Ala Ala Ala Ala Ala Gly Cys
                260                 265                 270
Ala Gly Ala Ala Ala Ala Ala Gly Gly Thr Cys Cys Ala Ala Thr
                275                 280                 285
Ala Thr Cys Ala Ala Thr Ala Ala Thr Ala Ala Cys Ala Ala Cys Ala
                290                 295                 300
Gly Thr Gly Ala Ala Cys Ala Ala Cys Thr Gly Ala Gly Ala Ala
305                 310                 315                 320
Thr Gly Cys Gly Gly Cys Thr Ala Thr Ala Ala Thr Gly Ala Ala
                325                 330                 335
Gly Ala Gly Gly Cys Thr Thr Cys Ala Gly Ala Gly Cys Cys Gly
                340                 345                 350
Ala Cys Cys Gly Ala Cys Cys Ala Gly Cys Thr Ala Thr Ala Cys Ala
                355                 360                 365
Ala Gly Thr Gly Gly Ala Gly Cys Gly Thr Cys Gly Thr Cys Ala Thr
                370                 375                 380
Cys Cys Ala Gly Gly Ala Thr Gly Cys Cys Ala Thr Cys Gly Gly
385                 390                 395                 400
Ala Thr Ala Gly Cys Gly Cys Ala Gly Cys Gly Gly Ala Ala Ala Thr
                405                 410                 415
Thr Ala Ala Ala Ala Ala Ala Gly Ala Ala Gly Gly Ala Ala Ala
                420                 425                 430
Gly Cys Cys Ala Thr Ala Gly Cys Ala Thr Cys Ala Thr Cys Gly Gly
                435                 440                 445
Ala Thr Ala Gly Thr Gly Ala Gly Cys Thr Thr Gly Ala Ala Ala Gly
                450                 455                 460
Cys Cys Thr Thr Ala Cys Thr Thr Ala Thr Cys Cys Gly Gly Ala Thr
465                 470                 475                 480
Ala Ala Ala Cys Cys Ala Ala Cys Ala Ala Ala Gly Thr Ala Ala
                485                 490                 495
Ala Thr Ala Ala Gly Ala Ala Ala Ala Ala Gly Thr Gly Gly Cys
                500                 505                 510
Gly Ala Ala Ala Gly Ala Gly Thr Cys Ala Gly Thr Thr Gly Cys Gly
                515                 520                 525
Gly Ala Thr Gly Cys Thr Thr Cys Thr Gly Ala Ala Ala Gly Thr Gly
                530                 535                 540
Ala Cys Thr Thr Ala Gly Ala Thr Thr Cys Thr Ala Gly Cys Ala Thr
545                 550                 555                 560
Gly Cys Ala Gly Thr Cys Ala Gly Cys Ala Gly Ala Thr Gly Ala Gly
                565                 570                 575
Thr Cys Thr Thr Cys Ala Cys Cys Ala Cys Ala Cys Cys Thr Thr
                580                 585                 590
Thr Ala Ala Ala Ala Gly Cys Ala Ala Ala Cys Cys Ala Cys Ala
                595                 600                 605
Ala Cys Cys Ala Thr Thr Thr Thr Cys Cys Thr Ala Ala Ala
                610                 615                 620
Gly Thr Ala Thr Thr Ala Ala Ala Ala Ala Ala Thr Ala Ala
625                 630                 635                 640
Ala Ala Gly Ala Thr Gly Cys Gly Gly Gly Ala Ala Ala Thr Gly
                645                 650                 655
```

-continued

Gly Gly Thr Ala Cys Gly Thr Gly Ala Thr Ala Ala Ala Thr Cys
                660                 665                 670

Gly Ala Cys Gly Ala Ala Ala Thr Cys Cys Thr Gly Ala Ala Gly
        675                 680                 685

Thr Ala Ala Ala Gly Ala Ala Gly Cys Gly Ala Thr Thr Gly Thr
690                 695                 700

Thr Gly Ala Thr Ala Ala Ala Gly Thr Gly Cys Ala Gly Gly Gly
705                 710                 715                 720

Thr Thr Ala Ala Thr Thr Gly Ala Cys Cys Ala Ala Thr Ala Thr
            725                 730                 735

Thr Ala Ala Cys Cys Ala Ala Ala Ala Gly Ala Ala Ala Ala Gly
            740                 745                 750

Thr Gly Ala Ala Gly Ala Gly Gly Thr Ala Ala Ala Thr Gly Cys Thr
        755                 760                 765

Thr Cys Gly Gly Ala Cys Thr Thr Cys Cys Gly Cys Cys Ala Cys
        770                 775                 780

Cys Ala Cys Cys Thr Ala Cys Gly Gly Ala Thr Gly Ala Ala Gly Ala
785                 790                 795                 800

Gly Thr Thr Ala Ala Gly Ala Cys Thr Thr Gly Cys Thr Thr Gly
        805                 810                 815

Cys Cys Ala Gly Ala Gly Ala Cys Ala Cys Ala Ala Thr Gly Cys
        820                 825                 830

Thr Thr Cys Thr Thr Gly Gly Thr Thr Thr Ala Ala Thr Gly Cys
        835                 840                 845

Thr Cys Cys Thr Gly Cys Thr Ala Cys Ala Thr Cys Ala Gly Ala Ala
850                 855                 860

Cys Cys Gly Ala Gly Cys Thr Cys Ala Thr Thr Cys Gly Ala Ala Thr
865                 870                 875                 880

Thr Thr Cys Cys Ala Cys Cys Ala Cys Cys Thr Ala Cys
            885                 890                 895

Gly Gly Ala Thr Gly Ala Ala Gly Ala Gly Thr Thr Ala Ala Gly Ala
        900                 905                 910

Cys Thr Thr Gly Cys Thr Thr Thr Gly Cys Cys Ala Gly Ala Gly Ala
        915                 920                 925

Cys Gly Cys Cys Ala Ala Thr Gly Cys Thr Thr Cys Thr Thr Gly Gly
        930                 935                 940

Thr Thr Thr Thr Ala Ala Thr Gly Cys Thr Cys Cys Thr Gly Cys Thr
945                 950                 955                 960

Ala Cys Ala Thr Cys Gly Gly Ala Ala Cys Cys Gly Ala Gly Cys Thr
            965                 970                 975

Cys Gly Thr Thr Cys Gly Ala Ala Thr Thr Cys Cys Ala Cys Cys
            980                 985                 990

Gly Cys Cys Thr Cys Cys Ala Ala  Cys Ala Gly Ala Ala  Gly Ala Thr
            995                     1000                 1005

Gly Ala  Ala Cys Thr Ala Gly  Ala Ala Ala Thr Cys  Ala Thr Cys
    1010                 1015                 1020

Cys Gly  Gly Gly Ala Ala Ala  Cys Ala Gly Cys Ala  Thr Cys Cys
    1025                 1030                 1035

Thr Cys  Gly Cys Thr Ala Gly  Ala Thr Thr Cys Thr  Ala Gly Thr
    1040                 1045                 1050

Thr Thr  Thr Ala Cys Ala Ala  Gly Ala Gly Gly  Gly Ala Thr
    1055                 1060                 1065

Thr Thr  Ala Gly Cys Thr Ala  Gly Thr Thr Thr Gly  Ala Gly Ala

```
Ala Ala Thr Gly Cys Thr Ala Thr Thr Ala Ala Thr Cys Gly Cys
        1085                1090                1095

Cys Ala Thr Ala Gly Thr Cys Ala Ala Ala Thr Thr Thr Cys
        1100                1105                1110

Thr Cys Thr Gly Ala Thr Thr Thr Cys Cys Cys Ala Cys Cys Ala
        1115                1120                1125

Ala Thr Cys Cys Cys Ala Cys Ala Gly Ala Ala Gly Ala Ala
        1130                1135                1140

Gly Ala Gly Thr Thr Gly Ala Ala Cys Gly Gly Gly Ala Gly Ala
        1145                1150                1155

Gly Gly Cys Gly Gly Thr Ala Gly Ala Cys Cys Ala
        1160                1165                1170

<210> SEQ ID NO 9
<211> LENGTH: 669
<212> TYPE: DNA
<213> ORGANISM: Artificial Sequence
<220> FEATURE:
<223> OTHER INFORMATION: actA

<400> SEQUENCE: 9
tttatcacgt acccattcc ccgcatcttt tatttttta aatactttag ggaaaaatgg      60 ttttttgattt gcttttaaag gttgtggtgt agactcgtct gctgactgca tgctagaatc    120
taagtcactt tcagaagcat ccacaactga ctctttcgcc acttttctct tatttgcttt    180
tgttggttta tctggataag taaggctttc aagctcacta tccgacgacg ctatggcttt    240
tcttcttttt ttaatttccg ctgcgctatc cgatgacaga cctggatgac gacgctccac    300
ttgcagagtt ggtcggtcga ctcctgaagc ctcttcattt atagccacat ttcctgtttg    360
ctcaccgttg ttattattgt tattcggacc tttctctgct tttgctttca acattgctat    420
taggtctgct ttgttcgtat ttttcacttt attcgatttt tctagttcct caatatcacg    480
tgaacttact tcacgtgcag tttcgtatct tggtcccgta tttacctcgc ttggctgctc    540
ttctgttttt tcttcttccc attcatctgt gtttagactg gaatcttcgc tatctgtcgc    600
tgcaaatatt atgtcggggt taatcgtaat gcagttggca gtaatgaaaa ctaccatcat    660
cgcacgcat                                                            669

<210> SEQ ID NO 10
<211> LENGTH: 390
<212> TYPE: PRT
<213> ORGANISM: Artificial Sequence
<220> FEATURE:
<223> OTHER INFORMATION: actA

<400> SEQUENCE: 10

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80
```

Ala Asp Leu Ile Ala Met Leu Lys Glu Lys Ala Glu Lys Gly Pro Asn
            85                  90                  95

Ile Asn Asn Asn Ser Glu Gln Thr Glu Asn Ala Ala Ile Asn Glu
        100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
        180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
        355                 360                 365

Gln Asn Phe Ser Asp Phe Pro Pro Ile Pro Thr Glu Glu Leu Asn
    370                 375                 380

Gly Arg Gly Gly Arg Pro
385                 390

<210> SEQ ID NO 11
<211> LENGTH: 1170
<212> TYPE: DNA
<213> ORGANISM: Artificial Sequence
<220> FEATURE:
<223> OTHER INFORMATION: actA

<400> SEQUENCE: 11
atgcgtgcga tgatggtggt tttcattact gccaattgca ttacgattaa ccccgacata      60
atatttgcag cgacagatag cgaagattct agtctaaaca cagatgaatg gaagaagaa     120 aaaacagaag agcaaccaag cgaggtaaat acgggaccaa gatacgaaac tgcacgtgaa     180
gtaagttcac gtgatattaa agaactagaa aaatcgaata aagtgagaaa tacgaacaaa     240
gcagacctaa tagcaatgtt gaaagaaaaa gcagaaaaag gtccaaatat caataataac     300

-continued

```
aacagtgaac aaactgagaa tgcggctata aatgaagagg cttcaggagc cgaccgacca    360
gctatacaag tggagcgtcg tcatccagga ttgccatcgg atagcgcagc ggaaattaaa    420
aaaagaagga aagccatagc atcatcggat agtgagcttg aaagccttac ttatccggat    480
aaaccaacaa aagtaaataa gaaaaaagtg gcgaaagagt cagttgcgga tgcttctgaa    540
agtgacttag attctagcat gcagtcagca gatgagtctt caccacaacc tttaaaagca    600
aaccaacaac cattttttccc taaagtattt aaaaaaataa aagatgcggg gaaatgggta    660
cgtgataaaa tcgacgaaaa tcctgaagta aagaaagcga ttgttgataa aagtgcaggg    720
ttaattgacc aattattaac caaaagaaa agtgaagagg taaatgcttc ggacttcccg     780
ccaccaccta cggatgaaga gttaagactt gctttgccag agacaccaat gcttcttggt    840
tttaatgctc ctgctacatc agaaccgagc tcattcgaat ttccaccacc acctacggat    900
gaagagttaa gacttgcttt gccagagacg ccaatgcttc ttggttttaa tgctcctgct    960
acatcggaac cgagctcgtt cgaatttcca ccgcctccaa cagaagatga actagaaatc    1020
atccgggaaa cagcatcctc gctagattct agttttacaa gaggggattt agctagtttg    1080
agaaatgcta ttaatcgcca tagtcaaaat ttctctgatt tcccaccaat cccaacagaa    1140
gaagagttga acgggagagg cggtagacca                                      1170
```

<210> SEQ ID NO 12
<211> LENGTH: 32
<212> TYPE: PRT
<213> ORGANISM: Listeria monocytogenes

<400> SEQUENCE: 12

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 13
<211> LENGTH: 19
<212> TYPE: PRT
<213> ORGANISM: Listeria monocytogenes

<400> SEQUENCE: 13

Lys Glu Asn Ser Ile Ser Ser Met Ala Pro Ala Ser Pro Pro Ala
1               5                   10                  15

Ser Pro Lys

<210> SEQ ID NO 14
<211> LENGTH: 14
<212> TYPE: PRT
<213> ORGANISM: Listeria monocytogenes

<400> SEQUENCE: 14

Lys Thr Glu Glu Gln Pro Ser Glu Val Asn Thr Gly Pro Arg
1               5                   10

<210> SEQ ID NO 15
<211> LENGTH: 28
<212> TYPE: PRT
<213> ORGANISM: Listeria monocytogenes

<400> SEQUENCE: 15

Lys Ala Ser Val Thr Asp Thr Ser Glu Gly Asp Leu Asp Ser Ser Met
1               5                   10                  15

-continued

Gln Ser Ala Asp Glu Ser Thr Pro Gln Pro Leu Lys
            20                  25

<210> SEQ ID NO 16
<211> LENGTH: 20
<212> TYPE: PRT
<213> ORGANISM: Listeria monocytogenes

<400> SEQUENCE: 16

Lys Asn Glu Glu Val Asn Ala Ser Asp Phe Pro Pro Pro Thr Asp
1               5                   10                  15

Glu Glu Leu Arg
            20

<210> SEQ ID NO 17
<211> LENGTH: 33
<212> TYPE: PRT
<213> ORGANISM: Listeria monocytogenes

<400> SEQUENCE: 17

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Ile Asp
            20                  25                  30

Arg

<210> SEQ ID NO 18
<211> LENGTH: 28
<212> TYPE: PRT
<213> ORGANISM: Listeria monocytogenes

<400> SEQUENCE: 18

Lys Glu Ser Val Val Asp Ala Ser Glu Ser Asp Leu Asp Ser Ser Met
1               5                   10                  15

Gln Ser Ala Asp Glu Ser Thr Pro Gln Pro Leu Lys
            20                  25

<210> SEQ ID NO 19
<211> LENGTH: 20
<212> TYPE: PRT
<213> ORGANISM: Listeria monocytogenes

<400> SEQUENCE: 19

Lys Ser Glu Glu Val Asn Ala Ser Asp Phe Pro Pro Pro Thr Asp
1               5                   10                  15

Glu Glu Leu Arg
            20

<210> SEQ ID NO 20
<211> LENGTH: 33
<212> TYPE: PRT
<213> ORGANISM: Listeria monocytogenes

<400> SEQUENCE: 20

Arg Gly Gly Arg Pro Thr Ser Glu Glu Phe Ser Ser Leu Asn Ser Gly
1               5                   10                  15

Asp Phe Thr Asp Asp Glu Asn Ser Glu Thr Thr Glu Glu Ile Asp
            20                  25                  30

Arg

-continued

```
<210> SEQ ID NO 21
<211> LENGTH: 19
<212> TYPE: PRT
<213> ORGANISM: Listeria monocytogenes

<400> SEQUENCE: 21

Arg Ser Glu Val Thr Ile Ser Pro Ala Glu Thr Pro Glu Ser Pro Pro
1               5                   10                  15

Ala Thr Pro

<210> SEQ ID NO 22
<211> LENGTH: 17
<212> TYPE: PRT
<213> ORGANISM: Streptococcus pyogenes

<400> SEQUENCE: 22

Lys Gln Asn Thr Ala Ser Thr Glu Thr Thr Thr Thr Asn Glu Gln Pro
1               5                   10                  15

Lys

<210> SEQ ID NO 23
<211> LENGTH: 17
<212> TYPE: PRT
<213> ORGANISM: Streptococcus equisimilis

<400> SEQUENCE: 23

Lys Gln Asn Thr Ala Asn Thr Glu Thr Thr Thr Thr Asn Glu Gln Pro
1               5                   10                  15

Lys

<210> SEQ ID NO 24
<211> LENGTH: 22
<212> TYPE: PRT
<213> ORGANISM: Artificial Sequence
<220> FEATURE:
<223> OTHER INFORMATION: E7 primer sequence

<400> SEQUENCE: 24

Gly Gly Cys Thr Cys Gly Ala Gly Cys Ala Thr Gly Gly Ala Gly Ala
1               5                   10                  15

Thr Ala Cys Ala Cys Cys
                20

<210> SEQ ID NO 25
<211> LENGTH: 28
<212> TYPE: PRT
<213> ORGANISM: Artificial Sequence
<220> FEATURE:
<223> OTHER INFORMATION: E7 primer sequence

<400> SEQUENCE: 25

Gly Gly Gly Gly Ala Cys Thr Ala Gly Thr Thr Thr Ala Thr Gly Gly
1               5                   10                  15

Thr Thr Thr Cys Thr Gly Ala Gly Ala Ala Cys Ala
            20                  25

<210> SEQ ID NO 26
<211> LENGTH: 31
<212> TYPE: PRT
<213> ORGANISM: Artificial Sequence
<220> FEATURE:
<223> OTHER INFORMATION: hly promoter and gene fragment F primer

<400> SEQUENCE: 26
```

```
Gly Gly Gly Gly Gly Cys Thr Ala Gly Cys Cys Cys Thr Cys Cys Thr
1               5                   10                  15

Thr Thr Gly Ala Thr Thr Ala Gly Thr Ala Thr Ala Thr Thr Cys
            20                  25                  30

<210> SEQ ID NO 27
<211> LENGTH: 28
<212> TYPE: PRT
<213> ORGANISM: Artificial Sequence
<220> FEATURE:
<223> OTHER INFORMATION: hly promoter and gene fragment R primer

<400> SEQUENCE: 27

Cys Thr Cys Cys Cys Thr Cys Gly Ala Gly Ala Thr Cys Ala Thr Ala
1               5                   10                  15

Ala Thr Thr Thr Ala Cys Thr Thr Cys Ala Thr Cys
            20                  25

<210> SEQ ID NO 28
<211> LENGTH: 55
<212> TYPE: PRT
<213> ORGANISM: Artificial Sequence
<220> FEATURE:
<223> OTHER INFORMATION: prfA gene amplification F primer

<400> SEQUENCE: 28

Gly Ala Cys Thr Ala Cys Ala Ala Gly Gly Ala Cys Gly Ala Thr Gly
1               5                   10                  15

Ala Cys Cys Gly Ala Cys Ala Ala Gly Thr Gly Ala Thr Ala Ala Cys
            20                  25                  30

Cys Cys Gly Gly Gly Ala Thr Cys Thr Ala Ala Ala Thr Ala Ala Ala
        35                  40                  45

Thr Cys Cys Gly Thr Thr Thr
    50                  55

<210> SEQ ID NO 29
<211> LENGTH: 27
<212> TYPE: PRT
<213> ORGANISM: Artificial Sequence
<220> FEATURE:
<223> OTHER INFORMATION: prfA gene amplification R primer

<400> SEQUENCE: 29

Cys Cys Cys Gly Thr Cys Gly Ala Cys Cys Ala Gly Cys Thr Cys Thr
1               5                   10                  15

Thr Cys Thr Thr Gly Gly Thr Gly Ala Ala Gly
            20                  25

<210> SEQ ID NO 30
<211> LENGTH: 25
<212> TYPE: PRT
<213> ORGANISM: Artificial Sequence
<220> FEATURE:
<223> OTHER INFORMATION: E7 F primer sequence

<400> SEQUENCE: 30

Gly Cys Gly Gly Ala Thr Cys Cys Cys Ala Thr Gly Gly Ala Gly Ala
1               5                   10                  15

Thr Ala Cys Ala Cys Cys Thr Ala Cys
            20                  25

<210> SEQ ID NO 31
```

```
<211> LENGTH: 22
<212> TYPE: PRT
<213> ORGANISM: Artificial Sequence
<220> FEATURE:
<223> OTHER INFORMATION: E7 R primer sequence

<400> SEQUENCE: 31

Gly Cys Thr Cys Thr Ala Gly Ala Thr Thr Ala Thr Gly Gly Thr Thr
1               5                   10                  15

Thr Cys Thr Gly Ala Gly
            20

<210> SEQ ID NO 32
<211> LENGTH: 9
<212> TYPE: PRT
<213> ORGANISM: Artificial Sequence
<220> FEATURE:
<223> OTHER INFORMATION: (PE)-conjugated E7 peptide

<400> SEQUENCE: 32

Arg Ala His Tyr Asn Ile Val Thr Phe
1               5

<210> SEQ ID NO 33
<211> LENGTH: 31
<212> TYPE: PRT
<213> ORGANISM: Artificial Sequence
<220> FEATURE:
<223> OTHER INFORMATION: hly promoter and gene fragment F primer

<400> SEQUENCE: 33

Gly Gly Gly Gly Thr Cys Thr Ala Gly Ala Cys Cys Thr Cys Cys Thr
1               5                   10                  15

Thr Thr Gly Ala Thr Thr Ala Gly Thr Ala Thr Ala Thr Thr Cys
            20                  25                  30

<210> SEQ ID NO 34
<211> LENGTH: 45
<212> TYPE: PRT
<213> ORGANISM: Artificial Sequence
<220> FEATURE:
<223> OTHER INFORMATION: hly promoter and gene fragment R primer

<400> SEQUENCE: 34

Ala Thr Cys Thr Thr Cys Gly Cys Thr Ala Thr Cys Thr Gly Thr Cys
1               5                   10                  15

Gly Cys Cys Gly Cys Gly Gly Cys Gly Cys Gly Thr Gly Cys Thr Thr
            20                  25                  30

Cys Ala Gly Thr Thr Thr Gly Thr Thr Gly Cys Gly Cys
        35                  40                  45

<210> SEQ ID NO 35
<211> LENGTH: 45
<212> TYPE: PRT
<213> ORGANISM: Artificial Sequence
<220> FEATURE:
<223> OTHER INFORMATION: ActA gene amplification F primer

<400> SEQUENCE: 35

Gly Cys Gly Cys Ala Ala Cys Ala Ala Ala Cys Thr Gly Ala Ala Gly
1               5                   10                  15

Cys Ala Gly Cys Gly Gly Cys Cys Gly Cys Gly Gly Cys Gly Ala Cys
            20                  25                  30

Ala Gly Ala Thr Ala G

<210> SEQ ID NO 36
<211> LENGTH: 42
<212> TYPE: PRT
<213> ORGANISM: Artificial Sequence
<220> FEATURE:
<223> OTHER INFORMATION: ActA gene amplification R primer

<400> SEQUENCE: 36

Thr Gly Thr Ala Gly Gly Thr Gly Thr Ala Thr Cys Thr Cys Cys Ala
1               5                   10                  15

Thr Gly Cys Thr Cys Gly Ala Gly Ala Gly Cys Thr Ala Gly Gly Cys
            20                  25                  30

Gly Ala Thr Cys Ala Ala Thr Thr Thr Cys
        35                  40

<210> SEQ ID NO 37
<211> LENGTH: 42
<212> TYPE: PRT
<213> ORGANISM: Artificial Sequence
<220> FEATURE:
<223> OTHER INFORMATION: E7 F primer sequence

<400> SEQUENCE: 37

Gly Gly Ala Ala Thr Thr Gly Ala Thr Cys Gly Cys Cys Thr Ala Gly
1               5                   10                  15

Cys Thr Cys Thr Cys Gly Ala Gly Cys Ala Thr Gly Gly Ala Gly Ala
            20                  25                  30

Thr Ala Cys Ala Cys Cys Thr Ala Cys Ala
        35                  40

<210> SEQ ID NO 38
<211> LENGTH: 42
<212> TYPE: PRT
<213> ORGANISM: Artificial Sequence
<220> FEATURE:
<223> OTHER INFORMATION: E7 R primer sequence

<400> SEQUENCE: 38

Ala Ala Ala Cys Gly Gly Ala Thr Thr Thr Ala Thr Thr Thr Ala Gly
1               5                   10                  15

Ala Thr Cys Cys Cys Gly Gly Gly Thr Thr Ala Thr Gly Gly Thr Thr
            20                  25                  30

Thr Cys Thr Gly Ala Gly Ala Ala Cys Ala
        35                  40

<210> SEQ ID NO 39
<211> LENGTH: 42
<212> TYPE: PRT
<213> ORGANISM: Artificial Sequence
<220> FEATURE:
<223> OTHER INFORMATION: prfA gene amplification F primer

<400> SEQUENCE: 39

Thr Gly Thr Thr Cys Thr Cys Ala Gly Ala Ala Ala Cys Cys Ala Thr
1               5                   10                  15

Ala Ala Cys Cys Cys Gly Gly Gly Ala Thr Cys Thr Ala Ala Ala Thr
            20                  25                  30

Ala Ala Ala Thr Cys Cys Gly Thr Thr Thr
        35                  40

```
<210> SEQ ID NO 40
<211> LENGTH: 28
<212> TYPE: PRT
<213> ORGANISM: Artificial Sequence
<220> FEATURE:
<223> OTHER INFORMATION: prfA gene amplification R primer

<400> SEQUENCE: 40

Gly Gly Gly Gly Gly Thr Cys Gly Ala Cys Cys Ala Gly Cys Thr Cys
1               5                   10                  15

Thr Thr Cys Thr Thr Gly Gly Thr Gly Ala Ala Gly
            20                  25

<210> SEQ ID NO 41
<211> LENGTH: 21
<212> TYPE: DNA
<213> ORGANISM: Artificial Sequence
<220> FEATURE:
<223> OTHER INFORMATION: dal gene forward primer

<400> SEQUENCE: 41
ccatggtgac aggctggcat c                                          21

<210> SEQ ID NO 42
<211> LENGTH: 27
<212> TYPE: DNA
<213> ORGANISM: Artificial Sequence
<220> FEATURE:
<223> OTHER INFORMATION: dal gene reverse primer

<400> SEQUENCE: 42
gctagcctaa tggatgtatt ttctagg                                    27

<210> SEQ ID NO 43
<211> LENGTH: 27
<212> TYPE: DNA
<213> ORGANISM: Artificial Sequence
<220> FEATURE:
<223> OTHER INFORMATION: minimal p60 promoter sequence forward primer

<400> SEQUENCE: 43
ttaattaaca aatagttggt atagtcc                                    27

<210> SEQ ID NO 44
<211> LENGTH: 36
<212> TYPE: DNA
<213> ORGANISM: Artificial Sequence
<220> FEATURE:
<223> OTHER INFORMATION: minimal p60 promoter sequence forward primer

<400> SEQUENCE: 44
gacgatgcca gcctgtcacc atggaaaact cctctc                          36

<210> SEQ ID NO 45
<211> LENGTH: 156
<212> TYPE: DNA
<213> ORGANISM: Artificial Sequence
<220> FEATURE:
<223> OTHER INFORMATION: truncated p60 promoter

<400> SEQUENCE: 45
caaatagttg gtatagtcct ctttagcctt tggagtatta tctcatcatt tgttttttag    60
gtgaaaactg ggtaaactta gtattatcaa tataaaatta attctcaaat acttaattac   120
gtactgggat tttctgaaaa aagagaggag ttttcc                            156
```

<210> SEQ ID NO 46
<211> LENGTH: 25
<212> TYPE: DNA
<213> ORGANISM: Artificial Sequence
<220> FEATURE:
<223> OTHER INFORMATION: oriRep forward primer

<400> SEQUENCE: 46
ggcgccacta actcaacgct agtag                                              25

<210> SEQ ID NO 47
<211> LENGTH: 27
<212> TYPE: DNA
<213> ORGANISM: Artificial Sequence
<220> FEATURE:
<223> OTHER INFORMATION: oriRep reverse primer

<400> SEQUENCE: 47
gctagccagc aaagaaaaac aaacacg                                            27

<210> SEQ ID NO 48
<211> LENGTH: 38
<212> TYPE: DNA
<213> ORGANISM: Artificial Sequence
<220> FEATURE:
<223> OTHER INFORMATION: oriRep forward primer

<400> SEQUENCE: 48
gtcgacggtc accggcgcca ctaactcaac gctagtag                                38

<210> SEQ ID NO 49
<211> LENGTH: 35
<212> TYPE: DNA
<213> ORGANISM: Artificial Sequence
<220> FEATURE:
<223> OTHER INFORMATION: oriRep reverse primer

<400> SEQUENCE: 49
ttaattaagc tagccagcaa agaaaaacaa acacg                                   35

<210> SEQ ID NO 50
<211> LENGTH: 29
<212> TYPE: DNA
<213> ORGANISM: Artificial Sequence
<220> FEATURE:
<223> OTHER INFORMATION: LLO-E7 gene forward amplification primer

<400> SEQUENCE: 50
atgaaaaaaa taatgctagt ttttattac                                          29

<210> SEQ ID NO 51
<211> LENGTH: 48
<212> TYPE: DNA
<213> ORGANISM: Artificial Sequence
<220> FEATURE:
<223> OTHER INFORMATION: LLO-E7 gene reverse amplification primer

<400> SEQUENCE: 51
gcggccgctt aatgatgatg atgatgatgt ggtttctgag aacagatg                     48

<210> SEQ ID NO 52
<211> LENGTH: 22
<212> TYPE: DNA
<213> ORGANISM: Artificial Sequence
<220> FEATURE:
<223> OTHER INFORMATION: Taqman primer-probe sets

<400> SEQUENCE: 52
gcaagtgtga ctctacgctt cg                                           22

<210> SEQ ID NO 53
<211> LENGTH: 21
<212> TYPE: DNA
<213> ORGANISM: Artificial Sequence
<220> FEATURE:
<223> OTHER INFORMATION: Taqman primer-probe sets

<400> SEQUENCE: 53
tgcccattaa caggtcttcc a                                            21

<210> SEQ ID NO 54
<211> LENGTH: 32
<212> TYPE: DNA
<213> ORGANISM: Artificial Sequence
<220> FEATURE:
<223> OTHER INFORMATION: Taqman primer-probe sets

<400> SEQUENCE: 54
tgcgtacaaa gcacacacgt agacattcgt ac                                32

<210> SEQ ID NO 55
<211> LENGTH: 24
<212> TYPE: DNA
<213> ORGANISM: Artificial Sequence
<220> FEATURE:
<223> OTHER INFORMATION: Taqman primer-probe sets

<400> SEQUENCE: 55
tgacatcgtt tgtgtttgag ctag                                         24

<210> SEQ ID NO 56
<211> LENGTH: 23
<212> TYPE: DNA
<213> ORGANISM: Artificial Sequence
<220> FEATURE:
<223> OTHER INFORMATION: Taqman primer-probe sets

<400> SEQUENCE: 56
gcagcgctct ctataccagg tac                                          23

<210> SEQ ID NO 57
<211> LENGTH: 38
<212> TYPE: DNA
<213> ORGANISM: Artificial Sequence
<220> FEATURE:
<223> OTHER INFORMATION: Taqman primer-probe sets

<400> SEQUENCE: 57
ttaatgtcca tgttatgtct ccgttatagc tcatcgta                          38

<210> SEQ ID NO 58
<211> LENGTH: 19
<212> TYPE: DNA
<213> ORGANISM: Artificial Sequence
<220> FEATURE:
<223> OTHER INFORMATION: primer to verify deletion of ActA

<400> SEQUENCE: 58
tgggatggcc aagaaattc                                               19

<210> SEQ ID NO 59

```
<211> LENGTH: 22
<212> TYPE: DNA
<213> ORGANISM: Artificial Sequence
<220> FEATURE:
<223> OTHER INFORMATION: primer to verify deletion of ActA

<400> SEQUENCE: 59
ctaccatgtc ttccgttgct tg                                              22

<210> SEQ ID NO 60
<211> LENGTH: 1256
<212> TYPE: DNA
<213> ORGANISM: Artificial Sequence
<220> FEATURE:
<223> OTHER INFORMATION: Lm-dd actA

<400> SEQUENCE: 60
gcgccaaatc attggttgat tggtgaggat gtctgtgtgc gtgggtcgcg agatgggcga      60
ataagaagca ttaaagatcc tgacaaatat aatcaagcgg ctcatatgaa agattacgaa     120
tcgcttccac tcacagagga aggcgactgg ggcggagttc attataatag tggtatcccg     180
aataaagcag cctataatac tatcactaaa cttggaaaag aaaaaacaga acagctttat     240
tttcgcgcct taaagtacta tttaacgaaa aaatcccagt ttaccgatgc gaaaaaagcg     300
cttcaacaag cagcgaaaga tttatatggt gaagatgctt ctaaaaaagt tgctgaagct     360
tgggaagcag ttgggggttaa ctgattaaca aatgttagag aaaaattaat tctccaagtg     420
atattcttaa ataattcat gaatattttt tcttatatta gctaattaag aagataacta     480
actgctaatc caatttttaa cggaacaaat tagtgaaaat gaaggccgaa ttttccttgt     540
tctaaaaagg ttgtattagc gtatcacgag gagggagtat aagtgggatt aaacagattt     600
atgcgtgcga tgatggtggt tttcattact gccaattgca ttacgattaa ccccgacgtc     660
gacccatacg acgttaattc ttgcaatgtt agctattggc gtgttctctt tagggggcgtt    720 tatcaaaatt attcaattaa gaaaaaataa ttaaaaacac agaacgaaag aaaaagtgag    780
gtgaatgata tgaaattcaa aaaggtggtt ctaggtatgt gcttgatcgc aagtgttcta    840
gtctttccgg taacgataaa agcaaatgcc tgttgtgatg aatacttaca acacccgca    900 gctccgcatg atattgacag caaattacca cataaactta gttggtccgc ggataacccg    960
acaaatactg acgtaaatac gcactattgg cttttttaaac aagcggaaaa aatactagct   1020
aaagatgtaa atcatatgcg agctaattta atgaatgaac ttaaaaaatt cgataaacaa   1080
atagctcaag gaatatatga tgcggatcat aaaaatccat attatgatac tagtacattt   1140
ttatctcatt tttataatcc tgatagagat aatacttatt gccgggttt tgctaatgcg   1200 aaaataacag gagcaaagta tttcaatcaa tcggtgactg attaccgaga agggaa       1256

<210> SEQ ID NO 61
<211> LENGTH: 28
<212> TYPE: DNA
<213> ORGANISM: Artificial Sequence
<220> FEATURE:
<223> OTHER INFORMATION: Her-2-Chimera (F) primer

<400> SEQUENCE: 61
tgatctcgag acccacctgg acatgctc                                        28

<210> SEQ ID NO 62
<211> LENGTH: 49
<212> TYPE: DNA
<213> ORGANISM: Artificial Sequence
```

<220> FEATURE:
<223> OTHER INFORMATION: HerEC1-EC2F primer

<400> SEQUENCE: 62
ctaccaggac acgattttgt ggaagaatat ccaggagttt gctggctgc        49

<210> SEQ ID NO 63
<211> LENGTH: 49
<212> TYPE: DNA
<213> ORGANISM: Artificial Sequence
<220> FEATURE:
<223> OTHER INFORMATION: HerEC1-EC2R primer

<400> SEQUENCE: 63
gcagccagca aactcctgga tattcttcca caaaatcgtg tcctggtag        49

<210> SEQ ID NO 64
<211> LENGTH: 50
<212> TYPE: DNA
<213> ORGANISM: Artificial Sequence
<220> FEATURE:
<223> OTHER INFORMATION: HerEC2-ICIF primer

<400> SEQUENCE: 64
ctgccaccag ctgtgcgccc gagggcagca gaagatccgg aagtacacga       50

<210> SEQ ID NO 65
<211> LENGTH: 50
<212> TYPE: DNA
<213> ORGANISM: Artificial Sequence
<220> FEATURE:
<223> OTHER INFORMATION: HerEC2-ICIR primer

<400> SEQUENCE: 65
tcgtgtactt ccggatcttc tgctgccctc gggcgcacag ctggtggcag       50

<210> SEQ ID NO 66
<211> LENGTH: 39
<212> TYPE: DNA
<213> ORGANISM: Artificial Sequence
<220> FEATURE:
<223> OTHER INFORMATION: Her-2-Chimera (R) primer

<400> SEQUENCE: 66
gtggcccggg tctagattag tctaagaggc agccatagg        39

<210> SEQ ID NO 67
<211> LENGTH: 28
<212> TYPE: DNA
<213> ORGANISM: Artificial Sequence
<220> FEATURE:
<223> OTHER INFORMATION: Her-2-EC1(F) primer

<400> SEQUENCE: 67
ccgcctcgag gccgcgagca cccaagtg        28

<210> SEQ ID NO 68
<211> LENGTH: 31
<212> TYPE: DNA
<213> ORGANISM: Artificial Sequence
<220> FEATURE:
<223> OTHER INFORMATION: Her-2-EC1(R)

<400> SEQUENCE: 68
cgcgactagt ttaatcctct gctgtcacct c        31

<210> SEQ ID NO 69
<211> LENGTH: 28
<212> TYPE: DNA
<213> ORGANISM: Artificial Sequence
<220> FEATURE:
<223> OTHER INFORMATION: Her-2-EC2(F) primer

<400> SEQUENCE: 69
ccgcctcgag tacctttcta cggacgtg                                    28

<210> SEQ ID NO 70
<211> LENGTH: 30
<212> TYPE: DNA
<213> ORGANISM: Artificial Sequence
<220> FEATURE:
<223> OTHER INFORMATION: Her- 2- EC2(R) primer

<400> SEQUENCE: 70
cgcgactagt ttactctggc cggttggcag                                  30

<210> SEQ ID NO 71
<211> LENGTH: 31
<212> TYPE: DNA
<213> ORGANISM: Artificial Sequence
<220> FEATURE:
<223> OTHER INFORMATION: Her-2- IC1(F) primer

<400> SEQUENCE: 71
ccgcctcgag cagcagaaga tccggaagta c                                31

<210> SEQ ID NO 72
<211> LENGTH: 30
<212> TYPE: DNA
<213> ORGANISM: Artificial Sequence
<220> FEATURE:
<223> OTHER INFORMATION: Her-2-IC1(R) primer

<400> SEQUENCE: 72
cgcgactagt ttaagcccct cggagggtg                                   30

<210> SEQ ID NO 73
<211> LENGTH: 7075
<212> TYPE: DNA
<213> ORGANISM: Artificial Sequence
<220> FEATURE:
<223> OTHER INFORMATION: pAdv164 sequence

<400> SEQUENCE: 73
cggagtgtat actggcttac tatgttggca ctgatgaggg tgtcagtgaa gtgcttcatg    60
tggcaggaga aaaaggctg caccggtgcg tcagcagaat atgtgataca ggatatattc   120
cgcttcctcg ctcactgact cgctacgctc ggtcgttcga ctgcggcgag cggaaatggc   180
ttacgaacgg ggcggagatt tcctggaaga tgccaggaag atacttaaca gggaagtgag   240
agggccgcgg caaagccgtt tttccatagg ctccgccccc ctgacaagca tcacgaaatc   300
tgacgctcaa atcagtggtg gcgaaacccg acaggactat aaagatacca ggcgtttccc   360
cctggcggct ccctcgtgcg ctctcctgtt cctgcctttc ggtttaccgg tgtcattccg   420
ctgttatggc cgcgtttgtc tcattccacg cctgacactc agttccgggt aggcagttcg   480
ctccaagctg gactgtatgc acgaaccccc cgttcagtcc gaccgctgcg ccttatccgg   540
taactatcgt cttgagtcca acccggaaag acatgcaaaa gcaccactgg cagcagccac   600
tggtaattga tttagaggag ttagtcttga agtcatgcgc cggttaaggc taaactgaaa   660

```
ggacaagttt tggtgactgc gctcctccaa gccagttacc tcggttcaaa gagttggtag    720
ctcagagaac cttcgaaaaa ccgccctgca aggcggtttt ttcgttttca gagcaagaga    780
ttacgcgcag accaaaacga tctcaagaag atcatcttat taatcagata aaatatttct    840
agccctcctt tgattagtat attcctatct taaagttact tttatgtgga ggcattaaca    900
tttgttaatg acgtcaaaag gatagcaaga ctagaataaa gctataaagc aagcatataa    960
tattgcgttt catctttaga agcgaatttc gccaatatta taattatcaa agagagggg   1020 tggcaaacgg tatttggcat tattaggtta aaaaatgtag aaggagagtg aaacccatga   1080
aaaaaataat gctagttttt attacactta tattagttag tctaccaatt gcgcaacaaa   1140
ctgaagcaaa ggatgcatct gcattcaata agaaaattc aatttcatcc atggcaccac    1200
cagcatctcc gcctgcaagt cctaagacgc caatcgaaaa gaaacacgcg gatgaaatcg   1260
ataagtatat acaaggattg gattacaata aaacaatgt attagtatac cacggagatg    1320
cagtgacaaa tgtgccgcca agaaaaggtt acaaagatgg aaatgaatat attgttgtgg   1380
agaaaaagaa gaaatccatc aatcaaaata atgcagacat tcaagttgtg aatgcaattt   1440
cgagcctaac ctatccaggt gctctcgtaa agcgaattc ggaattagta gaaaatcaac    1500
cagatgttct ccctgtaaaa cgtgattcat taacactcag cattgatttg ccaggtatga   1560
ctaatcaaga caataaaata gttgtaaaaa atgccactaa atcaaacgtt aacaacgcag   1620
taaatacatt agtggaaaga tggaatgaaa aatatgctca agcttatcca aatgtaagtg   1680
caaaaattga ttatgatgac gaaatggctt acagtgaatc acaattaatt gcgaaatttg   1740
gtacagcatt taaagctgta aataatagct tgaatgtaaa cttcggcgca atcagtgaag   1800
ggaaaatgca agaagaagtc attagttta aacaaattta ctataacgtg aatgttaatg    1860
aacctacaag accttccaga ttttcggca agctgttac taaagagcag ttgcaagcgc    1920
ttggagtgaa tgcagaaaat cctcctgcat atatctcaag tgtggcgtat ggccgtcaag   1980
tttatttgaa attatcaact aattcccata gtactaaagt aaaagctgct tttgatgctg   2040
ccgtaagcgg aaaatctgtc tcaggtgatg tagaactaac aaatatcatc aaaaattctt   2100
ccttcaaagc cgtaatttac ggaggttccg caaaagatga agttcaaatc atcgacggca   2160
acctcggaga cttacgcgat attttgaaaa aaggcgctac ttttaatcga gaaacaccag   2220
gagttcccat tgcttataca acaaacttcc taaaagacaa tgaattagct gttattaaaa   2280
acaactcaga atatattgaa acaacttcaa aagcttatac agatggaaaa attaacatcg   2340
atcactctgg aggatacgtt gctcaattca acatttcttg ggatgaagta aattatgatc   2400
tcgagaccca cctggacatg ctccgccacc tctaccaggg ctgccaggtg gtgcagggaa   2460
acctggaact cacctacctg cccaccaatg ccagcctgtc cttcctgcag gatatccagg   2520
aggtgcaggg ctacgtgctc atcgctcaca ccaagtgag gcaggtccca ctgcagaggc   2580
tgcggattgt gcgaggcacc cagctctttg gacaactac tgccctggcc gtgctagaca   2640
atggagaccc gctgaacaat accaccccctg tcacaggggc ctccccagga ggcctgcggg   2700
agctgcagct tcgaagcctc acagagatct tgaaaggagg ggtcttgatc cagcggaacc   2760
cccagctctg ctaccaggac acgattttgt ggaagaatat ccaggagttt gctggctgca   2820
agaagatctt tgggagcctg gcatttctgc cggagagctt tgatgggac ccagcctcca   2880 acactgcccc gctccagcca gagcagctcc aagtgtttga actctggaa gagatcacag   2940 gttacctata catctcagca tggccggaca gcctgcctga cctcagcgtc ttccagaacc   3000
```

```
tgcaagtaat ccggggacga attctgcaca atggcgccta ctcgctgacc ctgcaagggc    3060
tgggcatcag ctggctgggg ctgcgctcac tgagggaact gggcagtgga ctggccctca    3120
tccaccataa cacccacctc tgcttcgtgc acacggtgcc ctgggaccag ctctttcgga    3180
acccgcacca agctctgctc cacactgcca accggccaga ggacgagtgt gtgggcgagg    3240
gcctggcctg ccaccagctg tgcgcccgag ggcagcagaa gatccggaag tacacgatgc    3300
ggagactgct gcaggaaacg gagctggtgg agccgctgac acctagcgga gcgatgccca    3360
accaggcgca gatgcggatc ctgaaagaga cggagctgag gaaggtgaag gtgcttggat    3420
ctggcgcttt tggcacagtc tacaagggca tctggatccc tgatggggag aatgtgaaaa    3480
ttccagtggc catcaaagtg ttgagggaaa acacatcccc caaagccaac aaagaaatct    3540
tagacgaagc atacgtgatg gctggtgtgg gctccccata tgtctcccgc cttctgggca    3600
tctgcctgac atccacggtg cagctggtga cacagcttat gccctatggc tgcctcttag    3660
actaatctag acccgggcca ctaactcaac gctagtagtg gatttaatcc caaatgagcc    3720
aacagaacca gaaccagaaa cagaacaagt aacattggag ttagaaatgg aagaagaaaa    3780
aagcaatgat ttcgtgtgaa taatgcacga aatcattgct tatttttta aaaagcgata    3840
tactagatat aacgaaacaa cgaactgaat aaagaataca aaaaaagagc cacgaccagt    3900
taaagcctga gaaactttaa ctgcgagcct taattgatta ccaccaatca attaaagaag    3960
tcgagaccca aaatttggta aagtatttaa ttactttatt aatcagatac ttaaatatct    4020
gtaaacccat tatatcgggt ttttgagggg atttcaagtc tttaagaaga taccaggcaa    4080
tcaattaaga aaaacttagt tgattgcctt ttttgttgtg attcaacttt gatcgtagct    4140
tctaactaat taattttcgt aagaaggag aacagctgaa tgaatatccc ttttgttgta    4200
gaaactgtgc ttcatgacgg cttgttaaag tacaaattta aaaatagtaa aattcgctca    4260
atcactacca agccaggtaa aagtaaaggg gctattttg cgtatcgctc aaaaaaaagc    4320
atgattggcg gacgtggcgt tgttctgact tccgaagaag cgattcacga aaatcaagat    4380
acatttacgc attggacacc aaacgtttat cgttatggta cgtatgcaga cgaaaaccgt    4440
tcatacacta aaggacattc tgaaaacaat ttaagacaaa tcaataccttt ctttattgat    4500
tttgatattc acacggaaaa agaaactatt tcagcaagcg atatttttaac aacagctatt    4560
gatttaggtt ttatgcctac gttaattatc aaatctgata aaggttatca agcatatttt    4620
gtttttagaaa cgccagtcta tgtgacttca aaatcagaat ttaaatctgt caaagcagcc    4680
aaaataatct cgcaaaatat ccgagaatat tttggaaagt ctttgccagt tgatctaacg    4740
tgcaatcatt ttgggattgc tcgtatacca agaacggaca atgtagaatt ttttgatccc    4800
aattaccgtt attctttcaa agaatggcaa gattggtctt tcaaacaaac agataataag    4860
ggctttactc gttcaagtct aacggtttta agcggtacag aaggcaaaaa acaagtagat    4920
gaaccctggt ttaatctctt attgcacgaa acgaattttt caggagaaaa gggtttagta    4980
gggcgcaata gcgttatgtt taccctctct ttagcctact ttagttcagg ctattcaatc    5040
gaaacgtgcg aatataatat gtttgagttt aataatcgat tagatcaacc cttagaagaa    5100
aaagaagtaa tcaaaattgt tagaagtgcc tattcagaaa actatcaagg ggctaatagg    5160
gaatacatta ccattctttg caaagcttgg gtatcaagtg atttaaccag taagagttta    5220
tttgtccgtc aagggtggtt taaattcaag aaaaaagaa gcgaacgtca acgtgttcat    5280
ttgtcagaat ggaagaagaa tttaatggct tatattagca aaaaagcga tgtatacaag    5340
ccttatttag cgacgaccaa aaagagatt agagaagtgc taggcattcc tgaacggaca    5400
```

```
ttagataaat tgctgaaggt actgaaggcg aatcaggaaa ttttcttta a gattaaacca    5460 ggaagaaatg gtggcattca acttgctagt gttaaatcat tgttgctatc gatcattaaa    5520
ttaaaaaaag aagaacgaga aagctatata aaggcgctga cagcttcgtt taatttagaa    5580
cgtacattta ttcaagaaac tctaaacaaa ttggcagaac gccccaaaac ggacccacaa    5640
ctcgatttgt ttagctacga tacaggctga aaataaaacc cgcactatgc cattacattt    5700
atatctatga tacgtgtttg tttttctttg ctggctagct taattgctta tatttacctg    5760
caataaagga tttcttactt ccattatact cccattttcc aaaaacatac ggggaacacg    5820
ggaacttatt gtacaggcca cctcatagtt aatggtttcg agccttcctg caatctcatc    5880
catggaaata tattcatccc cctgccggcc tattaatgtg acttttgtgc ccggcggata    5940
ttcctgatcc agctccacca taaattggtc catgcaaatt cggccggcaa ttttcaggcg    6000
ttttcccttc acaaggatgt cggtcccttt caattttcgg agccagccgt ccgcatagcc    6060
tacaggcacc gtcccgatcc atgtgtcttt ttccgctgtg tactcggctc cgtagctgac    6120
gctctcgcct tttctgatca gtttgacatg tgacagtgtc gaatgcaggg taaatgccgg    6180
acgcagctga aacggtatct cgtccgacat gtcagcagac gggcgaaggc catacatgcc    6240
gatgccgaat ctgactgcat taaaaaagcc tttttcagc cggagtccag cggcgctgtt    6300
cgcgcagtgg accattagat tcttaacgg cagcggagca atcagctctt taaagcgctc    6360
aaactgcatt aagaaatagc ctctttcttt ttcatccgct gtcgcaaaat gggtaaatac    6420 cccttgcac tttaaacgag ggttgcggtc aagaattgcc atcacgttct gaacttcttc    6480
ctctgttttt acaccaagtc tgttcatccc cgtatcgacc ttcagatgaa aatgaagaga    6540 acctttttc gtgtggcggg ctgcctcctg aagccattca acagaataac ctgttaaggt    6600
cacgtcatac tcagcagcga ttgccacata ctccggggga accgcgccaa gcaccaatat    6660
aggcgccttc aatccctttt tgcgcagtga aatcgcttca tccaaaatgg ccacggccaa    6720
gcatgaagca cctgcgtcaa gagcagcctt tgctgtttct gcatcaccat gcccgtaggc    6780
gtttgctttc acaactgcca tcaagtggac atgttcaccg atatgttttt tcatattgct    6840 gacatttcc tttatcgcgg acaagtcaat ttccgcccac gtatctctgt aaaaaggttt    6900
tgtgctcatg gaaactcct ctcttttttc agaaaatccc agtacgtaat aagtatttg    6960 agaattaatt ttatattgat taatactaag tttacccagt tttcacctaa aaacaaatg    7020 atgagataat agctccaaag gctaagagg actataccaa ctatttgtta attaa        7075
```

<210> SEQ ID NO 74
<211> LENGTH: 9
<212> TYPE: PRT
<213> ORGANISM: Artificial Sequence
<220> FEATURE:
<223> OTHER INFORMATION: HLA-A2 restricted epitopes

<400> SEQUENCE: 74

His Leu Tyr Gln Gly Cys Gln Val Val
1               5

<210> SEQ ID NO 75
<211> LENGTH: 9
<212> TYPE: PRT
<213> ORGANISM: Artificial Sequence
<220> FEATURE:
<223> OTHER INFORMATION: HLA-A2 restricted epitopes

<400> SEQUENCE: 75

```
Lys Ile Phe Gly Ser Leu Ala Phe Leu
1               5
```

<210> SEQ ID NO 76
<211> LENGTH: 9
<212> TYPE: PRT
<213> ORGANISM: Artificial Sequence
<220> FEATURE:
<223> OTHER INFORMATION: HLA-A2 restricted epitopes

<400> SEQUENCE: 76

```
Arg Leu Leu Gln Glu Thr Glu Leu Val
1               5
```

<210> SEQ ID NO 77
<211> LENGTH: 30
<212> TYPE: DNA
<213> ORGANISM: Artificial Sequence
<220> FEATURE:
<223> OTHER INFORMATION: forward amplification primer actA promoter
      region

<400> SEQUENCE: 77
atcccgggtg aagcttggga agcagttggg                              30

<210> SEQ ID NO 78
<211> LENGTH: 32
<212> TYPE: DNA
<213> ORGANISM: Artificial Sequence
<220> FEATURE:
<223> OTHER INFORMATION: reverse amplification primer actA promoter
      region

<400> SEQUENCE: 78
attctagatt tatcacgtac ccatttcccc gc                           32

<210> SEQ ID NO 79
<211> LENGTH: 32
<212> TYPE: DNA
<213> ORGANISM: Artificial Sequence
<220> FEATURE:
<223> OTHER INFORMATION: chimera Her2/neu amplification F primer

<400> SEQUENCE: 79
attctagaac ccacctggac atgctccgcc ac                           32

<210> SEQ ID NO 80
<211> LENGTH: 67
<212> TYPE: DNA
<213> ORGANISM: Artificial Sequence
<220> FEATURE:
<223> OTHER INFORMATION: chimera Her2/neu amplification R primer

<400> SEQUENCE: 80
gtcgacacta gtctagtggt gatggtgatg atggagctca gatctgtcta agaggcagcc    60
atagggc                                                              67

<210> SEQ ID NO 81
<211> LENGTH: 2015
<212> TYPE: DNA
<213> ORGANISM: Listeria monocytogenes

<400> SEQUENCE: 81
atggcgcggg atggtatact atacaagcgt atggttcaaa aagatacttt gaattaagaa    60

| | | | | |
|---|---|---|---|---|
| gtacaataaa | gttaacttca | ttagacaaaa | agaaaaaaca | aggaagaata gtacatagtt | 120 |
| ataaatactt | ggagagtgag | gtgtaatatg | ggggcagctg | attttgggg tttcatatat | 180 |
| gtagtttcaa | gattagccat | tgttgcggca | gtagtttact | tcttatactt attgagaaaa | 240 |
| attgcaaata | aatagaaaaa | aagccttgtc | aaacgaggct | ttttttatgc aaaaaatacg | 300 |
| acgaatgaag | ccatgtgaga | caatttggaa | tagcagacaa | caaggaaggt agaacatgtt | 360 |
| ttgaaaaatt | tactgatttt | cgattattat | taacgcttgt | taatttaaac atctcttatt | 420 |
| tttgctaaca | tataagtata | caaagggaca | taaaaaggtt | aacagcgttt gttaaatagg | 480 |
| aagtatatga | aaatcctctt | ttgtgtttct | aaatttattt | ttaaggagtg gagaatgttg | 540 |
| aaaaaaaata | attggttaca | aaatgcagta | atagcaatgc | tagtgttaat tgtaggtctg | 600 |
| tgcattaata | tgggttctgg | aacaaaagta | caagctgaga | gtattcaacg accaacgcct | 660 |
| attaaccaag | ttttcccaga | tcccggccta | gcgaatgcag | tgaaacaaaa tttagggaag | 720 |
| caaagtgtta | cagaccttgt | atcacaaaag | gaactatctg | gagtacaaaa tttcaatgga | 780 |
| gataatagca | acattcaatc | tcttgcggga | atgcaatttt | tcactaattt aaaagaactt | 840 |
| catctatccc | ataatcaaat | aagtgacctt | agtcctttaa | aggatctaac taagttagaa | 900 |
| gagctatctg | tgaatagaaa | cagactgaaa | aatttaaacg | gaattccaag tgcttgttta | 960 |
| tctcgcttgt | ttttagataa | caacgaactc | agagatactg | actcgcttat tcatttgaaa | 1020 |
| aatctagaaa | tcttatctat | tcgtaataat | aagttaaaaa | gtattgtgat gcttggtttt | 1080 |
| ttatcaaaac | tagaggtatt | agatttgcat | ggtaatgaaa | taacaaatac aggtggacta | 1140 |
| actagattga | agaaagttaa | ctggatagat | ttaactggtc | agaaatgtgt gaatgaacca | 1200 |
| gtaaaatacc | aaccagaatt | gtatataaca | aatactgtca | aagacccaga tggaagatgg | 1260 |
| atatctccat | attacatcag | taatggtggg | agttatgtag | atggttgtgt cctgtgggaa | 1320 |
| ttgccagttt | atacagatga | agtaagctat | aagtttagcg | aatatataaa cgttggggag | 1380 |
| actgaggcta | tatttgatgg | aacagttaca | caacctatca | agaattagga cttgtgcaca | 1440 |
| cctgtatact | ttgagctctc | gtataatcac | gagagctttt | taaatatgta agtcttaatt | 1500 |
| atctcttgac | aaaaagaacg | tttattcgta | taaggttacc | aagagatgaa gaaactatt | 1560 |
| tatttacaat | tcaccttgac | accaaaaact | ccatatgata | tagtaaataa ggttattaaa | 1620 |
| caagaaagaa | gaagcaaccc | gcttctcgcc | tcgttaacac | gaacgttttc aggcaaaaaa | 1680 |
| ttcaaacttt | cgtcgcgtag | cttacgcgat | tttgaatgtg | cgggattgct gaaaagcagc | 1740 |
| ccgttttttt | atggcctccg | aacgaatgag | ttagcaggcc | gcagatttga acagctattt | 1800 |
| tctatcttgt | tgtaacaaaa | ttaagtggag | gtggctcacc | attagcaaag acatgttggt | 1860 |
| aaacgatggg | attcgtgcac | gtgaagtaag | attgatcgac | caagacggtg aacaattagg | 1920 |
| cgtgaagagt | aaaatcgatg | cgcttcaaat | tgctgaaaag | gctaatcttg atctagtgct | 1980 |
| tgttgctcca | acagcgaaac | cgccagtagc | tcgta | | 2015 |

<210> SEQ ID NO 82
<211> LENGTH: 1140
<212> TYPE: DNA
<213> ORGANISM: Artificial Sequence
<220> FEATURE:
<223> OTHER INFORMATION: sequence of DNA that is cloned in the
    temperature sensitive plasmid, pKSV7 to create inl C deletion
    mutant

<400> SEQUENCE: 82

| | | | | |
|---|---|---|---|---|
| gaattcatgg | cgcgggatgg | tatactatac | aagcgtatgg | ttcaaaaaga tactttgaat | 60 |

```
taagaagtac aataaagtta acttcattag acaaaaagaa aaaacaagga agaatagtac    120
atagttataa atacttggag agtgaggtgt aatatggggg cagctgattt ttggggtttc    180
atatatgtag tttcaagatt agccattgtt gcggcagtag tttacttctt atacttattg    240
agaaaaattg caaataaata gaaaaaaagc cttgtcaaac gaggcttttt ttatgcaaaa    300
aatacgacga atgaagccat gtgagacaat ttggaatagc agacaacaag gaaggtagaa    360
catgttttga aaaatttact gattttcgat tattattaac gcttgttaat ttaaacatct    420 cttattttg ctaacatata agtatacaaa gggacataaa aaggttaaca gcgtttgtta    480
aataggaagt atatgaaaat cctcttttgt gtttctaaat ttatttttaa ggagtggaga    540
ggatccggac ttgtgcacac ctgtatactt tgagctctcg tataatcacg agagcttttt    600
aaatatgtaa gtcttaatta tctcttgaca aaagaacgt ttattcgtat aaggttacca     660
agagatgaag aaactatttt atttacaatt caccttgaca ccaaaaactc catatgatat    720
agtaaataag gttattaaac aagaaagaag aagcaacccg cttctcgcct cgttaacacg    780
aacgttttca ggcaaaaaat tcaaactttc gtcgcgtagc ttacgcgatt ttgaatgtgc    840
gggattgctg aaaagcagcc cgttttttta tggcctccga acgaatgagt tagcaggccg    900
cagatttgaa cagctatttt ctatcttgtt gtaacaaaat taagtggagg tggctcacca    960
ttagcaaaga catgttggta aacgatggga ttcgtgcacg tgaagtaaga ttgatcgacc   1020
aagacggtga acaattaggc gtgaagagta aaatcgatgc gcttcaaatt gctgaaaagg   1080
ctaatcttga tctagtgctt gttgctccaa cagcgaaacc gccagtagct cgtactgcag   1140

<210> SEQ ID NO 83
<211> LENGTH: 1256
<212> TYPE: DNA
<213> ORGANISM: Listeria monocytogenes

<400> SEQUENCE: 83
gcgccaaatc attggttgat tggtgaggat gtctgtgtgc gtgggtcgcg agatgggcga     60
ataagaagca ttaaagatcc tgacaaatat aatcaagcgg ctcatatgaa agattacgaa    120
tcgcttccac tcacagagga aggcgactgg ggcggagttc attataatag tggtatcccg    180
aataaagcag cctataatac tatcactaaa cttggaaaag aaaaaacaga acagctttat    240
tttcgcgcct taaagtacta tttaacgaaa aaatcccagt ttaccgatgc gaaaaaagcg    300
cttcaacaag cagcgaaaga tttatatggt gaagatgctt ctaaaaaagt tgctgaagct    360
tgggaagcag ttggggttaa ctgattaaca atgttagaa aaaattaat tctccaagtg     420 atattcttaa aataattcat gaatattttt tcttatatta gctaattaag aagataacta    480
actgctaatc caattttttaa cggaacaaat tagtgaaaat gaaggccgaa ttttccttgt   540
tctaaaaagg ttgtattagc gtatcacgag gagggagtat aagtgggatt aaacagattt    600
atgcgtgcga tgatggtggt tttcattact gccaattgca ttacgattaa ccccgacgtc    660
gacccatacg acgttaattc ttgcaatgtt agctattggc gtgttctctt tagggcgtt     720 tatcaaaatt attcaattaa gaaaaaataa ttaaaaacac agaacgaaag aaaaagtgag   780
gtgaatgata tgaaattcaa aaaggtggtt ctaggtatgt gcttgatcgc aagtgttcta    840
gtctttccgg taacgataaa agcaaatgcc tgttgtgatg aatacttaca aacacccgca    900
gctccgcatg atattgacag caaattacca cataaactta gttggtccgc ggataacccg    960
acaaatactg acgtaaatac gcactattgg cttttttaaac aagcggaaaa aatactagct   1020
```

-continued

| | | | | | |
|---|---|---|---|---|---|
| aaagatgtaa | atcatatgcg | agctaattta | atgaatgaac | ttaaaaaatt | cgataaacaa  1080 |
| atagctcaag | gaatatatga | tgcggatcat | aaaaatccat | attatgatac | tagtacattt  1140 |
| ttatctcatt | tttataatcc | tgatagagat | aatacttatt | tgccgggttt | tgctaatgcg  1200 |
| aaaataacag | gagcaaagta | tttcaatcaa | tcggtgactg | attaccgaga | agggaa  1256 |

What is claimed is:

1. A method of reducing suppression of activated T cells by suppressor cells in an antigen non-specific manner in a subject having asthma or in a disease site within the subject, the method comprising the step of administering to the subject a composition comprising a live attenuated *Listeria* vaccine strain, wherein said *Listeria* vaccine strain comprises a recombinant nucleic acid comprising an open reading frame encoding an endogenous Proline, Glutamic acid, Serine, and Threonine (PEST)-containing polypeptide, wherein the PEST-containing polypeptide is not fused to a heterologous antigen, and wherein administration of said *Listeria* strain reduces the suppression of said activated T cell in said subject or in said disease site within the subject.

2. The method of claim 1, wherein said activated T cells are CD8+ T cells or CD4+ T cells.

3. The method of claim 1, wherein said suppressor cells are T-regulatory cells (Treg).

4. The method of claim 1, wherein said subject is human.

5. The method of claim 1, wherein said suppressor cells suppress an anti-tumor or cancer T cell response, or an anti-disease T cell response in said subject.

6. The method of claim 1, wherein said recombinant nucleic acid further comprises an additional open reading frame encoding a metabolic enzyme, wherein said metabolic enzyme complements an endogenous gene that is lacking in the chromosome of said attenuated *Listeria* strain.

7. The method of claim 6, wherein said metabolic enzyme encoded by said additional open reading frame is an alanine racemase enzyme or a D-amino acid transferase enzyme.

8. The method of claim 6, wherein said attenuated *Listeria* further comprises a mutation or a deletion of a genomic actA gene, a plcA gene, prfA gene or a plcB gene.

9. The method of claim 1, wherein said recombinant nucleic acid is integrated into the *Listeria* genome.

10. The method of claim 1, wherein said recombinant nucleic acid is in a plasmid that is stably maintained in said recombinant *Listeria* vaccine strain in the absence of antibiotic selection.

11. The method of claim 1, wherein said PEST-containing polypeptide is an N-terminal truncated Listeriolysin O (LLO) polypeptide, an N-terminal ActA polypeptide, or PEST-peptide.

12. The method of claim 1, wherein said suppressor cells are myeloid-derived suppressor cells (MDSC).

13. The method of claim 1, wherein said suppression of activated T cells comprises suppression of T-cell replication of the activated T-cells.

14. The method of claim 1, wherein said administrating is in combination with other therapeutic modalities useful for enhancing an immune response.

* * * * *